(12) United States Patent
Noggle et al.

(10) Patent No.: US 10,428,309 B2
(45) Date of Patent: *Oct. 1, 2019

(54) SYSTEMS AND METHODS FOR PRODUCING STEM CELLS AND DIFFERENTIATED CELLS

(71) Applicant: New York Stem Cell Foundation, Inc., New York, NY (US)

(72) Inventors: Scott Noggle, Long Island City, NY (US); Kevin Eggan, Boston, MA (US); Stephen Chang, Poway, CA (US); Susan Solomon, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 280 days.

This patent is subject to a terminal disclaimer.

(21) Appl. No.: 14/318,339

(22) Filed: Jun. 27, 2014

(65) Prior Publication Data

US 2015/0166964 A1 Jun. 18, 2015

Related U.S. Application Data

(63) Continuation-in-part of application No. 13/691,258, filed on Nov. 30, 2012.
(Continued)

(51) Int. Cl.
*C12M 1/00* (2006.01)
*C12M 1/32* (2006.01)
(Continued)

(52) U.S. Cl.
CPC .......... *C12N 5/0696* (2013.01); *C12M 23/12* (2013.01); *C12M 41/46* (2013.01); *C12M 41/48* (2013.01); *C12M 47/04* (2013.01)

(58) Field of Classification Search
CPC ..... C12N 5/0696; C12M 23/12; C12M 41/46; C12M 41/48; C12M 47/04
See application file for complete search history.

(56) References Cited

U.S. PATENT DOCUMENTS 7,879,601 B2 2/2011 Smith et al.
8,211,697 B2 7/2012 Sakurada et al.
(Continued)

FOREIGN PATENT DOCUMENTS

EP 2 423 302 A1 2/2012
EP 2 481 795 A1 8/2012
(Continued)

OTHER PUBLICATIONS

Abyzov, A. et al.: "Somatic copy number mosaicism in human skin revealed by induced pluripotent stem cells". Nature 492, 438-442 (2012).
(Continued)

*Primary Examiner* — William H. Beisner
*Assistant Examiner* — Danielle B Henkel
(74) *Attorney, Agent, or Firm* — DLA Piper LLP (US)

(57) ABSTRACT

The present invention provides various improved systems and methods for obtaining, generating, culturing, and handling cells, such as stem cells (including induced pluripotent stem cells or iPSCs) and differentiated cells, as well as cells and cell panels produced using such systems and methods, and uses of such cells and cell panels.

9 Claims, 77 Drawing Sheets
Specification includes a Sequence Listing.

Related U.S. Application Data

(60) Provisional application No. 61/840,271, filed on Jun. 27, 2013, provisional application No. 61/700,792, filed on Sep. 13, 2012, provisional application No. 61/580,007, filed on Dec. 23, 2011, provisional application No. 61/565,818, filed on Dec. 1, 2011.

(51) Int. Cl.
  *C12M 1/34* (2006.01)
  *C12M 1/36* (2006.01)
  *C12N 5/074* (2010.01)

(56) References Cited

U.S. PATENT DOCUMENTS

| | | | |
|---|---|---|---|
| 2001/0051374 | A1 | 12/2001 | McLaughlin-Taylor et al. |
| 2006/0179502 | A1 | 8/2006 | Kauselmann |
| 2007/0238175 | A1* | 10/2007 | Chi ................. C12N 5/0679 435/378 |
| 2009/0029462 | A1 | 1/2009 | Beardsley et al. |
| 2010/0167300 | A1 | 7/2010 | Esmaeli-Azad |
| 2010/0216181 | A1 | 8/2010 | Daigh et al. |
| 2010/0279403 | A1 | 11/2010 | Rajesh |
| 2011/0020814 | A1 | 1/2011 | Dimos |
| 2011/0171185 | A1 | 7/2011 | Klimanskaya |
| 2011/0200568 | A1 | 8/2011 | Ikeda et al. |
| 2011/0286978 | A1 | 11/2011 | Klimanskaya et al. |
| 2011/0306516 | A1 | 12/2011 | Kahler et al. |
| 2012/0135525 | A1 | 5/2012 | Brown |
| 2013/0345094 | A1 | 12/2013 | Noggle et al. |
| 2014/0220681 | A1* | 8/2014 | Valamehr ........... C12N 5/0696 435/366 |

FOREIGN PATENT DOCUMENTS

| | | |
|---|---|---|
| WO | WO 2003/087292 A2 | 12/2003 |
| WO | WO 2008/107695 A1 | 9/2008 |
| WO | WO 2011/026222 A1 | 3/2011 |
| WO | WO 2013/082509 A1 | 6/2013 |

OTHER PUBLICATIONS

Beers, J. et al.: "A cost-effective and efficient reprogramming platform for large-scale production of integration-free human induced pluripotent stem cells in chemically defined culture". Sci. Rep. 5, 11319 (2015).
Bock, C. et al.: "Reference maps of human ES and iPS cell variation enable high-throughput characterization of pluripotent cell lines". Cell 144, 439-452 (2011).
Cahan, P. & Daley, G.Q.: "Origins and implications of pluripotent stem cell variability and heterogeneity". Nat. Rev. Mol. Cell Biol. 14, 357-368 (2013).
Carey, B.W. et al.: "Reprogramming factor stoichiometry influences the epigenetic state and biological properties of induced pluripotent stem cells". Cell Stem Cell 9, 588-598 (2011).
Chen, K.G. et al: "Human pluripotent stem cell culture: considerations for maintenance, expansion, and therapeutics". Cell Stem Cell 14, 13-26 (2014).
Cheng, L. et al.: "Low incidence of DNA sequence variation in human induced pluripotent stem cells generated by nonintegrating plasmid expression". Stem Cell 10, 337-344 (2012).
Colman, A. & Dreesen, O.: "Pluripotent stem cells and disease modeling". Cell Stem Cell 5, 244-247 (2009).
Conway, M.K. et al.: "Scalable 96-well plate based iPSC culture and production using a robotic liquid handling system". J. Vis. Exp. 99, e52755 (2015).
Douvaras, P. et al.: "Efficient generation of myelinating oligodendrocytes from primary progressive multiple sclerosis patients by induced pluripotent stem cells". Stem Cell Reports 3, 250-259 (2014.
Fusaki, N. et al.: "Efficient induction of transgene-free human pluripotent stem cells using a vector based on Sendai virus, an RNA virus that does not integrate into the host genome". Proc. Jpn. Acad., Ser. B, Phys. Biol. Sci. 85, 348-362 (2009).
Hanna, J. et al.: "Direct cell reprogramming is a stochastic process amenable to acceleration". Nature 462, 595-601 (2009).
Hannan, N.R.F. et al.: "Production of hepatocyte-like cells from human pluripotent stem cells". Nat. Protoc. 8, 430-437 (2013).
Harris, P.A. et al.: "Research electronic data capture (REDCap)—a metadata-driven methodology and workflow process for providing translational research informatics support". J. Biomed. Inform. 42, 377-381 (2009).
Kajiwara, M. et al.: "Donor-dependent variations in hepatic differentiation from human-induced pluripotent stem cells". Proc. Natl. Acad. Sci. USA 109, 12538-12543 (2012).
Li, C. et al.: "Genetic heterogeneity of induced pluripotent stem cells: results from 24 clones derived from a single C57BL/6 mouse". PLoS One 10, e0120585 (2015).
Lian, X. et al.: "Directed cardiomyocyte differentiation from human pluripotent stem cells by modulating Wnt/β-catenin signaling under fully defined conditions". Nat. Protoc. 8, 162-175 (2013).
Liang, G. & Zhang, Y.: "Genetic and epigenetic variations in iPSCs: potential causes and implications for application". Cell Stem Cell 13, 149-159 (2013).
Martincorena, I. et al.: "Tumor evolution. High burden and pervasive positive selection of somatic mutations in normal human skin". Science (New York, N.Y.) 348, 880-886 (2015).
Mayshar, Y. et al.: "Identification and classification of chromosomal aberrations in human induced pluripotent stem cells". Cell Stem Cell 7, 521-531 (2010).
McKernan, R. & Watt, F.M.: "What is the point of large-scale collections of human induced pluripotent stem cells?" Nat. Biotechnol. 31, 875-877 (2013).
Mekhoubad, S. et al.: "Erosion of dosage compensation impacts human iPSC disease modeling". Cell Stem Cell 10, 595-609 (2012).
Morris, A.P. et al.: "Large-scale association analysis provides insights into the genetic architecture and pathophysiology of type 2 diabetes". Nat. Genet. 44, 981-990 (2012).
R Development Core Team: "R: A Language and Environment for Statistical Computing" (R Foundation for Statistical Computing, 2012).
Robinton, D.A. & Daley, G.Q.: "The promise of induced pluripotent stem cells in research and therapy". Nature 481, 295-305 (2012).
Rohani, L. et al.: "The aging signature: a hallmark of induced pluripotent stem cells?" Aging Cell 13, 2-7 (2014).
Santostefano, K.E. et al.: "A practical guide to induced pluripotent stem cell research using patient samples". Lab. Invest. 95, 4-13 (2015).
Taguchi, A. et al.: "Redefining the in vivo origin of metanephric nephron progenitors enables generation of complex kidney structures from pluripotent stem cells". Cell Stem Cell 14, 53-67 (2014).
Takahashi, K. et al.: "Induction of pluripotent stem cells from adult human fibroblasts by defined factors". Cell 131, 861-872 (2007).
Terstegge, S. et al.: "Automated maintenance of embryonic stem cell cultures". Biotechnol. Bioeng. 96, 195-201 (2007).
Thomas, R. et al.: "Automated, scalable culture of human embryonic stem cells in feeder-free conditions." Biotechnol. Bioeng. 102, 1636-1644 (2009).
Tyson, C. et al.: "Expansion of a 12-kb VNTR containing the REXO1L1 gene cluster underlies the microscopically visible euchromatic variant of 8q21.2". Eur. J. Hum. Genet. 22, 458-463 (2014).
Utikal, J. et al.: "Immortalization eliminates a roadblock during cellular reprogramming into iPS cells". Nature 460, 1145-1148 (2009).
Valamehr, B. et al.: "A novel platform to enable the high-throughput derivation and characterization of feeder-free human iPSCs". Sci. Rep. 2, 213 (2012).
Vallot, C. et al.: "Erosion of X chromosome inactivation in human pluripotent cells initiates with XACT coating and depends on a specific heterochromatin landscape". Cell Stem Cell 16, 533-546 (2015).
Warren, L. et al.: "Highly efficient reprogramming to pluripotency and directed differentiation of human cells with synthetic modified mRNA". Cell Stem Cell 7, 618-630 (2010).

(56) References Cited

OTHER PUBLICATIONS

Warren, L. et al.: "*Feeder-free derivation of human induced pluripotent stem cells with messenger RNA*". Sci. Rep. 2, 657 (2012).
Watanabe, K. et al.: "*A ROCK inhibitor permits survival of dissociated human embryonic stem cells*". Nat. Biotechnol. 25, 681-686 (2007).
Woodard, C.M. et al.: "*iPSC-derived dopamine neurons reveal differences between monozygotic twins discordant for Parkinson's disease*". Cell Reports 9, 1173-1182 (2014).
Zhou, H. et al.: "*Rapid and efficient generation of transgene-free iPSC from a small volume of cryopreserved blood*". Stem Cell Rev. 11, 652-665 (2015).
Anonymous: "*081-09.04.10: NRW-Konsortium baut "StemCellFactory"*; UKB Universitatsklinikum BONN / Medizinische Fakultat, Apr. 9, 2010 (Apr. 9, 2010), XP055176792, Retrieved from the Internet: URL:https://www.ukb.uni-bonn.de/42256BC8002AF3E7/vwWebPagesByID/E48E477507DEDBB9C125 77000030729D. With English translation (Anonymous:"*NRW Consortium to Build*"*Stem Cell Factory*"; Home News Archive; Apr. 9, 2010.).
Extended European Search Report dated Mar. 26, 2015, regarding EP 12 85 2680.
Japanese Office Action dated Sep. 6, 2016, regarding JP 2014-544949.
Kahler, David J. et al.: "*Improved Methods for Fibroblast Reprogramming*"; PLOS ONE, Mar. 2013, vol. 8:3; e59867.
International Search Report regarding PCT/US2014/044702.
International Search Report dated May 19, 2016, regarding PCT/US2015/000498.
Aasen, Trond, et al.: "*Efficient and rapid generation of induced pluripotent stem cells from human keratinocytes*"; Nature Biotechnology, vol. 26, No. 11, Nov. 1, 2008, pp. 1276-1284.
Extended European Search Report dated May 11, 2017, regarding EP 14 81 7538.3.
Phang, Rui-Zhe et al.: "*Zinc Finger Nuclease-Expressing Baculoviral Vectors Mediate Targeted Genome Integration of Reprogramming Factor Genes to Facilitate the Generation of Human Induced Pluripotent Stem Cells*"; Stem Cells Translational Medicine : SCTM, vol. 2, No. 12, Oct. 28, 2013, pp. 935-945.
Haupt, Simone et al.: "*Automated selection and harvesting of pluripotent stem cell colonies*"; Biotechnology and Applied Biochemistry, vol. 59, No. 2, Mar. 1, 2012, pp. 77-87.
Joannides, Alexis et al.: "*Automated mechanical passaging: a novel and efficient method for human embryonic stem cell expansion*"; Stem Cells, vol. 24, No. 2, Feb. 1, 2006, pp. 230-235.
Kami, Daisuke et al.: "*Large-scale cell production of stem cells for clinical application using the automated cell processing machine*"; BMC Biotechnology, 13:102, Nov. 15, 2013, 9 pages.
Partial Supplementary Search Report dated Feb. 13, 2017, regarding EP 14 81 7538.3.
Paull, Daniel et al.: "*Automated, high-throughput derivation, characterization and differentiation of induced pluripotent stem cells*"; Nature Methods, vol. 12, No. 9, Sep. 2015, pp. 885-892.
Techan Cellerity™ documents Published by Techan 2008-2009, pp. 1-18.
Ramalingam, Sivaprakash et al.: "*Generation and Genetic Engineering of Human Induced Pluripotent Stem Cells Using Designed Zinc Finger Nucleases*"; Stem Cell & Development, 2013, vol. 22, No. 4, pp. 595-610.
Byrne, Susan M. et al.: "*Genome Editing in Human Stem Cells*"; Methods in Enzymology, 2014, vol. 546, pp. 119-138.
Heintze, Jacob et al.: "*A CRISPRr CASe for high-throughput silencing*"; Frontiers in Genetics, Oct. 2013, vol. 4, Article 193, pp. 1-6.
Wagner, Kate and Welch, David: "*Cryopreserving and Recovering of Human iPS Cells using Complete KnockOut Serum Replacement Feeder-Free Medium*"; J. Visual Experiments, 2010, pp. 1-3.

\* cited by examiner

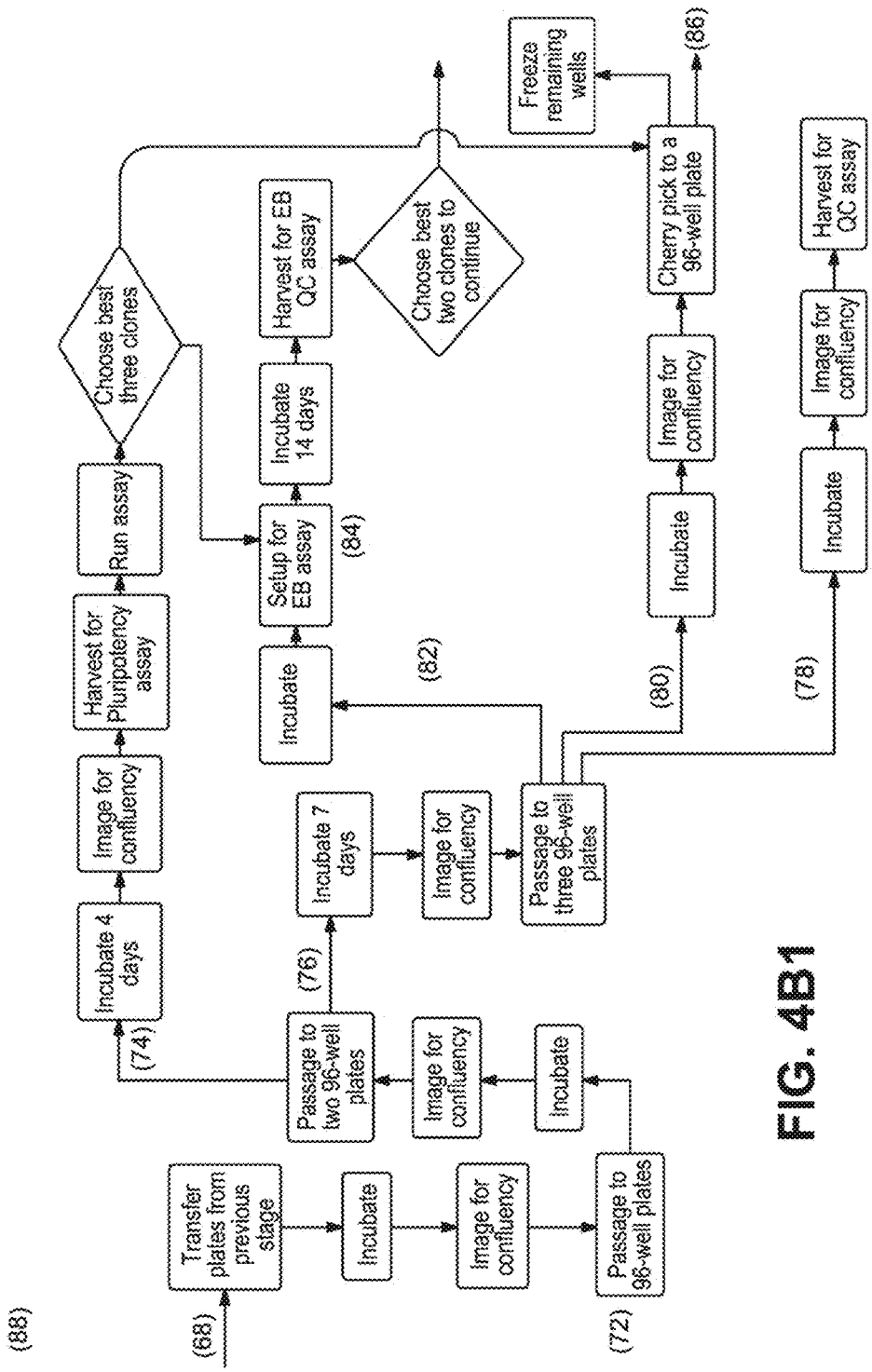
FIG. 4B1

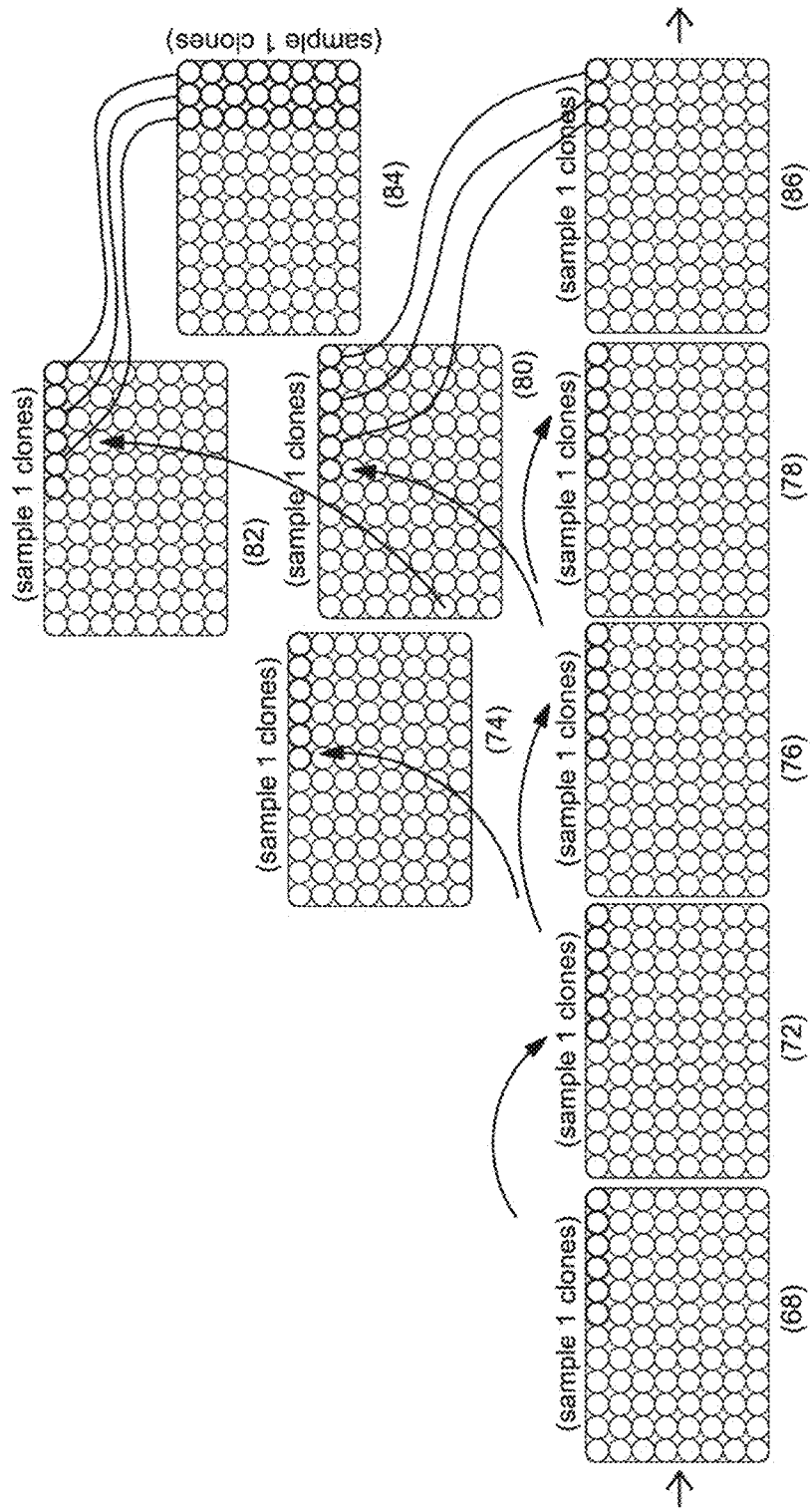
FIG. 4B2

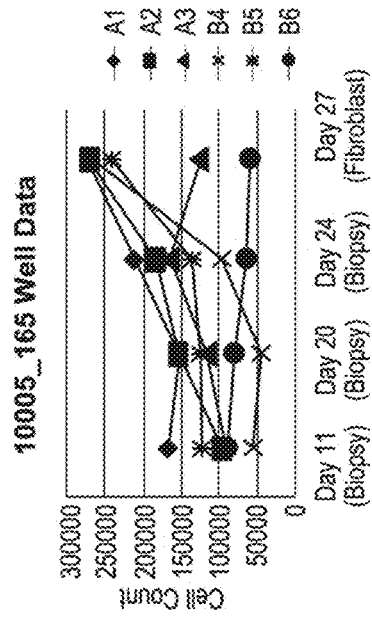
FIG. 6A
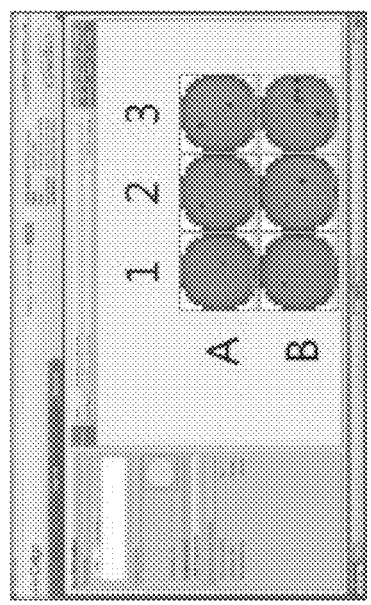
FIG. 6B
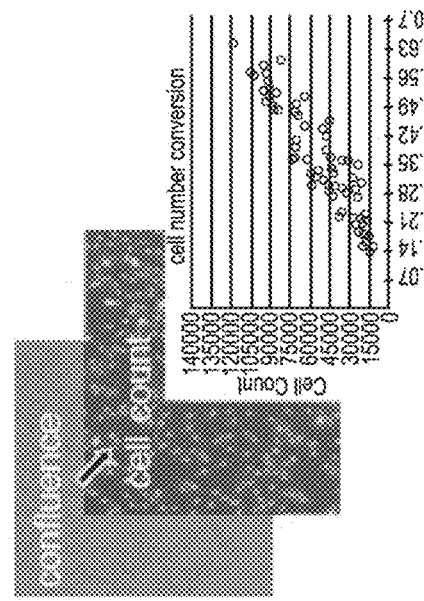
FIG. 6C
FIG. 6D

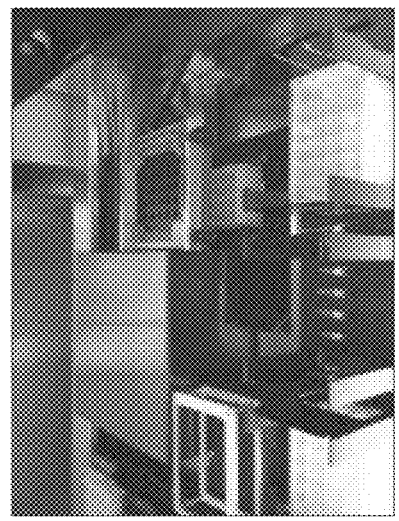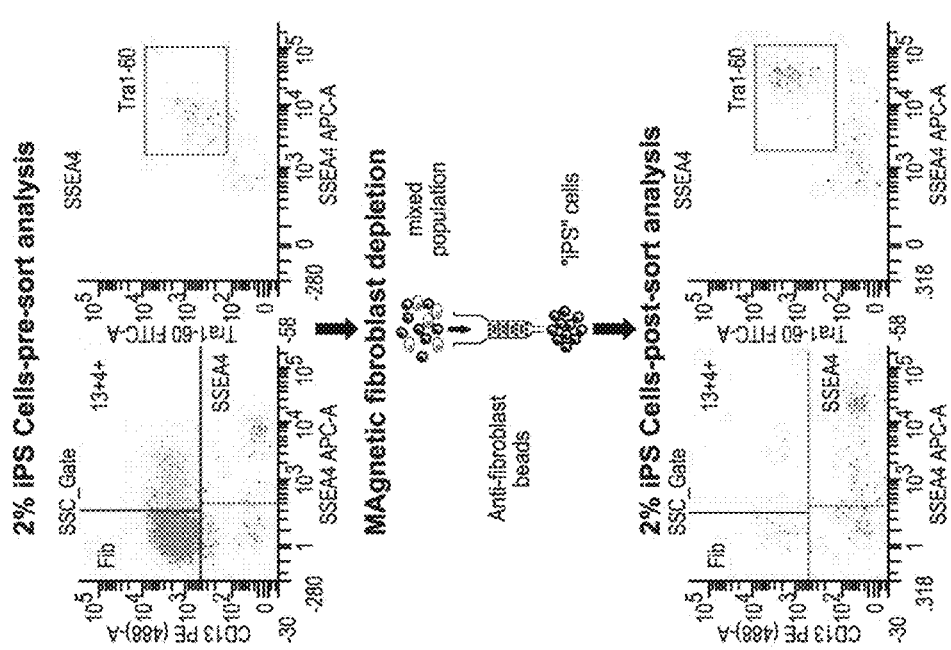

| Sorted Population | Sorted Cell# | Colonies |
|---|---|---|
| SSEA4+ | 5000 | 35 |
| SSEA4+ | 10000 | 129 |
| SSEA4+ Tra-1-60+ | 5000 | 132 |
| SSEA4+ Tra-1-60+ | 10000 | 363 |

FIG. 18A

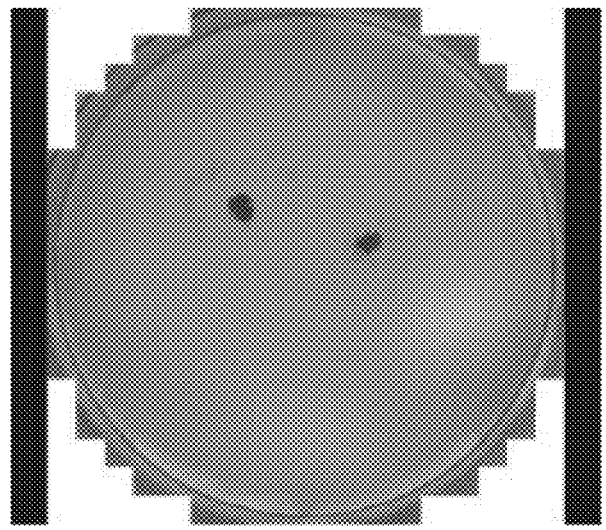
FIG. 20D(i)
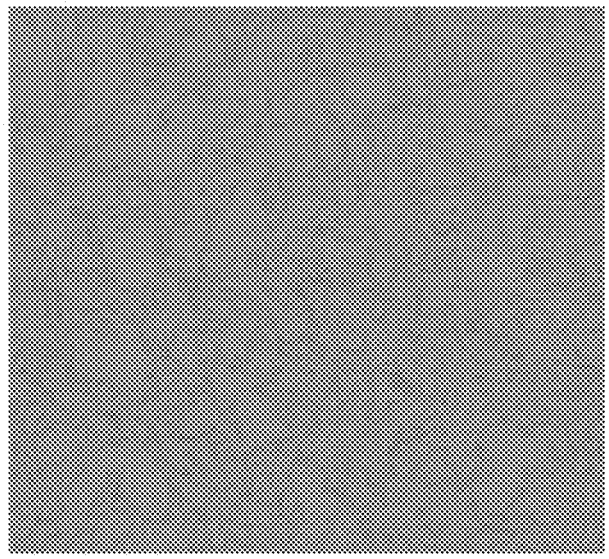
FIG. 20D(ii)

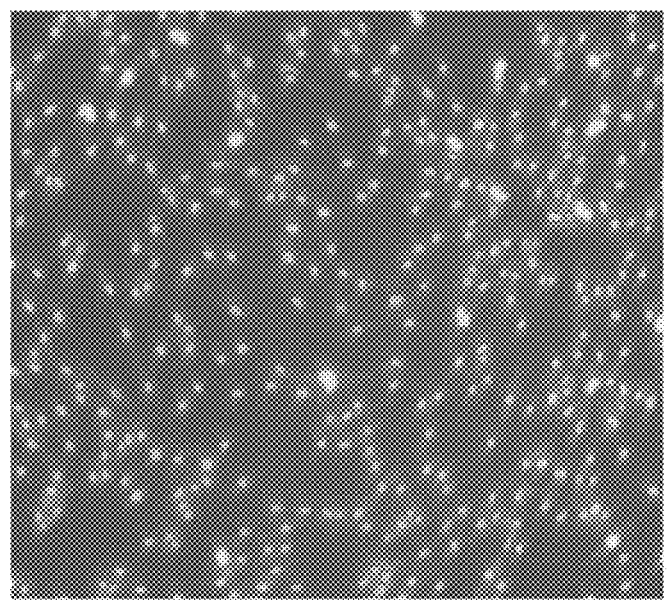
FIG. 20D(iii)
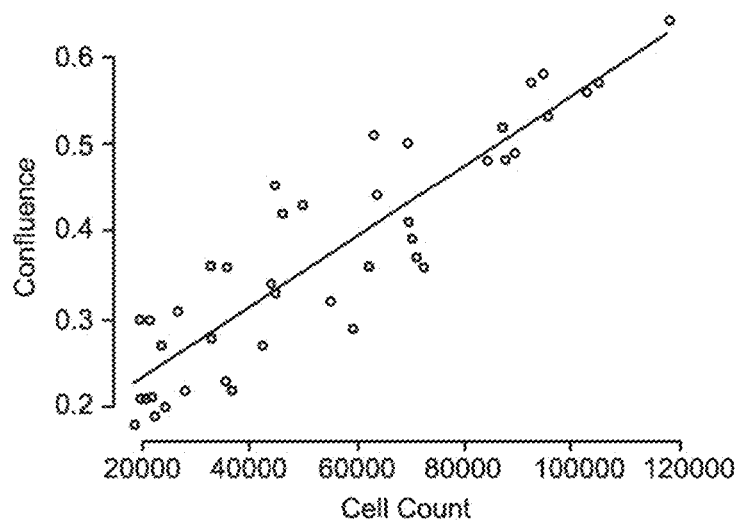
FIG. 20D(iv)

| Cell Line | Diff Score (Tmed) | Pluri Score (Tmed) | diff_mu | Pluri_mu |
|---|---|---|---|---|
| HUES 45 P34 | -3.393 | 1.595 | 5.455 | 12.240 |
| HUES 65 P28 | -2.715 | 2.225 | 5.468 | 12.496 |
| HUES 65 P33 | -1.034 | 2.789 | 5.903 | 12.268 |
| BC1 P30 | -0.381 | 1.390 | 6.193 | 10.846 |
| HUES 44 P29 | -0.139 | 1.531 | 5.956 | 12.153 |
| HUES 44 P32 | 0.639 | 1.953 | 6.030 | 11.997 |
| HUES 45 P31 | 0.079 | 2.084 | 6.088 | 12.157 |
| HUES 45 P33 | 0.190 | 1.778 | 6.119 | 11.979 |
| HUES 6 P32 | -1.015 | 2.050 | 5.865 | 12.311 |
| HUES 6 P36 | -1.932 | 1.892 | 5.515 | 12.354 |
| HUES 8 P34 | 0.836 | 1.450 | 6.134 | 11.873 |
| HUES 8 P35 | -2.621 | 0.822 | 5.369 | 11.959 |
| HUES 9 P31 | -0.051 | 2.266 | 6.074 | 12.105 |
| HUES 9 P33 | 0.816 | 1.986 | 6.149 | 12.089 |
| HUES 1 P34 | -4.058 | 2.291 | 5.082 | 12.069 |
| 10005_421F P2 | 1.288 | 0.750 | 6.446 | 10.745 |
| 10005_450F P2 | -0.175 | 0.984 | 6.193 | 11.741 |
| 10005_421F P2 | -1.175 | 1.663 | 5.800 | 11.733 |
| 10005_350F P2 | 1.018 | 0.019 | 6.459 | 11.532 |
| BJ P2 | -0.106 | 0.019 | 6.096 | 11.886 |
| BJ P2 | -0.211 | 1.734 | 6.155 | 11.600 |
| BJ P2 | -0.265 | 1.782 | 6.076 | 12.012 |
| 10005_569F P2 | -0.596 | 1.149 | 5.967 | 11.468 |
| 10005_568F P2 | 0.037 | 1.828 | 6.108 | 12.235 |
| BJ P2 | -0.686 | 1.632 | 6.064 | 12.140 |
| 10005_699 P2 | 0.011 | 3.095 | 5.956 | 12.927 |
| Fibroblast 1 | 4.948 | -14.167 | 8.428 | 5.699 |
| Fibroblast 2 | 3.243 | -14.540 | 8.266 | 5.678 |
| Fibroblast 3 | 5.197 | -14.025 | 8.473 | 5.726 |

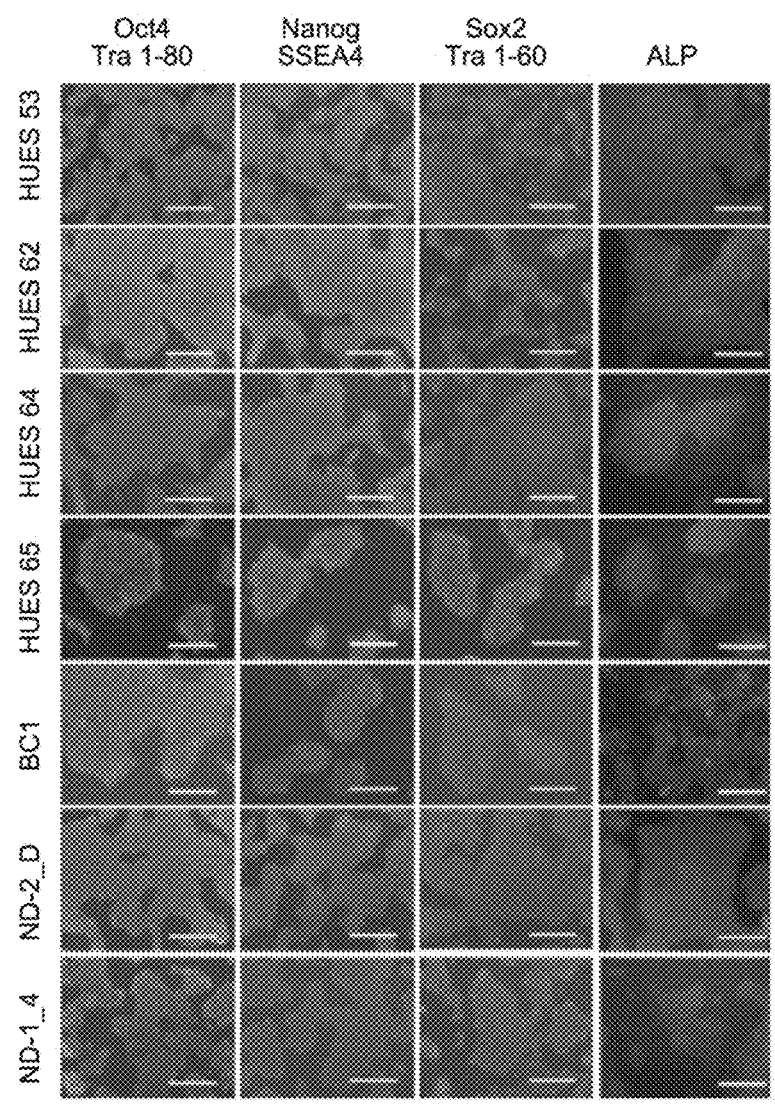
FIG. 32A(ii)

| Reference lines | EC | | ME | | EN |
|---|---|---|---|---|---|
| Hues 1 P30 | ⇨ | 0.07 ⇨ | -0.23 | ⇨ | 0.20 |
| Hues 9 P28 | ⇨ | -0.37 ⇨ | 0.47 | ⬀ | 0.84 |
| Hues 8 P30 | ⇨ | 0.49 ⬂ | -0.53 | ⇨ | -0.15 |
| Hues 64 P29 | ⇨ | 0.10 ⇨ | 0.01 | ⇨ | -0.09 |
| Hues 45 P31 | ⇨ | -0.30 ⇨ | -0.01 | ⇨ | 0.10 |
| Hues 53 P15 | ⇨ | -0.18 ⬀ | 0.60 | ⇨ | 0.33 |
| Hues 49 P20 | ⬀ | 0.94 ⇨ | -0.34 | ⬂ | -0.58 |
| Hues 44 P27 | ⇨ | 0.06 ⇨ | 0.33 | ⇨ | 0.38 |
| Hues 62 P16 | ⇨ | 0.01 ⇨ | 0.24 | ⇨ | -0.24 |
| Hues 65 P26 | ⬀ | 0.53 ⬂ | -1.12 | ⬂ | -1.33 |

FIG. 32B

SEQUENCE LISTING

<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
ccccagggcc ccattttggt acc                                              23

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggcacaaact ccaggttttc                                                  20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
acactgcccc tctcacacat                                                  20

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gggttttctc catgctgttt ct                                               22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
acccacacag gtgagaaacc tt                                               22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gttgggaact tgaccatgat tg                                               22

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
agcagaggag caaaagctca tt                                            22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccaaagtcca atttgaggca gt                                            22

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ccccagggcc ccattttggt acc                                           23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
aacctacagg tggggtcttt ca                                            22

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acactgcccc tctcacacat                                               20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aacctacagg tggggtcttt ca                                            22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gaccacctcg ccttacacat                                               20
```

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
aacctacagg tgggtctttt ca                                              22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
agcagaggag caaaagctca tt                                              22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
aacctacagg tggggtcttt ca                                              22

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
tagctgtgct cgggctact                                                  19

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tctctgctgg atgacgcg                                                   18

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gagaaggaga agctggagca                                                 20

<210> SEQ ID NO 20
<211> LENGTH: 20
<212> TYPE: DNA
<213> ORGANISM: Artificial Sequence
<220> FEATURE:
<223> OTHER INFORMATION: Primer

```
<400> SEQUENCE: 20
gtgaagtgag ggctcccata                                               20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agaaccccaa gatgcacaac                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tggagtggga ggaagaggta                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
acctggcgag tctgacatgg                                               20

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
tcttcatgtg taaggcgagg tgg                                           23
```

SYSTEMS AND METHODS FOR PRODUCING STEM CELLS AND DIFFERENTIATED CELLS

This application is a Continuation-In-Part application of U.S. application Ser. No. 13/691,258, filed Nov. 30, 2012, now pending, which claims benefit of priority under 35 U.S.C. § 119(e) of U.S. Provisional Patent Application No. 61/700,792, filed Sep. 13, 2012; U.S. Provisional Patent Application No. 61/580,007, filed Dec. 23, 2011; U.S. Provisional Patent Application No. 61/565,818, filed on Dec. 1, 2011; and which claims benefit of priority under 35 U.S.C. § 119(e) of U.S. Provisional Patent Application No. 61/840,271 filed Jun. 27, 2013, the entire contents of which are incorporated herein by reference in their entireties.

The material in the accompanying Sequence Listing is hereby incorporated by reference into this application. The accompanying sequence listing text file, name NYSC1210-1_Sequence_Listing_ST25.txt, was created on Dec. 8, 2014 and is 5 KB. The file can be assessed using Microsoft Word on a computer that uses Windows OS.

BACKGROUND OF THE INVENTION

Stem cells are unspecialized cells that self-renew for long periods through cell division, and can be induced to differentiate into cells with specialized functions, i.e., differentiated cells. These qualities give stem cells great promise for use in therapeutic applications to replace damaged cells and tissue in various medical conditions. Embryonic stem (ES) cells are derived from the blastocyst of an early stage embryo and have the potential to develop into endoderm, ectoderm, and mesoderm (the three germ layers) (i.e., they are "pluripotent"). In vitro, ES cells tend to spontaneously differentiate into various types of tissues, and the control of their direction of differentiation can be challenging. There are unresolved ethical concerns that are associated with the destruction of embryos in order to harvest human ES cells. These problems limit their availability for research and therapeutic applications.

Adult stem (AS) cells are found among differentiated tissues. Stem cells obtained from adult tissues typically have the potential to form a more limited spectrum of cells (i.e., "multipotent"), and typically only differentiate into the cell types of the tissues in which they are found, though recent reports have shown some plasticity in certain types of AS cells. They also generally have a limited proliferation potential.

Induced pluripotent stem cells (iPSC or iPSCs) are produced by laboratory methods from differentiated adult cells. iPSCs are widely recognized as important tools, e.g., for conducting medical research. Heretofore, the technology for producing iPSCs has been time-consuming and labor-intensive. Differentiated adult cells, e.g., fibroblasts, are reprogrammed, cultured, and allowed to form individual colonies which represent unique clones. Previously, identifying these types of cells has been difficult because the majority of the cells are not fully-reprogrammed iPSC clones. The standard is for iPSC clones to be selected based on the morphology of the cells, with desirable colonies possessing sharply demarcated borders containing cells with a high nuclear-to-cytoplasmic ratio. When clones are identified, they are manually-picked by micro-thin glass tools and cultured on "feeder" layers of cells typically, murine embryonic fibroblasts (MEFs). This step is performed typically at 14-21 days post-infection with a reprogramming vector. Then the clones are expanded for another 14-21 days or more, prior to undergoing molecular characterization.

Others have focused on developing techniques to rapidly and more accurately identify and characterize fully-reprogrammed adult fibroblasts and their downstream differentiation potential (Bock et al., 2011, *Cell* 144: 439-452; Boulting et al., 2011, *Nat Biotechnol* 29: 279-286). Also see, for example, co-owned U.S. Ser. No. 13/159,030, filed on Jun. 13, 2011, describing the use of Fluorescence Activated Cell Sorting (FACS) to identify and live sort unique subpopulations of stem cells as defined by unique expression patterns of surface proteins.

Thus, stem cells are an attractive source of cells for therapeutic applications, medical research, pharmaceutical testing, and the like. However, there remains a longstanding need in the art for an automated system for rapidly producing and isolating reproducible iPSC cell lines under standard conditions in order to meet these and other needs. There also there remains in the art a need for methods of making panels of iPSC cell lines, and differentiated cells produced therefrom, that are derived from multiple different individuals in a "population of interest."

SUMMARY OF THE INVENTION

The present invention provides various improved systems and methods for obtaining, generating, culturing, and handling cells, such as stem cells (including induced pluripotent stem cells or iPSCs) and differentiated cells, as well as cells and cell panels produced using such systems and methods, and uses of such cells and cell panels. The present invention builds upon, and provides certain improvements over, the systems and methods described previously in international patent application PCT/US2012/067417 (published on Jun. 6, 2013 with publication number WO/2013/082509) and U.S. patent application Ser. No. 13/691,258 (published on Dec. 26, 2013 with publication number 2013-0345094), the contents of each of which are hereby incorporated by reference in their entireties for those jurisdictions that permit incorporation by reference. Building on the work described in these prior patent applications, the Applicants have now developed certain improved methods and systems that can significantly reduce variability in obtaining, generating, culturing, and handling a variety of cell types, including differentiated cells and stem cells. Such improved systems and methods are particularly advantageous for automated and/or high-throughput applications—greatly facilitating the ability to work with large numbers of cells in a parallel manner.

For example, the Applicants have discovered that variability in the generation and culture and differentiated cells and stem cells can be reduced, allowing for more efficient parallel processing, if individual samples are selected and grouped according to various characteristics (such as growth characteristics or donor age), such that cells having similar characteristics are grown and handled together. In some parts of this application such methods may be referred to as "binning" methods, or "batching" methods, or "binning and batching" methods, or "data-driven batching" methods. Applicants also discovered that the efficiency of cellular reprogramming could be improved, and the variability in reprogramming efficiency reduced, when cells were grown in low serum or serum free medium for a certain amount of time prior to, and optionally also during, reprogramming. This finding was unexpected given the widely-held view that growth rates should be maximized for reprogramming. Indeed, consistent with this prevailing view, cells are typically grown in high serum media (e.g. containing 10% serum) prior to reprogramming and then subsequently switched to low serum or serum free medium at a later stage. While the Applicants, like others, found that increased growth rates were beneficial for reprogramming, Applicants' findings suggested that switching cells to low serum medium at the time of, or soon after, reprogramming may shock the cells and have a detrimental effect on reprogramming success. Applicants found that such effects could be mitigated by allowing the cells to adjust to low serum conditions for a certain amount of time prior to reprogramming. Applicants also found that differences in methods used to generate embryoid bodies (EBs) from pluripotent stem cells had significant and surprising effects on differentiation. For example, Applicants found that "hanging drop" methods for EB generation led to a bias towards endoderm differentiation, while the generation of EBs in V-bottom plates led to a more uniform differentiation potential, as well we being better suited to automated and high-throughput systems. These and other improvements to systems and methods for obtaining, generating, culturing and handling differentiated cells and stem cells, are described in further detail in this Summary of the Invention section, as well as throughout other sections of this patent application, including the Detailed Description, Examples, Drawings & Claims.

As mentioned above, Applicants have discovered that variability in the generation and culture of differentiated cells and stem cells can be reduced if individual samples are selected and grouped according to various characteristics, such that cells having similar characteristics are grown and handled together. Such methods can reduce variability in the generation and culture and differentiated cells and stem cells, which is particularly advantageous in applications requiring parallel processing of multiple different samples, such as in automated and/or high-throughput methods. Similarly, the ability to select, group and handle samples according to various particular characteristics may be useful for the generation of cell panels for use in a variety of applications, including for use in drug screening. The present invention provides a variety of methods and systems that can be used to select and group samples in such ways. Such methods and systems may be referred to herein as data-driven batching methods or systems. Accordingly, in one embodiment the present invention provides a method for the automated generation and/or manipulation of stem cells, the method comprising: (a) culturing multiple different samples of cells, wherein the cells comprise adult somatic cells or induced pluripotent stem cells, (b) determining the proliferation rate or cell doubling time of individual cell samples from among the multiple different samples of cells, (c) freezing individual cell samples from among the multiple different samples of cells, (d) selecting from the individual cell samples a subset of samples having similar proliferation rates or cell doubling times, (e) thawing the subset of samples selected in step (d), (f) plating the subset of samples in a multi-well plate, (g) culturing the subset of samples until they reach a desired confluency, and (h) where the cells comprise adult somatic cells, contacting the somatic cells with one or more reprogramming factors in order to produce iPSCs, or, where the cells comprise iPSCs, treating the iPSCs in order to produce differentiated cells. Similarly, in one embodiment the present invention provides a method for the efficient generation, culture and/or handling of multiple cell samples in parallel, the method comprising: (a) culturing multiple different cell samples, (b) determining, or obtaining information regarding one or more characteristics or properties of individual samples from among the multiple different cell samples (or of the donor/subject from which such samples were obtained), (c) selecting from the multiple different cell samples a subset of cell samples having a desired characteristic or property, (d) plating the subset of cell samples in a multi-well plate, and (e) culturing the subset of cell samples in the multi-well plate. Similarly, in other embodiment, the present invention provides a method for the efficient culture of multiple cell samples in parallel, the method comprising: (a) culturing multiple different cell samples, (b) determining, or obtaining information regarding, one or more characteristics or properties of individual samples from among the multiple different cell samples (or of the donor/subject from which such samples were obtained), (c) freezing individual cell samples from among the multiple different cell samples, (d) selecting from the multiple different cell samples a subset of cell samples having a desired characteristic or property, (e) thawing the subset of cell samples selected in step (d) plating the subset of cell samples in a multi-well plate, and (f) culturing the subset of cell samples in the multi-well plate. In some such embodiments the characteristic or property is the cellular proliferation rate or cell doubling time of a cell sample. In some such embodiments, the characteristic or property relates to the age, sex, race, ethnicity, diagnosis (e.g. for a disease or a disorder), genotype, phenotype, blood type, HLA type, treatment history, or drug response profile of the cell sample or of the donor/subject from which the cell sample was obtained. In some such embodiments cell samples are selected on the basis of at least two characteristics, including (i) the cellular proliferation rate or cell doubling time of the cell sample, and (ii) the age, sex, race, ethnicity, diagnosis (e.g. for a disease or a disorder), genotype, phenotype, blood type, HLA type, treatment history, or drug response profile of the cell sample or the donor/subject from which the cell sample was obtained. In some such embodiments the cell samples are adult somatic cells, such as adult somatic fibroblasts. In some such embodiments the cell samples are pluripotent stem cells, such as induced pluripotent stem cell (iPSCs). In some such embodiments the cell samples are differentiated cells derived from pluripotent stem cells. In some such embodiments one or more of the steps is automated. In some embodiments, each of the steps is automated. In some such embodiments the step of selecting from the multiple different cell samples a subset of the cell samples is automated and/or performed by a computer. In some such embodiments, where samples are selected based on having similar proliferation rates or cell doubling times, the selected samples have proliferation rates or cell doubling times that vary by less than 30% between samples, or by less than 25% between samples, or by less than 20% between samples, or by less than 15% between samples, or by less than 10% between samples, or by less than 5% between samples, or by less than 2% between samples.

In another embodiment, the present invention provides a method for the efficient generation of induced pluripotent stem cells from differentiated adult somatic cells, the method comprising: (a) culturing multiple different samples of differentiated adult somatic cells, (b) determining the proliferation rate or cell doubling time of individual samples from among the multiple different samples of differentiated adult somatic cells, (c) selecting from the multiple different samples of differentiated adult somatic cells a subset of samples having similar proliferation rates or cell doubling times, (d) plating the subset of the samples selected in a multi-well plate, such that each of the samples in the multi-well plate has a similar proliferation rate or cell doubling time, (e) culturing the cell samples in the multi-well plate until they reach a desired confluency, and (f) contacting the cell samples with one or more reprogramming factors in order to produce iPSCs. Similarly, in another embodiment, the present invention provides a method for the automated generation of induced pluripotent stem cells from differentiated adult somatic cells, the method comprising: (a) culturing multiple different samples of differentiated adult somatic cells, (b) determining the proliferation rate or cell doubling time of individual samples from among the multiple different samples of differentiated adult somatic cells, (c) freezing individual cell samples from among the multiple different cell samples, (d) selecting from the multiple different samples of differentiated adult somatic cells a subset of the samples having similar proliferation rates or cell doubling times, (e) thawing and plating the subset of the samples selected in step (d) into a multi-well plate, such that each of the samples in the multi-well plate has a similar proliferation rate or cell doubling time, (f) culturing the cell samples in the multi-well plate until they reach a desired confluency, and (g) contacting the cell samples with one or more reprogramming factors in order to produce iPSCs. In some such embodiments the differentiated adult somatic cells are fibroblasts. In some such embodiments the fibroblasts are derived from human donors/subjects. In some such embodiments one or more of the steps is automated. In some such embodiments, each of the steps is automated. In some such embodiments the step of selecting from the multiple different cell samples a subset of the cell samples having similar proliferation rates or cell doubling times is performed by a computer. In some such embodiments, where samples are selected based on having similar proliferation rates or cell doubling times, the selected samples have proliferation rates or cell doubling times that vary by less than 30% between samples, or by less than 25% between samples, or by less than 20% between samples, or by less than 15% between samples, or by less than 10% between samples, or by less than 5% between samples, or by less than 2% between samples. In some such embodiments the culturing of the somatic cells prior to contacting with reprogramming factors is performed in low serum medium or in serum free medium. In some such embodiments the step of selecting a subset of the cell samples further comprises selecting cell samples on the basis of the age, sex, race, ethnicity, diagnosis (e.g. for a disease or a disorder), genotype, phenotype, blood type, HLA type, treatment history, or drug response profile of the cell sample or the donor/subject from which the cell sample was obtained. In some such embodiments the method further comprises producing differentiated cells from the pluripotent stem cells, for example by contacting the pluripotent stem cells with one or more differentiation factors or by generating embryoid bodies (EBs). In some such embodiments, where EBs are generated from pluripotent stem cells, the EBs are generated in V-bottom plates.

In one embodiment, the present invention provides a method for the efficient generation of human induced pluripotent stem cells (iPSCs) from human donor fibroblasts, the method comprising: (a) culturing multiple different samples of human donor fibroblasts, (b) determining the proliferation rate or cell doubling time of individual samples from among the multiple different samples of human donor fibroblasts, (c) freezing individual cell samples from among the multiple different samples of human donor fibroblasts, (d) selecting from the multiple different samples of human donor fibroblasts a subset of the samples having similar proliferation rates or cell doubling times, (e) thawing the subset of samples selected in step (d), (f) culturing the subset of cell samples in a multi-well plate, such that each of the samples in the multi-well plate has a similar proliferation rate or cell doubling time, wherein the culturing comprises contacting the cell samples with low serum medium for at least 3 days, and (g) subsequently contacting the cell samples with one or more reprogramming factors in order to produce iPSCs. In one such embodiment one or more of the steps is automated. In one such embodiment each of the steps is automated. In one such embodiment the step of selecting from the multiple different cell samples a subset of the cell samples having similar proliferation rates or cell doubling times is automated and/or performed by a computer. In some such embodiments, where samples are selected based on having similar proliferation rates or cell doubling times, the selected samples have proliferation rates or cell doubling times that vary by less than 30% between samples, or by less than 25% between samples, or by less than 20% between samples, or by less than 15% between samples, or by less than 10% between samples, or by less than 5% between samples, or by less than 2% between samples. In one such embodiments the step of selecting a subset of the cell samples further comprises selecting cell samples on the basis of the age, sex, race, ethnicity, diagnosis (e.g. for a disease or a disorder), genotype, phenotype, blood type, HLA type, treatment history, or drug response profile of the cell sample or the donor/subject from which the cell sample was obtained.

In one embodiment, the present invention provides a method for the automated generation of differentiated cells from pluripotent stem cells, the method comprising: (a) culturing multiple different samples of pluripotent stem cells, (b) determining the proliferation rate or cell doubling time for individual samples from among the multiple different samples of pluripotent stem cells, (c) selecting from the multiple different samples of pluripotent stem cells a subset of samples having similar proliferation rates or cell doubling times, (d) plating the subset of the samples selected in step (c) into a multi-well plate, such that each of the samples in the multi-well plate has a similar proliferation rate or cell doubling time, (e) culturing the cell samples in the multi-well plate until they reach a desired passage number and/or confluency, and (f) producing differentiated cells from the pluripotent stem cells. Similarly, in another embodiment, the present invention provides a method for the automated generation of differentiated cells from pluripotent stem cells, the method comprising: (a) culturing multiple different samples of pluripotent stem cells, (b) determining the proliferation rate or cell doubling time for each of the multiple different samples of pluripotent stem cells, (c) freezing individual cell samples from among the multiple different cell samples, (d) selecting from the multiple different samples of pluripotent stem cells a subset of the samples having similar proliferation rates or cell doubling times, (e) thawing and plating the subset of the samples selected in step (x) into a multi-well plate, such that each of the samples in the multi-well plate has a similar proliferation rate or cell doubling time, (f) culturing the cell samples in the multi-well plate until they reach a desired passage number and/or confluency, and (g) producing differentiated cells from the pluripotent stem cells. In some such embodiments the pluripotent stem cells are induced the pluripotent stem cells (iPSCs). In some such embodiments one or more of the steps is automated. In some such embodiments the each of the steps is automated. In some such embodiments the step of selecting from the multiple different cell samples a subset of the cell samples having similar proliferation rates or cell doubling times is automated and/or performed by a computer. In some such embodiments, where samples are selected based on having similar proliferation rates or cell doubling times, the selected samples have proliferation rates or cell doubling times that vary by less than 30% between samples, or by less than 25% between samples, or by less than 20% between samples, or by less than 15% between samples, or by less than 10% between samples, or by less than 5% between samples, or by less than 2% between samples. In some such embodiments, the step of producing differentiated cells from the iPSCs comprises contacting the iPSCs with one or more differentiation factor. In some such embodiments the step of producing differentiated cells from the iPSCs comprises generating embryoid bodies (EBs). In some such embodiments the step of producing differentiated cells from the iPSCs comprises generating embryoid bodies (EBs) in V-bottom plates. In some such embodiments the step of selecting a subset of the cell samples further comprises selecting cell samples on the basis of the age, sex, race, ethnicity, diagnosis (e.g. for a disease or a disorder), genotype, phenotype, blood type, HLA type, treatment history, or drug response profile of the cell sample or the donor/subject from which the cell sample was obtained.

The present invention also provides automated "data-driven batching systems" that can be used to select and group (or "bin and/or batch") cell samples based on one or more properties or characteristics, as described above. Such automated data-driven batching systems systems can be used, for example, to select and group somatic cells (such as fibroblasts) for analysis or for subsequent iPSC generation, to select and group stem cells (such as iPSCs) for analysis or for subsequent differentiation, and/or to select and group cells (such as somatic cells obtained from donors, iPSCs, or differentiated cells derived from iPSCs) for inclusion in a cell panel. The components of the data-driven batching systems described here can comprise, or can be modified from, or can be used in conjunction with, the other automated systems, and components thereof, described herein and/or those described in international patent application PCT/US2012/067417 and U.S. patent application Ser. No. 13/691,258. Further, one of skill in the art will appreciate where and how the automated systems described herein (and in PCT/US2012/067417 and U.S. Ser. No. 13/691,258) can be modified to provide or include such data-driven batching systems.

For example, in some embodiments, the present invention provides an automated data-driven batching system that comprises: (a) a component/system for determining the cell proliferation rate or cell doubling time of a cell sample, (b) a component/system for selecting and/or retrieving cell samples having a desired cell proliferation rate or cell doubling time, and (c) a component/system for plating the selected samples in a multi-well plate. Similarly, in some embodiments, the present invention provides an automated data-driven batching system that comprises: (a) a component/system for determining the cell proliferation rate or cell doubling time of a cell sample, (b) a component/system for cryopreserving a cell sample, (c) a component/system for selecting and/or retrieving cryopreserved cell samples having a desired cell proliferation rate or cell doubling time, (d) a component/system for thawing the selected cryopreserved cell samples, and (e) a component/system for plating the selected samples in a multi-well plate. In some such embodiments, the component/system of the data-driven batching system used to determine the cell proliferation rate or cell doubling time of a cell sample may comprise an automated cell imager (such as a Celigo imager) or other automated device that can be used to measure cell confluency or cell numbers, or some other parameter from which cell proliferation rate or cell doubling time can be calculated (such as a confluency checking unit). In some such embodiments, the component/system for cryopreserving the cell sample may comprise a system for robotically transferring cell samples into cryopreservation tubes (such as barcoded cryopreservation tubes) and may comprise a 80° C. freezer. In some such embodiments, the component/system for selecting cell samples having a desired cell proliferation rate or cell doubling time may comprise a computer system programmed with desired selection criteria, and/or may comprise an automated sample access system, such as a −80° C. Sample Access Manager or "SAM" (Hamilton Storage Technologies). Such an automated sample access system may comprise an inventory database that allows for flexible recall and downstream process batching of cell samples, for example based on one or more factors such as cell proliferation rate, cell doubling time, or any other desired property or characteristic.

In some embodiments such data-driven batching systems form part of a larger automated system, such as the larger automated systems described herein for the generation of iPSCs and/or differentiated cells. For example, in one embodiment the present invention provides an automated system for generating and isolating iPSCs, comprising: (a) a somatic cell plating unit for placing somatic cells on a plate; (b) a data-driven batching system used to select somatic cell samples for reprogramming, and (c) an induction unit for automated reprogramming of the somatic cells by contacting the somatic cells on the somatic cell plating unit with reprogramming factors to produce iPSCs. In one such embodiment, the system further comprises a sorting unit for selectively sorting and isolating the iPSCs produced by the induction unit, e.g., by identifying iPSC specific markers, including, e.g., surface markers on the cells. In one illustrative example, the somatic cells are fibroblasts. Similarly, in another embodiment the present invention provides an automated system for generating and isolating differentiated adult cells from stem cells, e.g., iPSCs, embryonic stem (ES) cells or mesenchymal stem (MS) cells, comprising: (a) a stem cell plating unit for placing stem cells on a plate; (b) a data-driven batching system used to select stem cell samples for subsequent differentiation and (c) an induction unit for automated differentiation of stem cells, for example by contacting the cells on the with one or more differentiation factors to produce differentiated cells. In one such embodiment, the system further comprises a sorting unit for selectively sorting and isolating the differentiated cells produced by the induction unit.

As described above, it is a discovery of the present invention that the efficiency of cellular reprogramming can be improved, and variability in reprogramming efficiency reduced, when cells are grown in low serum or serum free medium for a certain amount of time prior to, and optionally also during, contacting cells with reprogramming factors. While the Applicants, like others, found that increased growth rates were beneficial for reprogramming, Applicants' findings suggested that switching cells to low serum medium at the time of, or soon after, reprogramming may shock the cells and have a detrimental effect on reprogramming success. Applicants found that such effects could be mitigated by allowing the cells to adjust to low serum conditions for a certain amount of time prior to reprogramming. Accordingly, in one embodiment the present invention provides a method for the generation of induced pluripotent stem cells (iPSCs) from differentiated adult somatic cells, the method comprising: (a) obtaining adult somatic cells, (b) culturing the adult somatic cells in low serum medium days, and (c) subsequently contacting the adult somatic cells with one or more reprogramming factors, in order to produce iPSCs. In some such embodiments the population of adult somatic cells obtained in step (a) had previously been frozen. In some such embodiments the population of adult somatic cells had been thawed in low serum medium. In some such embodiments the adult somatic cells are fibroblasts. In some such embodiments the adult somatic cells are cultured in low serum medium for more than 1 day prior to contacting the adult somatic cells with one or more reprogramming factors. In some such embodiments the adult somatic cells are cultured in low serum medium for more than 2 days prior to contacting the adult somatic cells with one or more reprogramming factors. In some such embodiments the adult somatic cells are cultured in low serum medium for more than 3 days prior to contacting the adult somatic cells with one or more reprogramming factors. In some such embodiments the adult somatic cells are cultured in low serum medium for more than 4 days prior to contacting the adult somatic cells with one or more reprogramming factors. In some such embodiments the adult somatic cells are cultured in low serum medium for more than 5 days prior to contacting the adult somatic cells with one or more reprogramming factors. In some such embodiments the adult somatic cells are cultured in low serum medium for more than 6 days prior to contacting the adult somatic cells with one or more reprogramming factors. In some such embodiments the adult somatic cells are cultured in low serum medium for more than 7 days prior to contacting the adult somatic cells with one or more reprogramming factors. In some such embodiments the adult somatic cells are cultured in low serum medium for 5-7 days prior to contacting the adult somatic cells with one or more reprogramming factors. In some such embodiments the adult somatic cells are cultured in low serum medium for 4-8 days prior to contacting the adult somatic cells with one or more reprogramming factors. In some such embodiments the adult somatic cells are cultured in low serum medium for 3-9 days prior to contacting the adult somatic cells with one or more reprogramming factors. In some such embodiments the adult somatic cells are cultured in low serum medium for 2-10 days prior to contacting the adult somatic cells with one or more reprogramming factors. In some such embodiments the step of contacting the adult somatic cells with one or more reprogramming factors is performed while the adult somatic cells are in low serum medium. In some such embodiments the low serum medium comprises less than 5% serum. In some such embodiments the low serum medium comprises less than 4% serum. In some such embodiments the low serum medium comprises less than 3% serum. In some such embodiments the low serum medium comprises less than 2% serum. In some such embodiments the low serum medium comprises less than 1% serum. In some such embodiments the low serum medium is serum free. In some such embodiments the low serum medium comprises a serum replacement. Several different serum replacements are known in the art and any such serum replacement can be used.

In certain embodiments the present invention also provides cells, such as somatic cells (e.g. donor-derived fibroblasts), pluripotent stem cells (such as iPSCs), differentiated cells produced from pluripotent stem cells (such as hematopoetic cells, muscle cells, cardiac muscle cells, liver cells, cartilage cells, epithelial cells, urinary tract cells, and neuronal cells), and transdifferentiated cells, such as those produced using the methods and systems described herein. The present invention also provides "arrays" or "panels" or "banks" comprising such cells. In some embodiments such cell arrays, panels or banks may comprise cells derived from multiple different individuals, for example multiple different individuals in a "population of interest." The population of interest can be any population desired, including, but not limited to, the world population, the population of a particular country, the population of a particular continent, the population of a particular geographic region, the population of a particular racial or ethnic group, a population of a particular age, a population of a particular sex (male or female), a population having a particular disease or disorder, a population having a particular mutation, a population having a particular genotype, a population having a particular phenotype, a population having a particular blood type, a population having a particular HLA type, a population having a particular drug response profile, and the like. In some embodiments the individuals from whom cells are derived are selected in order to be representative of the variation in the particular population of interest. For example, if the population of interest is the U.S. population, the individuals from whom cells are derived are preferably selected to be representative of the U.S. population (e.g. in terms of race/ethnicity and/or any other desired characteristic), for example based on census data or some other suitable criteria. In some embodiments the cell panels comprise isogenic control cells. For example, in embodiments where the cell panels contain cells having a certain mutation, the panels may comprise control cells in which that mutation is not present (for example if it has been corrected) but where the cells are otherwise genetically identical. In some embodiments the cells in the cell panels comprise a reporter gene, such as a reporter gene that can be used to report expression of a gene or gene product that is or may be involved in a disease, or is in a pathway that is or may be involved in a disease. In some embodiments the cell panels comprise both sporadic and familial lines. For example, in the case of a panel containing samples from subjects having a certain disease, the panel may comprise samples from subjects in which that disease arose as the result of a sporadic mutation, as well as samples from subjects in which that disease was inherited. In some embodiments, the cell panels comprise 3 or more cell lines/clones from each subject, in order to provide replicates of samples from each subject. In some embodiments the present invention provides populations of stem cells (such as iPSCs) or differentiated cells wherein the populations of cells are derived from at least 96, or at least 384, or at least 1596 different individuals from the population of interest. In preferred embodiments cells from different individuals are provided in separate vessels, such as separate wells of a 96-well, 384-well, or 1596-well microtiter plate.

The cells, arrays, panels and banks of the invention may be useful in a variety of different applications, for example in studying or determining the efficacy, toxicity, teratogenicity or safety of, one or more candidate drugs on cells of different individuals in a population of interest. As such the cell panels of the invention can be used to perform "clinical trials in a dish."

In some embodiments the present invention also provides gene sets and probe sets that may be useful for detection of iPSCs or differentiated cells, such as those made using the automated systems of the present invention. Such gene and probe sets can be used in as part of one of the automated systems of the invention or in other applications, as desired.

In one embodiment the present invention provides a "Pluri25" gene/probe set comprising the following genes, or probes for detecting expression of the following genes: retroviral tOct4, retroviral tSox2, retroviral tKlf4, retroviral tC-Myc, Sendai tOct4, Sendai tSox2, Sendai tKlf4, Sendai tC-Myc, Sendai vector (SeV), POU5F1 (Oct4), SOX2, KLF4, MYC, LIN28, NANOG, ZFP42, SOX17, AFP, NR2F2, ANPEP (CD13), ACTB, POLR2A, ALAS1, SRY and XIST.

In another embodiment the present invention provides a gene/probe set for detection of iPSCs comprising the following genes, or probes for detecting expression of the following genes: Sendai tOct4, Sendai tSox2, Sendai tKlf4, Sendai tC-Myc, Sendai vector (SeV), POU5F1 (Oct4), SOX2, KLF4, MYC, LIN28, NANOG, ZFP42, SOX17, AFP, NR2F2, ANPEP (CD13), ACTB, POLR2A, ALAS1, SRY and XIST.

In another embodiment the present invention provides a gene/probe set for detection of iPSCs comprising the following genes, or probes for detecting expression of the following genes: retroviral tOct4, retroviral tSox2, retroviral tKlf4, retroviral tC-Myc, POU5F1 (Oct4), SOX2, KLF4, MYC, LIN28, NANOG, ZFP42, SOX17, AFP, NR2F2, ANPEP (CD13), ACTB, POLR2A, ALAS1, SRY and XIST.

In another embodiment the present invention provides a gene/probe set for detection of iPSCs comprising the following genes, or probes for detecting expression of the following genes: POU5F1 (Oct4), SOX2, KLF4, MYC, LIN28, NANOG, ZFP42, SOX17, AFP, NR2F2, ANPEP (CD13), ACTB, POLR2A, ALAS1, SRY and XIST.

In another embodiment the present invention provides a gene/probe set referred to as the "3GLSC100" gene/probe set, which is useful for detection of iPSCs and which comprises the genes, or probes for detecting expression of the genes, listed in Table 2 in the Detailed Description section of the present application.

In some embodiments the present invention also provides gene/probe sets for detection of cells that have begun to differentiate into cardiomyocytes. One such gene/probe set, referred to as the "cardiac 1" gene/probe set, comprises the following genes, or probes for detecting expression of the following genes: ACTN1, BMP4, GATA4, GJA1, IRX-4, ISL1, KDR, MEF2A, MEF2C, MESP1, MYH6, MYH7, MYL2, MYL7, NKX2-5, NPPA, PDGFRa, SIRPA, TBX20, TBX5, TNNI3, TNNT2, VCAM1, VWF, MIXL1, NANOG, OCT4, SOX17, Brachury T and KCNJ2. Another such gene/probe set, referred to as the "cardiac 2" gene/probe set, comprises the following genes, or probes for detecting expression of the following genes: ACTN1, BMP4, GATA4, GJA1, IRX-4, ISL1, KDR, MEF2A, MEF2C, MESP1, MYH6, MYH7, MYL2, MYL7, NKX2-5, NPPA, PDGFRa, SIRPA, TBX20, TBX5, TNNI3, TNNT2, VCAM1, VWF, MIXL1, NANOG, OCT4, SOX17, Brachury T, KCNJ2, GAPDH, GUSB, HPRT1, and TBP.

In another embodiment the present invention provides methods for obtaining reprogrammed human fibroblasts from mixed cell populations (for example using the automated methods described herein) by isolating cells that are CD13-negative, SSEA4-positive and Tra-1-60-positive, wherein the CD13-negative, SSEA4-positive and Tra-1-60-positive cells are reprogrammed human fibroblasts. In some embodiments such methods utilize fluorescence activated cell sorting (FACS).

BRIEF DESCRIPTION OF THE DRAWINGS

FIGS. 4A-4C. Examples of a flow of patient samples through multi-well tissue culture plates during an automated reprogramming process.

FIGS. 6A-6C. Automated biopsy outgrowth tracking system. In FIG. 6A, biopsies or discarded tissue are plated in multiple wells of a 6-well dish and maintained by an automated system that feeds, images, passages, and freezes fibroblast outgrowths. Examples of the image analysis interface are shown for a typical sample. FIG. 6B: Cell numbers are extrapolated from confluence measurements based on linear regression from a standard curve generated independently. FIGS. 6C and 6D: An example of cell counts for a typical biopsy outgrowth maintained on an automated system provided by the invention. Extrapolated cell numbers per patient sample are plotted for each well independently (FIG. 6C) allowing calculation of total output from the sample (FIG. 6D).

FIG. 7A FACS gating scheme used for analysis. FIG. 7B: A substantial proportion of cells co-expressing traditional pluripotency surface markers SSEA4 & TRA-1-60 retain the fibroblast marker CD13 at all time points during reprogramming using viral vectors to introduce reprogramming factors such as Oct4, Sox2, Klf4 and c-Myc. Box plots indicating aggregated data from 131 experiments (Retrovirus, n=66, Sendai virus, n=65) are shown. While Sendai mediated reprogramming produces more SSEA4/TRA-1-60 double positive cells, (FIG. 7C) there is a delay in elimination of CD13 from the surface. (FIG. 7D) Example staining pattern of a patient cell line reprogrammed using Sendai/Cytotune system on an automated system provided by the invention. At both 7 and 13 days post infection (dpi), more than half of SSEA4/TRA-1-60 double positive cells have lost CD13. Additionally, at both time points assayed, CD13 negative/Nanog positive cells are present in this fraction, suggesting these can be isolated by negative selection against CD13.

FIGS. 8A-8C. FACs pre-sort analyses and a part of the automated system to demonstrate enrichment and clone selection of iPSCs. FIG. 8A shows Non-reprogrammed cell populations can be depleted from cultures of iPSCs by negative selection by a fibroblast marker. In the example, fibroblasts are efficiently removed from the culture containing 2% established iPSCs leaving TRA-1-60 positive iPSCs untouched. FIG. 8B shows a Miltenyi MultiMACS system integrated into Hamilton liquid handler that can sort 24 samples in parallel. FIG. 8C is an illustration of the iPSC-enriched fraction from the anti-fibroblast magnetic negative selection step that is plated on 96-well imaging plates at limiting dilution. These plates are screened using live-cell staining for the pluripotency surface marker TRA-1-60 or TRA-1-81. Wells with TRA-1-60 positive iPSCs are identified by automated image analysis using the Celigo software capable of single colony confirmation. Wells that meet both criteria of containing a single colony that is positive for the surface marker are selected for passaging, expansion, and QC.

(FIG. 9A) Transcript counts after normalization to HK gene expression for two human ESC lines, Sendai positive control, fibroblast negative control, and iPSC lines derived by FACS sorting assayed at passage 5 and 10. All assays are run relative to a panel of normal human ESC and iPSC lines maintained under similar conditions. (FIG. 9B) Second stage of a quality control screen, which uses an additional 83 germ layer/lineage markers to monitor differentiation capability in embryoid body assays. Single EBs are generated and pooled to collect RNA for expression analysis of germ layer markers in the embryoid body scorecard assay. Shown is a cluster dendrogram analysis of gene expression in EBs collected from nine different embryonic stem cells lines. After normalization, data generated from direct lysis of six EBs compares favorably to data generated from total RNA extracted and purified from EBs prepared from bulk culture.

(FIG. 10A) is an example of the nCounter Karyotype assay on BC1 iPSCs; (FIG. 10B) is an example of the nCounter Karyotype assay on 1016 fibroblasts with partial gain and loss of chromosome arms. Comparison to Affymetrix SNP 6.0 chip data demonstrating copy number gains on a portion of the q arm of Chr1 (top track, 1q21.2-1q43) and loss of part of the long arm of Chr6 (bottom track, 6q16.3-6q26).

(FIG. 11A) CD13NEGSSEA4POSTra-1-60NEG and CD13NEGSSEA4POSTra-1-60POS populations from the manually derived 1018 clone were sorted onto MEF feeder layers and expanded for 20 days prior to reanalysis by flow cytometry to assess retention of sorted surface markers. dpi=days post infection. dps=days post sort. (FIG. 11B) CD13NEGSSEA4POS and CD13NEGSSEA4POSTra-1-60POS populations were sorted onto MEF layers at seven days post infection and imaged at 3 and 17 dps to assess colony formation. (FIG. 11C) Colony counts arising from the sorted cell populations shown in Panel B at 17 dps (25 dpi). (FIG. 11D) Gating structure used in the analysis of CD13POS cells present within the SSEA4POSTra-1-60POS population at 7 dpi. (FIG. 11E) Fluorescence microscopy demonstrating NANOG expression in CD13POS cell at 7 dpi. 40× magnification. CD13 shown in red. Nanog in shown Green. Values designated % T indicates proportion of total cells within the culture positive for the indicated combinations of surface markers. Values without T designation indicate the proportion of CD13NEGSSEA4POS cells that are Tra-1-60POS or Tra-1-60NEG in Panel A and D.

(FIG. 12A) Foreskin (0825) and adult dermal fibroblast (1018 and 1023) lines underwent four factor retroviral reprogramming and were analyzed by flow cytometry for the emergence of the $CD13^{NEG}SSEA4^{POS}Tra-1-60^{POS}$ population at seven day intervals post infection. Values designated % T indicates proportion of total cells within the culture positive for the indicated combinations of surface markers. Values without T designation indicate the proportion of cells positive within the parent gate. (FIG. 12B) Gating structure used to sort the $CD13^{NEG}SSEA4^{POS}Tra-1-60^{POS}$ populations for all cell lines derived in this study. Live cell are first defined using forward (FSC) and Side (SSC) light scattering properties. The $CD13^{NEG}SSEA4^{POS}$ population is then selected from the live cell gate (blue cells). The highest $Tra-1-60^{POS}$ expressing cells are then selected from the $CD13^{NEG}SSEA4^{POS}$ population (Green cells) and sorted for expansion and characterization. (FIG. 12C) Comparison of $SSEA4^{POS}Tra-1-60^{POS}$ populations present in Retro (R) or Sendai (S) viral infected fibroblast cultures during first two weeks of programming. (FIG. 12D) Comparison of $CD13^{POS}$ cells present within the $SSEA4^{POS}Tra-1-60^{POS}$ populations during first two weeks of programming following Retro (R) or Sendai (S) infection. Dpi 1-7: (R) n=29, (S) n=21. Dpi 8-14: (R) n=32, (S) n=46. Total n=228. Statistical significance was assessed via Student's t-Test. *p<=0.05, p<=0.001, *p<=0.001, ****p<=0.0001.

(FIG. 13C) Three sorted and three picked lines from patient 1023 were used to compare the ability of both methods to generate independent clones. 10μ of genomic DNA were cut overnight with BglII and submitted to Southern blotting. The HUES line HES2 was used as a positive control for endogenous KLF4/OCT4, and as a negative control for transgene insertions. Samples were first blotted for KLF4, then stripped and reblotted for OCT4. Picked clones 1023 C and E are consistent with being the same clone by both KLF4 and OCT4 blotting. * indicated the predicted endogenous KLF4/OCT4 bands, and ** indicated a consistent band found in all samples blotted with OCT4.

(FIG. 14D) Teratomas from FACS (FIG. 14D) or manually derived (FIG. 14E) clones of 1023 fibroblast line indicating in vitro differentiation potential by formation of three germ layers.

(FIG. 16G) Expression levels of transcription factors common to the indicated germ layers from EB generated by the indicated IPSC lines.

FIGS. 18A-18B. Karyotype of FACS (FIG. 18A) and Manually (FIG. 18B) Derived retroviral iPS lines possess a normal karyotype and match the parent fibroblast. Karyotype was assessed using 20 G-banded metaphase cells from each fibroblast and reprogrammed lines at passages indicated. All lines possess a normal karyotype and match the parent fibroblast. Karyotype was assessed using 20 G-banded metaphase cells from each fibroblast and reprogrammed lines at passages indicated. Fibroblasts and FACS derived lines possess a normal karyotype and match the parent fibroblast. Three out of 20 cells from the manually derived line displayed an unbalanced translocation between the short arm of chromosomes 11 and 22 resulting in trisomy of the short arm of chromosome 11.

(FIG. 19C) qRTPCR showing expression of endogenous gene expression and silencing (FIG. 19D) of retroviral genes.

FIGS. 20A-20G. Automated fibroblast and iPSC production. (FIG. 20A) Schematic of workflow through automation system from donor biopsy collection through to iPS expansion and freezing. (FIG. 20B) Image of system for automated fibroblast production consisting of a liquid handling device, imager, centrifuge and capper/decaper contained in a biosafety cabinet, connected to an automated incubator and managed by system control software. (FIG. 20C) Phase contrast image of representative fibroblast outgrowth from a biopsy. (10×) (FIG. 20D) Fibroblast biopsy outgrowth (i) as visualized following automated imaging. Confluence measurements (ii) and Hoechst stained nuclei (iii) are compared against each other to generate a regression model (iv) for calculating count values from unstained samples with confluence measurements. (FIG. 20E) Histogram of fibroblast doubling times calculated from confluence scans of fibroblasts during expansion. (FIG. 20F) Scatterplot of doubling time vs. age of donor. (FIG. 20G) Fibroblast doubling times from fibroblasts thawed and recovered for reprogramming.

(FIG. 21A) Experimental scheme for automated fibroblast thawing and reprogramming. (FIG. 21B) Image of robotic system for automated fibroblast thawing and mRNA transfections. (FIG. 21C) Timecourse of mRNA transfection showing development of colonies over 22 days. (FIG. 21D) Image-based identification and counting of TRA-1-60 positive colonies to determine reprogramming efficiency. (FIG. 21E) FACS analysis of reprogrammed cultures from automated mRNA transfection demonstrating that higher proportion of cells after reprogramming by mRNA stain double positive for the pluripotency markers TRA-1-60/SSEA4 and lack of the fibroblast surface marker CD13. (FIG. 21F, FIG. 21G, FIG. 21H AND FIG. 21I) Effect plots of poisson regression analysis of factors that contribute to reprogramming success. Gray area and bars indicate confidence intervals.

(FIG. 22A) Schematic illustration of bulk method of unreprogrammed fibroblast cell depletion from reprogramming 24 well plates, consolidation and freezing. (FIG. 22B) Image of integrated magnetic bead selection robot. (FIG. 22C) Representative images of 96-well for bulk sorted cells from first day post sorting (1 dps) to 9 days post sorting (9 dps), and TRA-1-60 expression pattern captured by automated imaging. (FIG. 22D) Example of a 96-well plate of sorted iPSCs derived from mRNA mediated reprogramming. Three samples are represented on the plate in three-point two fold serial dilution. (FIG. 22E) Representative images for retrospective identification of clonal lines derived from sorted cells from a single cell identified on the second day post sorting (2 dps) to its colony at 10 days post sorting (10 dps), and TRA-1-60 expression pattern captured by Celigo Tumorsphere application. (FIG. 22F) FACS analysis for TRA-1-60/SSEA4/CD13 on sorted cells after consolidation and prior to freezing. (FIG. 22G) Histogram of doubling time for iPSCs during growth after sorting before freezing. Frequency bins are 6 hrs. Median doubling time was 42 hr, n=826 samples.

(FIG. 23A) Boxplot of the pluripotency scores for reference hESC lines, iPSC lines, and fibroblast lines. (FIG. 23B) Boxplot of differentiation scores for the three categories of cell lines.

(FIG. 24A) Image of 96-well freezing and passaging robot. (FIG. 24B) Bright field images of iPS cells in the same well in a 96W plate recovering after automated thawing method. Confluence was monitored over 5 days. (FIG. 24C) Correlation of confluence data from the Celigo prior to cryotube freeze and post-thaw. Both the freezing and thawing of cryotubes were performed on the integrated automated system. (FIG. 24D) FACS analysis of TRA-1-60/SSEA4 double positive population before and after automated passaging for control hESCs and iPSCs derived on the system. (FIG. 24E) FACS analysis of iPSCs before freezing and recovered from thawing using automated methods. (FIG. 24F) Example growth rates of a robotically passaged iPSC plate over 3 days culture.

(FIG. 25A) Boxplot of the differentiation propensities (EC=ectoderm, ME=mesoderm, EN=endoderm) for the 10 hESC reference lines with segments showing the average differentiation propensities observed for iPSC lines derived using three different methods. (FIG. 25B) Representative image of the Greiner 96 well v-bottom plate with EBs is shown after passage to form EBs by automation. The EBs were generated from iPSC lines ubiquotously expressing GFP. (FIG. 25C) Image of EBs by stereomicroscopy. (FIG. 25D, FIG. 25E, FIG. 25F) Correlation of differentiation propensity for all samples generated using the reference lines used in this study with previously published scorecard reference data (Bock et al., 2011).

(FIG. 27A) Mycoplasma detection of samples from in-house automated luminescence assay. Marginal values were confirmed negative with PCR validation. No mycoplasma positive samples have been generated in house during biopsy collection and outgrowth expansion on the automated systems. (FIG. 27B) Representative traces of fibroblasts karyotyped using the Nanostring Karyotype assay with representative traces of normal diploid fibroblasts (a) 46, XX, (b) 46, XY and an aneuploid fibroblast showing a loss of one X chromosome (c) 45, X.

(FIG. 28A) Pluripotency staining of mRNA derived lines and example of a phase contrast image of iPSC produced by mRNA transfection. Scale bars are 50 μm. (FIG. 28B) Well image of Sendai reprogramming after 20 days showing colonies and TRA-1-60 live stain of the same well in the bottom panel. Only a subset of colonies stain positive for the pluripotency marker. (FIG. 28C) Pluripotency marker staining of established cell lines from automated reprogramming by Sendai virus. Scale bars are 50 μm. (FIG. 28D) FACS analysis of reprogrammed cultures from automated mRNA transfection demonstrating that higher proportion of cells after reprogramming by mRNA stain double positive for the pluripotency markers TRA-1-60/SSEA4 and lack of the fibroblast surface marker CD13. (FIG. 28E) Variation of gene expression of the germ layer and pluripotency markers shown in (FIG. 28D) for BJ fibroblasts reprogrammed on the automated system by mRNA transfection or Sendai infection and isolated by manual colony picking Means are not significantly different. N=33.

(FIG. 29A) iPSC:fibroblast (1:20 to 1:100) were mixed, 5% of total cells before and after magnetic bead negative selection using anti-fibroblast microbeads were analyzed using FACS. Representative data is shown pre and post-sort of a mixture of iPSCs and adult human fibroblasts at a 1:50 ratio. (FIG. 29B) Representative FACS result for 5% of total cells before and after magnetic bead negative selection using anti-fibroblast microbeads. (FIG. 29C) Examples of clonal lines derived by automated sorting method.

(FIG. 30A) Pluri25 scorecard assay values for T scores and gene expression means. (FIG. 30B) Immunofluoresence result for Nanog expression in consolidated cells in 96 well format. (FIG. 30C) Example of overgrown well demonstrating spontaneous differentiation detectible by the Pluri25 scorecard assays.

(FIG. 31A) Schematic of thawing and passaging and plate replication in 96 well format. (FIG. 31B) Percent coefficient of variation was calculated for 3 plates from the replication passages of a representative cell line using data from confluence scans from 3 different time points. (FIG. 31C) Immunostaining of iPS lines derived on the robotic platform as well as control hES cell lines showing the presence of POU5FI and TRA_1-81; SSEA4 and NANOG, and SOX2 and TRA-1-81. (FIG. 31D) FACS analysis of TRA-1-60/SSEA4 double positive population before and after automated passage 1:3 for control hESC lines and iPSC lines derived on the system. (FIG. 31E) Detection of an aneuploid line in 4 of 38 independent iPSC lines tested using the Nanostring karyotyping assay. (FIG. 31F, FIG. 31G and FIG. 32H) Nanostring identity test data comparing Fibroblast lines to iPSCs derived by the automated process.

FIGS. 32A-32B. (FIG. 32A) Pluripotency marker analysis of reference lines used for lineage scorecard analysis after adaptation to serum-free media used to grow iPSCs on the system. EBs were generated from these lines by the automated system under identical conditions to those used to generate EBs from iPSCs generated on the system. (FIG. 32B) Scorecard analysis of EBs generated from reference HUES lines under automated conditions.

(FIG. 33A) Comparisons of standard deviation of gene expression values for different types of cell lines considering only a single replicate per sample. (FIG. 33B) Significance test: −log 10(p-value) using the Wilcoxen signed rank test that tests the null hypothesis that the median of these paired distributions is the same (non-parametric test).

DETAILED DESCRIPTION

Figure 1:
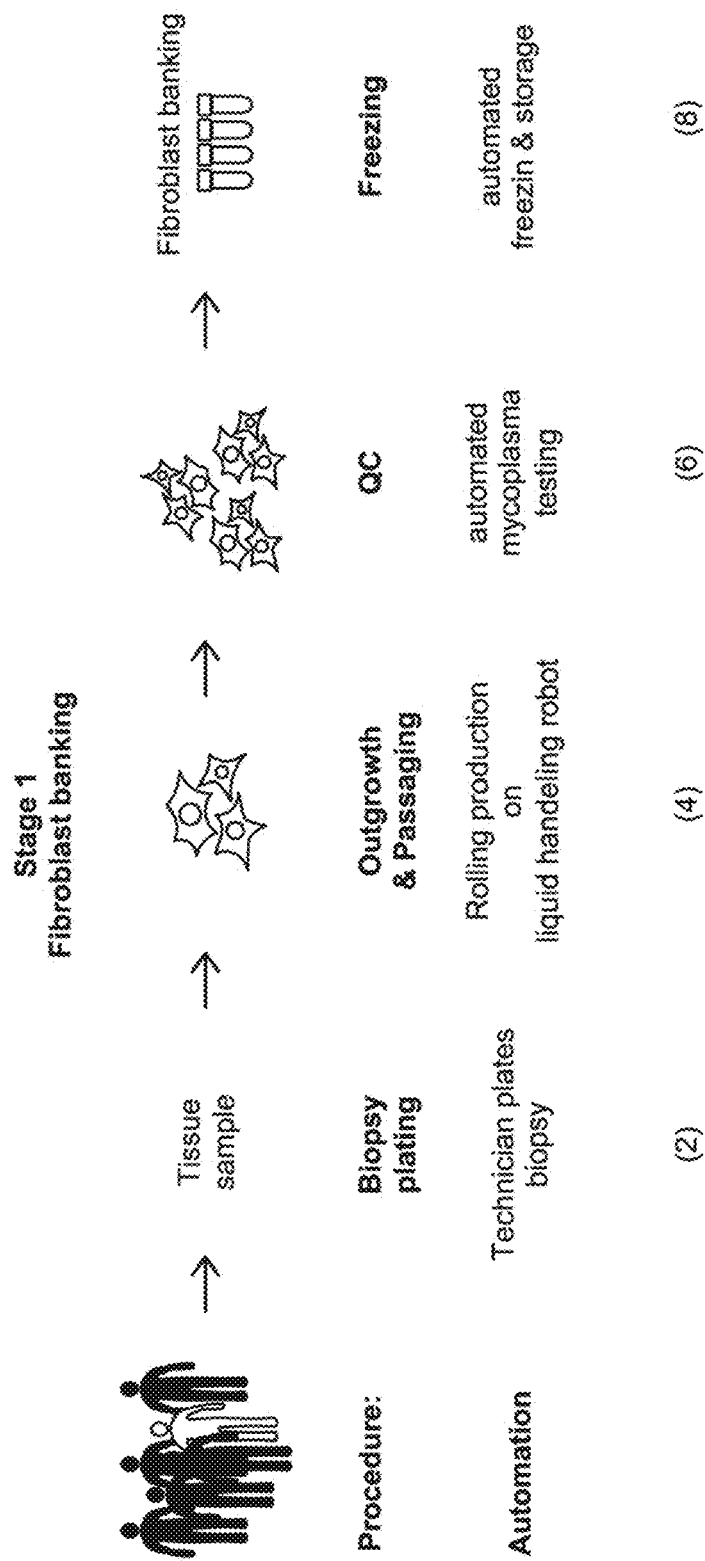
FIG. 1. Steps for acquiring a fibroblast cell bank.

The present invention provides various improved systems and methods for obtaining, generating, culturing, and handling cells, such as stem cells (including induced pluripotent stem cells or iPSCs) and differentiated cells, as well as cells and cell panels produced using such systems and methods, and uses of such cells and cell panels. The present invention builds upon, and provides certain improvements over, the systems and methods described previously in international patent application PCT/US2012/067417 (published on Jun. 6, 2013 with publication number WO/2013/082509) and U.S. patent application Ser. No. 13/691,258 (published on Dec. 26, 2013 with publication number 2013-0345094), the contents of each of which are hereby incorporated by reference in their entireties for those jurisdictions that permit incorporation by reference. Building on the work described in these prior patent applications, the Applicants have now developed certain improved methods and systems that can significantly reduce variability in obtaining, generating, culturing, and handling a variety of cell types, including differentiated cells and stem cells. Such improved systems and methods are particularly advantageous for automated and/or high-throughput applications—greatly facilitating the ability to work with large numbers of cells in a parallel manner.

Several of the major embodiments of the present invention are described in the above "Summary of the Invention" section of this application, as well as in the Examples, Figures, and Claims sections of this patent application. In order to avoid unnecessary duplication, such embodiments may not be described in full in this Detailed Description section. Rather this Detailed Description provides certain additional information regarding the invention, which is intended to be read together and in conjunction with the Summary of the Invention section of the application and all other sections of this patent application. Furthermore, the various embodiments described in each section of this patent application are intended to be combined in various ways, as will be apparent to those of skill in the art.

As used herein "adult" means post-fetal, i.e., an organism from the neonate stage through the end of life, and includes, for example, cells obtained from delivered placenta tissue, amniotic fluid and/or cord blood.

As used herein, the term "adult differentiated cell" encompasses a wide range of differentiated cell types obtained from an adult organism, that are amenable to producing iPSCs using the instantly described automation system. Preferably, the adult differentiated cell is a "fibroblast." Fibroblasts, also referred to as "fibrocytes" in their less active form, are derived from mesenchyme. Their function includes secreting the precursors of extracellular matrix components including, e.g., collagen. Histologically, fibroblasts are highly branched cells, but fibrocytes are generally smaller and are often described as spindle-shaped. Fibroblasts and fibrocytes derived from any tissue may be employed as a starting material for the automated workflow system on the invention.

As used herein, the term, "induced pluripotent stem cells" or, iPSCs, means that the stem cells are produced from differentiated adult cells that have been induced or changed, i.e., reprogrammed into cells capable of differentiating into tissues of all three germ or dermal layers: mesoderm, endoderm, and ectoderm. The iPSCs produced do not refer to cells as they are found in nature.

Mammalian "somatic cells" useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

The term "totipotency" refers to a cell with a developmental potential to make all of the cells in the adult body as well as the extra-embryonic tissues, including the placenta. The fertilized egg (zygote) is totipotent, as are the cells (blastomeres) of the morula (up to the 16-cell stage following fertilization).

The term "pluripotent" as used herein refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). A pluripotent cell has a lower developmental potential than a totipotent cell. The ability of a cell to differentiate to all three germ layers can be determined using, for example, a nude mouse teratoma formation assay. In some embodiments, pluripotency can also evidenced by the expression of embryonic stem (ES) cell markers, although the preferred test for pluripotency of a cell or population of cells generated using the compositions and methods described herein is the demonstration that a cell has the developmental potential to differentiate into cells of each of the three germ layers. In some embodiments, a pluripotent cell is termed an "undifferentiated cell." Accordingly, the terms "pluripotency" or a "pluripotent state" as used herein refer to the developmental potential of a cell that provides the ability for the cell to differentiate into all three embryonic germ layers (endoderm, mesoderm and ectoderm). Those of skill in the art are aware of the embryonic germ layer or lineage that gives rise to a given cell type. A cell in a pluripotent state typically has the potential to divide in vitro for a long period of time, e.g., greater than one year or more than 30 passages.

The term "multipotent" when used in reference to a "multipotent cell" refers to a cell that has the developmental potential to differentiate into cells of one or more germ layers, but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

The term "embryonic stem cell" as used herein refers to naturally occurring pluripotent stem cells of the inner cell mass of the embryonic blastocyst (see, e.g., U.S. Pat. Nos. 5,843,780; 6,200,806; 7,029,913; 7,584,479, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent.

As used herein, the distinguishing characteristics of an embryonic stem cell define an "embryonic stem cell phenotype." Accordingly, a cell has the phenotype of an embryonic stem cell if it possesses one or more of the unique characteristics of an embryonic stem cell, such that that cell can be distinguished from other cells not having the embryonic stem cell phenotype. Exemplary distinguishing embryonic stem cell phenotype characteristics include, without limitation, expression of specific cell-surface or intracellular markers, including protein and microRNAs, gene expression profiles, methylation profiles, deacetylation profiles, proliferative capacity, differentiation capacity, karyotype, responsiveness to particular culture conditions, and the like. In some embodiments, the determination of whether a cell has an "embryonic stem cell phenotype" is made by comparing one or more characteristics of the cell to one or more characteristics of an embryonic stem cell line cultured within the same laboratory.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells. In some aspects described herein, a "somatic pluripotent cell" refers to a somatic cell, or a progeny cell of the somatic cell, that has had its developmental potential altered, i.e., increased, to that of a pluripotent state by contacting with, or the introduction of, one or more reprogramming factors using the compositions and methods described herein.

The term "progenitor cell" is used herein to refer to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated, pluripotent, embryonic stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. Unless otherwise indicated, the compositions and methods for reprogramming a somatic cell described herein can be performed both in vivo and in vitro (where in vivo is practiced when a somatic cell is present within a subject, and where in vitro is practiced using an isolated somatic cell maintained in culture).

The term "differentiated cell" encompasses any somatic cell that is not, in its native form, pluripotent, as that term is defined herein. Thus, the term a "differentiated cell" also encompasses cells that are partially differentiated, such as multipotent cells, or cells that are stable, non-pluripotent partially reprogrammed, or partially differentiated cells, generated using any of the compositions and methods described herein. In some embodiments, a differentiated cell is a cell that is a stable intermediate cell, such as a non-pluripotent, partially reprogrammed cell. It should be noted that placing many primary cells in culture can lead to some loss of fully differentiated characteristics. Thus, simply culturing such differentiated or somatic cells does not render these cells non-differentiated cells (e.g. undifferentiated cells) or pluripotent cells. The transition of a differentiated cell (including stable, non-pluripotent partially reprogrammed cell intermediates) to pluripotency requires a reprogramming stimulus beyond the stimuli that lead to partial loss of differentiated character upon placement in culture. Reprogrammed and, in some embodiments, partially reprogrammed cells, also have the characteristic of having the capacity to undergo extended passaging without loss of growth potential, relative to parental cells having lower developmental potential, which generally have capacity for only a limited number of divisions in culture. In some embodiments, the term "differentiated cell" also refers to a cell of a more specialized cell type (i.e., decreased developmental potential) derived from a cell of a less specialized cell type (i.e., increased developmental potential) (e.g., from an undifferentiated cell or a reprogrammed cell) where the cell has undergone a cellular differentiation process.

The term "reprogramming" as used herein refers to a process that reverses the developmental potential of a cell or population of cells (e.g., a somatic cell). Stated another way, reprogramming refers to a process of driving a cell to a state with higher developmental potential, i.e., backwards to a less differentiated state. The cell to be reprogrammed can be either partially or terminally differentiated prior to reprogramming. In some embodiments of the aspects described herein, reprogramming encompasses a complete or partial reversion of the differentiation state, i.e., an increase in the developmental potential of a cell, to that of a cell having a pluripotent state. In some embodiments, reprogramming encompasses driving a somatic cell to a pluripotent state, such that the cell has the developmental potential of an embryonic stem cell, i.e., an embryonic stem cell phenotype. In some embodiments, reprogramming also encompasses a partial reversion of the differentiation state or a partial increase of the developmental potential of a cell, such as a somatic cell or a unipotent cell, to a multipotent state. Reprogramming also encompasses partial reversion of the differentiation state of a cell to a state that renders the cell more susceptible to complete reprogramming to a pluripotent state when subjected to additional manipulations, such as those described herein. Such manipulations can result in endogenous expression of particular genes by the cells, or by the progeny of the cells, the expression of which contributes to or maintains the reprogramming. In certain embodiments, reprogramming of a cell using the synthetic, modified RNAs and methods thereof described herein causes the cell to assume a multipotent state (e.g., is a multipotent cell). In some embodiments, reprogramming of a cell (e.g. a somatic cell) using the synthetic, modified RNAs and methods thereof described herein causes the cell to assume a pluripotent-like state or an embryonic stem cell phenotype. The resulting cells are referred to herein as "reprogrammed cells," "somatic pluripotent cells," and "RNA-induced somatic pluripotent cells." The term "partially reprogrammed somatic cell" as referred to herein refers to a cell which has been reprogrammed from a cell with lower developmental potential by the methods as disclosed herein, such that the partially reprogrammed cell has not been completely reprogrammed to a pluripotent state but rather to a non-pluripotent, stable intermediate state. Such a partially reprogrammed cell can have a developmental potential lower that a pluripotent cell, but higher than a multipotent cell, as those terms are defined herein. A partially reprogrammed cell can, for example, differentiate into one or two of the three germ layers, but cannot differentiate into all three of the germ layers.

The term a "reprogramming factor," as used herein, refers to a developmental potential altering factor, as that term is defined herein, such as a gene, protein, RNA, DNA, or small molecule, the expression of which contributes to the reprogramming of a cell, e.g. a somatic cell, to a less differentiated or undifferentiated state, e.g. to a cell of a pluripotent state or partially pluripotent state. A reprogramming factor can be, for example, transcription factors that can reprogram cells to a pluripotent state, such as SOX2, OCT3/4, KLF4, NANOG, LIN-28, c-MYC, and the like, including as any gene, protein, RNA or small molecule, that can substitute for one or more of these in a method of reprogramming cells in vitro. In some embodiments, exogenous expression of a reprogramming factor, using the synthetic modified RNAs and methods thereof described herein, induces endogenous expression of one or more reprogramming factors, such that exogenous expression of one or more reprogramming factors is no longer required for stable maintenance of the cell in the reprogrammed or partially reprogrammed state. "Reprogramming to a pluripotent state in vitro" is used herein to refer to in vitro reprogramming methods that do not require and/or do not include nuclear or cytoplasmic transfer or cell fusion, e.g., with oocytes, embryos, germ cells, or pluripotent cells. A reprogramming factor can also be termed a "de-differentiation factor," which refers to a developmental potential altering factor, as that term is defined herein, such as a protein or RNA, that induces a cell to de-differentiate to a less differentiated phenotype, that is a de-differentiation factor increases the developmental potential of a cell.

As used herein, the term "differentiation factor" refers to a developmental potential altering factor, as that term is defined herein, such as a protein, RNA, or small molecule, that induces a cell to differentiate to a desired cell-type, i.e., a differentiation factor reduces the developmental potential of a cell. In some embodiments, a differentiation factor can be a cell-type specific polypeptide, however this is not required. Differentiation to a specific cell type can require simultaneous and/or successive expression of more than one differentiation factor. In some aspects described herein, the developmental potential of a cell or population of cells is first increased via reprogramming or partial reprogramming using synthetic, modified RNAs, as described herein, and then the cell or progeny cells thereof produced by such reprogramming are induced to undergo differentiation by contacting with, or introducing, one or more synthetic, modified RNAs encoding differentiation factors, such that the cell or progeny cells thereof have decreased developmental potential.

In the context of cell ontogeny, the term "differentiate", or "differentiating" is a relative term that refers to a developmental process by which a cell has progressed further down a developmental pathway than its immediate precursor cell. Thus in some embodiments, a reprogrammed cell as the term is defined herein, can differentiate to a lineage-restricted precursor cell (such as a mesodermal stem cell), which in turn can differentiate into other types of precursor cells further down the pathway (such as a tissue specific precursor, for example, a cardiomyocyte precursor), and then to an end-stage differentiated cell, which plays a characteristic role in a certain tissue type, and may or may not retain the capacity to proliferate further.

As used herein, the term "without the formation of a pluripotent intermediate cell" refers to the transdifferentiation of one cell type to another cell type, preferably, in one step; thus a method that modifies the differentiated phenotype or developmental potential of a cell without the formation of a pluripotent intermediate cell does not require that the cell be first dedifferentiated (or reprogrammed) and then differentiated to another cell type. Instead, the cell type is merely "switched" from one cell type to another without going through a less differentiated phenotype. Accordingly, transdifferentiation refers to a change in the developmental potential of a cell whereby the cell is induced to become a different cell having a similar developmental potential, e.g., a liver cell to a pancreatic cell, a pancreatic alpha cell into a pancreatic beta cell, etc. The system and methods of the invention are well suited for transdifferentiation of cells.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

As used herein, the term "transcription factor" refers to a protein that binds to specific parts of DNA using DNA binding domains and is part of the system that controls the transcription of genetic information from DNA to RNA.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "exogenous" as used herein refers to a nucleic acid (e.g., a synthetic, modified RNA encoding a transcription factor), or a protein (e.g., a transcription factor) that has been introduced by a process involving the hand of man into a biological system such as a cell or organism in which it is not normally found, or in which it is found in lower amounts. A factor (e.g. a synthetic, modified RNA encoding a transcription factor, or a protein, e.g., a polypeptide) is considered exogenous if it is introduced into an immediate precursor cell or a progeny cell that inherits the substance. In contrast, the term "endogenous" refers to a factor or expression product that is native to the biological system or cell (e.g., endogenous expression of a gene, such as, e.g., SOX2 refers to production of a SOX2 polypeptide by the endogenous gene in a cell). In some embodiments, the introduction of one or more exogenous factors to a cell, e.g., a developmental potential altering factor, using the compositions and methods comprising synthetic, modified RNAs described herein, induces endogenous expression in the cell or progeny cell(s) thereof of a factor or gene product necessary for maintenance of the cell or progeny cell(s) thereof in a new developmental potential.

The term "isolated cell" as used herein refers to a cell that has been removed from an organism in which it was originally found, or a descendant of such a cell. Optionally the cell has been cultured in vitro, e.g., in the presence of other cells. Optionally, the cell is later introduced into a second organism or re-introduced into the organism from which it (or the cell or population of cells from which it descended) was isolated.

The term "isolated population" with respect to an isolated population of cells as used herein refers to a population of cells that has been removed and separated from a mixed or heterogeneous population of cells. In some embodiments, an isolated population is a "substantially pure" population of cells as compared to the heterogeneous population from which the cells were isolated or enriched. In some embodiments, the isolated population is an isolated population of pluripotent cells which comprise a substantially pure population of pluripotent cells as compared to a heterogeneous population of somatic cells from which the pluripotent cells were derived.

As used herein, the terms "synthetic, modified RNA" or "modified RNA" refer to an RNA molecule produced in vitro, which comprise at least one modified nucleoside as that term is defined herein below. Methods of the invention do not require modified RNA. The synthetic, modified RNA composition does not encompass mRNAs that are isolated from natural sources such as cells, tissue, organs etc., having those modifications, but rather only synthetic, modified RNAs that are synthesized using in vitro techniques. The term "composition," as applied to the terms "synthetic, modified RNA" or "modified RNA," encompasses a plurality of different synthetic, modified RNA molecules (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 75, at least 90, at least 100 synthetic, modified RNA molecules or more). In some embodiments, a synthetic, modified RNA composition can further comprise other agents (e.g., an inhibitor of interferon expression or activity, a transfection reagent, etc.). Such a plurality can include synthetic, modified RNA of different sequences (e.g., coding for different polypeptides), synthetic, modified RNAs of the same sequence with differing modifications, or any combination thereof.

As used herein, the term "polypeptide" refers to a polymer of amino acids comprising at least 2 amino acids (e.g., at least 5, at least 10, at least 20, at least 30, at least 40, at least 50, at least 60, at least 70, at least 80, at least 90, at least 100, at least 125, at least 150, at least 175, at least 200, at least 225, at least 250, at least 275, at least 300, at least 350, at least 400, at least 450, at least 500, at least 600, at least 700, at least 800, at least 900, at least 1000, at least 2000, at least 3000, at least 4000, at least 5000, at least 6000, at least 7000, at least 8000, at least 9000, at least 10,000 amino acids or more). The terms "protein" and "polypeptide" are used interchangeably herein. As used herein, the term "peptide" refers to a relatively short polypeptide, typically between about 2 and 60 amino acids in length.

Microarrays and particularly "cell arrays" or "cell panels" are currently needed for screening of large biomolecule libraries, such as RNAs, DNAs, proteins and small molecules with respect to their biological functions and for fundamental investigation of cell and gene-functions. Many research facilities both in academia and in industry need advanced high-density arrays to improve their screening-efficiency, velocity and quality. Many screens will first become possible or significantly more affordable with the development of next generation microarrays and cell arrays/cell panels, respectively. An invention array or cell panel should typically fit onto a customary microtiter scaled plate to ensure the usability of conventional microplate handling robots and microscopes. In one embodiment cell arrays or cell panels can comprise any collection of cell lines that need to be assayed as a unit under identical conditions, for example where the only variable is the genotype of the cell lines. An example could be a collection of normal and disease specific iPSC lines, or their differentiated derivatives, plated in microtiter plates in wells adjacent to each other. The cell panels may comprise cells derived from multiple individuals in any "population of interest" and can be selected such that the cells (or individuals from whom the cells are derived) are representative of the diversity of that population of interest. The cells in the cell panels may be stem cells, differentiated cells made from such stem cells, or differentiated cells made by trans-differentiation from cells of another type (e.g. by trans-differentiation). Such cell panels can be used, for example, to probe the activity of a single factor (e.g. small molecule) on multiple genotypes simultaneously to discover genotype specific effects of that factor using the appropriate assays.

One advantage of the present invention is that it provides methods and systems for generating an essentially limitless supply of isogenic or synegenic human cells (such as iPSCs and differentiated cells derived therefrom) that may be suitable for transplantation, use in drug discovery assays, and/or for disease modeling. Such cells (such as iPSCs) may be tailored specifically to the patient, therefore, potentially obviating the significant problem associated with current transplantation methods, such as, rejection of the transplanted tissue, which may occur because of host versus graft or graft versus host rejection. When utilized for drug discovery the cells demonstrate each person's response to chemicals when used in drug discovery or their individual manifestation of diseases in disease models. Several kinds of iPSCs or fully differentiated somatic cells prepared from iPSCs derived from somatic cells derived from humans can be stored in an iPSC bank as a library of cells, and one kind or more kinds of the iPSCs in the library can be used for preparation of somatic cells, tissues, or organs that are free of rejection by a patient to be subjected to stem cell therapy.

In one embodiment the present invention provides methods of making panels of cells or "cell panels" that are derived from multiple individuals in a "population of interest" and that may, in some embodiments, be representative of the diversity of that population of interest. Such cell panels can be made, for example, using the automated systems of the present invention or other suitable systems known the art. The cells in the cell panels may be somatic cells, stem cells, differentiated cells made from such stem cells, or differentiated cells made by trans-differentiation from cells of another type (e.g. by trans-differentiation). Such cell panels can be made in multiple formats and can be frozen and stored to form frozen banks of cell panels. Such cell panels may be useful for a variety of different applications, including, but not limited to, use in assays designed to screen for new drugs that might be effective in a given population of interest, and/or to test the efficacy, safety, and/or toxicity of drugs in a given population of interest.

The cell panels of the present invention may include samples obtained from, and/or be designed to be representative of, any "population of interest" desired, including, but not limited to, the world population, the population of a particular country, the population of a particular continent, the population of a particular geographic region (e.g. Northern Italian, Indian sub-continent, etc.), the population of a particular racial or ethnic group (e.g. Ashkenazi Jews, Maoris, etc.), a population of a particular age, a population of a particular sex (male or female), a population having a particular disease or disorder (e.g. a specific cancer, metastatic cancer, Huntington disease, Parkinson's disease, psoriasis, asthma, post-traumatic stress disorder, traumatic brain injury, autism, or any other disease or disorder of interest), a population having a particular mutation, a population having a particular genotype, a population having a particular phenotype, a population having a particular HLA type, a population having a particular blood group, a population having a particular drug response profile, and the like. In some embodiments the panels of the present invention may be designed to be representative of the population of interest (e.g. in terms or race, ethnicity, sex, age, genotype, phenotype or any other desired characteristic), for example based on population Census data. In some embodiments the cell panels may comprise engineered lines, such as those created to test for the effects of particular mutations.

For some applications it will be desirable to use "control" panels of cells, or panels comprising "control" cells. Such controls can be used for comparison to cells from the populations of interest. For example, if a panel comprises cell samples having a particular mutation (such as a mutation related to a particular disease) it may desirable to have a control panel comprising control cell samples, or to include control cell samples in the panel. In some embodiments, such control cells samples may comprise isogenic control cell samples, such as cell samples in which a mutation has been corrected.

In some embodiments the present invention provides panels of stem cells that are derived from multiple individuals in a population of interest. In some embodiments the stem cells may comprise induced pluripotent stem cells (iPSCs). Such panels can be made, for example, by obtaining differentiated somatic cells from an adult or child and using iPSC methods known in the art to convert those cells to pluripotent stem cells, for example using the automated systems of the invention. In some embodiments the stem cells may comprise embryonic stem cell (ESCs), for example ESCs derived from donated embryos (such as those created in an IVF procedure) or ESCs made by a nuclear transfer technique.

In some embodiments the present invention provides panels of differentiated cells that are derived from multiple individuals in a population of interest. Types of differentiated cells that may be provided using in the format of a panel according to the invention include, but are not limited to: oligodendrocytes, beta cells, cortical neurons, dopaminergic neurons, cardiomyocytes, and cells of certain mesenchymal lineages (osteoblasts).

In some embodiments the cell panels of the present invention are made in, and/or provided in, the form of tissue culture vessels, such as tissue culture plates, bottles, or vials. In one embodiment the cell panels of the present invention are made in, and/or provided in, microtiter plates, such as those having 6, 24, 96, 384, 1536, 3456 or 9600 wells in one plate. In some embodiments, each well in such a microtiter plate may comprise cells derived from one individual (such as one human individual) with every well containing cells from different individuals. For example, 96 different individuals may be represented in one 96-well plate, 384 different individuals may be represented in one 384-well plate, and 1596 different individuals may be represented in one 1596-well plate within the population group of interest. In other embodiments multiple wells within one plate may comprise cells from the same individual.

In one embodiment the panels of the present invention are made using an automation platform, such as that described herein or in U.S. patent application Ser. No. 13/691,257, the contents of which are hereby incorporated by reference. In other embodiments these cell panels may be made manually or by any other suitable means known in the art.

The cell panels of the present invention have a variety of uses. In some embodiments the cell panels can be used for disease modeling, drug screening, toxicology testing (e.g. for testing the toxicity of drugs on specific populations of interest), efficacy studies (e.g. for testing efficacy of drugs on specific populations of interest), studying basic biology, studying developmental biology, for generating cell products (e.g. materials generated using cells as "factories"), or identifying groups of individuals similarly affected by drugs. As such, the cell panels can be used in methods that resemble clinical trials but that are performed in vitro, allowing drugs to be tested on cells from large cohorts of different individuals. In this way it may be possible, for example, to identify subgroups of individuals that respond in a particular way to drugs before the drugs are used in clinical trials or are approved and used in the population at large.

The cell panels of the present invention can be provided in various forms. In one embodiment they can be provided as growing/living cells, for example in the form of a microtiter plate, or plates, of living cells. Such plates of living cells can be passaged as needed to maintain, continue or expand the cell panel(s). In some embodiments the plates of cells can be passaged using an automated system such as that described herein. In some embodiments the cell panels of the present invention are provided as frozen cells, for example in one or more plates or vials. In some embodiments the panels of the present invention may be frozen and/or thawed using an automated system such as that described herein.

In one aspect the present invention provides automated systems suitable for generating, maintaining and handling a variety types, such as iPSCs and differentiated cells produced therefrom. The invention system greatly improves the efficiency and reproducibility of making and handling standardized iPSC lines and other cell lines. Typically, researchers generate iPSCs by hand, which limits the cells utility due to researcher variability and an inability to generate large numbers of cells. The invention system circumvents these problems with a completely automated system from receipt of the tissue or cell sample to banking of large stocks of well-defined iPSC lines and/or differentiated cells produced therefrom. The system allows for consistency in the generation of large numbers of cells from many donors, which will facilitate the use of iPSC technology to discover treatments and cures for many diseases. Various embodiments and components of the automated systems of the invention are described herein. In addition, each of such embodiments can be modified by inclusion of a data-driven batching system, or a component thereof, as described in other sections of this patent application.

In one embodiment, the workflow system of the invention includes an automated system for generating and isolating iPSCs, comprising: a somatic cell, e.g., fibroblast, plating unit for placing cells on a plate; and an induction unit for automated reprogramming of cells by contacting the cells on the plating unit with reprogramming factors to produce iPSCs. In some embodiments the system further comprises a data-driven batching system, or a component thereof. In a further embodiment, the invention system includes a sorting unit for selectively sorting and isolating the iPSCs produced by the induction unit by identifying iPSC specific markers, including, e.g., surface markers or green fluorescent proteins inserted by a transfection vector. Somatic cells can be obtained from cell lines, biopsy or other tissue samples, including blood, and the like.

In another embodiment, the invention provides an automated system for generating and isolating differentiated adult cells from stem cells, e.g., iPSCs, embryonic stem (ES) cells or mesenchymal stem (MS) cells, comprising: a stem cell plating unit for placing cells, e.g., iPSCs, ES or MS cells, on a plate; and an induction unit for automated reprogramming of cells by contacting the cells on the stem cell plating unit with reprogramming factors to produce differentiated adult cells. In some embodiments the system further comprises a data-driven batching system, or a component thereof. In one embodiment, the system further includes a sorting unit for selectively sorting and isolating the differentiated adult cells produced by the induction unit by identifying markers specific to the differentiated adult cells.

In yet another embodiment, the invention provides an automated system for generating and isolating differentiated adult cells from induced pluripotent stem cells (iPSCs), comprising: an iPSC plating unit for placing iPSCs on a plate; and an induction unit for automated reprogramming of iPSCs by contacting the iPSCs on the iPSC plating unit with reprogramming factors to produce differentiated adult cells. In some embodiments the system further comprises a data-driven batching system, or a component thereof. In one embodiment, the system further includes a sorting unit for selectively sorting and isolating the differentiated adult cells produced by the induction unit by identifying markers specific to the differentiated adult cells.

The invention provides an automated workflow system for producing iPSCs from differentiated adult cells. Broadly, the inventive workflow system provides a new workflow system that starts with adult differentiated cells (e.g., isolated or tissue samples) and results in either iPSCs or adult cells derived from pluripotent cells. In some embodiments the workflow system comprises a data-driven batching system, or a component thereof. In one embodiment, the adult differentiated cells are preferably fibroblasts obtained, e.g., from skin biopsies. The adult fibroblasts are converted into induced pluripotent stem cells (iPSCs) by the inventive workflow that incorporates automation and robotics. The inventive workflow system is capable of generating thousands of iPSCs in parallel resulting in an accelerated timeframe, in a period of months instead of the years, which would have previously been required. The inventive workflow system can be adapted to any cell isolation system for starting material and be applied to direct or indirect reprogramming and transdifferentiation, for example. The inventive workflow system will allow production employing cellular arrays of cells from 6, 24, 96, 384, 1536 sized arrays, or greater (such as 3456 or 9600 sized arrays). The inventive workflow system is flexible and will allow for multiple iterations and flexibility in cell type and tissue. The description herein is shown with fibroblasts as an illustrative somatic cell. As noted herein, other cell types are used in the system. The example is not meant to be limited in this way.

The Workflow System

The workflow system is broken down into four independently-operated units:
(1) Quarantine Somatic Cell Isolation and Growth (System 1);
(2) Quarantine Assay (System 2);
(3) Thawing, Infection and Identification (Systems 3, 4, and 5); and
(4) Maintenance, QC, Expansion, and Freezing. (Systems 6, 7, and 8)

Additionally, an automated −80 storage and retrieval system for storing fibroblasts and final clones in 1.4 mL Matrix screw cap tubes, is part of the system. The systems, and the steps and operations that each unit will perform, will be described below.

System 1, Part A: Quarantine Somatic Cell Isolation and Growth Workflow, Biopsy Processing Pre-Mycoplasma Test
1. Technician will plate 40 biopsies per week in 6-well dishes;
2. 6-well plates will be maintained in quarantine incubator with 200-plate capacity;
3. Periodic confluency checks are performed on an integrated Cyntellect Celigo Cytometer.

The system components that may be used to perform these automated steps include by way of example, STARlet Manual Load, a Modular Arm for 4/8/12 ch./MPH, 8 channels with 1000 µl Pipetting Channels and an iSWAP Plate Handler, all available from Hamilton Science Robotics. If centerfuging is needed or desired, an Agilent VSpin Microplate Centerfuge can be used. The software may be Celigo API Software. The incubator may be a Cytomat Incubator. For plate handling a Cytomat 24 Barcode Reader, Cytomat 23 mm Stackers, and a Cytomat 400 mm transfer station may be used. For plate tilting, one may use a MultiFlex Tilt Module. The system controller may be a Dell PG with a Windows XP operating system. The carrier package may be a Q Growth Carrier Package.

System 1, Part B: Quarantine Growth Workflow, Mycoplasma Test
1. Retrieve from incubator to deck of Quarantine Growth STARlet, remove media from wells to plate for ELISA based mycoplasma test.
2. Manually transfer 96-well assay plates to Quarantine Assay STARlet.

System 1, Part C: Quarantine Growth Workflow, after Passing Mycoplasma Testing
1. Expanded fibroblasts distributed into multiple cryovials, capped, transferred to SAM −80° C.

The system components that may be used to perform these automated steps may be selected from the same components used in the Quarantine Growth Workflow, except a STARlet Auto Load may be used. A Spectramax L Reader may be used as a spectral acquisition device.

System 2: Quarantine Assay Workflow
1. Test using glow luminescence method, Lonza MycoAlert.
2. Perform luminescence plate read on spectral acquisition device.

The system components that may be used to perform these automated steps include STARlet Manual Load, a Modular Arm for 4/8/12 ch./MPH, 8 channels with 1000 μl Pipetting Channels and an iSWAP Plate Handler, all available from Hamilton Science Robotics. For luminescence assays the BioTek Synergy HT Reader may be used. The system controller may be a Dell PG with a Windows XP operating system. The carrier package may be a Q Growth Carrier Package.

Systems 3, 4, and 5: Thawing, Infection and Identification
Thawing Module & Infection Module
1. Retrieve cryotubes from SAM −80° C. (61, 190)
2. Thaw on warming block (122)
3. Decap (Hamilton Capper Decapper) (126)
4. Add media to dilute cryoprotectants (122)
5. Spin (128)
6. Resuspend in plating data (122)
7. Plate one sample per well of 6-well (62, 122)
8. Move to incubator (130, 132)
9. Fibroblasts recover for about 3-4 days
10. Confluence check on Cyntellect Celigo Cytometer (124)
11. Fibroblast passaging of all wells on the same day for reprogramming (122)
12. In batches, tryspin passage wells (122)
13. Count cells on Cyntellect Celigo Cytometer (124)
14. Plate a defined number per well on one-to-three wells of a 24-well plate consolidating samples onto as few as 24-well plates as possible (64, 122)
15. Return plates to the incubator overnight (130, 132)
16. Retrieve plates and thaw virus in tube format and add to each well of the fibroblasts in the 24-well plates (130, 122)
17. Daily partial media exchanges (122)

Magnetic Sorting Module
18. Harvest cultures with accutase to single-cell suspension (134)
19. Dilute in staining buffer (134)
20. Stain with magnetic beads against fibroblast surface marker (134)
21. Wash step (134)
22. Apply to magnet (for Dynal beads) or column (for Miltenyi system) (134, 136)
23. Retrieve non-magnetic fraction to new wells (134)
24. Count cells on Cyntellect Celigo Cytometer (124)
25. Dilute to appropriate cell density for delivering 1-10 cells per well to 96-well plate in passaging media (66, 134)
26. Retrieve new Matrigel or matrix-coated 96-well plate from 4° C. incubator (142)
27. Distribute cells to 96-well matrix plates, number based on cell count for example, two per plates per infection (66, 134)
28. Return plates to incubator (132)
29. Daily partial media exchanges (122)

Colony Identification Module
30. Retrieve 96-well plates from incubator to Colony identification liquid handler (66, 132, 138)
31. Perform live cell stain with pluripotency surface marker (138)
32. Image on Cyntellect Celigo Cytometer (140)
33. Identify wells with a single-marker positive colony that has a sharp colony border (140)
34. Techs review hits and select 6 per original sample for passage and retrieve plate and positive well IDs.
35. Cherry-pick wells with single positive colonies (138)
36. Retrieve new Matrigel or matrix coated 96-well plate from 4° C. incubator (68, 142)
37. Harvest selected wells and passage to new 96-well matrix plate consolidating clones onto as few plates as possible and plating each in passaging media (68, 138)
38. Daily partial media exchanges (122)

The system components that may be used to perform these automated steps may be selected from the same components used in the Quarantine Growth Workflow with the addition of one or more CORE 96 PROBEHEAD II 1000 μl model probe heads.

Systems 6, 7, and 8: Maintenance, QC, Expansion, and Freezing
Maintenance Module
39. Will serially-passage clones 1:1 into new 96-well matrix-coated plates until colony density is high enough (68-72, 160)
40. Daily feeding of all plates with ~75% media exchange with 96-tip head (160)
41. Periodic monitoring of colony density and growth rates on Cyntellect Celigo Cytometer (166)
42. Plate replication to produce plates for QC of clones (74-86, 160)
43. Goal is to expand clones onto multiple plates for use in several QC assays to eliminate poorly-performing clones until left with two-to-three high-quality clones per original sample
44. Will also cherry-pick and re-array clones that pass QC steps as the poor clones are eliminated to consolidate clones onto as few plates as possible (80, 86, 160)
45. Daily feeding throughout this process (160)

QC Module
46. Harvest cells (74, 150)
47. Count cells (164)
48. Plate a defined cell number in V-bottom plates (range of 5000-10000 cells/well) in 2-6 replicates per line (84, 150)
49. Return to incubator—(1 g aggregation) (172)
50. Media exchange after two days (150)
51. Incubate for additional 12 days in incubator (172)
52. Partial media exchange every two days (150)
53. Transfer to nucleic acid prep station to remove media from wells leaving embryoid bodies in the well (84, 192)

54. Resuspend in RNA lysis buffer and combine and mix replicates for each sample and make plates available for analysis in Nanostring nCounter assay (84, 192)

Freezing Module

55. Begins with a 96-well plate after an expansion passage (88)
56. Incubate 6 days in incubator (172)
57. Partial media exchange every day (154)
58. Remove plate from incubator (88, 162)
59. Remove media (needs to be complete) (154)
60. Add cool Pre-freeze media (diluted matrigel in growth media) (154)
61. Incubate in incubator for 1 h (172)
62. Remove media (needs to be complete) (154)
63. Addition of cold freezing media—low volume (154)
64. Seal plate (88, 164
65. Samples taken off-line to −80° C. storage to freeze (190)
66. Store in vapor phase Liquid Nitrogen Cryovial Storage 67. Begins with a 96-well plate after an expansion passage (90)
68. Incubate 6 days (172)
69. Daily partial media exchanges (154)
70. Passage wells 1:1 to a 24-well plate (92, 154)
71. Incubate 6 days (172)
72. Daily partial media exchanges (154)
73. Passage wells 1:1 to a 6-well plate (94, 154)
74. Incubate 4-6 days (172)
75. Daily partial media exchanges (154)
76. Remove plate from incubator (162)
77. Partial media exchange with pre-freeze media (154)
78. Incubate in incubator for 1 h (172)
79. Harvest cells for freezing as for normal passage (154)
80. Move to matrix tubes, two-to-three tubes per well (96, 154)
81. Spin and remove media (168, 154)
82. Addition of cold freezing media (154)
83. Cap tubes (170)
84. Samples taken off-line to −80° C. storage (190)

The system components that may be used to perform these automated steps may be selected from the same components used in the Quarantine Growth Workflow.

The iPSCs of the present invention may be differentiated into a number of different cell types to treat a variety of disorders by methods known in the art. For example, iPSCs may be induced to differentiate into hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition or used to advance medical research or in to develop drug discovery assays. Thus, the methods of the present invention may be used to as a treatment or to develop a treatment for a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, Huntington's disease, amyotrophic lateral sclerosis (ALS), lysosomal storage diseases, multiple sclerosis, spinal cord injuries, genetic disorders, and similar diseases, where an increase or replacement of a particular cell type/tissue or cellular de-differentiation is desirable.

In one embodiment, the inventive system can also be used to obtain cell populations enriched in fully reprogrammed cells, from among cells that have undergone differentiation in established iPSC cell lines that were cultured under both murine embryonic fibroblast (MEF) feeder layer, as well as feeder reconditions. The inventive system further enables the live-sorting of defined subpopulations of fully-reprogrammed, or differentiated, iPSC cells into 96-well plates for use in high-throughput screening campaigns.

FIG. 1 shows the steps performed by System 1, including plating of a biopsy (2), outgrowth and passaging (4) (rolling production on liquid handling robot), QC (6) (automated testing for mycoplasma), and (8) automated freezing on liquid handling robot.

Figure 2:
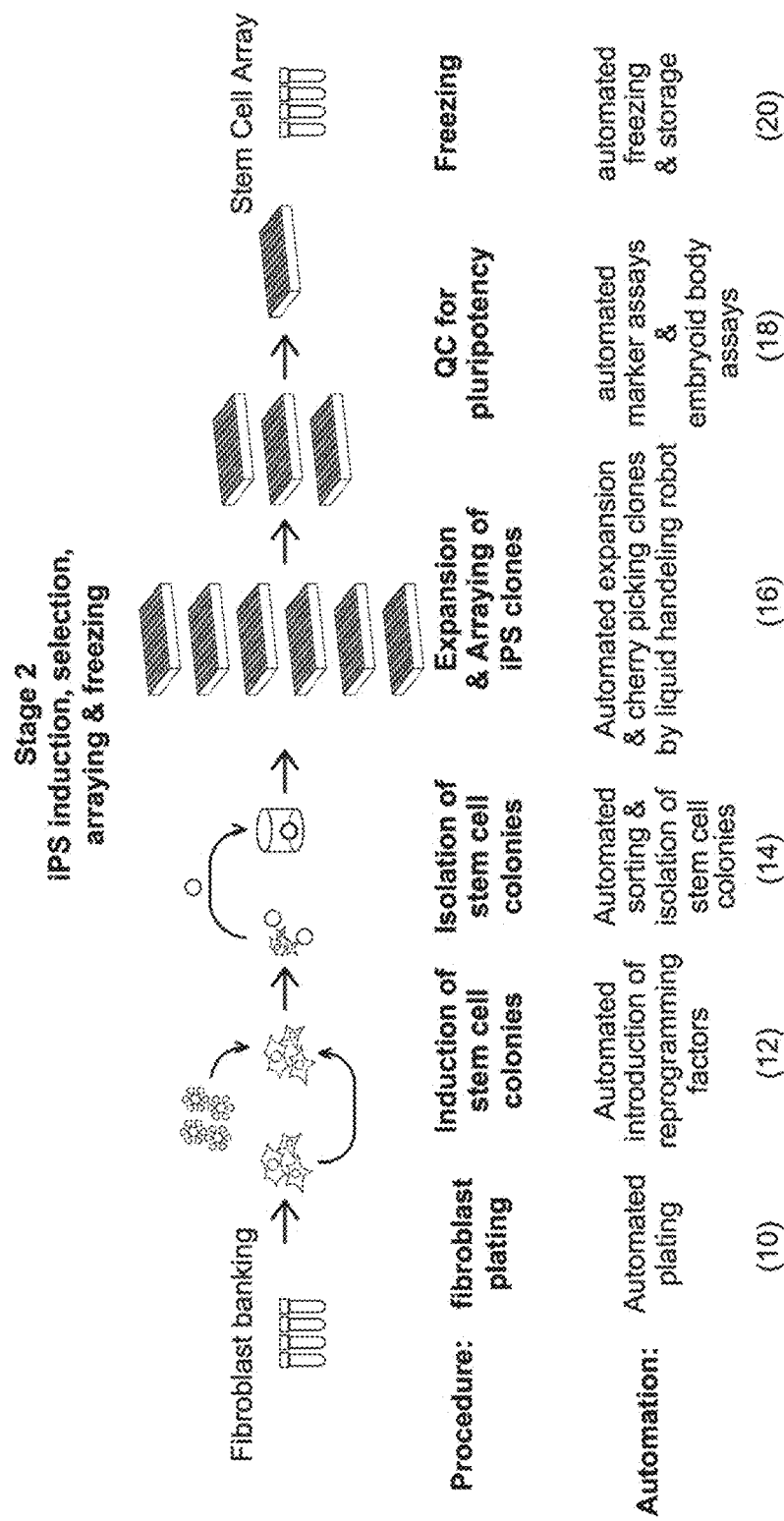
FIG. 2. Steps for obtaining a stem cell array from a fibroblast bank.

FIG. 2 shows the steps performed by Systems 2, 3, and 4. Fibroblasts are plated by the automated system (10), reprogramming factors are introduced by the automated system (12), iPSCs are isolated by automated sorting and isolation (14), desired clones are selected and expanded by the automated system (16), automated quality checks (QC) for pluripotent status by marker assays and embryoid body assays (18), followed by automated freezing and storage of desired cells (20).

Figure 3:
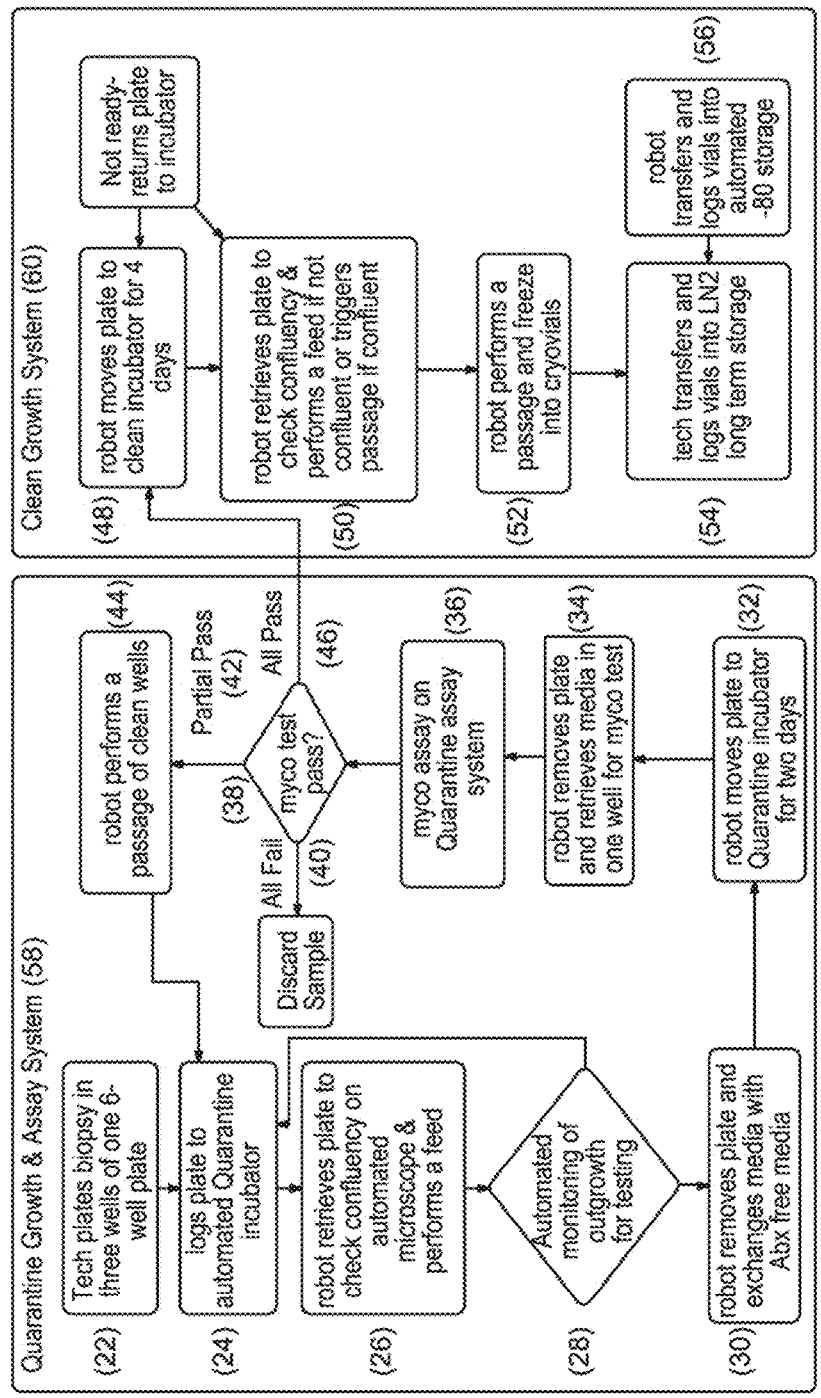
FIG. 3. Flowchart showing steps in a system for producing iPSCs.

FIG. 3 is a flowchart showing the step (22) through (60) involved in System 1.

FIG. 3 illustrates an example of the workflow and decision tree for production of fibroblasts from biopsies. The workflow is divided into Quarantine (58) and Clean phases (60). As biopsies enter the facility, a technician plates biopsies in 6-well plates (22) and logs the plates into the automated incubator (24). After biopsies are given time to attach to the plate, the liquid handling robot retrieves the plates from the automated incubator to feed and check confluency of the outgrowths on an automated microscope (26). The plates are returned to the incubator and allowed to outgrow (28). The liquid handler removes the plate from the incubator and exchanges the media for antibiotic and antimycotic free media (30). The robot moves the plate to the incubator for another five days (32). The robot then removes the plate and retrieves media to daughter plates for mycoplasma test (34). The daughter plates are moved to the Quarantine Assay system for mycoplasma testing (36). A choice is then made based on a positive signal from the assay (38). If all wells of a 6-well plate fail with a positive mycoplasma assay result (40) they are discarded. If all wells of a 6-well plate are negative and free of mycoplasma, they are transferred out of quarantine into the clean growth system (46). If some wells are positive and some wells are negative, the negative wells are maintained in quarantine (42). The negative wells are passaged (44) to new plates, transferred to the incubator, and the source plates containing positive wells are discarded. These cultures proceed through steps to retest for mycoplasma (24, 26, 28, 30, 32, 34, 36, 38). Clean cultures are monitored for growth (50), passaged (52) and frozen in cryovials (54, 56).

Figure 4A:
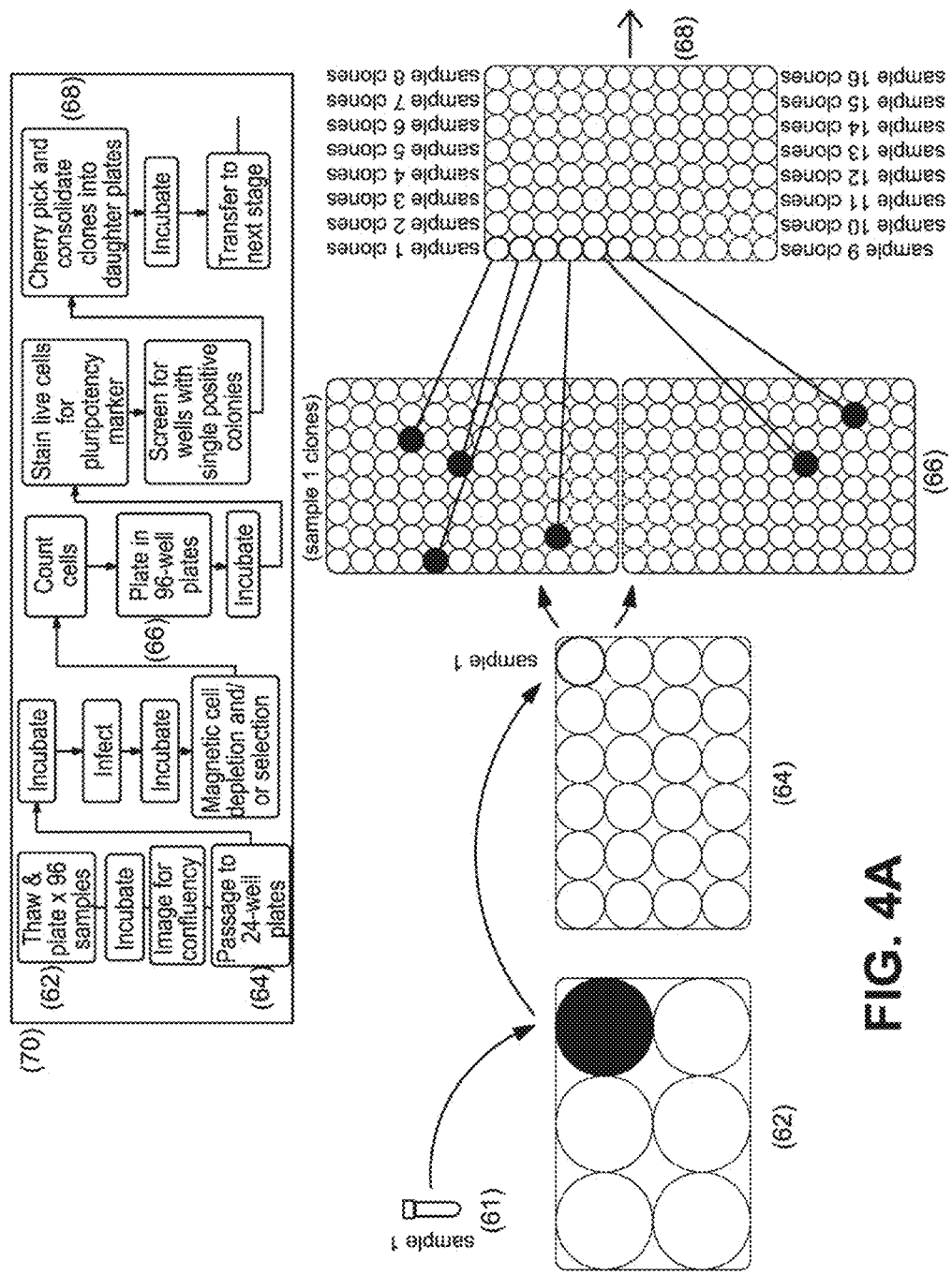
Figure 4C:
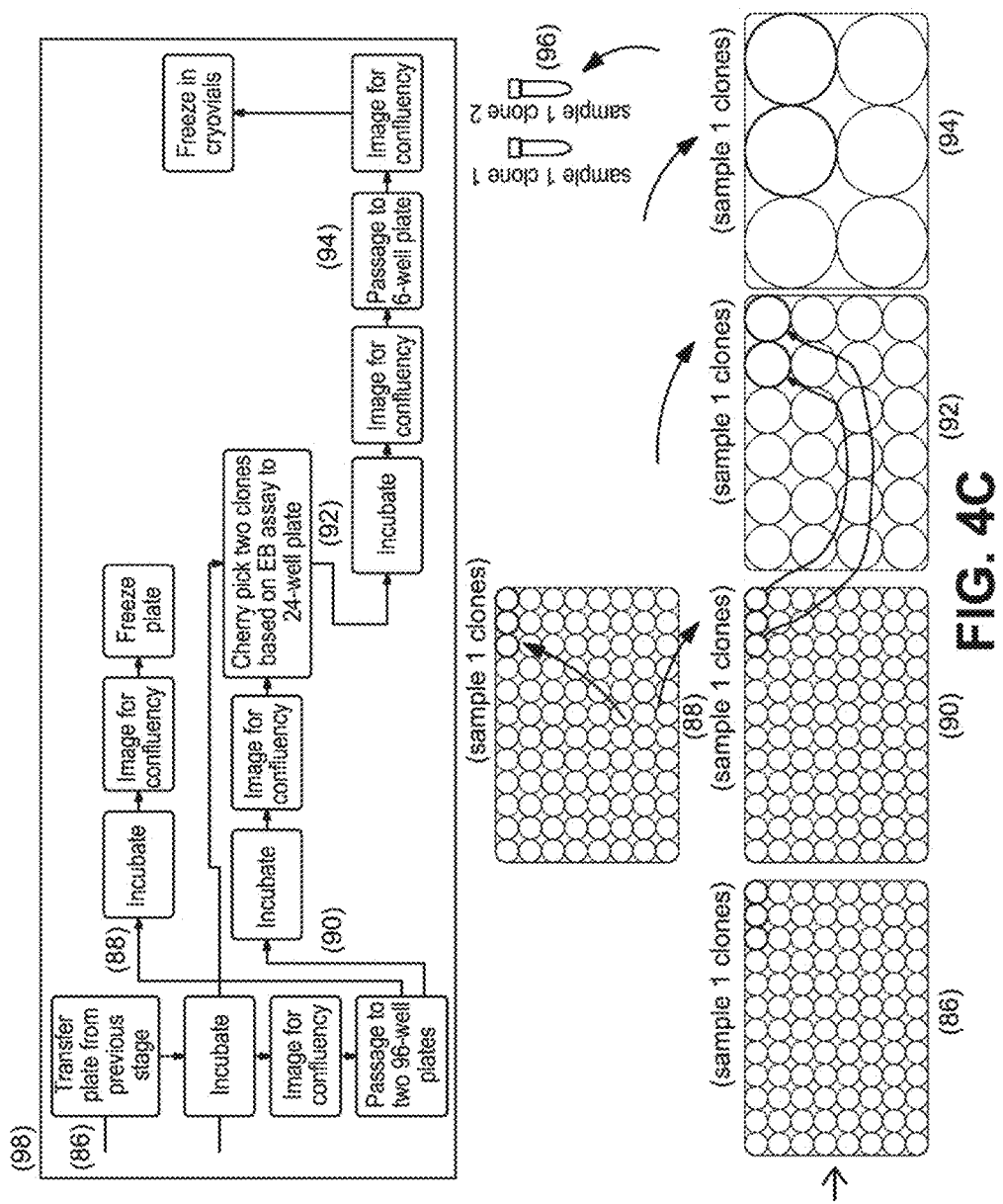

FIGS. 4A, 4B1, 4B2, and 4C illustrate an example of the flow of patient samples through multi-well tissue culture plates during the automated reprogramming process. At the top of each diagram, a flowchart describes the flow of procedures performed at each step of the workflow (70, 88, 98). At the bottom of each diagram, multi-well cell culture plates are shown with platemaps for example samples represented by shaded wells or groups of wells marked with sample labels (61-68, 72-86, 88-96). Transfer of a sample from plate-to-plate or well-to-well through the procedure is shown from left to right as indicated by arrows. As shown in FIG. 4A, the automated iPSC derivation process begins when patient samples and control fibroblast samples (61) are plated in individual wells of a 6-well plate (62). These are passaged at defined cell number into individual wells of a 24-well plate (64) for infection using viruses encoding reprogramming factors or other means of introducing reprogramming factors to the cells. In the next step, reprogrammed samples are depleted of non-reprogrammed cells by cell sorting or, as is preferred, using magnetic bead based enrichment and plated at clonal density in multiple wells in 96-well plates (66). Two such plates are shown in this example. In this example, 6 wells, as indicated by wells with a dot in the middle (66) are identified containing a single clone positive for a pluripotency surface marker as assayed by immunofluorescent analysis on automated imager. These clones are passaged and cherry picked to reformat the clones into a minimum number of 96-well plates (68). The example figure shows six clones per individual starting sample and indicates that clones from 16 starting sample can be arrayed onto a 96-well plate. To facilitate plate processing, this cherry picking step can be performed over multiple passages to consolidate the clones onto a minimum number of plates. As show in FIGS. 4B1 and 4B2, these clones are serially passaged until confluence of stem cell colonies within a well is achieved for each starting sample (72). Each plates' samples are then replicated onto duplicate plates (74-86), to allow for the quality control (6) and selection of clones that demonstrate appropriate stem cell characteristics. To begin the QC process, one plate is generated by the system for a Pluripotency quality control assay needed to determine pluripotent status of the individual clones (74) and one plate is generated for carrying forward in subsequent passages (76). The plate that is carried forward is passaged again into three plates (78, 80, 82) for further quality control and expansion. One plate is harvested for QC assays to characterize Karyotype and genetic diversity (78). A second plate (82) is passaged onto v-bottom plates to form embryoid bodies (84) for a QC assay that assesses differentiation capability of the iPS clones. The final plate (80) is carried forward for further expansion. Individual clones that do not pass quality control from previous pluripotency QC assays are not carried forward as shown by the "X" in the wells indicated in FIGS. 4A, 4B1, 4B2 and 4C. In the example shown in FIG. 4B2, the consolidated plate (86) will contain iPS lines (or differentiated lines) from up to 32 individuals represented by 3 iPS clones per individual on a single 96 well plate or up to 96 individuals if represented by a single clone each. Remaining clones are consolidated onto as few plates as possible until one to three clones remain (86-92). As shown in FIG. 4C, these are expanded for cryopreservation while attached to the plate (88) or further expanded (92-94) and cryopreserved in cryovials (96). Any or all information from the pluripotency marker screen shown in FIG. 4A (70), and the quality control assays shown in FIG. 4B1 can be used alone or in combination to decide which clones to select for consolidation and arraying in the automated process.

Methods for transfecting and transforming or reprogramming adult cells to form iPSC lines are generally known, e.g., Takahashi et al., 2007 *Cell*, 131: 861-872, 2007, Yu et al., 2007, *Science*, vol. 318, pp. 1917-1920. iPSC are induced from somatic cells with reprogramming factors. Reprogramming factors are contemplated to include, e.g., transcription factors. The method for reprogramming adult cells includes, e.g., introducing and expressing a combination of specific transcription factors, e.g., a combination of Oct3/4, Sox2, Klf4 and c-Myc genes. Others have demonstrated that other transcription factors may be employed in transforming or reprogramming adult cells. These other transcription factors include, e.g., Lin28, Nanog, hTert and SV40 large T antigen as described, for example, by Takahashi et al., 2006 *Cell*, 126: 663-676 and Huiqun Yin, et al. 2009, *Front. Agric. China* 3(2): 199-208, incorporated by reference herein.

In another aspect, iPSCs can be generated using direct introduction of RNAs into a cell, which, when translated, provide a desired protein or proteins. Higher eukaryotic cells have evolved cellular defenses against foreign, "non-self," RNA that ultimately result in the global inhibition of cellular protein synthesis, resulting in cellular toxicity. This response involves, in part, the production of Type I or Type II interferons, and is generally referred to as the "interferon response" or the "cellular innate immune response." The cellular defenses normally recognize synthetic RNAs as foreign, and induce this cellular innate immune response. In certain aspects where the ability to achieve sustained or repeated expression of an exogenously directed protein using RNA is hampered by the induction of this innate immune response, it is desirable to use synthetic RNAs that are modified in a manner that avoids or reduces the response. Avoidance or reduction of the innate immune response permit sustained expression from exogenously introduced RNA necessary, for example, to modify the developmental phenotype of a cell. In one aspect, sustained expression is achieved by repeated introduction of synthetic, modified RNAs into a target cell or its progeny. The inventive methods include natural or synthetic RNAs.

The natural, modified, or synthetic RNAs in one aspect, can be introduced to a cell in order to induce exogenous expression of a protein of interest in a cell. The ability to direct exogenous expression of a protein of interest using the modified, synthetic RNAs described herein is useful, for example, in the treatment of disorders caused by an endogenous genetic defect in a cell or organism that impairs or prevents the ability of that cell or organism to produce the protein of interest. Accordingly, in some embodiments, compositions and methods comprising the RNAs described herein can be used for the purposes of gene therapy.

The RNAs described can advantageously be used in the alteration of cellular fates and/or developmental potential. The ability to express a protein from an exogenous RNA permits either the alteration or reversal of the developmental potential of a cell, i.e., the reprogramming of the cell, and the directed differentiation of a cell to a more differentiated phenotype. A critical aspect in altering the developmental potential of a cell is the requirement for sustained and prolonged expression of one or more developmental potential altering factors in the cell or its immediate progeny. Traditionally, such sustained expression has been achieved by introducing DNA or viral vectors to a cell. These approaches have limited therapeutic utility due to the potential for insertional mutagenesis.

One of the areas that can most benefit from the ability to express a desired protein or proteins over a sustained period of time from exogenous RNAs as described herein is the generation of pluripotent or multipotent cells from cells initially having a more differentiated phenotype. In this aspect, RNAs encoding a reprogramming factor or factors are used to reprogram cells to a less differentiated phenotype, i.e., having a greater developmental potential.

A major goal of stem cell technology is to make the stem cell differentiate into a desired cell type, i.e., directed differentiation or produce cells via transdifferentiation. Not only are the compositions and methods described herein useful for reprogramming cells, they are also applicable to this directed differentiation and transdifferentiation of cells to a desired phenotype. That is, the same technology described herein for reprogramming is directly applicable to the differentiation of the reprogrammed cell, or any other stem cell or precursor cell, for that matter, to a desired cell type.

In some embodiments of this aspect and all such aspects described herein, the synthetic, modified RNA molecule comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In one such embodiment of this aspect and all such aspects described herein, the at least two modified nucleosides are 5-methylcytidine (5mC) and pseudouridine. (see e.g., Rossi US 2012/0046346, herein incorporated by reference).

Genes, proteins or RNA used in the methods of the invention include but are not limited to OCT4, SOX1, SOX 2, SOX 3, SOX15, SOX 18, NANOG, KLF1, KLF 2, KLF 4, KLF 5, NR5A2, c-MYC, l-MYC, n-MYC, REM2, TERT, and LIN28.

It has also been shown that a single transcription factor may be employed in reprogramming adult fibroblasts to iPSCs with the addition of certain small molecule pathway inhibitors. Such pathway inhibitors include e.g., the transforming growth factor-beta (TGFb) pathway inhibitors, SB431542 (4-[4-(1,3-benzodioxol-5-yl)-5-(2-pyridinyl)-1H-imidazol-2-yl]-benzamide), and A-83-01 [3-(6-Methyl-2-pyridinyl)-N-phenyl-4-(4-quinolinyl)-1H-pyrazole-1-carbothioamide], the extracellular signal-regulated kinases (ERK) and microtubule-associated protein kinase (MAPK/ERK) pathway inhibitor PD0325901 (N-[(2R)-2,3-dihydroxypropoxy]-3,4-difluoro-2-[(2-fluoro-4-iodophenyl)amino]-benzamide), the GSK3 inhibitor CHIR99021 [6-((2-((4-(2,4-Dichlorophenyl)-5-(4-methyl-1H-imidazol-2-yl)pyrimidin-2-yl)amino)ethyl)amino)nicotinonitrile] which activates Wnt signaling by stabilizing beta-catenin, the lysine-specific demethylase1 Parnate (a/k/a tranylcypromine), the small molecule activator of 3'-phosphoinositide-dependent kinase-1 (PDK1) PS48 [(2Z)-5-(4-Chlorophenyl)-3-phenyl-2-pentenoic acid], the histone deacetylase (HDAC) inhibitors sodium butyrate and valproic acid, small molecules that modulate mitochondrial oxidation (e.g., 2,4-dinitrophenol), glycolytic metabolism (fructose 2,6-bisphosphate and oxalate), HIF pathway activation (N-oxaloylglycine and Quercetin) Zhu et al., 2010, *Cell Stem Cell* 7: 651-655, incorporated by reference herein it its entirety. Zhu et al showed that Oct4 combined with Parnate and CHIR99021 was sufficient to reprogram adult human epidermal keratinocytes.

Although individual protocols differ, a general reprogramming protocol consists of expanding differentiated adult cells from tissue samples, e.g., skin biopsies and contacting them with reprogramming factors as discussed above, e.g., infecting them, i.e., transfecting, with e.g., expression vectors, such as viral constructs containing transcripts for pluripotent transcription factors. The fibroblasts are obtained by art-known methods, e.g., by mechanically disrupting the tissue followed by enzymatic dissociation to release the fibroblasts, and culturing the fibroblasts by art-known methods, e.g., as described by Dimos et. al., 2008, *Science Vol.* 321 (5893): 1218-1221.

While illustrative aspects of the invention use vectors, e.g., viral vectors, plasmid vectors, in some aspects vectors are not required for transfection techniques, including those transferring mRNA molecules to cells.

Transfection of the fibroblasts with an expression vector is carried out according to instructions provided with the desired vector. After a time (e.g., ranging from about 2 to about 10 days post-transfection, the cells are dissociated and contacted with fluorescent tagged antibodies raised against the $CD13^{NEG}$, $SSEA4^{POS}$ and $Tra-1-60^{POS}$ surface markers. The dissociated and antibody-labeled cells are then resuspended in a phosphate buffered saline solution and moved to an automated sorting and isolation of iPSC clones. Surface marker positive cells are sorted by tag color or absence thereof directly into sterile tubes containing tissue culture media or multi-well (6-96 well) tissue culture plates coated with MEFs or cell free biological matrices and cultured until formation of visible colonies occurs.

Colonies are then further confirmed as iPSC by light microscopic inspection of the resulting clones or optionally by microscopic fluorescence inspection of clones labeled with fluorescent tagged antibodies. Optionally, in certain embodiments, one or more of the vectors also insert a green fluorescence protein (GFP) expression marker, for convenience in sorting and identification. Several individual colonies possessing morphological characteristics consistent with pluripotent ES cell lines are plucked from cultures and expanded individually to form monoclonal cultures.

In some embodiments of the present invention cells are subjected to analysis to provide early confirmation and identification of iPSCs. Preferably, such analysis is conducted by Southern blot, or other art-known methods which include, but are not limited, to MicroArray, NanoString, quantitative real time PCR (qPCR), whole genome sequencing, immunofluorescence microscopy, flow cytometry, and fluorescence activated cell sorting.

In one embodiment detection of enzymatic activity of alkaline phosphatase, positive expression of the cell membrane surface markers SSEA3, SSEA4, Tra-1-60, Tra-1-81 and the expression of the KLF4, Oct3/4, Nanog, Sox2 transcription factors in, for example, presumptively reprogrammed human fibroblasts, confirms that a clone is an iPSC. In one embodiment all of the markers are present, but in some embodiments a subset of the markers are present.

In another embodiment positive expression of the cell membrane surface markers SSEA4 and Tra-1-60 and negative expression of CD13 provides an improved method for identifying reprogrammed human fibroblasts and confirming that a clone is an iPSC. This improved system is described in more detail in Example 3, whereby fluorescence activated cell sorting (FACS) is used to identify and isolate cells/clones that are CD13-negative, SSEA4-positive and Tra-1-60-positive resulting in improved yield/selection of reprogrammed IPSCs and depletion of both parental and contaminating partially reprogrammed cells.

In some aspects the present invention provides "gene sets" comprising genes whose expression can be used to detect, or confirm the presence or generation of, particular cells such as iPSCs or other pluripotent cells or differentiated cells derived from such iPSCs or other pluripotent cells. Such gene sets, and methods and compositions (such as probes and/or other detection agents) that allow detection of the expression of genes from such gene sets, can be used in a variety of different situations. For example they can be used in accordance with the automated systems described herein (for example as part of a colony identification step or a quality control step), or they can be used in any other situation in which it is desired to detect, or confirm the presence or generation of pluripotent stem cells, such as iPSCs, or differentiated cells produced therefrom.

In one embodiment the present invention provides the "Pluri25" gene set, and nucleic acid probes or other agents (such as antibodies) capable of detecting expression of genes in the Pluri25 gene set (which may be referred to as a Pluri25 probe set). Such a gene/probe set may be used to detect, or confirm the presence or generation of, iPSCs. The Pluri25 gene/probe set comprises the following genes, or probes or other agents for detection of the expression of the following genes: four retrovial transgenes (tOct4, tSox2, tKlf4, and tC-Myc), four Sendai transgenes (tOct4, tSox2, tKlf4, tC-Myc) plus Sendai vector marker (SeV), seven pluripotency markers (POU5F1 (Oct4), SOX2, KLF4, MYC, LIN28, NANOG, and ZFP42), three spontaneous differentiation markers (SOX17, AFP, and NR2F2), one fibroblast marker (ANPEP (CD13)), three house-keeping markers (ACTB, POLR2A, and ALAS1) and two sex markers (SRY and XIST)—for a total of 25 markers. The genes in the Pluri25 gene set are also listed in Table 1, below:

TABLE 1

Pluri25 Gene Set

| Retro-viral | Sendai transgenes | Pluripotency Markers | Spontaneous Differentiation | Fibro-blasts | House-keeping |
|---|---|---|---|---|---|
| tOct4 | S-tOct4 | POU5F1 (OCT4) | SOX17 | ANPEP (CD13) | ACTB |
| tSox2 | S-tKlf4 | SOX2 | AFP | | POLR2A |
| tKlf4 | S-tC-myc | KLF4 | NR2F2 | | ALAS1 |
| tC-Myc | S-tSox2 | MYC | | | |
| | SeV | LIN28 | | | |
| | | NANOG | | | |
| | | ZFP42 | | | |

A Pluri25 probe set may comprise nucleic acid probes or other agents (such as antibodies) capable of detecting expression or expression products of each of the genes in the Pluri25 gene set. Individual probes or detection agents may be used for each gene or, where appropriate, single probes or detection agents spanning several of the genes or gene expression products may be used. For example, a single nucleic acid probe spanning all of the four retroviral transgenes may be used. The sequences of each of the genes in the Pluri25 gene set are known in the art, and nucleic acid probes or other detection agents (such as antibodies) capable of detecting expression of each of these genes may be available in the art or may be made using standard methods known in the art. The Pluri25 gene set or probe set can be used to monitor pluripotency in human stem cell cultures, analyze contamination with differentiated cells or human fibroblasts, monitoring the sex of the cells, and monitor expression of retroviral and/or Sendai transgenes or vector components. The Pluri25 gene or probe set also contains a probe (SeV) for monitoring Sendai virus expression independent of expression of any transgenes. Further description of the Pluri25 gene/probe set, including validation studies and other data generated using the Pluri25 gene/probe set, is provided in Example 3, and Table 1.

In some embodiments variations on the Pluri25 gene or probe set may be used. For example, in some embodiments the Pluri25 gene or probe set may be modified so as to exclude the retroviral transgene markers but keep the Sendai transgene and/or Sendai vector markers. In other embodiments, the Pluri25 gene or probe set may be modified so as to exclude the Sendai transgene and/or Sendai vector markers but keep the retrovial transgene markers. In other embodiments the Pluri25 gene or probe set may be modified so as to exclude both the Sendai transgene/vector markers and the retrovial transgene markers. Thus, in one embodiment, the present invention provides a gene or probe set comprising: seven pluripotency markers (POU5F1 (Oct4), SOX2, KLF4, MYC, LIN28, NANOG, and ZFP42), three spontaneous differentiation markers (SOX17, AFP, and NR2F2), one fibroblast marker (ANPEP (CD13)), three house-keeping markers (ACTB, POLR2A, and ALAS1) and two sex markers (SRY and XIST)—for a total of 16 markers.

In another embodiment the "3GLSC100" gene set, and in particular nucleic acid probes or other agents (such as antibodies) capable of detecting expression products of genes in the 3GLSC100 gene set (which may be referred to as a 3GLSC100 probe set) may be used to detect, or confirm the presence or generation of iPSCs (similarly to the Pluri25 gene set) and can also be used to monitor differentiation of pluripotent stem cells by embryoid body assays (either directed or undirected) and can be used in accordance with the analysis methods described by Bock et al. (2011) "Reference Maps of human ES and iPS cell variation enable high-throughput characterization of pluripotent cell lines," Cell 144: 439-452, the contents of which are hereby incorporated by reference. The 3GLSC100 gene set comprises 83 genes selected from among the published germlayer scorecard of Bock et al. and 17 additional genes that are a subset of the Pluri25 gene set. The genes in the 3GLSC100 gene set are listed in Table 2 below.

TABLE 2

3GLSC100 Gene Set

| Mesoderm | Ectoderm | Endoderm | Retroviral | Sendai | Pluripotent | Other | Housekeeping |
|---|---|---|---|---|---|---|---|
| ABCG2 | ABCG2 | APOE | tOct4 | tOct4 | POU5F1 | SRY | ACTB |
| ADIPOQ | APOE | CD44 | tSox2 | tSox2 | NANOG | XIST | POLR2A |
| ANPEP | CD44 | CDH2 | tKlf4 | tKlf4 | ZFP42 | | ALAS1 |
| CD34 | CDH2 | CDX2 | tC-Myc | tC-Myc | | | |
| CD36 | CRABP2 | CTNNB1 | | SeV | | | |
| CD4 | EN1 | FOXA2 | | | | | |
| CD44 | FAS | GATA4 | | | | | |
| CDH1 | FGFR2 | GATA6 | | | | | |
| CDH2 | FUT4 | GCG | | | | | |
| CDH5 | GATA2 | HNF1A | | | | | |
| CEACAM1 | GATA3 | HNF1B | | | | | |
| DLL1 | HAND1 | ISL1 | | | | | |
| FUT4 | ICAM1 | ITGA6 | | | | | |
| GATA3 | ITGA4 | ITGB1 | | | | | |

TABLE 2-continued

3GLSC100Gene Set

| Mesoderm | Ectoderm | Endoderm | Retroviral | Sendai | Pluripotent | Other | Housekeeping |
|---|---|---|---|---|---|---|---|
| GATA4 | ITGA6 | NEUROG3 | | | | | |
| HHEX | ITGB1 | NKX2-5 | | | | | |
| ICAM1 | MAP2 | PAX6 | | | | | |
| INHBA | MAPT | PDX1 | | | | | |
| ITGA4 | MCAM | SLC2A2 | | | | | |
| ITGA6 | MNX1 | SST | | | | | |
| ITGAL | NCAM1 | SYP | | | | | |
| ITGAM | NEFL | THY1 | | | | | |
| ITGAV | NES | | | | | | |
| ITGAX | NEUROG3 | | | | | | |
| ITGB1 | NGFR | | | | | | |
| ITGB3 | NOG | | | | | | |
| KDR | NOTCH1 | | | | | | |
| KIT | OTX2 | | | | | | |
| LEF1 | PAX3 | | | | | | |
| MCAM | PAX6 | | | | | | |
| MME | PAX7 | | | | | | |
| MYOD1 | PDGFRA | | | | | | |
| MYOG | SNAI2 | | | | | | |
| NCAM1 | SOX10 | | | | | | |
| NES | SOX2 | | | | | | |
| NGFR | SOX9 | | | | | | |
| NOTCH1 | SYP | | | | | | |
| PECAM1 | TDGF1 | | | | | | |
| SDC1 | TH | | | | | | |
| SPI1 | THY1 | | | | | | |
| SRF | | | | | | | |
| STAT3 | | | | | | | |
| T | | | | | | | |
| THY1 | | | | | | | |
| TNFRSF1A | | | | | | | |
| TWIST1 | | | | | | | |

A 3GLSC100 probe set may comprise nucleic acid probes or other agents (such as antibodies) capable of detecting expression or expression products of each of the genes in the 3GLSC100 gene set. Individual probes or detection agents may be used for each gene or, where appropriate, single probes or detection agents spanning several of the genes or gene expression products may be used. For example, a single nucleic acid probe spanning all of the four retroviral transgenes in the 3GLSC100 gene set may be used. The sequences of each of the genes in the 3GLSC100 gene set are known in the art, and nucleic acid probes or other detection agents (such as antibodies) capable of detecting expression of each of these genes may be available in the art or may be made using standard methods known in the art. The 3GLSC100 gene set or probe set can be used in the same ways that the Pluri25 gene set is used and can also be used (as described above). Further description of the 3GLSC100 gene/probe set, including validation studies and other data generated using the 3GLSC100 gene/probe set, is provided in Example 3.

In some embodiments variations on the 3GLSC100 gene or probe set may be used. For example, in some embodiments the 3GLSC100 gene or probe set may be modified so as to exclude the retroviral transgene markers but keep the Sendai transgene and/or Sendai vector markers. In other embodiments, the 3GLSC100 gene or probe set may be modified so as to exclude the Sendai transgene and/or Sendai vector markers but keep the retrovial transgene markers. In other embodiments the 3GLSC100 gene or probe set may be modified so as to exclude both the Sendai transgene/vector markers and the retroviral transgene markers.

In another embodiment the "cardiac 1" or "cardiac 2" gene set (collectively the "cardiac gene sets"), and in particular nucleic acid probes or other agents (such as antibodies) capable of detecting expression products of genes in such gene sets (which may be referred to as a cardiac probe sets) may be used to detect, or confirm the presence or generation of, cells that are on a path towards differentiation into cardiomyocytes, such as cells that are have been derived from iPSCs or other pluiropotent cells and have been treated to encourage differentiation down a cardiomyocyte lineage. The "cardiac 1" gene set comprises the following genes: ACTN1, BMP4, GATA4, GJA1, IRX-4, ISL1, KDR, MEF2A, MEF2C, MESP1, MYH6, MYH7, MYL2, MYL7, NKX2-5, NPPA, PDGFRa, SIRPA, TBX20, TBX5, TNNI3, TNNT2, VCAM1, VWF, MIXL1, NANOG, OCT4, SOX17, Brachury T and KCNJ2—for a total of 30 genes. The "cardiac 2" gene set comprises the all of the genes in the cardiac 1 gene set and the following four additional genes: GAPDH, GUSB, HPRT1, and TBP—for a total of 34 genes.

A cardiac probe set may comprise nucleic acid probes or other agents (such as antibodies) capable of detecting expression or expression products of each of the genes in the cardiac gene set. Individual probes or detection agents may be used for each gene or, where appropriate, single probes or detection agents spanning several of the genes or gene expression products may be used. The sequences of each of the genes in the cardiac gene set are known in the art, and nucleic acid probes or other detection agents (such as antibodies) capable of detecting expression of each of these genes may be available in the art or may be made using standard methods known in the art.

The cardiac gene sets or probe sets can be used to establish the differentiation stage of pluripotent stem cells when pushed to differentiate towards a cardiomyocyte phenotype. The cardiac gene sets comprise pluripotency markers, cardiac mesoderm markers, cardiac progenitor markers, immature cardiomyocyte markers, and mature cardiomyocyte markers. They also include vascular markers and surface markers expressed by cardiomyocytes during differentiation to facilitate purification, for example by via flow cytometry or by a method using magnetic beads. In some embodiments variations on the cardiac 1 and cardiac 2 gene or probe sets may be used.

Any art-known transfection vector may be employed as a reprogramming factor, including, e.g., an RNA such as mRNA, microRNA, siRNA, antisense RNA and combinations thereof. Other expression vectors that may be employed include, e.g., a retrovirus, a lentivirus, an adenovirus, an adeno associated virus, a herpes virus, a Sindbis virus, a pox virus, a bacula virus, a bacterial phage, a Sendai virus and combinations thereof. Preferably, an employed vector is a non-replicative vector such as, e.g., Sendai virus vectors engineered to be nonreplicative. The preferred Sendai virus vector, while incapable of replication, remains capable of productive expression of nucleic acids encoding protein(s) carried by the vector, thereby preventing any potential uncontrolled spread to other cells or within the body of a vaccinee. This type of Sendai vector is commercially available as a CytoTune™-iPSC Sendai viral vector kit (DNAVEC, DV-0301).

Any art-known transfection method may be employed to insert such vectors into the adult fibroblasts, including, e.g., electroporation, gene gun, and the like. Chemical transfection is optionally conducted by means of a transfecting agent e.g., a polymer, calcium phosphate, a cationic lipid, e.g., for lipofection, and the like. Cell penetrating peptides are also optionally employed to carry vectors or other agents into the adult fibroblast cells. In brief, cell-penetrating peptides include those derived from proteins, e.g., protein transduction domains and/or amphipathic peptides that can carry vectors or other agents into the cell include peptides. The subject of cell-penetrating peptides has been reviewed, e.g., by Heitz et al., 2009 *British Journal of Pharmacology*, 157: 195-206, incorporated by reference herein in its entirety. Other cell penetrating peptides are art-known, and are disclosed by Heitz, Id. Other cell-penetrating technologies including, e.g., liposomes and nanoparticles, are also contemplated to be employed in the methods of the present invention. Liposomes and nanoparticles are also described by Heitz, Id.

Antibodies can be employed in order to identify the transformed cells. Four antibodies against stem cell specific surface proteins are commonly used to identify and characterize human pluripotent stem cell populations; SSEA3, SSEA4, Tra-1-60 and Tra-1-81. The Stage Specific Embryonic Antigens 3 and 4 (SSEA3 and SSEA4) are two monoclonal antibodies which recognize sequential regions of a ganglioside present on human 2102Ep cells (Henderson et al., 2002 *Stem Cells* 20: 329-337; Kannagi et al., 1983, *Embo J* 2: 2355-2361). The Tra-1-60 and Tra-1-81 antibodies were originally raised against human embryonal carcinoma (EC) cells (P W et al., 1984, *Hybridoma* 3: 347-361) and have been shown to specifically recognize a carbohydrate epitope on a keratan sulfated glycoprotein identified as podocalyxin, a member of the CD34-related family of sialomucins (Badcock et al., 1999, *Cancer Research* 59: 4715-4719; Nielsen et al., 2007, PLoS ONE 2: e237; Schopperle and DeWolf, 2007, *Stem Cells* 25: 723-730). Several other surface markers have been shown to be expressed on ES cells and include CD326 or EpCam (Sundberg et al., 2009, *Stem Cell Res* 2: 113-124), CD24 (Heat Stable Antigen) and CD133 (Barraud et al., 2007, *Journal of Neuroscience Research* 85, 250-259) (Gang et al., 2007, *Blood* 109: 1743-1751). Chan et al., 2009, Id. reported that the identification of bona fide IPSc from fibroblasts undergoing reprogramming via four factor retro viral transduction can be achieved via live cell imaging and by the observation, over time, that fibroblasts lose expression of the cell surface markers CD13 and D7Fib, and gain expression of the pluripotent stem cell markers SSEA4 and Tra-1-60 (Chan et al., 2009, Id.).

Also contemplated to be within the scope of the invention are compositions comprising iPSCs, e.g., compositions employed as research tools, or as pharmaceutical compositions, comprising effective amounts of iPSCs prepared by the inventive automated system.

The invention further relates to treating a disease or disorder in an animal or person in need thereof by administering the iPSCs, e.g., methods of treatment and/or tissue/organ repair by administering iPSCs produced by the inventive automated system, or differentiated cells derived therefrom. Appropriate differentiated cells (of ectodermal, mesodermal or endodermal lineage) may be derived from iPSCs produced by the inventive methods. The mode of administration can be determined by a person of skill in the art depending on the type of organ/injury to be treated. For example, iPSCs or differentiated cells derived therefrom, may be administered by injection (as a suspension) or implanted on a biodegradable matrix.

In addition, the invention relates to methods of testing pharmaceuticals by contacting iPSCs, transdifferentiated, or differentiated cells derived therefrom, for example, with one or more pharmaceutical agents of interest, and then detecting the effect of the applied pharmaceutical agent(s) on the contacted cells. For efficiency, pharmaceutical agent(s) are applied to a battery of iPSCs, or differentiated cells derived therefrom. The cells can vary in tissue source, in differentiated cell type, or allelic source, to allow identification of cells or tissue types that react favorably or unfavorably to one or more pharmaceutical agents of interest.

Further, the iPSCs produced by the inventive automated system may be used as a vehicle for introducing genes to correct genetic defects, such as osteogenesis imperfecta, diabetes mellitus, neurodegenerative diseases such as, for instance, Alzheimer's disease, Parkinson's disease, the various motor neuron diseases (MND), e.g., amyotrophic lateral sclerosis (ALS), primary lateral sclerosis (PLS), progressive muscular atrophy (PMA) and the like.

iPSCs produced by the inventive automated system may also be employed to provide specific cell types for biomedical research, as well as directly, or as precursors, to produce specific cell types for cell-based assays, e.g., for cell toxicity studies (to determine the effect of test compounds on cell toxicity), to determine teratogenic or carcinogenic effects of test compounds by treating the cells with the compound and observing and/or recording the compound's effects on the cells, e.g. effect on cellular differentiation.

The present invention may be better understood by reference to the following non-limiting Examples. The following examples are presented in order to more fully illustrate the preferred embodiments of the invention. They should in no way be construed, however, as limiting the broad scope of the invention.

EXAMPLES

Example 1

Illustrative Automated Systems

Figure 5A:
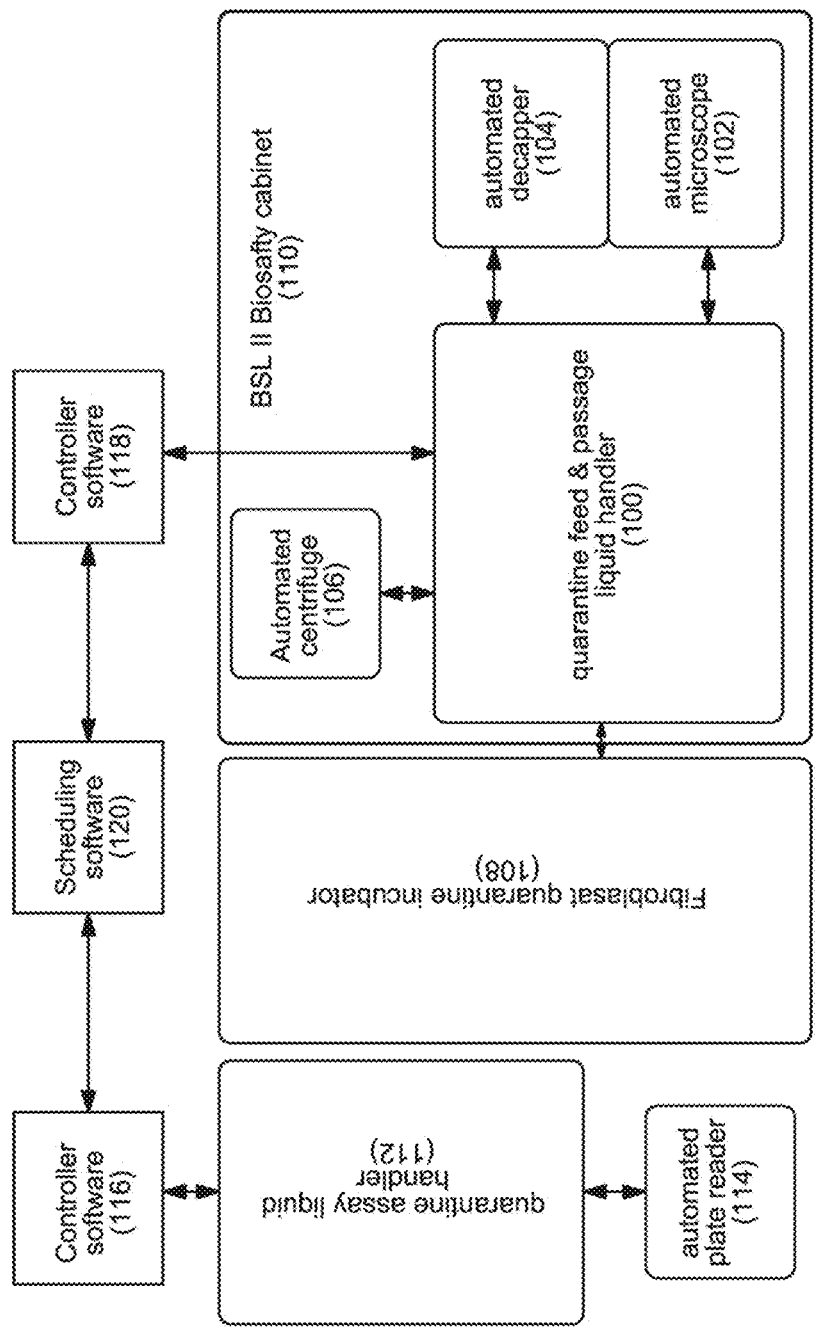
FIGS. 5A-5C. Example of an equipment configuration to accomplish the workflow.
Figure 5B:
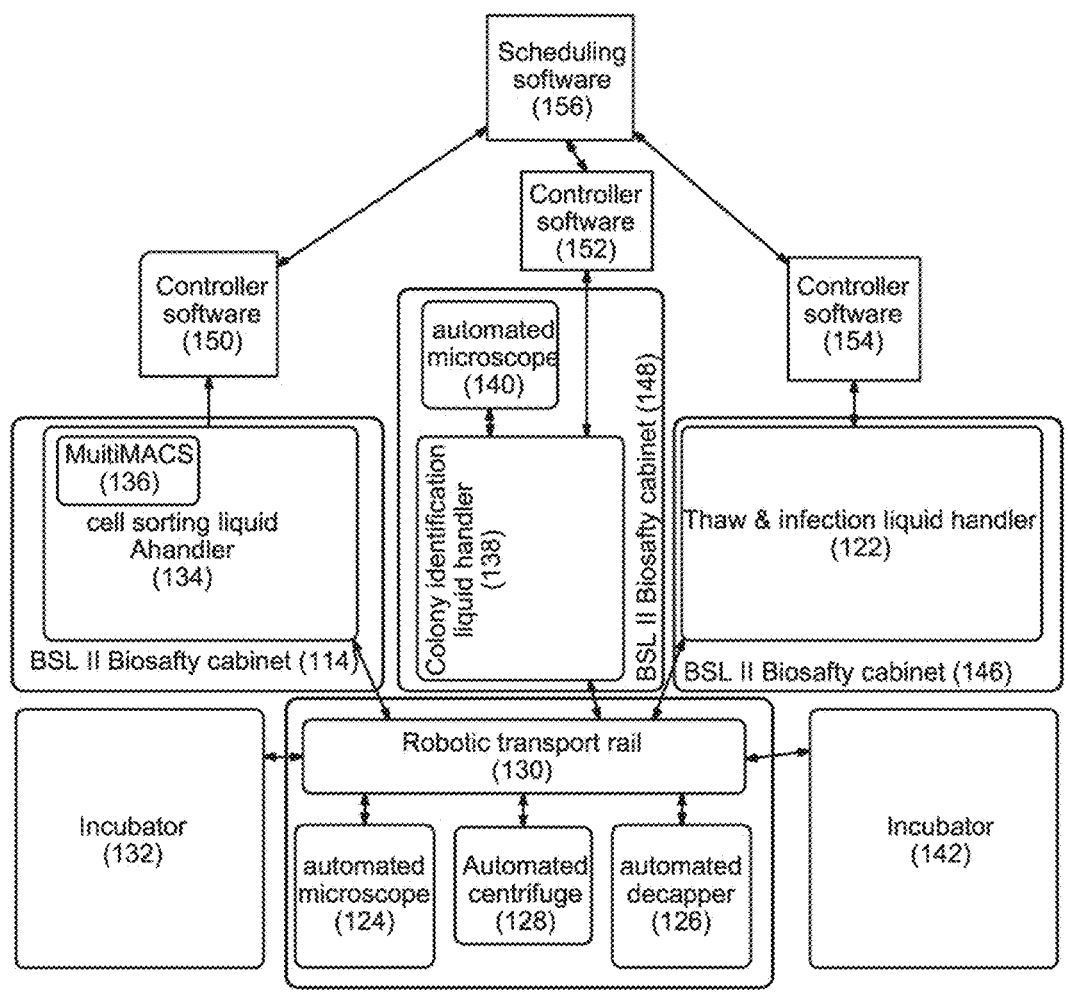
Figure 5C:
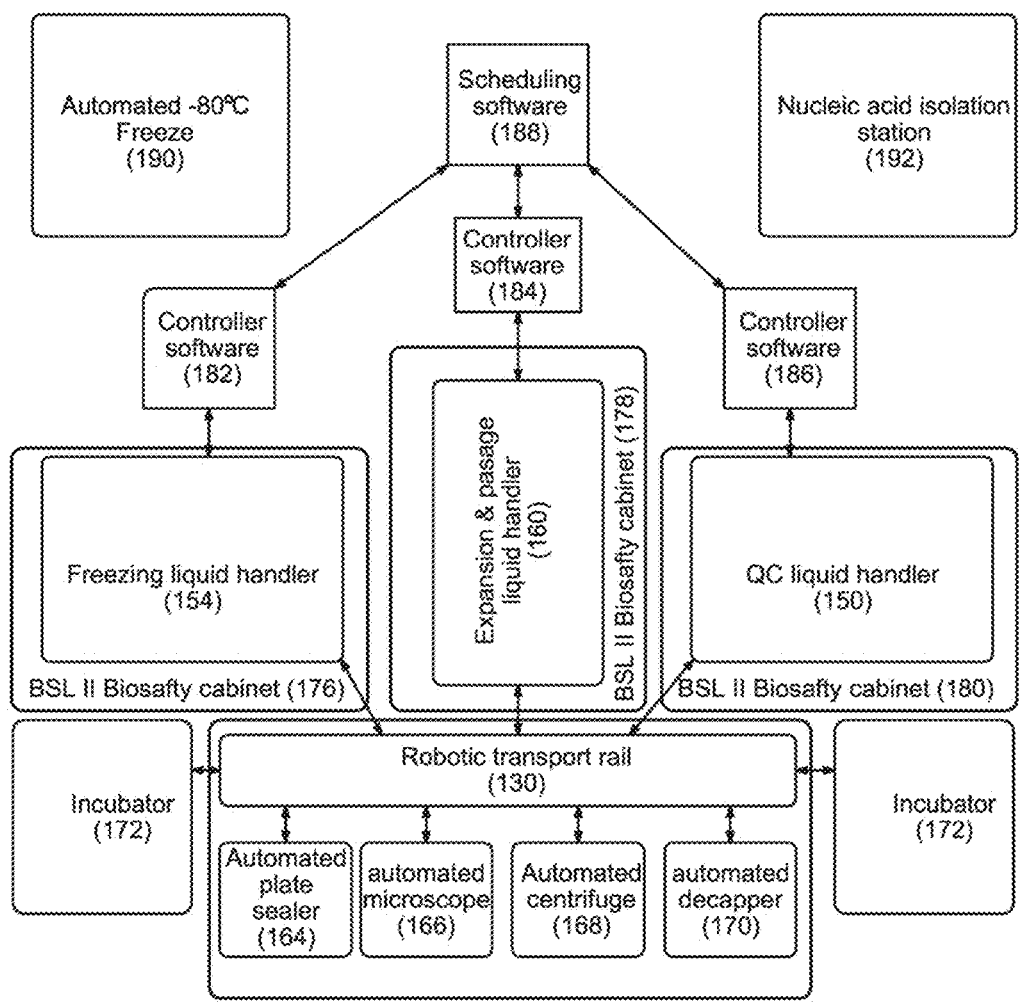
Figure 7A:
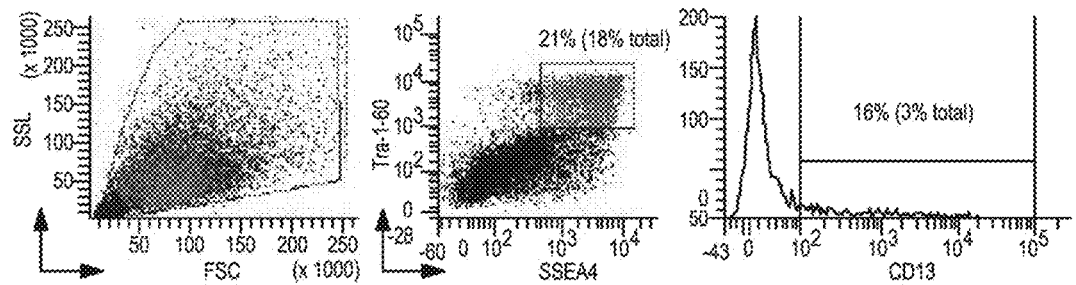
FIGS. 7A-7D. FACS analyses and graphs showing automated iPSC reprogramming. Expression levels of pluripotent surface markers on reprogrammed human fibroblasts were followed over a 3 week period to observe reprogramming kinetics and determine optimal time points at which to isolate defined cell populations.
Figure 7B:
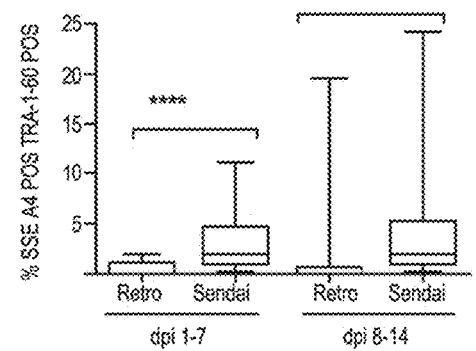
Figure 7C:
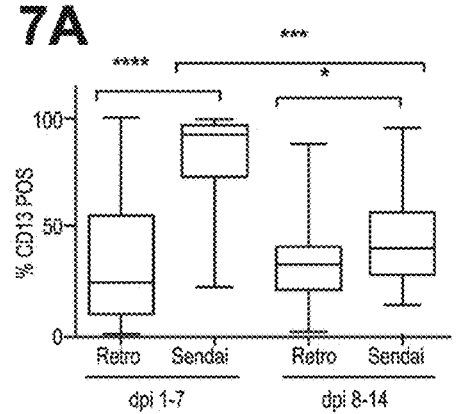
Figure 7D:
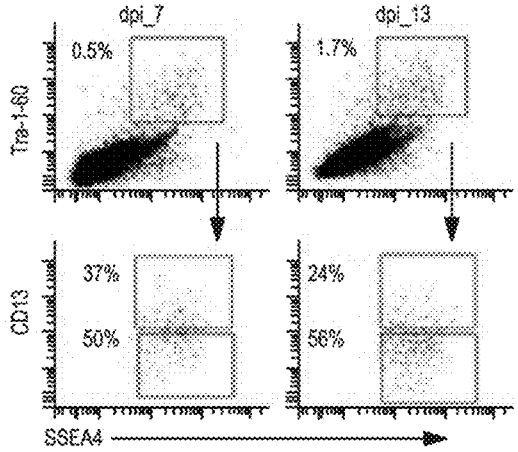

FIG. 5A, 5B, 5C illustrate an example of the equipment configuration needed to accomplish the workflow. FIG. 5A shows a system configuration for the automated expansion and quality control of a fibroblast bank. FIG. 5B shows a system configuration for the automated thawing of patient samples, such as fibroblasts, automated introduction of reprogramming factors with the patient samples, such as fibroblasts, automated cell sorting with MultiMACS, and automated colony identification and reformatting. FIG. 5C shows a system configuration for the automated expansion of iPS clones, automated Embryoid Body production, and automated freezing.

Automated Derivation of a Fibroblast Cell Bank

As an example, the hardware configuration used to accomplish the derivation of a fibroblast bank consists of a Hamilton STARlet liquid handling robot (100) connected to the following hardware components: a Cytomat 24C GLS automated incubator (108) that allows for the incubation of cell cultures, a Cyntellect Celigo cytometer (102) for automated image acquisition and analysis, an Agilent V-Spin automated centrifuge (106) for the centrifugation of cells in plates or tubes, and a Hamilton Capper DeCapper (104) for the automated capping and decapping of cryotubes. These components are further controlled by programmable software (118) on a PC that communicates with all instruments and controls the manipulation of cell culture-ware and cells among the hardware components. The controller software further communicates with scheduling software (120) to link System interactions. The Hamilton STARlet (100) is equipped with a Modular Arm for 4/8/12 channel pipetting, 8 pipetting channels, iSWAP plate handler, CO-RE Gripper for plate and lid handling, MultiFlex tilt Module for tilting plates during media exchanges, Hamilton Heated Shaker 2.0, as well as a Carrier Package for flexible layout of the liquid handling platform with plate and lid parks, pipette stackers, daughter plate stackers and troughs for holding media. The Cyntellect Celigo (102) is comprised of an imaging unit and programmable software on a PC for control of image acquisition and image analysis. The Celigo is preferred because it does not move the cell culture plates during imaging thereby reducing agitation of plated biopsies. The Hamilton Capper Decapper (104) and the Agilent V-Spin centrifuge (106) are contained with the Hamilton STARlet within a NuAire BSL II biosafety cabinet (110) to maintain a sterile operating environment during manipulation of cell culture plates.

To control plate handling on the automated system, MICROLAB STAR VENUS TWO Base Pack 4.3 software (118) with VENUS Dynamic Scheduler 5.1 (120) are used in conjunction with individual attached hardware component drivers for the centrifuge (106), Capper Decapper (104), Celigo (102), and Cytomat 24 (108) and Cytomat transfer station to integrate the operation of the system. The following methods programmed using the provided controller software (118) are needed for functionality of the system and can be combined in defined sequence to accomplish the derivation of fibroblast lines from patient skin biopsies:

1. Load 6-well biopsy plates (22, 24) onto the STARlet (100) and transfer to the Cytomat incubator (108).
2. Confluency check (26, 28) on Celigo (102) and a media exchange on the STARlet (100).
3. Confluency check (28) on Celigo (102).
4. Media change (30) on the STARlet (100) for full media exchange.
5. Assay plate preparation (34) on STARlet (100) and Agilent V-Spin centrifuge (106).
6. Passaging (44) on the STARlet (100).
7. Passage and cherry pick (42) on the STARlet (100).
8. Passage, harvest and freeze on the STARlet (100).
9. Retrieve plates (46, 40) onto the STARlet (100) from the Cytomat (108).

Automated Mycoplasma Testing on Quarantine Assay System

An independent hardware configuration is used to accomplish the mycoplasma testing of a fibroblast bank and consists of a Hamilton STARlet liquid handling robot (112) connected to a BioTek Synergy HT Reader (114). These components are further controlled by programmable software (116) on a PC that communicates with all instruments and controls the manipulation of cell culture-ware and cells between the hardware components. The Hamilton STARlet (112) is equipped with a Modular Arm for 4/8/12 channel pipetting, 8 pipetting channels, iSWAP plate handler, CO-RE Gripper for plate and lid handling, as well as a Carrier Package for flexible layout of the liquid handling platform with plate and lid parks, pipette stackers, daughter plate stackers and plate parks and troughs for holding reagents needed for the assay.

To control plate handling on the automated system, MICROLAB STAR VENUS TWO Base Pack 4.3 software (116) is used in conjunction with the attached hardware component drivers for the BioTek Synergy HT Reader (114) to integrate the operation of the system. A method is programmed using this software that allows execution of the MycoAlert Mycoplasma Detection assay (36) and data analysis to determine assay result (38).

Automated System for Thawing, Infection, and Identification of Reprogrammed Cells The hardware configuration needed to thaw fibroblasts, infect fibroblasts with reprogramming viruses, magnetic sort of reprogrammed cells, and identification of stem cell colonies is composed of three Hamilton STAR liquid handling units (122, 136, 138), two Cytomat 48C incubators (132), one Cytomat 2C 425 incubator (142), two Cyntellect Celigo cytometers (124, 140), Hamilton Capper DeCapper (126), Agilent V-Spin (128), Miltenyi MultiMACS magnetic separation device (136). The liquid handlers, a Celigo, the Hamilton Capper Decapper and Agilent V-Spin are all connected by a Hamilton Rack Runner robotic rail (130). Each Hamilton STAR is equipped with a Modular Arm for 4/8/12 channel pipetting, 8 pipetting channels, iSWAP plate handler, CO-RE Gripper for plate and lid handling, one or more MultiFlex tilt Module for tilting plates during media exchanges, one or more Hamilton Heated Shaker 2.0, as well as carrier packages for flexible layout of the liquid handling platform with plate and lid parks, pipette stackers, daughter plate stackers and troughs for holding media. One of the Hamilton STAR liquid handlers (122) is also equipped with a 96-well pipetting head. One Celigo (140) and the Cytomat 2C incubator (142) are connected directly to one of the Hamilton STARs (138) to facilitate automated cell sorting. The Hamilton STARs are contained within NuAire BSL II biosafety cabinets (144, 146,148) to maintain a sterile operating environment during manipulation of cell culture plates. The remaining components are enclosed in a Hepa filtered hood to maintain a sterile operating environment during transportation of cell culture plates among the devices. The Cytomat 48C incubator (132) is connected to the other components of the system by the Rack Runner transport rail (130).

To control plate handling on the automated system, MICROLAB STAR VENUS TWO Base Pack 4.3 software controllers (150, 152, 154) with VENUS Dynamic Scheduler 5.1 (156) are used in conjunction with individual attached hardware component drivers for all of the Hamilton STARs (122, 134, 138), the centrifuge (128), the Capper/ decapper (126), the two Celigos (140, 124), the Rack Runner (130), and Cytomat 24 (132), the Cytomat 2C (142), and associated Cytomat transfer stations to integrate the operation of the system. The following methods programmed using the provided controller software (150, 152, 154) are needed for functionality of the system and can be combined in a defined sequence to accomplish derivation of iPS colonies from fibroblasts:

1. Load mycoplasma free 6-well biopsy plates (48) onto the STAR (122) and transfer to the Cytomat incubator (132) under clean growth conditions (60).
2. Confluency check (50) on Celigo (124) and a media exchange on the STAR (122).
3. Passage, harvest (52) and freeze (54, 56) on the STAR (122).
4. A thawing method whereby cryotubes containing fibroblasts (61) are loaded and thawed on the STAR (122), followed by decapping of tubes (126) and washing of fibroblast, followed by resuspending cells in plating media and plating fibroblasts on 6 well plates (62) and transferring to Cytomat incubator (132).
5. Media change on the STARlet (122) for full media exchange.
6. Confluency check on Celigo (124).
7. Passaging and seeding of fibroblasts in 24-well plates (64) on the STARlet (122).
8. A method for infection of fibroblasts (64) on the STARlet (122).
9. A method to add a defined volume of media to wells on STAR (122, 138, 144).
10. A method for executing a half media exchange on STAR (122, 138, 144).
11. A method for magnetic sorting, dilution and plating (66) on the STAR (144) attached to the Miltenyi MultiMACS (136) and Celigo (124).
12. A method for a three quarter media exchange on the STAR (122, 138, 144).
13. A method for a executing an immunocytochemical stain on live colonies followed by automated imaging of the colonies (66) using a STAR (138) and Celigo (140).
14. A method for harvesting, cherry picking and replating colonies (68) from selected wells on a STAR (138).
15. Retrieve plates onto the STARlet (122, 138, 144) from the Cytomat (132).

Automated System for Expansion, Quality Control, and Freezing of Reprogrammed Cells The hardware configuration needed to expand reprogrammed Stem Cell Colonies, generate plates of colonies for quality control assays and generate plates and tubes for cryostorage is composed of three Hamilton STAR liquid handling units (150, 154, 160), Cytomat 24C incubator (172), one Cytomat 2C 425 incubator (174), one Cyntellect Celigo cytometer (166), Hamilton Capper DeCapper (170), Agilent V-Spin (168), and Agilent PlateLoc plate sealer (164). The liquid handlers, a Celigo, the Hamilton Capper Decapper, Agilent V-Spin, and Agilent PlateLoc plate sealer are all connected by a Hamilton Rack Runner robotic rail (162). The Hamilton STARs and STARlet are equipped with Modular Arms for 4/8/12 channel pipetting, 8 pipetting channels, iSWAP plate handlers, CO-RE Grippers for plate and lid handling, one or more MultiFlex tilt Modules for tilting plates during media exchanges, one or more Hamilton Heated Shaker 2.0s, as well as a carrier packages for flexible layout of the liquid handling platforms with plate and lid parks, pipette stackers, daughter plate stackers and troughs for holding media. One of the STARs (160) also has a 96 channel Multichannel pipetting head to facilitate media exchanges and passaging. The Cytomat 2C and Cytomat 24C incubators are connected to the Hamilton STARs by a Hamilton Rack Runner transport rail (162) to facilitate automated media exchanges. The Hamilton STARs are contained within a NuAire BSL II biosafety cabinet (176, 178, 180) to maintain a sterile operating environment during manipulation of cell culture plates. The remaining components are enclosed in a Hepa filtered hood to maintain a sterile operating environment during transportation of cell culture plates among the devices.

To control plate handling on the automated system, MICROLAB STAR VENUS TWO Base Pack 4.3 software controllers (182, 184, 186) with VENUS Dynamic Scheduler 5.1 (188) are used in conjunction with individual attached hardware component drivers for the centrifuge, decapper, plate sealer, Celigo, and Cytomat incubators and Cytomat transfer station to integrate the operation of the system. The following methods are needed for functionality of the system and can be combined in a defined sequence to expand cell cultures in plates for quality control assays and freezing in plates or cryovials:

1. A loading method on the STAR (160) to receive plates (68) from the previous stage into the Cytomat incubator (172).
2. Media change on the STAR (150, 154, 160) for full media exchanges using tilt modules and 8-channel pipetting arms.
3. Confluency check on Celigo (166) with associated methods to transport plates to and from the STARs (150, 154, 160) and Cytomat incubator (172).
4. A method for passaging and seeding of iPSCs in 96-well plates (68-90) on the STARs (150, 154, 160).
5. A method for executing a partial media exchanges on the STARs (150, 154, 160).
6. A method for harvesting, cherry picking and replating colonies from selected 96-well wells to new 96-well plates (80, 82, 86, 88) on a STAR (150, 154, 160).
7. A method for harvesting, cherry picking and replating colonies from selected 96-well wells to new 24-well plates (90, 92) on a STAR (154).
8. A method for harvesting and cherry picking and replating colonies from selected 24-well wells to new 6-well plates (92, 94) on a STAR (154).
9. Passage, harvest and distribute cells in freezing plates (88) on the STAR (154).
10. Passage, harvest and distribute cells in cryotubes (96) on the STAR (154).
11. Retrieve plates onto the STARs (150, 154, 160) from the Cytomat 24C (172) or Cytomat 2C (174).

Example 2

Production of a Fibroblast Bank for Reprogramming

The first step in the workflow to derive iPSCs from patient samples is to obtain and expand adult cells. This is accomplished, for example, by obtaining a skin punch biopsy or discarded dermal tissue, then isolating and expanding cultures of fibroblasts from the tissue. In the workflow described in the present Example, this is accomplished by the automated system comprised of Systems 1 and 2. The automated components of System 1 and 2 (100-120) and System 3 (122-132, 154, 190) perform the steps needed to derive a fibroblast bank stored in cryotubes (61) from patient samples, including plating of a patient biopsy (2, 22-24), outgrowth and passaging (4, 26-32) (rolling production on liquid handling robot), QC (6, 34-46) (automated testing for mycoplasma), and automated freezing on the liquid handling robot (8, 48-56). For example, the workflow and decision tree for production of fibroblasts from biopsies is divided into Quarantine (58) and Clean phases (60). As biopsies enter the facility, a technician plates biopsies in 6-well plates (22) and logs the plates into the automated incubator (24) to begin the quarantine workflow. After biopsies are given time to attach to the plate, the liquid handling robot retrieves the plates from the automated incubator to feed and check confluency of the outgrowth of adult fibroblasts from the plated tissue on an automated microscope (26). The plates are returned to the incubator and allowed to continue to outgrow (28). The liquid handler removes the plate from the incubator and exchanges the media for antibiotic and antimycotic free media (30) to prepare for mycoplasma testing. The robot moves the plate to the incubator for another five days (32). The robot then removes the plate and retrieves media to daughter plates for mycoplasma test (34). The daughter plates are moved to the Quarantine Assay system for mycoplasma testing (36). A choice is then made based on a positive signal from the assay (38). If all wells of a 6-well plate fail with a positive assay result (40) they are discarded. If all wells of a 6-well plate are negative and free of mycoplasma, they are transferred out of quarantine into the clean growth environment provided by Systems 3, 4, 5 (46). If some wells are positive and some wells are negative, the negative wells are maintained in quarantine (42). The negative wells are passaged (44) to new plates, transferred to the incubator, and the source plates containing positive wells are discarded. These cultures proceed through steps to retest for mycoplasma (24-38). Clean cultures are monitored for growth (50), passaged (52) and frozen in cryovials (54, 56, 61).

Production of Stem Cell Arrays

To produce iPSCs, Fibroblasts in cryotubes (61) are plated by the automated system (10), reprogramming factors are introduced by the automated system (12), iPSCs are isolated by automated sorting and isolation in System (14), desired clones are selected by the automated system (16), and expanded by the automated system (16), automated quality checks by the automated system (QC) for pluripotent status by marker assays and embryoid body assays (18), followed by automated freezing and storage of desired cells by the automated system (20). These steps are accomplished on the automated systems 3, 4, 5, 6, 7, and 8 (122-192).

For example, the automated iPS derivation process begins when 96 patient and control fibroblast samples in cryotubes (61) are plated in individual wells of a 6-well plate (62). These are passaged at defined cell number into individual wells of a 24-well plate for infection using viruses encoding reprogramming factors (64). In the next step, reprogrammed samples are depleted of non-reprogrammed cells by cell sorting or magnetic bead-based enrichment and plated at clonal density in multiple wells in 96-well plates (66). In this example, 6 wells (66) are identified containing a single clone positive for a pluripotency surface marker. These clones are cherry picked and consolidated into a minimum number of 96-well plates (68). These clones are serially passaged until confluence within a well is achieved for each starting sample (72). Each plates' samples are then replicated onto duplicate plates (74, 76), one plate for a Pluripotency quality control assay needed to determine pluripotent status of the individual clones (74) and one plate for carrying forward in subsequent passages (76). The plate that is carried forward is passaged again into three plates (78, 80, 82). One plate is harvested for QC assay that assesses Karyotype and genetic diversity (78), one plate (82) is passaged onto v-bottom plates to form embryoid bodies (84) for a QC assay that assesses differentiation capability of the iPS clones, and the final plate (80) is carried forward for further expansion. Individual clones that do not pass quality control from previous pluripotency QC assays are not carried forward as indicated by "X" in the wells in FIGS. 4B2 and 4C (80, 82, 90). Remaining clones are consolidated onto as few plates as possible until one to three clones remain (86). These clones are expanded for cryopreservation while attached to the plate (88) or further expanded (92, 94) and cryopreserved in cryovials (96).

Embryonic stem cells (ES) are also contemplated to be used with the automated system of the invention to generate differentiated adult cells. ES cells are derived from the blastocyst of an early stage embryo and have the potential to develop into endoderm, ectoderm, and mesoderm (the three germ layers) (i.e., they are "pluripotent"). In vitro, ES cells tend to spontaneously differentiate into various types of tissues, and the control of their direction of differentiation can be challenging. However, some progress has been achieved in the directed differentiation of ES cells to particular types of differentiated daughter cells. For example, it is now possible to direct the differentiation of human ES cells to functional midbrain dopaminergic neurons using defined factors added to the cell cultures at defined stages of their stepwise differentiation (see, e.g., Kriks et al., 2011 Nature, November 6. doi: 10.1038/nature10648 (Epub)). As differentiation is not homogenous, it remains necessary to isolate populations of interest for further study or manipulation. The process and instrumentation described here could be used to first derive and expand pluripotent embryonic stem cells and also isolate subpopulations of their differentiated derivatives by automated methods including automated magnetic cell isolation.

For example, whole human blastocysts can be plated on matrices in multi-well plates amenable to the automated process. Outgrowths from these plated blastocysts could be isolated using the same automated magnetic isolation procedures performed by the robotic instrumentation and methods described for the isolation of induced pluripotent stem cells. The resulting human embryonic stem cell lines could be expanded, selected by quality control assays and frozen using the same automated procedures described herein.

Further, using pluripotent stem cells, either blastocyst derived or induced by defined factors or by somatic cell nuclear transfer, differentiated derivatives can be isolated using the described workflow and instrumentation. The differentiated derivatives can be obtained by directed application of defined factors required to induce a cell fate change or after spontaneous differentiation. For example, inhibitors of the TGF beta pathway can be used to induce neural cell fates from pluripotent stem cells. Neural cells can be subsequently isolated from non-neural by magnetic bead immunolabeling of surface antigens, such as NCAM. The described workflow and instrumentation can be used to magnetically isolate, select, culture and expand differentiated cells like neurons. This process is also applicable to other differentiated cell types, like cardiac cells, for which there exist antibodies that recognize cell surface antigens specific to the cell type of interest.

Multipotent stems cells are also contemplated to be used with the automated systems of the invention to generate differentiated adult cells. In particular, mesenchymal stem (MS) cells can be employed to generate differentiated adult cells using the automated systems of the invention. MS cells are the formative pluripotent blast or embryonic-like cells found in bone marrow, blood, dermis, and periosteum and placenta that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues. Examples include differentiation of MS cells into differentiated cells with the properties of chondrocytes for cartilage repair, e.g., see U.S. Pat. No. 8,048,673.

Chromosomal Testing

In some aspects, the Nanostring nCounter Plex2 Assay Kit is used to target the 400 genomic loci, often known to be invariant among the population, allows for integrated molecular karyotype analysis coupled with "fingerprint" tracking of cell line identity. The molecular karyotype analysis utilizes an average of 8 probes per chromosome arm to verify genomic stability during the course of cell culture derivation and expansion of iPSC lines. Identity analysis will also be performed on all lines based on 30 common copy number variations (CNVs) of polymorphic loci, which allows for unambiguous identification of individual genomes.

Pluripotency Analysis

In one aspect, surface marker staining is performed to show that cells are positive for Tra-1-60 surface marker, which is monitored e.g., with the Celigo automated imager. PSC lines must show a significant level of the pluripotency genes. In one example, a probe set of 100 gene makers (described below) was utilized that includes the six markers for pluripotency (Oct4, Klf4, cMyc, Nanog, Lin28, ZFP42, and Sox2). To perform this analysis a sample of cells was lysed and RNA was harvested. The nCounter Plex2 Assay Kit was used to analyze expression levels in multiple samples and hundreds of gene targets simultaneously enabling the high-throughput approach to PSC characterization. As the nCounter gene expression assays are quantitative, selection criteria is based on expression levels falling within a range relative to a control panel of established hESC lines analyzed grown under identical conditions. Lines that pass pluripotency gene expression criteria will be further expanded and differentiated in vitro in embryoid body (EB) assays.

EB Formation Gene Expression Assay

It has been shown that epigenetic and transcriptional variation is common among human pluripotent cell lines and that this variation can have significant impact on a cell line's utility. In an illustrative example, the panels of gene markers includes: 83 different gene markers selected from each of the 3 germ layers (83), 5 retrovirus transgene (4 factors with single detection probe, 1 probe), 5 sendai transgenes (4 factors+vector only, 5), Oct4, Klf4, cMyc, Nanog, Lin28, ZFP42 (pluripotency, Sox2 is in germlayer group, 6 probes), sex markers (SRY, XIST (2)—donor sex must match or lines will be rejected), and housekeeping genes, ACTB, POLR2A, ALAS1 (3 probes).

hPSC Line Expansion and Storage

Automated Expansion:

Cell lines are expanded through plating of the initial cells into 2 separate wells of a 6-well plates then placing them within a CO2 incubator and allowing them to grow up to a maximum of 95% confluence.

Storage

The vials are first placed within the SAM −80 freezer to perform the initial slow cool. This system has automated monitoring of temperature and logs of time the system is accessed.

Next, the vials are placed in LN2 for long-term storage. Quality control for monitoring is detailed later in this proposal. Each vial is individually marked with a unique 2D barcode and inventory is tracked within the LIMS.

hPSC Line Characterization iPSC and EB gene expression analysis-Set of probes covering lineage differentiation assay scorecard (100 genes) to monitor germ layer differentiation in EB assays, pluripotency markers, sex markers and transgene expression Freeze-Thaw Analysis Cells are counted following recovery and plated in one well of a 6-well plate. Colonies are photographed on the first day of appearance and then 5 days later, colonies must display a doubling time no larger than 36 hours.

Surface Marker Analysis

Perform surface marker analysis using automated system using high content imaging of Tra-1-60 staining using the Celigo automated imager.

iPSC and EB Gene Expression Analysis

Pluripotency gene expression—iPSC clones must show a significant level of the pluripotency genes. A probe set of 100 gene makers (described below) was used that includes the six markers for pluripotency (Oct4, Klf4, cMyc, Nanog, Lin28, ZFP42, and Sox2). To perform this analysis a sample of cells is lysed for each of the selected clones and RNA is harvested. The nCounter Plex2 Assay Kit was used to analyze expression levels in multiple samples and hundreds of gene targets simultaneously enabling the high-throughput approach to iPSC characterization. As the nCounter gene expression assays are quantitative, selection criteria is based on expression levels falling within a range relative to a control panel of established hESC lines analyzed grown under identical conditions. Selected clones that pass pluripotency gene expression criteria will be further expanded and differentiated in vitro in embryoid body assays.

EB formation gene expression assay—In order to firmly establish the nature and magnitude of epigenetic variation that exists among human pluripotent stem cell lines, three genomic assays were applied to 20 established embryonic stem cell (ESC) lines and 12 iPSC lines that were recently derived and functionally characterized. As a step toward lowering the experimental burden of comprehensive cell line characterization, and to improve the accuracy over standard existing assays, all of the data from these studies are combined using the three genomic assays into a bioinformatics scorecard, which enables high-throughput prediction of the quality and utility of any pluripotent cell line. This scorecard was used to analyze gene expression data from the EBs formed from each clone of the iPSC lines. To test differentiation potential, the automated system was used to generate EBs in 96-well v-bottom plates and ends in RNA harvest for Nanostring nCounter Plex2 Assay Kit. The score card comprised 83 different gene markers selected from each of the 3 germ layers (83), 5 retrovirus transgenes (4 factors with single detection probe, 1 probe), 5 sendai transgenes (4 factors+vector only, 5), Oct4, Klf4, cMyc, Nanog, Lin28, ZFP42 (pluripotency, Sox2 is in germlayer group, 6 probes), sex markers (SRY, XIST (2)), and housekeeping genes (ACTB, POLR2A, ALAS1 (3 probes).

Karyotype and Identity Analysis

Prior to accepting a line and at the end of each expansion, the Nanostring nCounter Plex2 Assay Kit was used to target the 400 genomic loci allowed for integrated molecular karyotype analysis coupled with "fingerprint" tracking of cell line identity. The molecular karyotype analysis utilizes an average of 8 probes per chromosome arm to verify genomic stability during the course of cell culture derivation and expansion of iPSC lines. The "fingerprint" identity tracking analysis will rely on a combinatorial signature based on 30 common copy number variations (CNVs) of polymorphic loci, which allows for unambiguous identification of individual genomes. Additionally to avoid misidentification, tissue donors known to be relatives will not be processed in the same batch, as it is theoretically possible they will have similar CNVs. The data from the identity analysis will be cross-referenced with the initial CNV data to ensure that the LIMS system properly tracked all cell lines.

Freeze-Thaw Analysis

Freeze-Thaw Analysis: one vial is thawed after cryopreservation. Cells are counted following recovery and plated in one well of a 6-well plate. Cultures are observed daily. Colonies are photographed on the first day of appearance and then 5 days later. Colonies must at least double in diameter within 5 days after first observation.

Automated Biopsy Outgrowth Tracking

Using the invention system, one can track the outgrowth of biopsies as well as other tissue sources by automated and traceable image analysis. As shown in FIGS. 6A-6D, images and growth rates are tracked during the production process. In FIG. 6A, biopsies or discarded tissue are plated in multiple wells of a 6-well dish and maintained by an automated system that feeds, images, passages, and freezes fibroblast outgrowths. Examples of the image analysis interface is shown for a typical sample. A single plate is used per donated sample to minimize cross contamination. (FIG. 6B) Cell numbers are extrapolated from confluence measurements based on linear regression from a standard curve generated independently. (FIG. 6C and FIG. 6D) An example of cell counts for a typical biopsy outgrowth maintained on the automated system. Extrapolated cell numbers per patient sample are plotted for each well independently (FIG. 6C) allowing calculation of total output from the sample (FIG. 6D).

FIGS. 7A-7D show FACS analyses and graphs showing automated iPSC reprogramming. Expression levels of pluripotent surface markers on reprogrammed human fibroblasts were followed over a 3 week period to observe reprogramming kinetics and determine optimal time points at which to isolate defined cell populations. (FIG. 7A) FACS gating scheme used for analysis. (FIG. 7B) A substantial proportion of cells co-expressing traditional pluripotency surface markers SSEA4 & TRA-1-60 retain the fibroblast marker CD13 at all timepoints during reprogramming using either retroviral or Sendai vectors to introduce reprogramming factors Oct4, Sox2, Klf4 and c-Myc. Box plots indicating aggregated data from 131 experiments (Retrovirus, n=66, Sendai virus, n=65) are shown. While Sendai mediated reprogramming produces more SSEA4/TRA-1-60 double positive cells, (FIG. 7C) there is a delay in elimination of CD13 from the surface. (FIG. 7D) Example staining pattern of a patient cell line reprogrammed using Sendai/Cytotune system on the automated system. At both 7 and 13 dpi, more than half of SSEA4/TRA-1-60 double positive cells have lost CD13. Additionally, at both timepoints assayed, CD13 negative/Nanog positive cells are present in this fraction, suggesting these can be isolated by negative selection against CD13.

FIGS. 8A-8C shows FACs pre-sort analyses and a part of the automated system to demonstrate enrichment and clone selection of iPSCs. (FIG. 8A) Non-reprogrammed cell populations can be depleted from cultures of iPSCs by negative selection by a fibroblast marker. This strategy leaves iPSCs untouched. In the example, fibroblasts are efficiently removed from the culture containing 2% established iPSCs leaving TRA-1-60 positive iPSCs untouched. (FIG. 8B) A Miltenyi MultiMACS system integrated into Hamilton liquid handler can sort 24 samples in parallel. (FIG. 8C) An example colony of newly derived iPSCs derived by negative selection using anti-fibroblast antibody conjugated magnetic beads on the MultiMACS system. Phase contrast, nuclear stain by Sytox, surface marker stain by TRA-1-60 and nuclear Nanog staining. The iPS enriched fraction from the anti-fibroblast magnetic negative selection step is plated on 96-well imaging plates at limiting dilution. These plates are screened using live-cell staining for the pluripotency surface marker TRA-1-60 or TRA-1-81. Wells with TRA-1-60 positive iPSCs are identified by automated image analysis using the Celigo software capable of single colony confirmation. Wells that meet both criteria of containing a single colony that is positive for the surface marker are selecting for passaging and expansion and QC. Colonies produced by automated Sendai infection of adult fibroblasts.

iPSC induction has also been demonstrated by automated transfection of modified mRNA. iPSC colonies from BJ fibroblasts were efficiently recovered after 10 days of automated delivery of a transfection mix containing modified mRNA. After an additional two days culture, the same well was stained with TRA-1-60 to identify undifferentiated cells. iPSCs in the well demonstrate that these are undifferentiated iPSCs. iPSC colonies isolated by purification away from non-reprogrammed cells using magnetic bead depletion on the automated system were efficiently recovered.

Figures 9A, 9B:
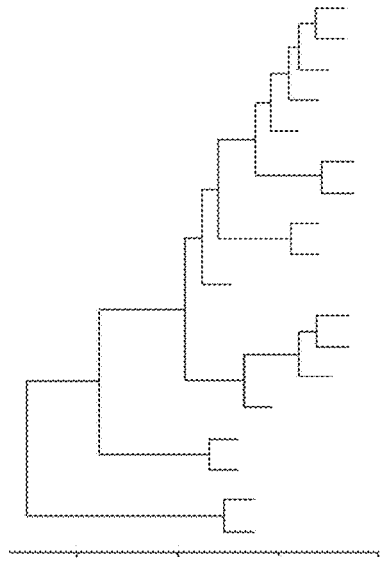
FIGS. 9A-9B. Illustration for the scorecard assays described herein. The first stage of the quality control screen uses a panel of pluripotency differentiation and transgene markers to choose an initial set of three clones.

High throughput scorecard assays for gene expression have been generated. The first stage of a quality control screen uses a panel of pluripotency differentiation and transgene markers to choose an initial set of three clones. FIG. 9A shows transcript counts after normalization to HK gene expression for two HESC lines, Sendai positive control, fibroblast negative control, and iPS lines derived by FACS sorting assayed at passage 5 and 10. All assays are run relative to a panel of normal HESC and iPS lines maintained under similar conditions. Not shown was an example image of an Embryoid body generated on the system in 96-well V-bottom plates. The arrow points to the EB. FIG. 9B illustrates the second stage of a quality control screen uses an additional 83 germ layer/lineage markers to monitor differentiation capability in embryoid body assays. Single EBs are generated and pooled to generate RNA for expression analysis of germ layer markers in the embryoid body scorecard assay. Shown is a cluster dendrogram analysis of gene expression in EBs collected from nine different embryonic stem cells lines. After normalization, data generated from direct lysis of six EBs compares favorably to data generated from total RNA extracted and purified from EBs prepared from bulk culture.

Figure 10A:
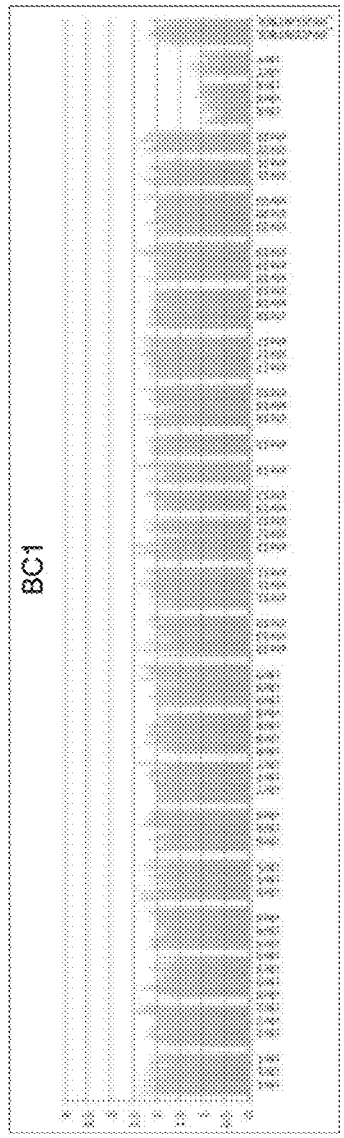
FIGS. 10A-10B. High throughput karyotyping of iPSCs based on Nanostring nCounter assays for CNVs.
Figure 10B:
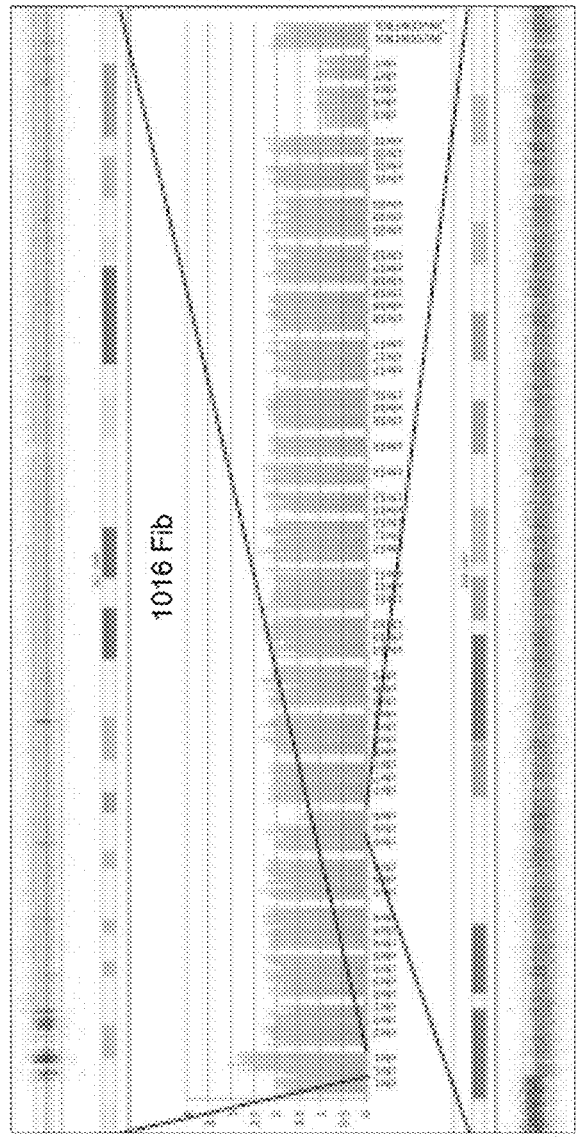

FIGS. 10A-10B demonstrate high throughput karyotyping of iPSCs based on Nanostring nCounter assays for CNVs. FIG. 10A is an example of the nCounter Karyotype assay on BC1 iPSCs; FIG. 10B is an example of the nCounter Karyotype assay on 1016 fibroblasts with partial gain and loss of chromosome arms. Comparison to Affymetrix SNP 6.0 chip data demonstrating copy number gains on a portion of the q arm of Chr1 (top track, 1q21.2-1q43) and loss of part of the long arm of Chr6 (bottom track, 6q16.3-6q26).

Example 3

Improved Methods for Reprogramming Human Dermal Fibroblasts

The work described in the present Example, including the associated figures, tables and drawings, was published by one or more of the inventors of the present application and others. The citation for the publication is Kahler et al. (2013) "Improved Methods for Reprogramming Human Dermal Fibroblasts Using Fluorescence Activated Cell Sorting," PLoS ONE 8(3): e59867, published Mar. 29, 2013, and the entire contents of Kahler et al. 2013, including its figures, supplemental figures, and supplemental tables, are incorporated herein by reference in their entirety.

Current methods to derive induced pluripotent stem cell (iPSC) lines from human dermal fibroblasts by viral infection rely on expensive and lengthy protocols. One major factor contributing to the time required to derive lines is the ability of researchers to identify fully reprogrammed unique candidate clones from a mixed cell population containing transformed or partially reprogrammed cells and fibroblasts at an early time point post infection. Failure to select high quality colonies early in the derivation process results in cell lines that require increased maintenance and unreliable experimental outcomes. Here, an improved method is described for the derivation of iPSC lines using fluorescence activated cell sorting (FACS) to isolate single cells expressing the cell surface marker signature CD13NEGSSEA4POSTra-1-60POS on day 7-10 after infection. This technique prospectively isolates fully reprogrammed iPSCs, and depletes both parental and "contaminating" partially reprogrammed fibroblasts, thereby substantially reducing the time and reagents required to generate iPSC lines without the use of defined small molecule cocktails. FACS derived iPSC lines express common markers of pluripotency, and possess spontaneous differentiation potential in vitro and in vivo. To demonstrate the suitability of FACS for high-throughput iPSC generation, 228 individual iPSC lines were derived using either integrating (retroviral) or non-integrating (Sendai virus) reprogramming vectors and performed extensive characterization on a subset of those lines. The iPSC lines used in this study were derived from 76 unique samples from a variety of tissue sources, including fresh or frozen fibroblasts generated from biopsies harvested from healthy or disease patients.

Introduction

The discovery that differentiated somatic cells could be reprogrammed to an embryonic stem cell-like state by forced expression of four transcription factors (Oct4, Klf4, Sox2, cMyc) has revolutionized the stem cell field [1]. Reprogrammed, or induced pluripotent stem cells (iPSCs), show remarkable similarities to embryonic stem cells (ESCs) and hold great promise for in vitro disease modeling, drug discovery, and therapeutic interventions because they provide a potentially unlimited source of differentiated cells from individuals with specific diseases [2], [3], [4], [5], [6].

However, initial derivation of stable iPSC clones by viral transduction of dermal fibroblasts is a slow (4-6 weeks) and inefficient (≤0.01% of total fibroblasts) process. Current methods of identifying colonies of bona fide iPSCs early in the reprogramming process (2-3 weeks post-infection) utilize light microscopy and manual isolation of candidate colonies, which requires training and expertise in advanced cell culture techniques. To enable future clinical applications requiring de novo iPSC derivation, there remains a need for standardized and validated methods for identifying, isolating and purifying reprogrammed cells.

Previous imaging studies based on tracking of cell-of-origin suggest that early events occur during defined factor reprogramming, including a change in cell proliferation rates and morphology [7], downregulation of CD13, a marker of mesenchymal cells including fibroblasts [8], as well as upregulation of the cell surface markers of pluripotency SSEA4 and TRA-1-60 [9]. These studies demonstrate that both partially and fully reprogrammed iPSCs can be identified by combined use of surface expression of multiple markers. Recently, a method of enriching reprogrammed fibroblasts by fluorescence activated cell sorting (FACS) for cells with dual expression of the pluripotency surface markers SSEA4 and TRA-1-81 arising late during reprogramming was described [10]. While a step forward, this method relies heavily on the use of a defined small molecule cocktail, and multiple rounds of sorting and extensive screening to identify fully reprogrammed clones. This suggests that pluripotency markers alone are not sufficient to purify fully reprogrammed iPSCs. Additionally, it is likely that the high variability among clones seen within this population is compounded by the use of integrating vectors to deliver the reprogramming factors. Here, results confirm that throughout the reprogramming process a significant proportion of SSEA4POSTra-1-60POS cells retain the fibroblast surface marker, CD13. Through the use of negative selection against CD13, fully reprogrammed iPSCs were purified from partially reprogrammed cells and parental fibroblasts by FACS. This method removes contaminating cells at an early stage and can be used with a variety of cell populations including: cells reprogrammed with DNA-integrating or non-integrating viruses; fibroblasts harvested from healthy or specific disease patients. Using this method, 228 iPSC lines have been generated and characterized from 76 fibroblast lines obtained from multiple sources including fresh biopsies, frozen stocks, and cell line repositories.

Materials and Methods

Fibroblast Cell Culture

Explants of 3-mm dermal biopsies were minced and placed in a 60-mm tissue culture dish under a sterile coverslip held down by sterilized silicon grease. Fibroblast medium [Dulbecco's modified Eagle's medium (DMEM), supplemented with 10% fetal bovine serum, Glutamax™, and penicillin/streptomycin (Invitrogen, Carlsbad, Calif.)] was added, and dishes incubated at 37° C. in a humidified 5% $CO_2$ atmosphere with media exchange every 5 days. Fibroblast outgrowths were harvested by trypsinization, expanded in a T25 flask in fibroblast medium, and allowed to reach ~90% confluence prior to freezing or splitting for reprogramming as described below. For reprogramming, fibroblasts were used within the first three passages from biopsy or within one passage after a thawing. All parent fibroblast and reprogrammed lines were subjected to cytogenetic analysis (Cell Line Genetics) and for DNA fingerprinting by short tandem repeat (STR) analysis.

Fibroblast Reprogramming

Fibroblasts were reprogrammed using high titer stocks of vesicular stomatitis virus G (VSVG)-coated retroviruses containing Oct4, Sox2, cMyc, and Klf4 (Harvard Gene Therapy Initiative at Harvard Medical School) as previously described [12], or the non-integrating CytoTune™—Sendai viral vector kit (Life Technologies, A13780). Fibroblasts reprogrammed with retroviruses were infected at 1×10$^4$ cells/well in 1 ml of human ESC medium (HUESM) [Knockout™ DMEM supplemented with 20% Knockout™ serum replacement (Invitrogen), 10 ng/ml bFGF (Invitrogen), nonessential amino acids (Invitrogen), (β-mercaptoethanol (Invitrogen), L-glutamine, and penicillin/streptomycin (Invitrogen)]. The medium was exchanged on day 2 to HUESM containing ALK5 inhibitor SB431542 (2 µM; Stemgent), MEK inhibitor PD0325901 (0.5 µM; Stemgent), and ROCK inhibitor [13] Thiazovivin (0.5 µM; Stemgent)] and changed daily thereafter. For Sendai virus mediated reprogramming, 5×105 fibroblasts were infected in fibroblast medium at a multiplicity of infection of 3 (MOI3) for two days with daily (HUESM) media exchanges. At day 7-10 days post-infection by retro or Sendai viral protocols, cells were subjected to FACS analysis or passaged onto feeder cells by enzymatic dissociation using Dispase (GIBCO) and/or Accutase (Sigma-Aldrich) then passaged onto γ-irradiated murine embryonic fibroblasts (MEFs; Globalstem) or Matrigel™ (BD Biosciences) coated plates in HUESM at 2×103 cells/cm2.

Fluorescent Activated Cell Sorting of Reprogrammed Fibroblasts

Cells enzymatically harvested as described above were filtered through a 35 µm cell strainer (BD biosciences) to obtain a single cell suspension prior to resuspension in 100 µl of a sterile iPSC staining buffer [DPBS containing 0.5% bovine serum albumin fraction V (BSA; Invitrogen), 100 U/ml penicillin/streptomycin (Invitrogen), 2 mM EDTA (Invitrogen), and 20 mM glucose (Sigma)]. A cocktail of fluorescence-conjugated antibodies [1 µl each anti-CD13 (555394) anti-SSEA4 (560219) and anti-Tra-1-60 (560173), obtained from BD, CA] was added to the cells and incubated at room temperature (RT) for 15 minutes shielded from light. Stained cells were washed once with iPSC staining buffer and sorted immediately on a 5 laser BD Biosciences ARIA-IIu™ SOU Cell Sorter using "gentle FACS" sorting conditions based on the work of Pruszak et al. (100 µm ceramic nozzle, 20 psi) [14]. Some experiments included antibodies against SSEA3 (BD, 560237), or CD326 (BD, 347200) in the cocktail to confirm the pluripotent status of the reprogrammed cells. Target cell populations were sorted directly onto MEF layers (ARIA plate holder at 37° C.) at between 2×103 and 5×104 cells/well in a 6-well plate containing HUESM plus 20 µM Y-27632 (ROCK inhibitor; Calbiochem). Two days after sorting, the ROCK inhibitor was removed from the medium and replaced with SB431542 (2 µM), PD0325901 (0.5 µM), and Thiazovivin (0.5 µM) [13] with daily media exchange. Several individual colonies were picked 7-10 days after sorting and expanded for characterization.

Quantitative RT-PCR

Total RNA was isolated from duplicate or triplicate cell samples using the RNeasy kit (QIAGEN, 74136). cDNA synthesis was performed on 1 µg RNA with SuperScript™ III First-Strand system (Invitrogen 18080-051) and oligo (dT) primers. The cDNA was diluted to a final volume of 200 µl and 1 µl was added to 500 nM of the forward and reverse primers in a final volume of 10 µl per PCR reaction. Quantitative real-time PCR was performed using the GoTaq® SYBR Green Master kit (Promega, A6001) and Mx3000p QPCR system (Stratagene). Primer sequences are provided in Table 3, below.

TABLE 3

Quantitative real-time PCR Primers (S1)

| GENE | FORWARD PRIMER 5'-3' | REVERSE PRIMER 5'-3' |
| --- | --- | --- |
| Oct 4 (endogenous) | CCCCAGGGCCCCATT TTGGTACC (SEQ ID NO: 1) | GGCACAAACTCCAGG TTTTC (SEQ ID NO: 2) |
| Sox2 (endogenous) | ACACTGCCCCTCTCA CACAT (SEQ ID NO: 3) | GGGTTTTCTCCATGC TGTTTCT (SEQ ID NO: 4) |
| Klf4 (endogenous) | ACCCACACAGGTGAG AAACCTT (SEQ ID NO: 5) | GTTGGGAACTTGACC ATGATTG (SEQ ID NO: 6) |
| C-Myc (endogenous) | AGCAGAGGAGCAAAA GCTCATT (SEQ ID NO: 7) | CCAAAGTCCAATTTG AGGCAGT (SEQ ID NO: 8) |
| Oct4 (transgene) | CCCCAGGGCCCCATT TTGGTACC (SEQ ID NO: 9) | AACCTACAGGTGGGG TCTTTCA (SEQ ID NO: 10) |
| Sox2 (transgene) | ACACTGCCCCTCTCA CACAT (SEQ ID NO: 11) | AACCTACAGGTGGGG TCTTTCA (SEQ ID NO: 12) |
| Klf4 (transgene) | GACCACCTCGCCTTA CACAT (SEQ ID NO: 13) | AACCTACAGGTGGGG TCTTTCA (SEQ ID NO: 14) |
| C-Myc (transgene) | AGCAGAGGAGCAAAA GCTCATT (SEQ ID NO: 15) | AACCTACAGGTGGGG TCTTTCA (SEQ ID NO: 16) |
| B2M | TAGCTGTGCTCGGGC TACT (SEQ ID NO: 17) | TCTCTGCTGGATGAC GCG (SEQ ID NO: 18) |

Southern Blotting

Probes for human Oct4, Sox2, and KLF4 were generated by PCR using the digoxigenin (DIG) probe synthesis kit (Roche) and Southern blotting was performed using DIG System detection reagents (Roche). Genomic DNA was isolated from human ESCs, parent fibroblast cells, and iPSCs using the Qiagen DNA Mini kit. DNA samples (5-10 µg) were digested overnight with BglII to generate a single cut in the integrated viral backbone of each transgene, and digests were resolved on a 0.8% agarose gel (without ethidium bromide), which was then denatured with 0.5% NaOH and neutralized. The gel was transferred to a nylon membrane by overnight capillary transfer. Wet membranes were crosslinked with 120 mJ UV (HL-2000 Hybrilinker, UVP) and allowed to dry. Membranes were pre-hybridized with DIG Easy Hyb buffer for at least 1 h at 55° C., then incubated with the appropriate probe overnight at 55° C. Membranes were washed thoroughly using the DIG Wash and Block kit, blocked for at least 1 h, and incubated with anti-DIG antibody for 30 min. Membranes were then washed and treated with CDP-Star reagent to detect DIG-incorporated bands. Blots were stripped and re-probed according to the manufacturer's instructions. Probe sequences are provided in Table 4, below.

TABLE 4

Southern Blot Primers (S2)

| GENE | FORWARD PRIMER 5'-3' | REVERSE PRIMER 5'-3' |
|---|---|---|
| Oct 4 (endogenous) | GAGAAGGAGAAGCTGGAGCA (SEQ ID NO: 19) | GTGAAGTGAGGGCTCCCATA (SEQ ID NO: 20) |
| Sox2 (endogenous) | AGAACCCAAGATGCACAAC (SEQ ID NO: 21) | TGGAGTGGGAGGAAGAGGTA (SEQ ID NO: 22) |
| Klf4 (endogenous) | ACCTGGCGAGTCTGACATGG (SEQ ID NO: 23) | TCTTCATGTGTAAGGCGAGGTGG (SEQ ID NO: 24) |

NanoString nCounter Assay

Total RNA was isolated from each iPSC clone between passage 10 and 15 using the RNeasy kit (Qiagen). A 100-ng sample of RNA was then profiled using the NanoString nCounter system (NanoString, Seattle, Wash.) using one of two custom-designed codesets. The pluripotency codeset contains 25 probes for detection of the Sendai and retroviral transgenes, pluripotency and spontaneous differentiation markers, and housekeeping genes (Table 5). The lineage codeset is derived from a previous study [15] and contains 85 probes for the three germ layers in addition to probes for retroviral and Sendai transgenes, and housekeeping genes (Table 6). RNA from a retrovirus-positive or Sendai-positive control line, a fibroblast line (1043), and two human ESC lines (HUES42 and Hues16) was included in each run. Data were analyzed using the nSolver Analysis Software v1.0 (NanoString) and plotted using Prism (Graphpad Software, La Jolla, Calif.). Data quality control and normalization to geometric mean for both internal positive controls, and subsequently for housekeeping genes, was performed in the nSolver analysis software.

TABLE 5

Pluripotency Codeset (S3)

| Retroviral | Sendai transgenes | Pluripotency Markers | Spontaneous Differentiation | Fibroblasts | Housekeeping |
|---|---|---|---|---|---|
| tOct4 | S-tOct4 | POU5F1 (OCT4) | SOX17 | ANPEP (CD13) | ACTB |
| tSox2 | S-tKlf4 | SOX2 | AFP | | POLR2A |
| tKlf4 | S-tC-myc | KLF4 | NR2F2 | | ALAS1 |
| tC-Myc | S-tSox2 | MYC | | | |
| | SeV | LIN28 | | | |
| | | NANOG | | | |
| | | ZFP42 | | | |

TABLE 6

Lineage Codeset (S4)

| Mesoderm | Ectoderm | Endoderm | Retroviral | Sendai | Pluripotent | Other | Housekeeping |
|---|---|---|---|---|---|---|---|
| ABCG2 | ABCG2 | APOE | tOct4 | tOct4 | POU5F1 | SRY | ACTB |
| ADIPOQ | APOE | CD44 | tSox2 | tSox2 | NANOG | XIST | POLR2A |
| ANPEP | CD44 | CDH2 | tKlf4 | tKlf4 | ZFP42 | | ALAS1 |
| CD34 | CDH2 | CDX2 | tC-Myc | tC-Myc | | | |
| CD36 | CRABP2 | CTNNB1 | | SeV | | | |
| CD4 | EN1 | FOXA2 | | | | | |
| CD44 | FAS | GATA4 | | | | | |
| CDH1 | FGFR2 | GATA6 | | | | | |
| CDH2 | FUT4 | GCG | | | | | |
| CDH5 | GATA2 | HNF1A | | | | | |
| CEACAM1 | GATA3 | HNF1B | | | | | |
| DLL1 | HAND1 | ISL1 | | | | | |
| FUT4 | ICAM1 | ITGA6 | | | | | |
| GATA3 | ITGA4 | ITGB1 | | | | | |
| GATA4 | ITGA6 | NEUROG3 | | | | | |
| HHEX | ITGB1 | NKX2-5 | | | | | |
| ICAM1 | MAP2 | PAX6 | | | | | |
| INHBA | MAPT | PDX1 | | | | | |
| ITGA4 | MCAM | SLC2A2 | | | | | |
| ITGA6 | MNX1 | SST | | | | | |
| ITGAL | NCAM1 | SYP | | | | | |
| ITGAM | NEFL | THY1 | | | | | |
| ITGAV | NES | | | | | | |
| ITGAX | NEUROG3 | | | | | | |
| ITGB1 | NGFR | | | | | | |
| ITGB3 | NOG | | | | | | |
| KDR | NOTCH1 | | | | | | |
| KIT | OTX2 | | | | | | |
| LEF1 | PAX3 | | | | | | |
| MCAM | PAX6 | | | | | | |
| MME | PAX7 | | | | | | |
| MYOD1 | PDGFRA | | | | | | |
| MYOG | SNAI2 | | | | | | |
| NCAM1 | SOX10 | | | | | | |
| NES | SOX2 | | | | | | |
| NGFR | SOX9 | | | | | | |
| NOTCH1 | SYP | | | | | | |
| PECAM1 | TDGF1 | | | | | | |
| SDC1 | TH | | | | | | |
| SPI1 | THY1 | | | | | | |
| SRF | | | | | | | |
| STAT3 | | | | | | | |

TABLE 6-continued

| Lineage Codeset (S4) | | | | | | | |
|---|---|---|---|---|---|---|---|
| Mesoderm | Ectoderm | Endoderm | Retroviral | Sendai | Pluripotent | Other | Housekeeping |
| T | | | | | | | |
| THY1 | | | | | | | |
| TNFRSF1A | | | | | | | |
| TWIST1 | | | | | | | |

Embryoid Body Formation

Embryoid bodies (EB) were formed by placing clumps of iPSCs in 96-well non-tissue culture treated V-bottom plates (Evergreen 222-8031-01V) containing HUESM. After 5 weeks of culture, EBs were harvested, fixed in 4% paraformaldehyde (PFA) for 30 min at RT and processed in 15% and 30% sucrose solutions for one day each prior embedding in O.C.T., freezing, sectioning into 10 μm slices and mounting on glass slides. EB sections were immunostained with antibodies against the markers shown in Table 7, below. Briefly, EB sections were incubated with blocking solution 10% donkey serum in PBST (PBS with 0.1% Triton-100) for 1 h at RT, followed by an overnight incubation at 4° C. with primary antibodies. After washing three times with PBST, sections were incubated for 1 h at RT with appropriate secondary antibodies obtained from Molecular Probes. Finally, sections were washed and counterstained with DAPI (1:1000 in PBS) for 15 min at RT.

TABLE 7

Primary Antibodies for Immunofluorescence (S5)

| Antibody | Company | Catalog # | Dilution |
|---|---|---|---|
| Oct4 | Stemgent | 09-0023 | 1:250 |
| Sox2 | Stemgent | 09-0024 | 1:250 |
| Tra-1-60 | Millipore | MAB4381 | 1:250 |
| SSEA4 | R&D Systems | MAB1435 | 1:250 |
| Nanog | R&D Systems | AF1997 | 1:250 |
| SSEA3 | R&D Systems | MAB1434 | 1:250 |
| Smooth Muscle | DAKO | M085101 | 1:500 |
| Alpha-1-Fetoprotein | DAKO | A0502 | 1:500 |
| TUJ1 | Covance | MMS-435P | 1:500 |
| Nestin | Millipore | AB5922 | 1:500 |
| MAP2 | Abcam | ab32454 | 1:500 |

Teratoma Assay

Manually (1023_C) and FACS-derived (1023_D2) cells were dissociated using Dispase (Gibco 17105-041) for 15 minutes at 37° C. to produce small clumps containing approximately 100-200 iPSCs/clump. The clumps were suspended in 100 μl of HUESM containing 100 μl Matrigel™ (BD Biosciences) and injected subcutaneously into NOD-SCID Il2rg-null mice (Jackson Laboratory) following an intraperitoneal injection of carprofen (Pfizer) at 5 mg/kg. Teratomas were allowed to grow for 6-8 weeks, isolated by dissection and fixed in 4% PFA overnight at 4° C. Fixed tissues were embedded in paraffin, sectioned at 10 μm and stained with hematoxylin and eosin (H&E).

Results

FACS Derivation of iPSCs

Previous studies have demonstrated downregulation of the human fibroblast marker CD13 [8], and upregulation of the pluripotency markers SSEA4 and TRA-1-60 occurs during reprogramming [9]. These studies suggest that isolation of fully reprogrammed iPSCs during early stages of reprogramming may be accomplished by FACS using a combination of positive and negative surface markers. While current sorting strategies for purification of pluripotent cells rely on positive selection[7], it is possible that a significant proportion of clones isolated using this method may not be fully reprogrammed. To test this hypothesis, first the conditions for survival of live-cell sorted, fully reprogrammed cells was optimized by examining the expression levels of three surface markers in a manually derived, early passage clone (p4) of an iPSC line (1018) cultured on MEFs.

Figure 11A:
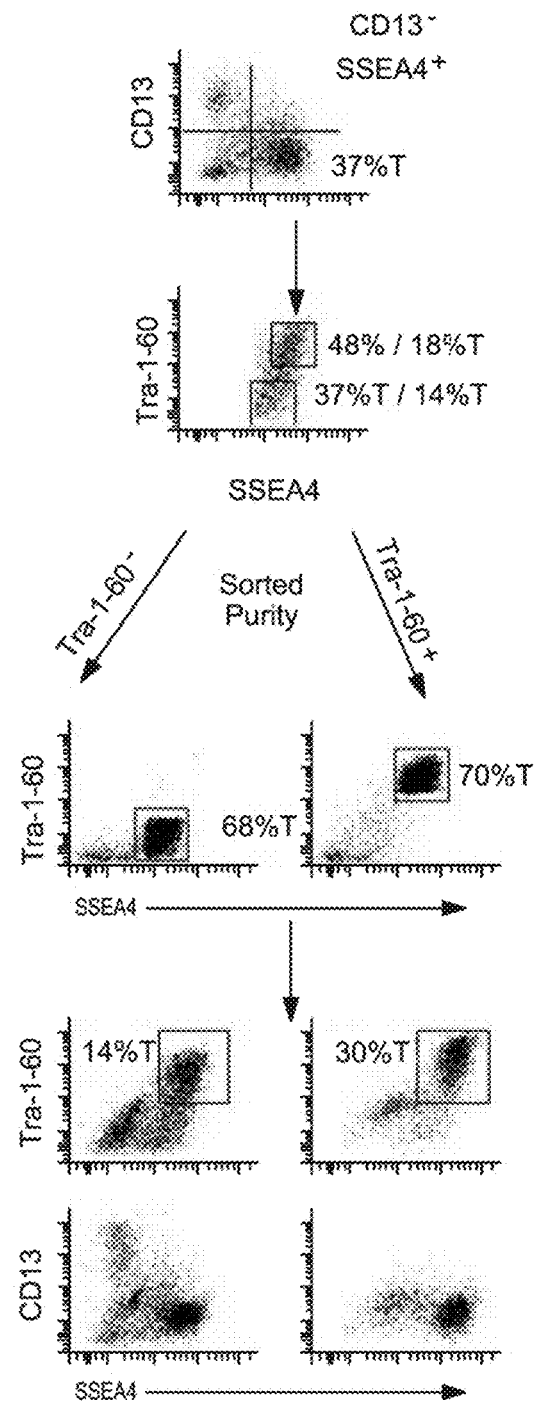
FIGS. 11A-11E. Enhanced derivation and maintenance of virally reprogrammed fibroblasts using Fluorescence Activated Cell Sorting.

Populations of cells expressing all three markers were found in the culture suggesting a heterogeneous mixture of cells containing parental and partially reprogrammed fibroblasts FIG. 11A. Then the CD13NEGSSEA4POSTra-1-60POS (Tra-1-60POS) population was sorted and, as a control, the CD13NEGSSEA4POSTra-1-60NEG (Tra-1-60NEG) population was sorted to approximately 70% purity directly into one well of a 6 well plate containing MEFs in the presence of ROCK inhibitor Y-27632. The sorted populations were maintained for 20 days on MEFs without ROCK inhibitor or removal of differentiated cells or splitting prior to reanalysis by flow cytometry (FCM). At 20 days post-sorting (dps), the cultures originating from the enriched Tra-1-60POS population contained fewer Tra-1-60NEG differentiated cells and no detectable CD13POS parental fibroblasts. The Tra-1-60POS population was present in these cultures at approximately double the proportion found in the Tra-1-60NEG enriched culture (30% vs. 14%). Conversely, at 20 dps the culture originating from the Tra-1-60NEG enriched population contained a Tra-1-60POS population at a similar proportion to the originally sorted culture (18% T vs. 14% T). However, these cultures also contained a higher proportion of differentiated or transformed cells (CD13NEGSSEA4NEGTra-1-60NEG) as well as adult fibroblasts (CD13POS) suggesting that these FACS conditions allow for purification of fully reprogrammed cells from contaminating cell types.

Figures 11B, 11C:
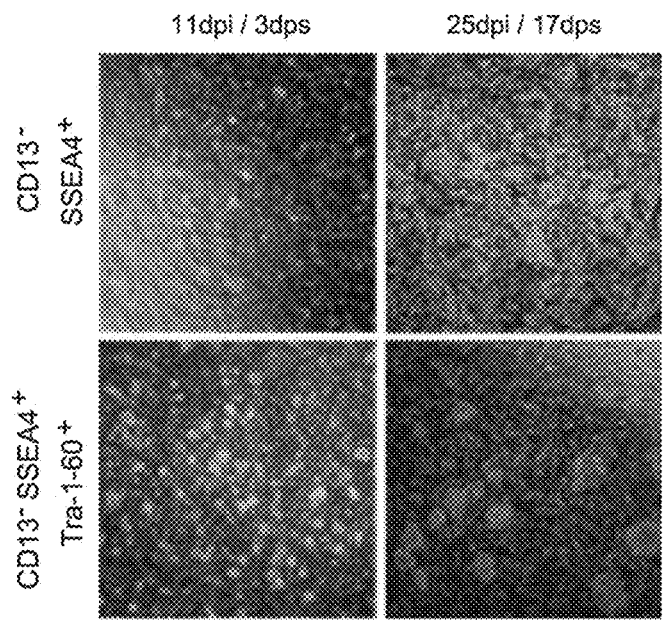

To confirm this strategy, adult skin fibroblasts at 8 days post infection (dpi) were sorted based on the CD13NEGSSEA4POSTra-1-60POS surface marker profile. As a control, the CD13NEGSSEA4POS population that contained two subpopulations of cells expressing either Tra-1-60POS or Tra-1-60NEG was isolated in parallel. 5,000 or 10,000 cells from each population were sorted directly into MEF-containing plates, and monitored for the formation of colonies. Small but distinct colonies were evident in both sorted populations as early as 3 days post sort (dps), with the CD13NEGSSEA4POSTra-1-60POS population producing larger and more abundant colonies than the CD13NEGSSEA4POS population (3 dps, 11 dpi; FIG. 11B). Following an additional 2 weeks of expansion without manual removal of differentiated cells, wells containing the CD13NEGSSEA4POS population had become overgrown with transformed and differentiated cells, whereas wells containing the sorted CD13NEGSSEA4POSTra-1-60POS cells contained large, well-separated colonies with few differentiated cells between the colonies and lacked cells with transformed morphology (17 dps, 25 dpi; FIG. 11B). A 3-4 fold increase was observed in the number of colonies present in wells containing the sorted CD13NEGSSEA4POSTra-1-60POS cells compared to the sorted CD13NEGSSEA4POS cells FIG. 11C.

Figure 11D:
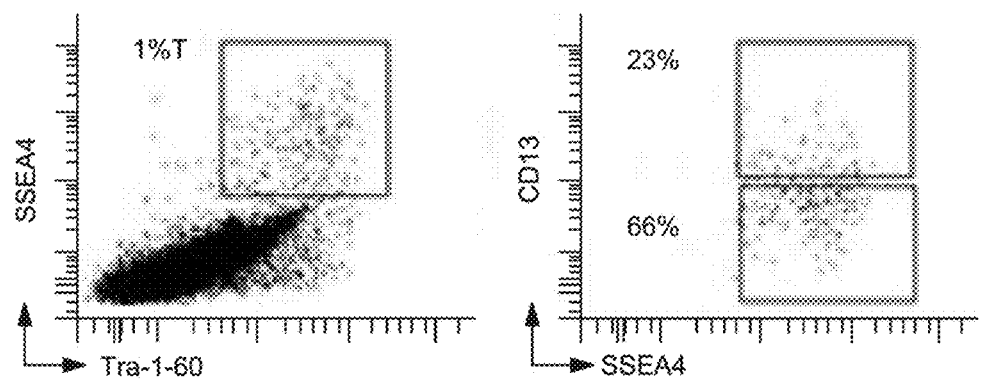
Figure 11E:
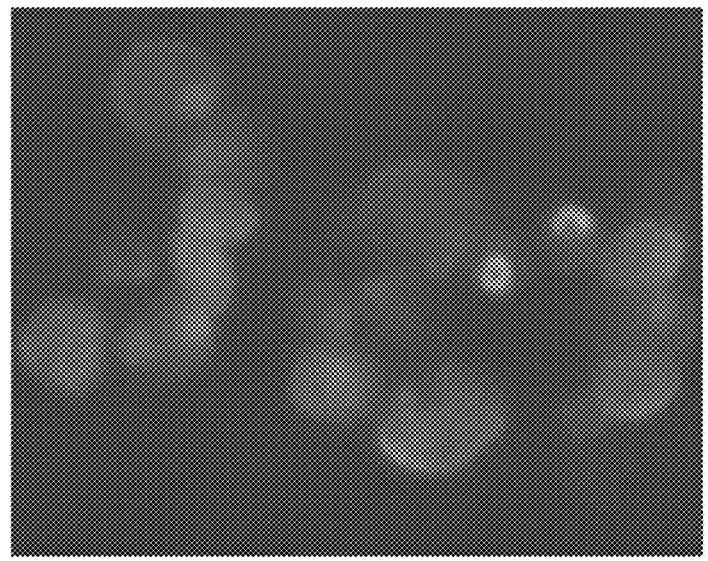

CD13 expression was then analyzed within the SSEA4POSTra-1-60POS population of reprogrammed fibroblasts at 7 dpi. Roughly one quarter of the SSEA4POSTra-1-60POS population expressed CD13 indicating the presence of a heterogeneous population of fully reprogrammed, transformed, or transitioning cells (23% CD13POS, 66% CD13—; FIG. 11D), some of which expressed both Nanog and CD13 FIG. 11E.

Figure 12A:
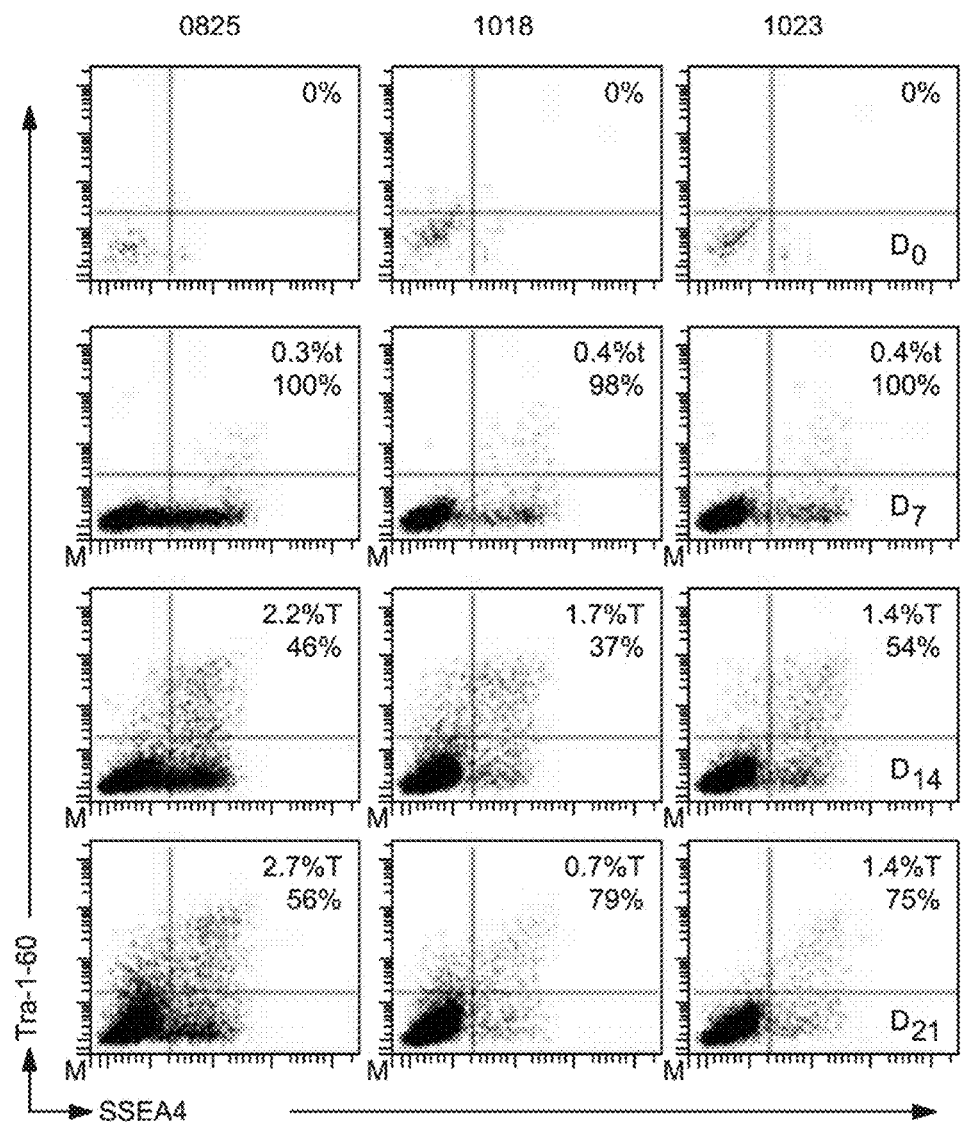
FIGS. 12A-12D. Fibroblasts undergoing viral reprogramming exhibit characteristic expression levels of surface markers at early time points post infection.

Because surface marker expression during reprogramming is dynamic, the earliest time point was first identified at which to enrich fully reprogrammed iPSCs. Time course analysis conducted by flow cytometry following retroviral reprogramming suggested that SSEA4POSTra-1-60POS cells were detectable as early as 7 dpi, and their proportion increased up to 21 dpi, then remained constant as marker negative cells outgrew the reprogrammed cells Table 3. The SSEA4POSTra-1-60POS population also expressed the SSEA3 and CD326 pluripotency markers [16], [17], [18], [19]. SSEA4POSCD13POS cells appeared by 7 dpi and while most of this population disappeared by 14 dpi, a proportion remained in the culture. To test whether this timing was consistent among different skin samples, cultures derived from a foreskin fibroblast line (0825), a healthy adult control fibroblast line (1023), and a fibroblast line from a subject with type I diabetes (1018) were analyzed for up to 21 dpi. The three fibroblast cell lines showed a consistent emergence of pluripotent surface markers with SSEA4POSTra-1-60POS cells present at low numbers at 7 dpi (D7, 0.3%-0.4% FIG. 12A), increasing in proportion at 14 dpi (D14, 1.4%-2.2%), and decreasing by day 21 as other cells overtook the culture (D21, 0.7%), suggesting a consistent appearance of potentially early reprogrammed cells between 7 and 14 dpi. However, at early time points, the majority of SSEA4POSTra-1-60POS cells also expressed CD13 (D7, 98%-100%). The proportion of CD13POSSSEA4POSTra-1-60POS decreased approximately half by day 14 post infection (D14, 37%-54%), suggesting loss of this fibroblast marker on cells undergoing reprogramming. Interestingly, the CD13POSSSEA4POSTra-1-60POS population increased again by day 21, suggesting that this population was expanding or that CD13NEG cells were lost from the culture.

Figure 12B:
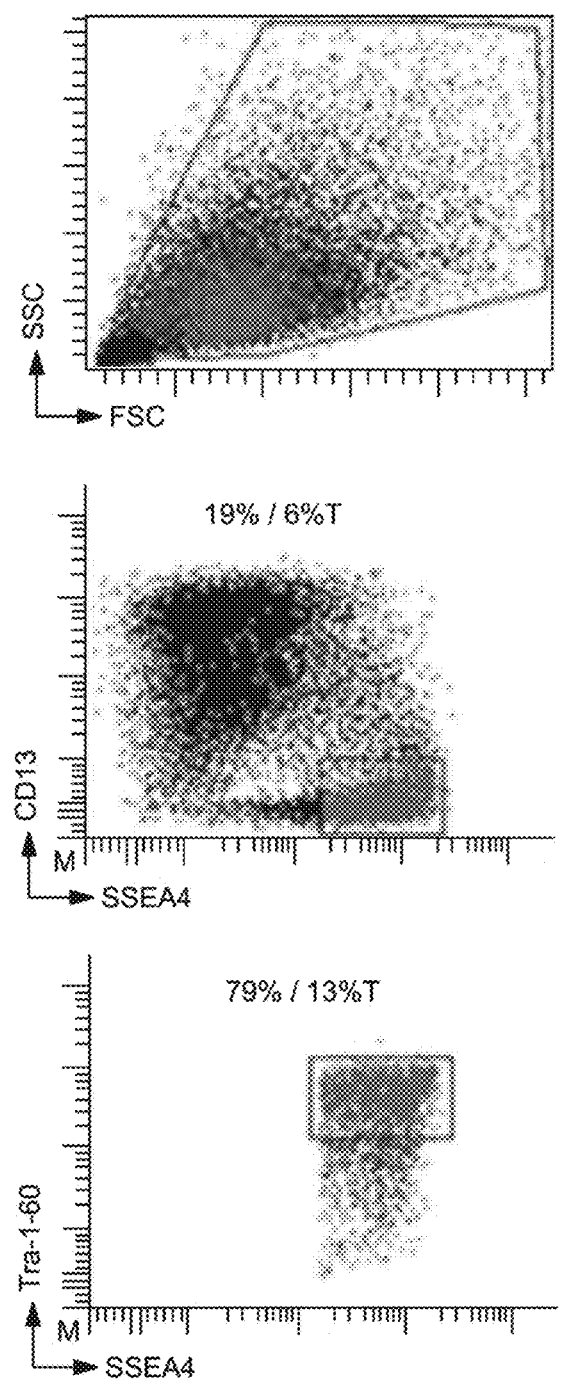
Figure 12C:
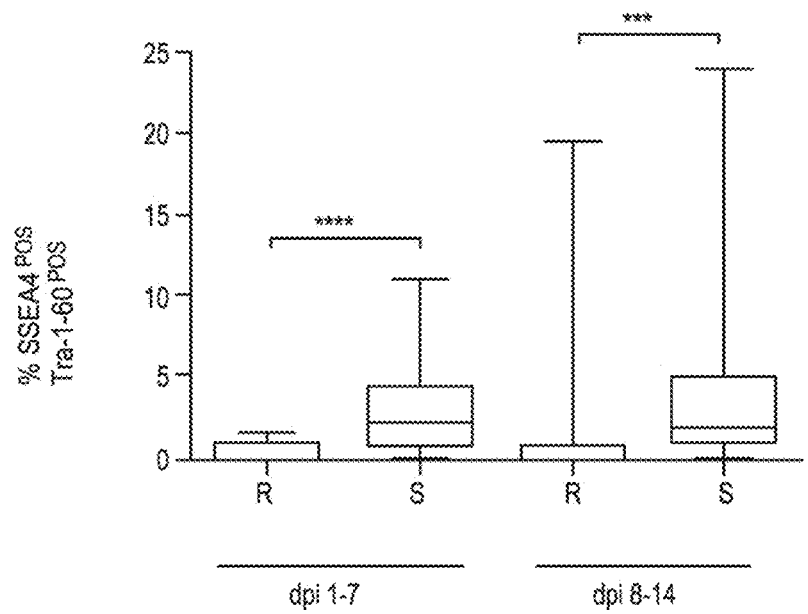
Figure 12D:
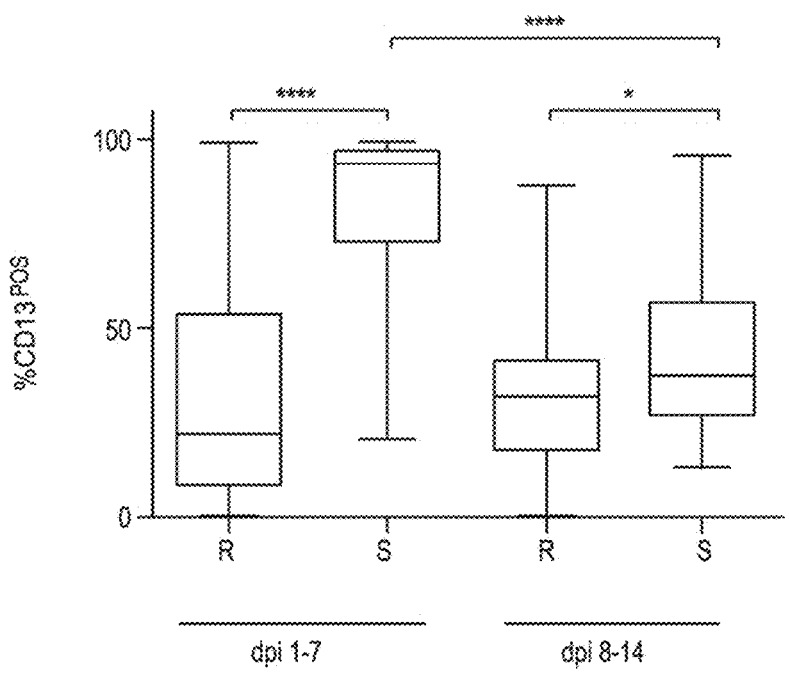

Based on these results, the sorting strategy shown in FIG. 12B was developed which omits the contaminating partially reprogrammed CD13POSSSEA4POS population by selecting the highest Tra-1-60POS expressing cells within the CD13NEGSSEA4POS population. Using this strategy FACS was used to derive 228 individual iPSC lines from over 75 fresh or frozen fibroblast lines generated from biopsies harvested from healthy or disease patients using either integrating (retroviral) or non-integrating (Sendai virus) reprogramming vectors and extensive characterization was performed on a subset of those lines which is described in the data that follows. The first 2 weeks of the reprogramming process was further characterized on 128 FACS derived iPSC lines using the analysis structure shown in FIG. 11D. As shown in FIG. 12C, a higher percentage of SSEA4POSTra-1-60POS cells were generated in Sendai infections compared to retroviral infections over the entire time course. However, Sendai infections demonstrated a delayed reduction in the proportion of CD13POSSSEA4POSTra-1-60POS cells FIG. 12D. By the second week of induction, the proportion of the CD13POS population between the cultures was similar.

FACS Derived Lines are Pluripotent

To further characterize this defined selection strategy, the phenotype and function of the FACS-derived iPSC clones were compared to manually picked clones. First, the 0825, 1018, and 1023 fibroblast lines shown in FIG. 12A reprogrammed using the 4-factor retroviral protocol were subjected to either FACS derivation at 7 dpi or standard picking techniques. For each method, one clone from each line was randomly selected for expansion and further characterization by a standard battery of assays, including karyotypic analysis, DNA fingerprint, pluripotent surface marker expression, qRT-PCR, and Embryoid body (EB) and teratoma formation. All fibroblasts and reprogrammed iPSC lines displayed normal karyotypes, and had DNA fingerprints matching the parental fibroblast line (Table 4). Clones from the 0825 foreskin fibroblast line had a DNA fingerprint that matched a major subpopulation in the parental fibroblasts that contained a contaminating subpopulation with a different genotype, suggesting isolation of clonal cultures from a mixed population.

Figure 13A:
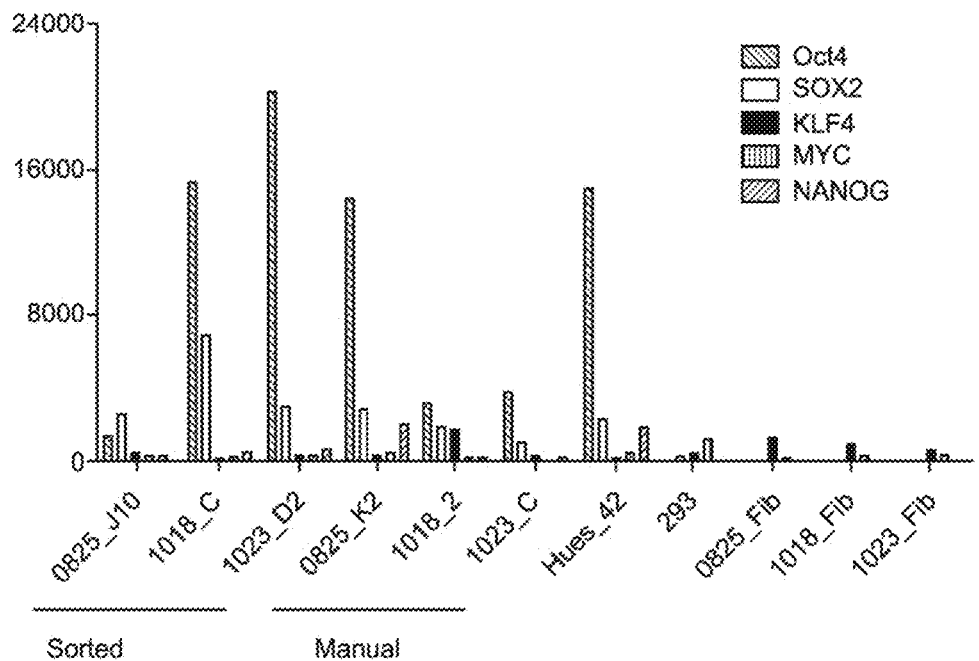
FIGS. 13A-13C. Fluorescence Activated Cell Sorting generates higher quality independent clones than manual derivation. Modified pluripotent scorecard assay was performed on manually and FACS derived clones to demonstrate (FIG. 13A) activation of endogenous gene expression and (FIG. 13B) silencing of gene expression and presence of unreprogrammed and transformed fibroblasts $CD13^{POS}$ in manually derived clones.
Figure 13B:
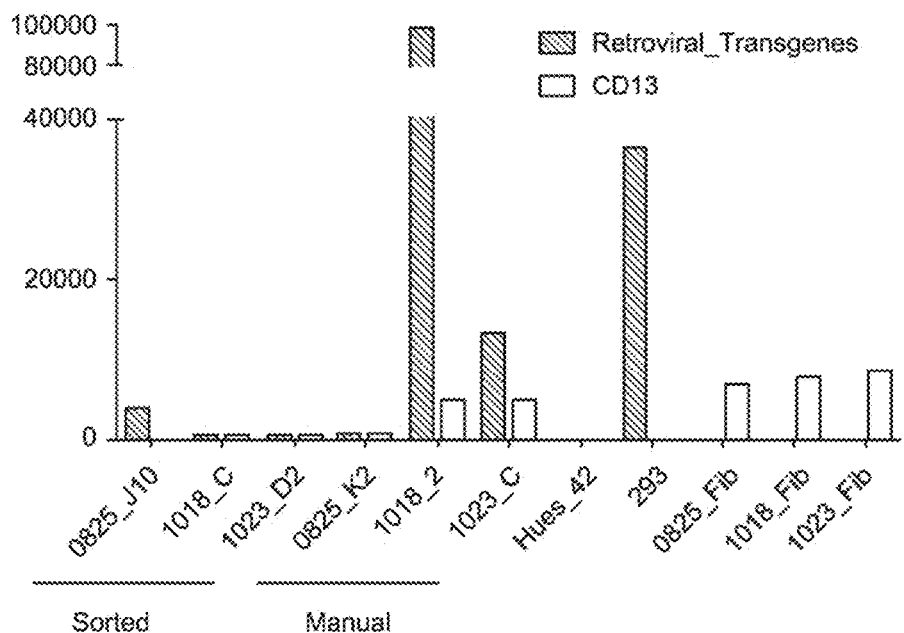
Figure 19A:
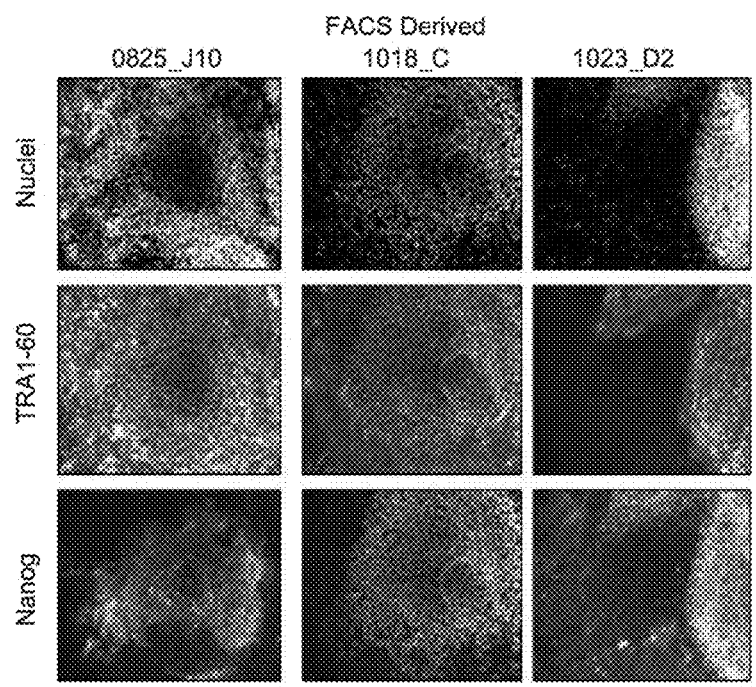
FIGS. 19A-19D. FACS and Manually Derived Sendai iPS lines express pluripotency markers. FACS (FIG. 19A) or Manually (FIG. 19B) derived clones were expanded on MEF feeder layers and stained for two common markers of pluripotency: Tra-1-60 and Nanog. 10× Magnification. All lines show consistent expression of pluripotency markers.
Figure 19B:
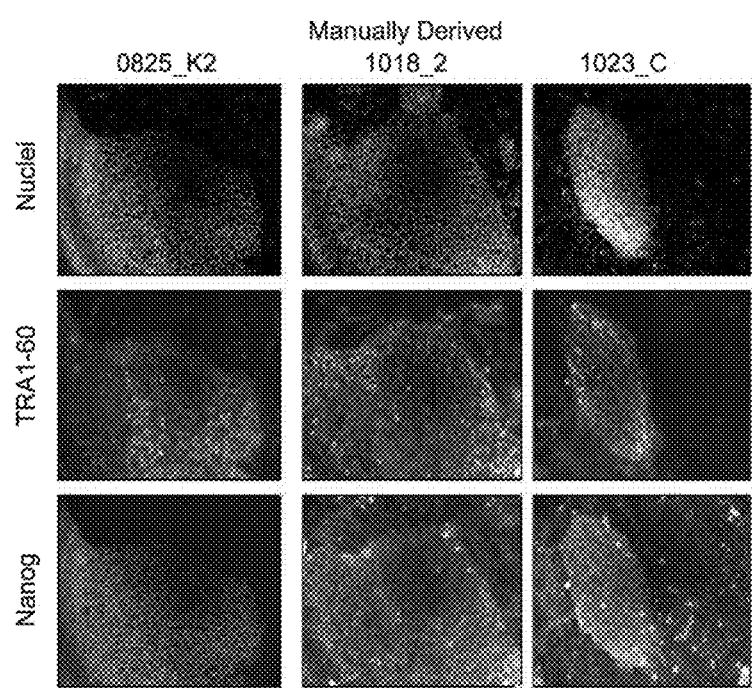
Figure 19C:
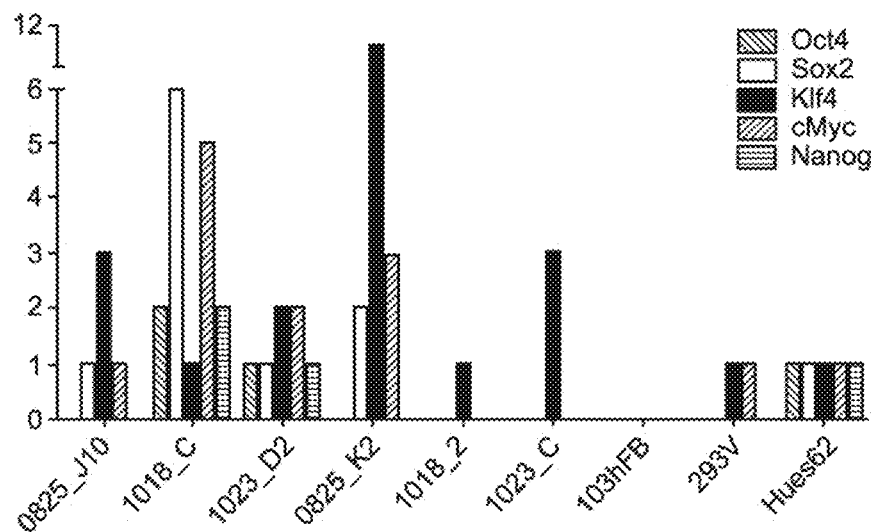
Figure 19D:
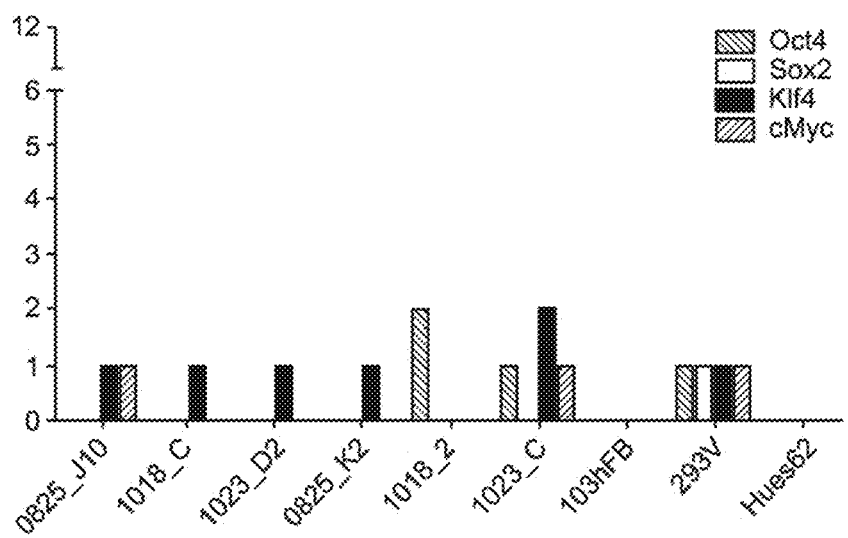

Both the manually and FACS-derived iPSC lines expressed common markers of pluripotency, including the surface marker Tra-1-60 and the transcription factor Nanog, and generated compact colonies morphologically consistent with normal hESCs, FIG. 19A-19B. Next, the cell lines were expanded for ten passages and the expression of endogenous Nanog, Oct4, Sox2, cMyc, and Klf4, and silencing of the viral transgenes Oct4, Sox2, Klf4, and cMyc were assayed. A probe-based Nanostring nCounter transcript quantification assay was used to assess pluripotency by detecting both activation of endogenous gene expression FIG. 13A and silencing of retroviral transgenes FIG. 13B. These data were further confirmed by qPCR FIGS. 19A-19D and revealed a similar pattern of endogenous gene expression in all iPSC lines compared to undifferentiated hESC controls FIG. 13A, FIGS. 19A-19D. However, two of the three manually derived clones (1018_2 and 1023_C) maintained much higher expression of the viral transgenes than the sorted clones FIG. 3B. Additionally, the 1018_2 cultures expressed CD13, indicating the presence of non-reprogrammed or partially transformed human fibroblasts in the manually picked lines FIG. 13B. These analyses suggest that selection of single cells based on CD13NEGSSEA4POSTra-1-60POS expression can be used to select against partially reprogrammed or contaminating cell types in reprogrammed cultures. The full data set for these experiments is provided in Table S7 (see Kahler et al, 2013, incorporated herein by reference).

Modified pluripotent scorecard assay was performed on manually and FACS derived clones to demonstrate (A) activation of endogenous gene expression and (B) silencing of gene expression and presence of unreprogrammed and transformed fibroblasts CD13POS in manually derived clones. (C) Three sorted and three picked lines from patient 1023 were used to compare the ability of both methods to generate independent clones. 10μ of genomic DNA were cut overnight with BglII and submitted to Southern blotting. The HUES line HES2 was used as a positive control for endogenous KLF4/OCT4, and as a negative control for transgene insertions. Samples were first blotted for KLF4, then stripped and reblotted for OCT4. Picked clones 1023 C and E are consistent with being the same clone by both KLF4 and OCT4 blotting. * indicated the predicted endogenous KLF4/OCT4 bands, and ** indicated a consistent band found in all samples blotted with OCT4.

Figure 14A:
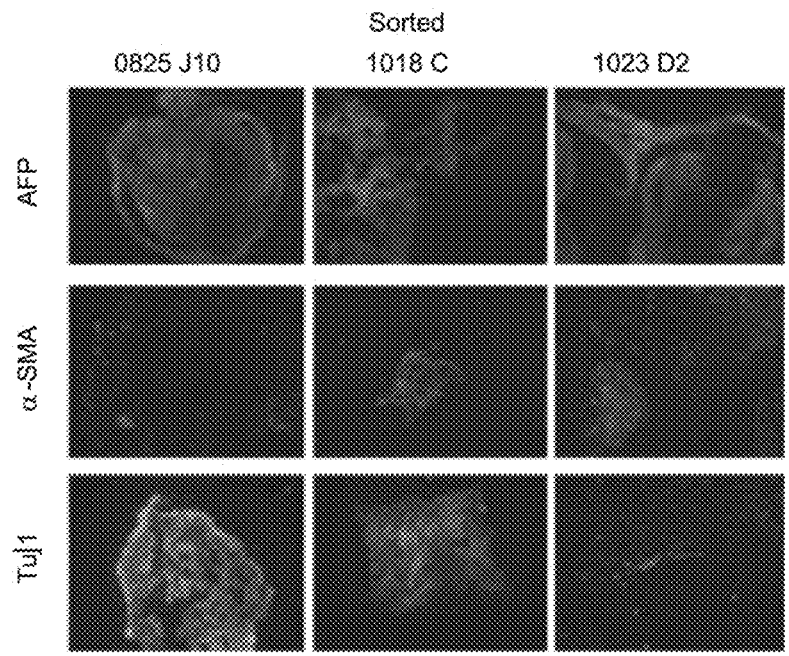
FIGS. 14A-14E. hIPSC lines derived by Fluorescence Activated Cell Sorting possess in vitro and in vivo spontaneous differential potential. Embryoid bodies were derived from FACS (FIG. 14A) or manually derived clones (FIG. 14B) and stained for expression of alpha fetoprotein, smooth muscle actin and beta III tubulin (Tuj1) to demonstrate differentiation potential in vitro potential. 10× Magnification (FIG. 14C) Differentiation potential of the derived lines for expression of germ layer genes present in the Lineage scorecard assay.
Figure 14B:
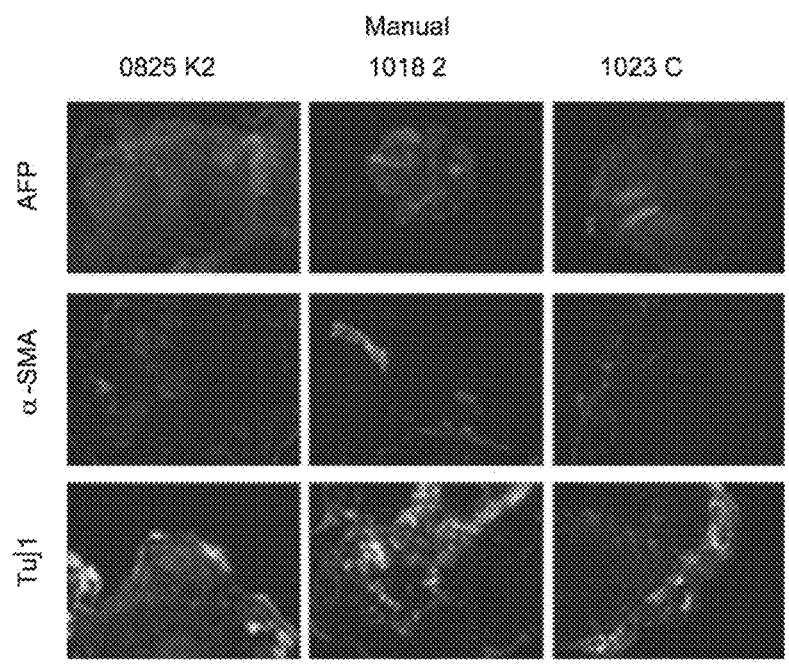
Figure 14C:
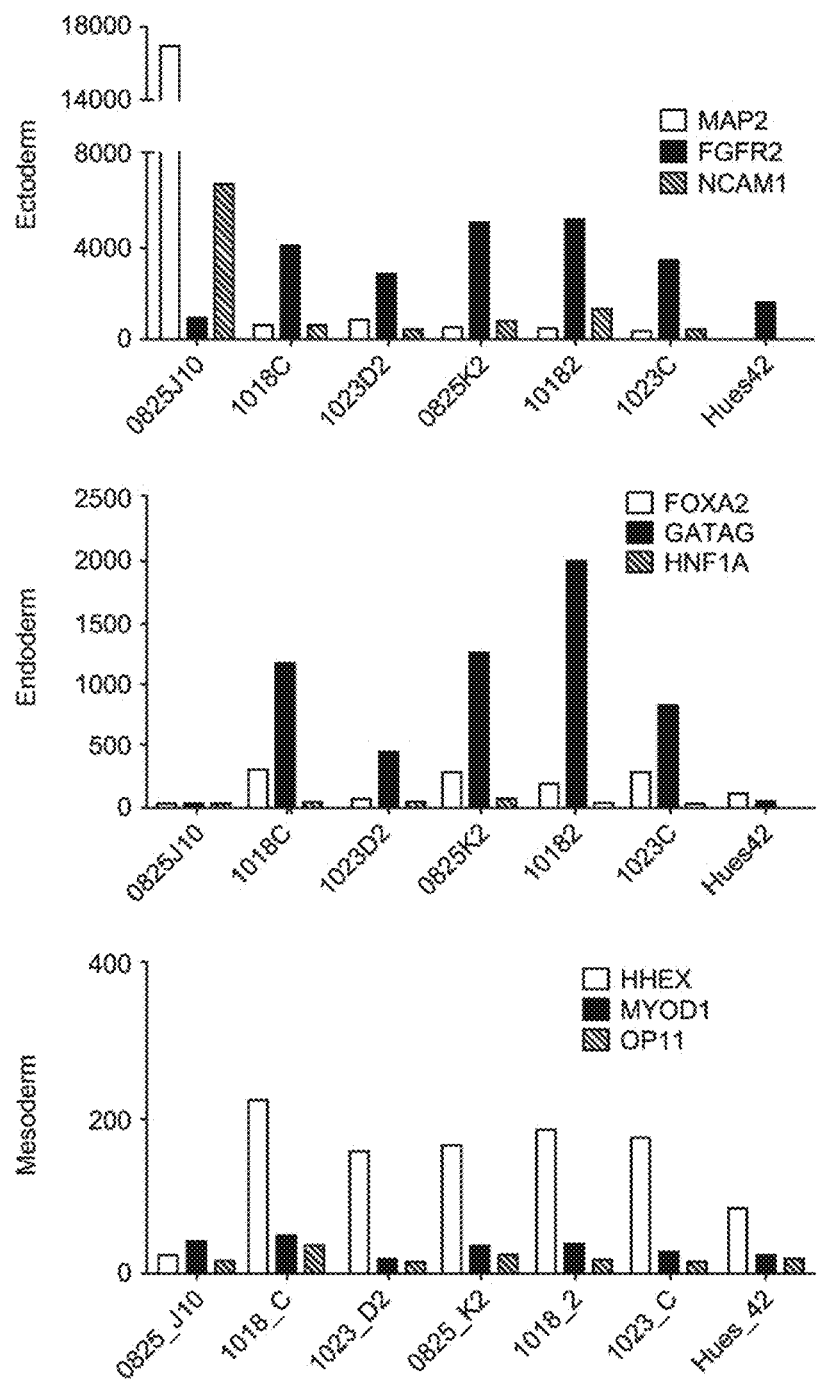

We next examined undirected EB formation to measure the in vitro differentiation potential of FACS and manually-derived iPSCs clones. Following differentiation for 5 weeks, EBs were collected and assayed for markers of three embryonic germ layers endoderm, mesoderm, and ectoderm by immunohistochemistry for α1-fetoprotein (AFP), smooth muscle actin (αSMA), and beta III tubulin (Tuj1), respectively. EBs derived from FACS or manually picked clones expressed markers associated with formation of the three germ layers FIGS. 14A-14B. To further define the differentiation potential of the derived lines, RNA from the EBs were collected after two weeks of differentiation and tested against a panel of lineage-specific nCounter probes Table S4 previously validated to detect expression of genes commonly found in the three germ layers [15] FIG. 14C. With the exception of the FACS-derived 0825 line, all lines expressed comparable levels of the germ layer-associated genes, indicating they have similar potential to spontaneously differentiate in vitro into any germ layer. The full data set for these experiments is provided in Table S8 (see Kahler et al, 2013, incorporated herein by reference).

Embryoid bodies were derived from FACS (A) or manually derived clones (B) and stained for expression of alpha fetoprotein, smooth muscle actin and beta III tubulin (Tuj1) to demonstrate differentiation potential in vitro potential. 10× Magnification (C) Differentiation potential of the derived lines for expression of germ layer genes present in the Lineage scorecard assay. (D) Teratomas from FACS (D) or manually derived (E) clones of 1023 fibroblast line indicating in vitro differentiation potential by formation of three germ layers.

Figure 14D:
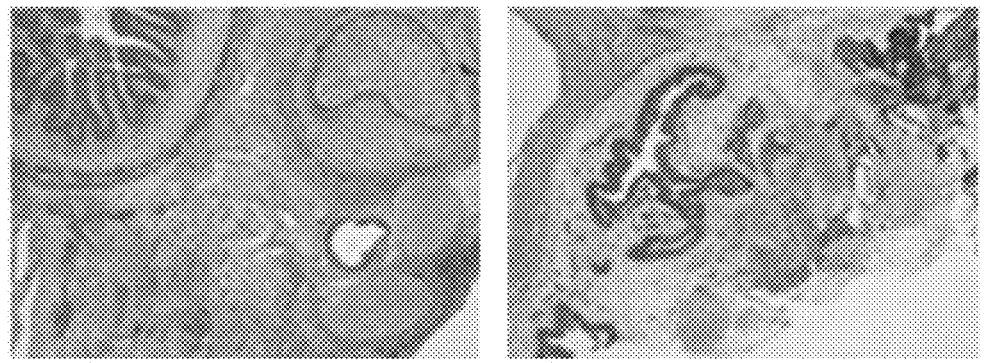
Figure 14E:
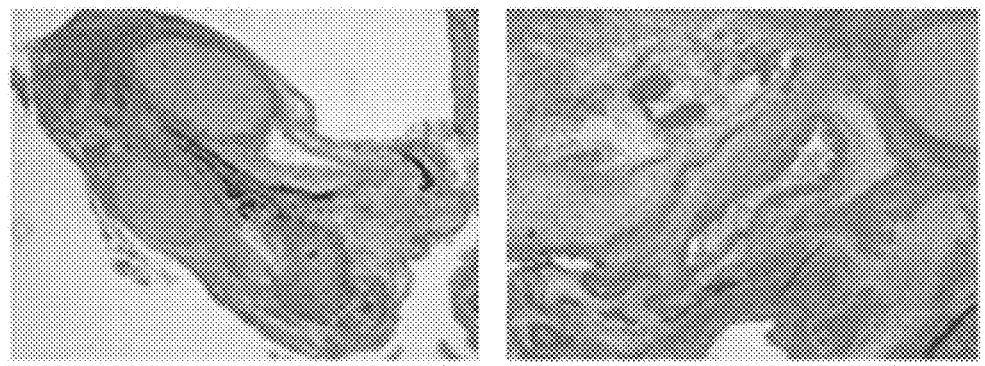

To measure the in vivo differentiation potential of the iPSCs, immunocompromised mice were injected with FACS or manually derived clones from the 1023 fibroblast line. The resulting teratomas were sectioned and examined by H&E staining. This analysis showed that teratomas generated from sorted FIG. 14D or manually derived FIG. 14E clones formed all three germ layer tissues, including gut-like epithelial tissues (endoderm), cartilage (mesoderm), and retinal pigment epithelium (ectoderm). Together, these analyses validate the use of CD13NEGSSEA4POSTra-1-60POS expression as a surface marker signature compatible with FACS that can be used to isolate a population of fully reprogrammed iPSCs.

FACS Derivation Produces Independent Clones

Figure 13C:
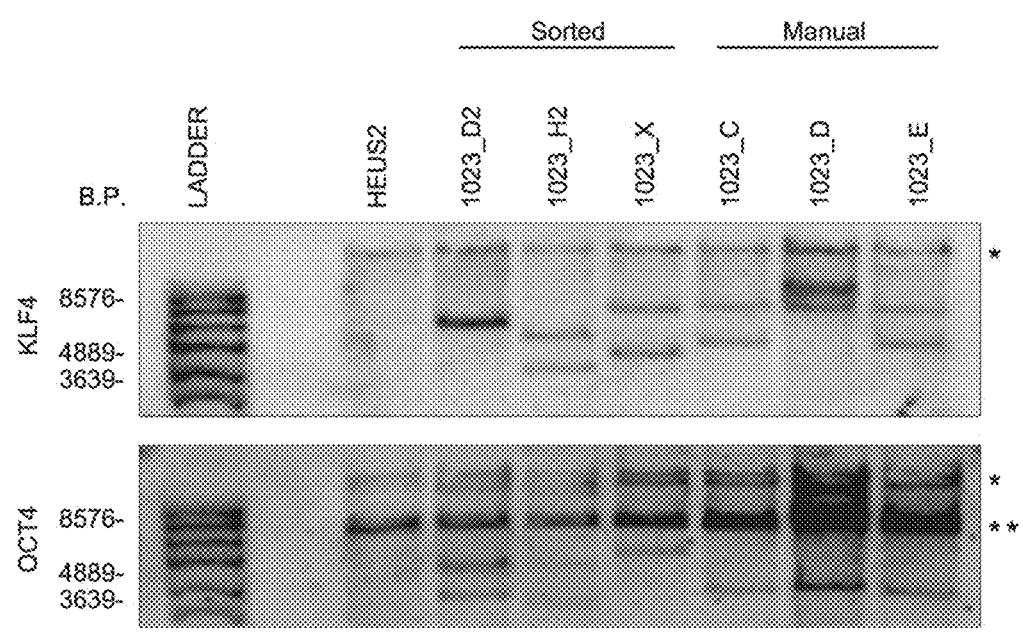

Because iPSC lines can arise from rare apparently stochastic events at early time points during reprogramming, it was important to establish that FACS sorting could isolate multiple independent reprogramming events. To determine whether FACS derivation can produce unique cell lines in a similar manner to manual picking, Southern blotting was performed on several clones derived by both methods. Klf4 and Oct4 probes were used to identify the endogenous and virally integrated forms of the genes. Different banding patterns indicate differences in the chromosomal integration sites and, in some cases, varying numbers of detectable integration events. As shown in FIG. 13C, all three sorted clones from line 1023 have different integration sites for both Klf4 and Oct4, demonstrating they are independent clones. In contrast, two of the three picked clones from line 1023 have identical banding patterns for Klf4 and Oct4, suggesting they are the same clone. Of the iPSC lines generated from three different fibroblast lines, 8/9 FACS-derived lines were independent clones, while 7/9 manually picked lines were independent (data not shown), suggesting equivalent ability to generate clonal cultures. Therefore, FACS sorting between 7-14 dpi using of CD13NEGSSEA4POSTra-1-60POS can generate independent clonal cultures following retroviral reprogramming.

FACS Derived Lines are Stable at Later Passages

Figure 15A:
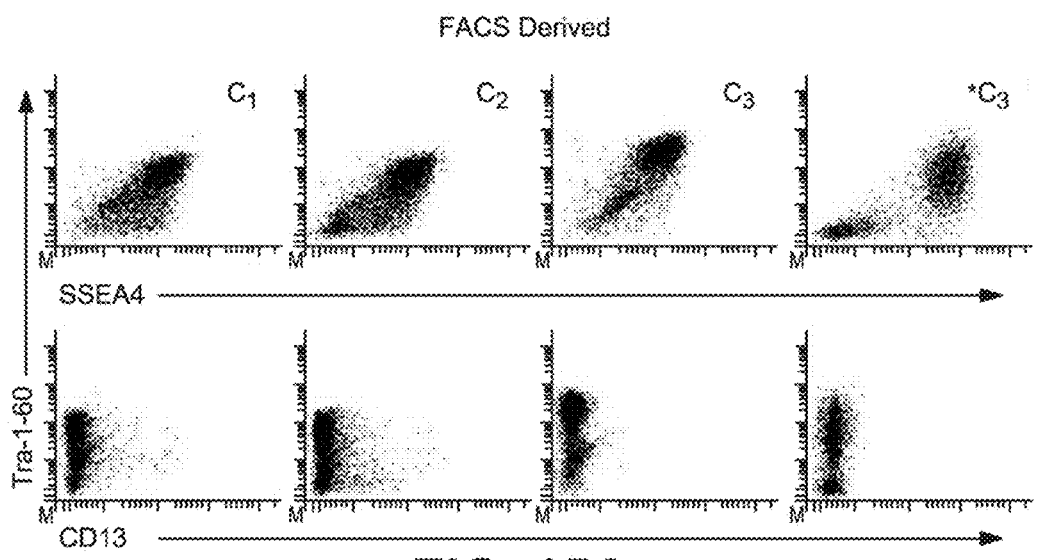
FIGS. 15A-15B. Stability of Fluorescence Activated Cell Sorted and Manually Derived IPSC Lines. Three individual clones were selected from foreskin (0819) fibroblasts lines which previously underwent four factor retroviral reprogramming and were derived by either FACS (FIG. 15A, $C_1$-$C_3$) or manual (FIG. 15B, $C_4$-$C_6$) techniques were analyzed by flow cytometry for pluripotent surface marker expression following expansion on murine embryonic fibroblasts for 12-14 passages. Clones C3 and C6 were adapted to Matrigel and mTSER media around passage11 and expanded for several passages prior to surface marker analysis by flow cytometry to demonstrate stability following changes in culture conditions. Events displayed in the 2D scatter plots are "live" cells as defined by forward and side scatter properties expressing indicated surface markers.
Figure 15B:
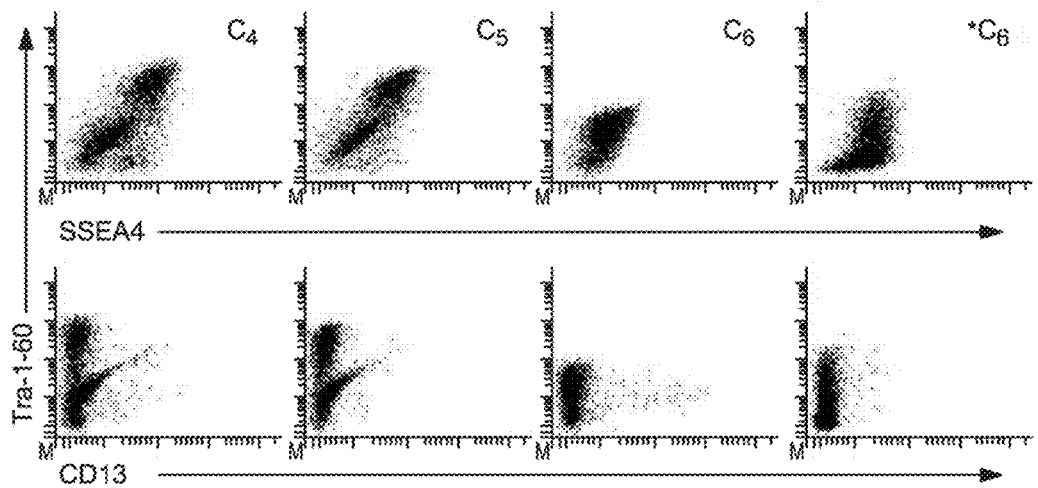

To demonstrate the stability of FACS derived iPS clones at later passages, a foreskin fibroblast line (0819) was retrovirally reprogrammed using both FACS and manual derivation methods. Three individual clones were chosen from each derivation method and expanded on MEFs to asses pluripotent surface marker expression by FCM at later passages. As shown in the first row of FIGS. 15A-15B, cultures of all clones (C1-C6) resulting from each derivation method possessed populations of cells positively expressing both SSEA4 and Tra-1-60 at varying proportions indicating stability at between 12-14 passages. Although not shown in FIGS. 15A-15B, cultures of these clones were stable at earlier (p4-p11) and later (p20-p25) passages. Clones C3 and C6 were adapted to matrigel and mTser media (*C3 and *C6 in FIGS. 15A-15B) following 11 passages on MEFS and expanded for 3-5 passages to demonstrate the stability of FACS derived iPS lines following changes in substrate and media conditions. FCM analysis of Matrigel adapted iPS lines show stable surface marker expression with less SSEA4POSTra-1-60NEG populations than the manually derived clone C6. Small populations of CD13POS expressing both Tra-1-60POS and Tra-1-60NEG (second row of FIGS. 15A-15B) were present in all cultures with the exception of the FACS derived C3 and *C3 clones indicating the variability present in individual clones derived under DNA integrating reprogramming techniques. Similar results are observed within clones derived using the non-integrating Sendai viral platform. These results demonstrate that FACS derived iPS clones remain stable over multiple passages and following adaptation to feeder free conditions.

Three individual clones were selected from foreskin (0819) fibroblasts lines which previously underwent four factor retroviral reprogramming and were derived by either FACS (A, C1-C3) or manual (B, C4-C6) techniques were analyzed by flow cytometry for pluripotent surface marker expression following expansion on murine embryonic fibroblasts for 12-14 passages. Clones C3 and C6 were adapted to Matrigel and mTSER media around passage11 and expanded for several passages prior to surface marker analysis by flow cytometry to demonstrate stability following changes in culture conditions. Events displayed in the 2D scatter plots are "live" cells as defined by forward and side scatter properties expressing indicated surface markers.

Utility for Multiple Reprogramming Methods

Figure 18A:
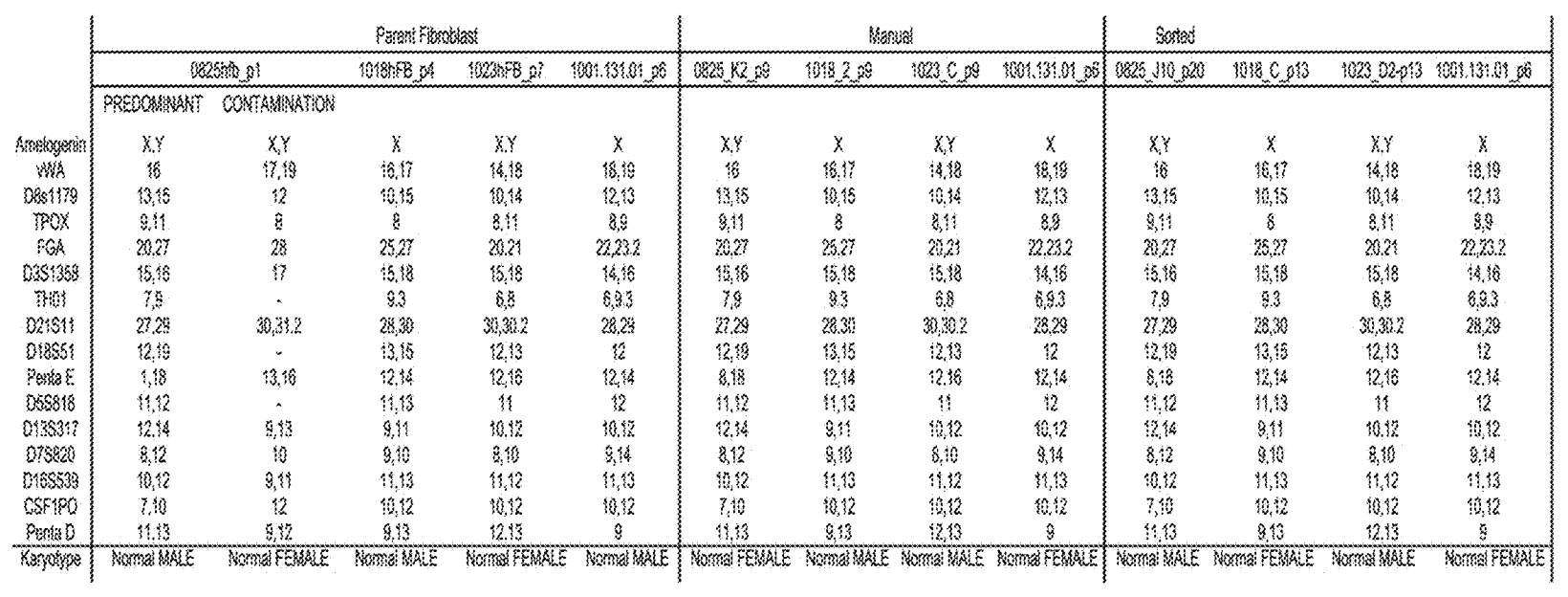
Figure 18B:
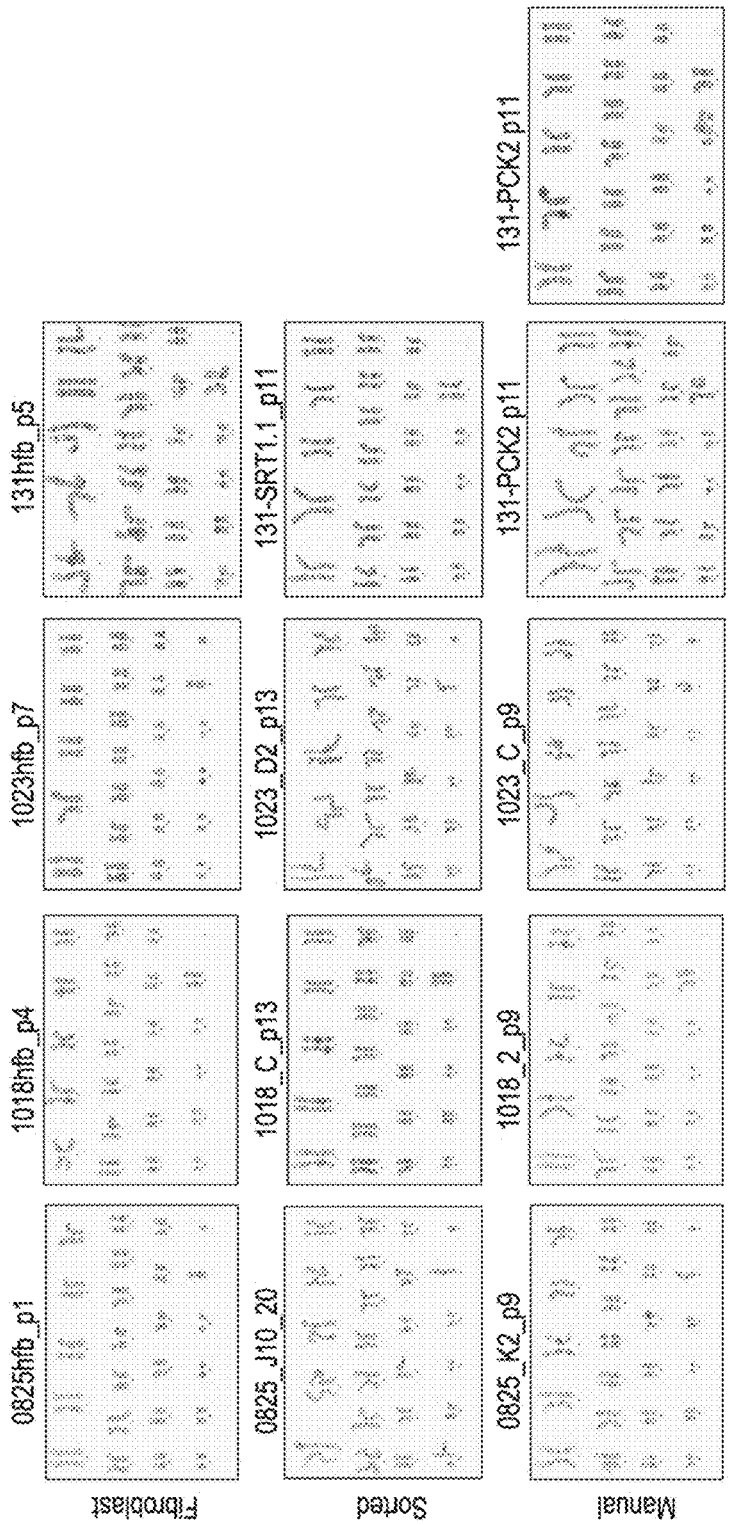

To further validate that the FACS surface marker panel can be used for multiple reprogramming methods, fibroblasts were reprogrammed using non-integrating Sendai viral constructs carrying the four Yamanaka reprogramming factors and compared the FACS and manual derivation methods to determine if there were differences between the integrating and non-integrating reprogramming systems. For these studies, an adult fibroblast line (131) was infected and subjected to either FACS sorting at 11 dpi or to manual derivation. At 11 dpi, the fraction of SSEA4POSTRA-1-60POS cells that were also CD13POS was significantly lower (1-2%) than with retroviral reprogramming (37-54%, FIG. 12C), suggesting an accelerated rate of reprogramming. As before with the retroviral lines, several clones from each derivation technique were selected and expanded for characterization following confirmation that the parent fibroblast line possessed a normal karyotype and DNA fingerprint, and was free of contaminating cell lines (FIGS. 18A-18B).

Figure 16A:
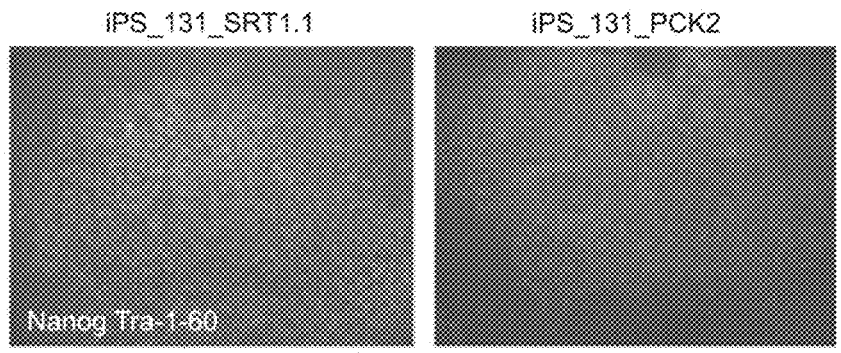
FIGS. 16A-16G. Characterization of Fluorescence Activated Cell Sorted and Manually Derived IPSC Lines by Sendai virus. Immunofluroescence microscopy of the 1001.131.01 line demonstrating expression of common markers of pluripotency by FACS or Manually Derived IPSC lines. Nuclear Transcription Factors shown in Green, Surface Markers shown in Red, Nucleus stained with DAPI in Blue (FIG. 16A) Nanog/Tra-1-60 (FIG. 16B) Oct4/Tra-1-81 (FIG. 16C) Sox2/SSEA4 (FIG. 16D) Oct4/Alkaline Phosphatase. 10× Magnification (FIG. 16E) Expression of endogenous pluripotent transcription factors (FIG. 16F) Silencing of viral transcription factors occur by passage 5.
Figure 16B:
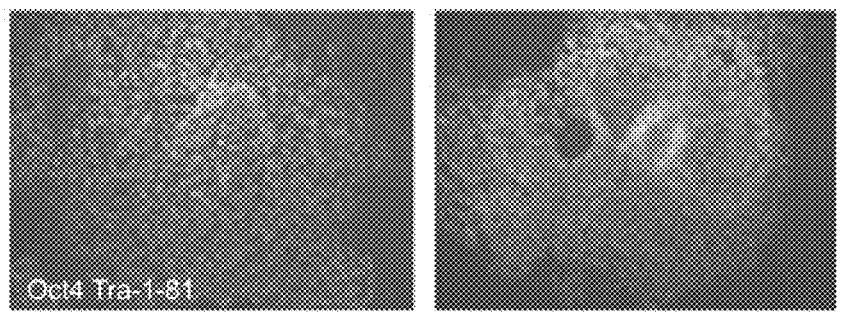
Figure 16C:
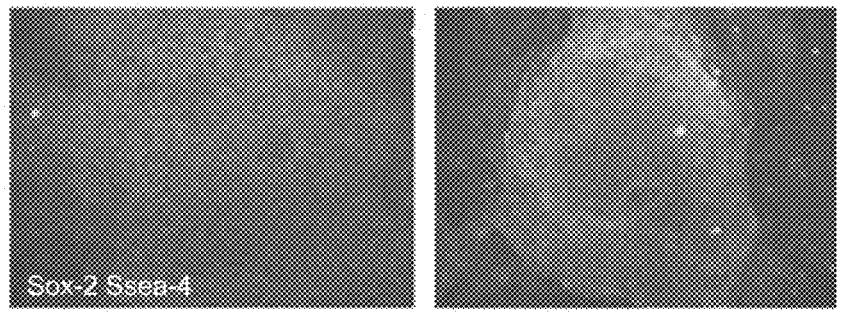
Figure 16D:
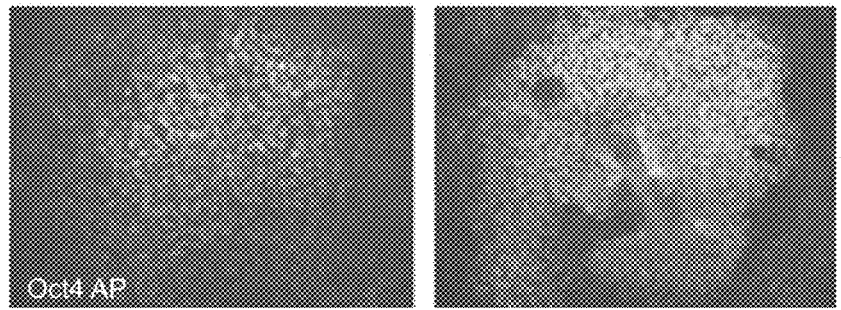
Figure 16E:
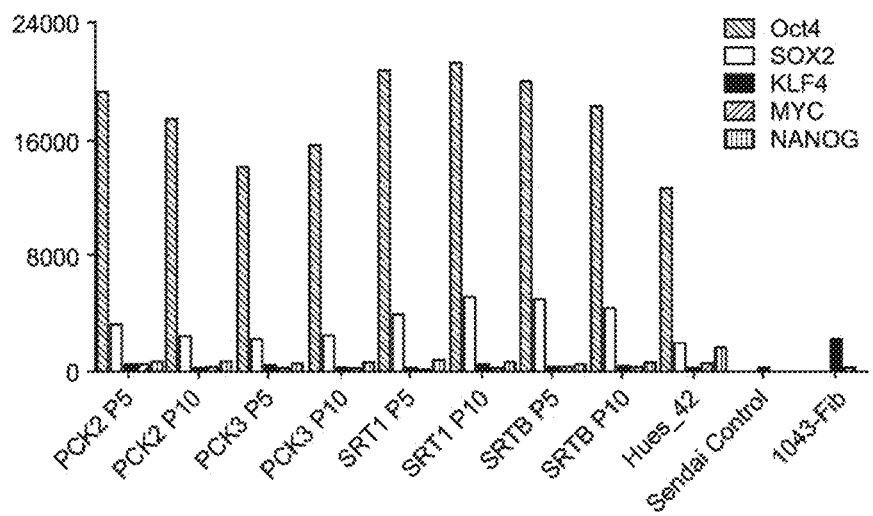
Figure 16F:
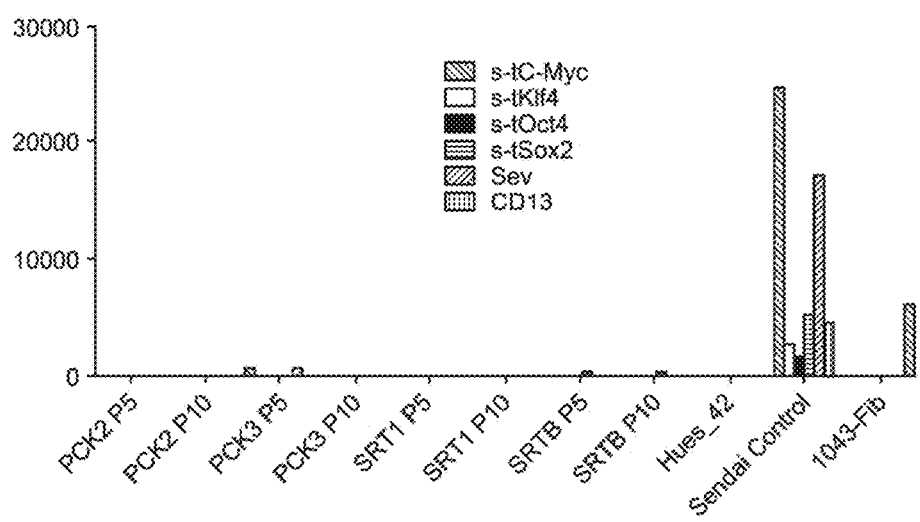

As before, individual clones selected from both FACS and manual derivation techniques expressed the common markers of pluripotency, as revealed by immunostaining FIGS. 16A-16D. In addition, the sorted (SRT) and picked (PCK) clones showed comparable levels of endogenous Oct4, Sox2, KLF4, MYC, and Nanog gene expression as early as passage 5, which remained relatively constant to passage 10, FIG. 16E. Similarly, though greatly reduced compared to control infected fibroblasts, Sendai virus gene expression was slightly above background at passage 5 in one sorted and one picked clone. However, this Sendai gene expression was eliminated by passage 10 in both cases, FIG. 16F. The full data set for these experiments is provided in Table S9 (see Kahler et al, 2013, incorporated herein by reference).

Immunofluroescence microscopy of the 1001.131.01 line demonstrating expression of common markers of pluripotency by FACS or Manually Derived IPSC lines. Nuclear Transcription Factors shown in Green, Surface Markers shown in Red, Nucleus stained with DAPI in Blue (A) Nanog/Tra-1-60 (B) Oct4/Tra-1-81 (C) Sox2/SSEA4 (D) Oct4/Alkaline Phosphatase. 10× Magnification (E) Expression of endogenous pluripotent transcription factors (F) Silencing of viral transcription factors occur by passage 5. (G) Expression levels of transcription factors common to the indicated germ layers from EB generated by the indicated IPSC lines.

Figure 16G:
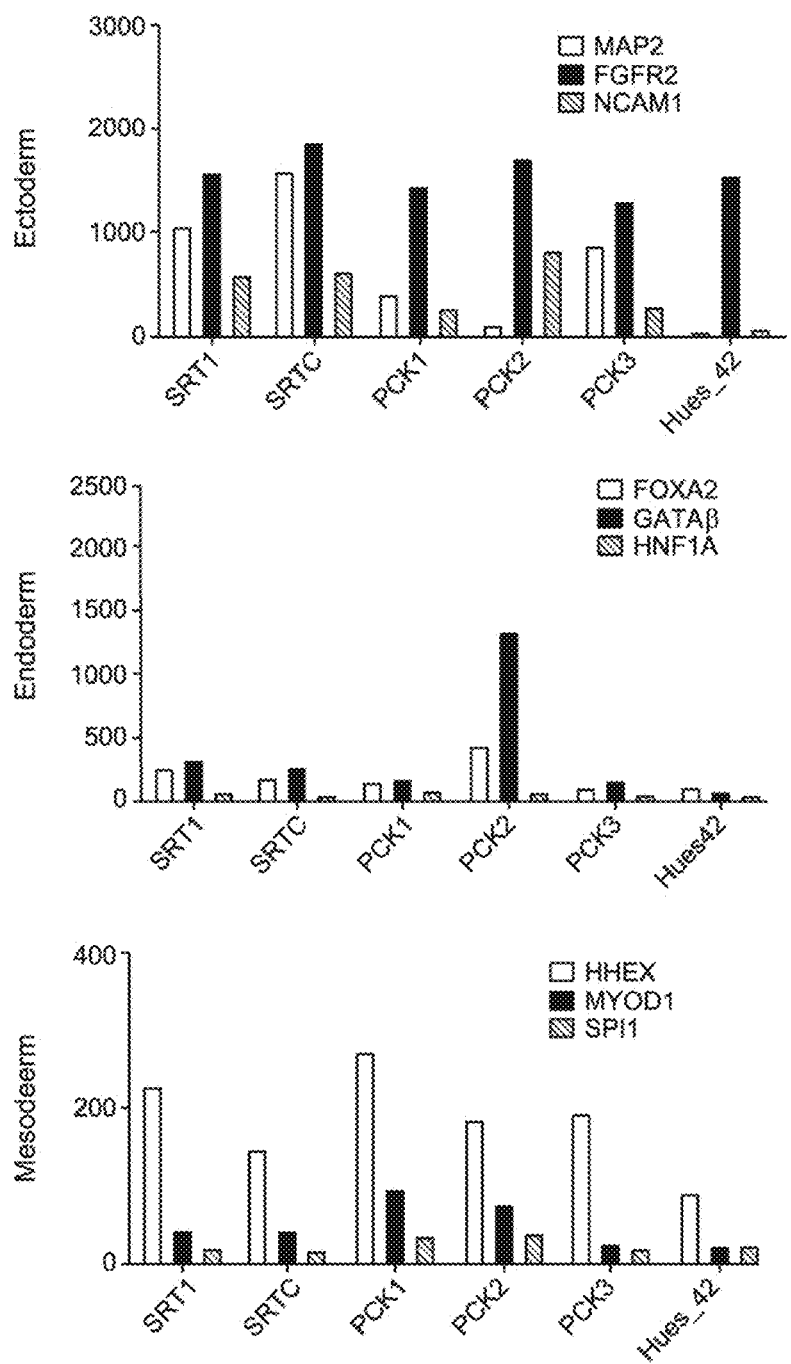
Figure 17:
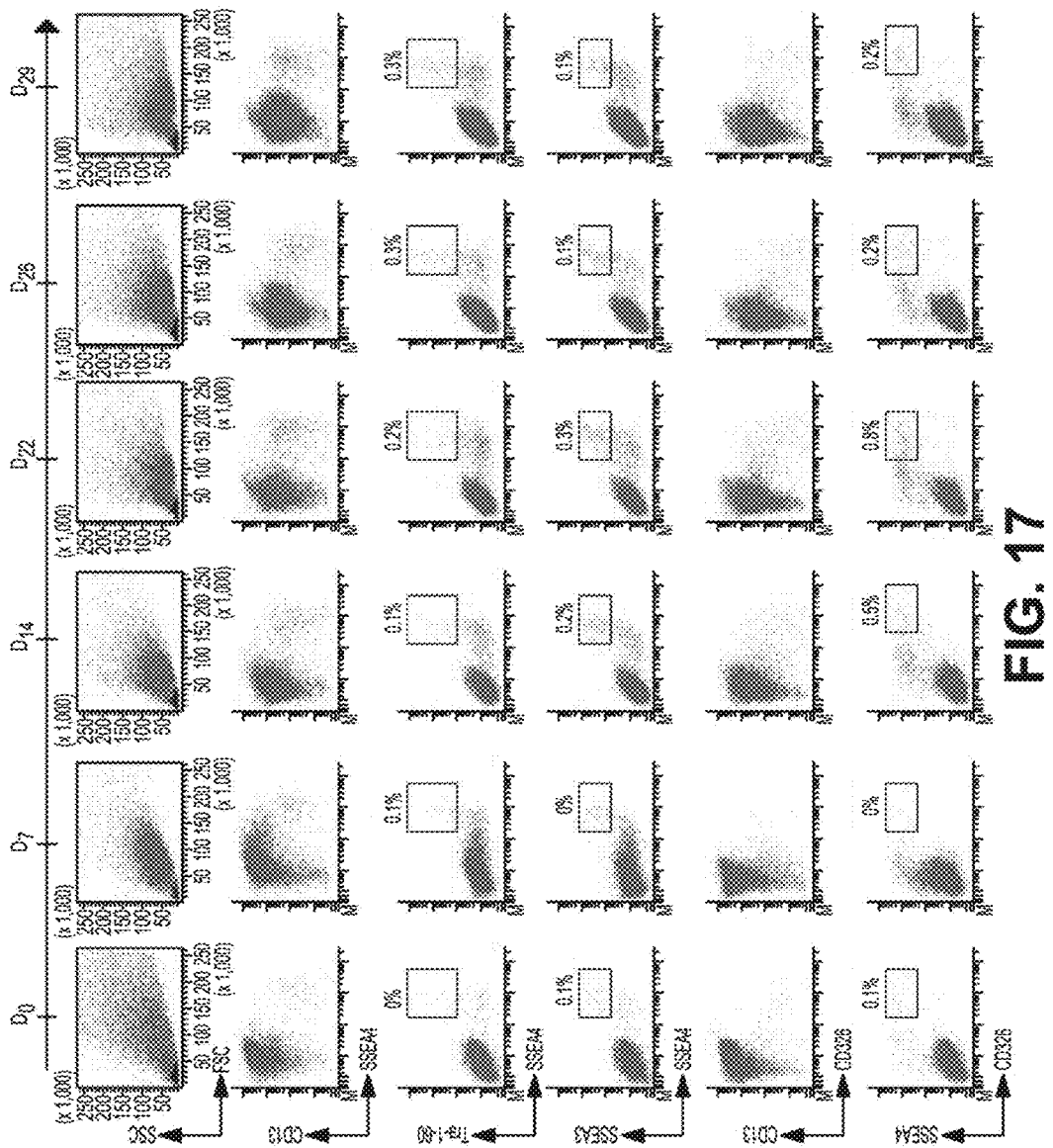
FIG. 17. Time Course analysis of retroviral reprogrammed fibroblasts. The 0825 foreskin fibroblast line was analyzed for changes in pluripotent surface marker expression by flow cytometry at ~7 dpi intervals following retroviral reprogramming to determine earliest time point at which the $CD13^{NEG}SSEA4^{POS}Tra\text{-}1\text{-}60^{POS}$ population appears. Values indicate percent of total cells in the culture expressing the indicated markers.

The in vitro differentiation potential of FACS and manually derived iPSC clones reprogrammed by the Sendai virus protocol was evaluated by EB formation and a lineage specific nCounter assay as above. Similar trends in gene expression were observed for clones derived under both methods, FIG. 16G. Both sorted and picked lines expressed levels of the ectodermal marker FGFR2 comparable to that of the control HUES42 line but higher levels of the mesodermal marker HHEX. Most clones showed levels of endodermal gene expression comparable to the HUES42 line with the exception of a manually derived clone that expressed higher levels of GATA6 than the remaining picked lines or FACS-derived lines. The full data set for these experiments is provided in Table S10 (see Kahler et al, 2013, incorporated herein by reference). Collectively, these data demonstrate that using FACS to purify the CD13NEGSSEA4POSTra-1-60POS cells from either retroviral or Sendai viral 4-factor reprogramming protocols consistently produces high quality iPSC lines.

Discussion

Clinical application of iPSC technology will require standardized and reproducible methods for each step of derivation and differentiation into relevant cell types. The majority of manually derived iPSC lines were found to contain CD13POS cells even after prolonged culture suggesting that these lines were either not fully reprogrammed or that CD13POS cells were carried over during passage. While both manual picking and FACS sorting methods [10] have been used to isolate reprogrammed pluripotent cells, inclusion of a negative selection marker such as CD13 has significant advantages in improving the purity of reprogrammed cultures. This fact was previously demonstrated [13]. Here, findings have validated a surface marker profile that enables selection of early reprogrammed iPSCs following reprogramming with either DNA-integrating or non-integrating viruses by FACS. Employing this strategy as early as 7 dpi isolates a highly purified starting population of fully functional CD13NEGSSEA4POSTra-1-60POS cells that are depleted of contaminating non-transduced and transformed fibroblasts. 228 individual iPSC lines have been successfully generated and characterized in 2 years from 76 fibroblast lines obtained from fresh biopsies, frozen stocks, and cell line repositories harvested from healthy and individuals possessing various forms of diabetes, neurodegenerative, cardiac and autoimmune diseases. Table 8, below.

TABLE 8

Summary of FACS Derived hIPSC Lines (S6)

| Model* | Cell Lines | Total Derivations | Retro | Sendai |
|---|---|---|---|---|
| Alzheimer | 11 | 20 | 19 | 1 |
| Parkinsons | 4 | 8 | 2 | 6 |
| FTD | 2 | 2 | 0 | 2 |
| GAN | 5 | 14 | 14 | 0 |
| Cardiac_LMNA | 3 | 7 | 6 | 1 |
| Cardiac_LongQT | 6 | 14 | 14 | 0 |
| MODY | 11 | 34 | 24 | 10 |
| T1D | 3 | 24 | 17 | 7 |
| T2D | 1 | 8 | 8 | 0 |
| MS_RR | 1 | 2 | 0 | 2 |
| MS_SP | 1 | 1 | 0 | 1 |
| Control | 28 | 94 | 51 | 43 |
| Totals | 76 | 228 | 155 | 73 |

*MS_RR Multiple Sclerosis Relapsing Remitting, MS_SP Multiple Sclerosis Secondary Progressive, FTD Frontal Temporal Dementia, GAN Giant Axonal Neuropathy, LMNA Lamin A/C, MODY Mature Onset Diabetes of the Young Moreover, FACS is routinely used for maintenance of established cell lines to remove differentiated cells and to dispense graded numbers of highly purified CD13NEGSSEA4POSTra-1-60POS populations cells for use in high-throughput derivation and screening assays which include directed differentiation and automated drug screening and phenotyping experiments. This is an important property because the results of these assays could be unequivocally attributed to a defined population of reprogrammed cells rather than to a heterogeneous mixture of cells. Taken together, these results suggest that isolation of the CD13NEGSSEA4POSTra-1-60POS population following reprogramming, including integrating or non-integrating viral technologies, allows for the rapid isolation of high quality iPSC lines. Negative selection against CD13POS cells significantly reduces the appearance of transformed cells in ipsc cultures and suggests that negative selection for a marker present on the starting somatic cells can be used to exclude non-reprogrammed or transformed cells from the cultures. Future studies will be needed to determine if this strategy applies to derivation from other somatic cell types or reprogramming methods.

References for Example 3

1. Takahashi K, Yamanaka S (2006) Induction of pluripotent stem cells from mouse embryonic and adult fibroblast cultures by defined factors. Cell 126: 663-676. doi: 10.1016/j.cell.2006.07.024.
2. Kiskinis E, Eggan K (2010) Progress toward the clinical application of patient-specific pluripotent stem cells. J Clin Invest 120: 51-59. doi: 10.1172/JCI40553.
3. Lee G, Papapetrou E P, Kim H, Chambers S M, Tomishima M J, et al. (2009) Modelling pathogenesis and treatment of familial dysautonomia using patient-specific iPSCs. Nature 461: 402-406. doi: 10.1038/nature08320.
4. Maehr R, Chen S, Snitow M, Ludwig T, Yagasaki L, et al. (2009) Generation of pluripotent stem cells from patients with type 1 diabetes. Proc Natl Acad Sci USA 106: 15768-15773. doi: 10.1073/pnas.0906894106.

5. Zhu S, Li W, Zhou H, Wei W, Ambasudhan R, et al. (2010) Reprogramming of Human Primary Somatic Cells by OCT4 and Chemical Compounds. Cell stem cell 7: 651-655. doi: 10.1016/j.stem.2010.11.015.
6. Inoue H, Yamanaka S (2011) The Use of Induced Pluripotent Stem Cells in Drug Development. Clin Pharmacol Ther 89(5): 655-661.
7. Smith Z D, Nachman I, Regev A, Meissner A (2010) Dynamic single-cell imaging of direct reprogramming reveals an early specifying event. Nat Biotechnol 28: 521-526. doi: 10.1038/nbt.1632.
8. Sorrell J M, Baber M A, Brinon L, Carrino D A, Seavolt M, et al. (2003) Production of a monoclonal antibody, DF-5, that identifies cells at the epithelial-mesenchymal interface in normal human skin. APN/C D13 is an epithelial-mesenchymal marker in skin. Exp Dermatol 12: 315-323. doi: 10.1034/j.1600-0625.2003.120312.x.
9. Chan E M, Ratanasirintrawoot S, Park I H, Manos P D, Loh Y H, et al. (2009) Live cell imaging distinguishes bona fide human iPS cells from partially reprogrammed cells. Nat Biotechnol 27: 1033-1037. doi: 10.1038/nbt.1580.
10. Valamehr B, Abujarour R, Robinson M, Le T, Robbins D, et al. (2012) A novel platform to enable the high-throughput derivation and characterization of feeder-free human iPSCs. Sci Rep 2: 213. doi: 10.1038/srep00213.
11. Noggle S, Fung H L, Gore A, Martinez H, Satriani K C, et al. (2011) Human oocytes reprogram somatic cells to a pluripotent state. Nature 478: 70-75. doi: 10.1038/nature10397.
12. Boulting G L, Kiskinis E, Croft G F, Amoroso M W, Oakley D H, et al. (2011) A functionally characterized test set of human induced pluripotent stem cells. Nat Biotechnol 29: 279-286. doi: 10.1038/nbt.1783.
13. Lin T, Ambasudhan R, Yuan X, Li W, Hilcove S, et al. (2009) A chemical platform for improved induction of human iPSCs. Nat Methods 6: 805-808. doi: 10.1038/nmeth.1393.
14. Pruszak J, Sonntag K C, Aung M H, Sanchez-Pernaute R, Isacson O (2007) Markers and methods for cell sorting of human embryonic stem cell-derived neural cell populations. Stem Cells 25: 2257-2268. doi: 10.1634/stemcells.2006-0744.
15. Bock C, Kiskinis E, Verstappen G, Gu H, Boulting G, et al. (2011) Reference Maps of human ES and iPS cell variation enable high-throughput characterization of pluripotent cell lines. Cell 144: 439-452. doi: 10.1016/j.cell.2010.12.032.
16. Sundberg M, Jansson L, Ketolainen J, Pihlajamaki H, Suuronen R, et al. (2009) CD marker expression profiles of human embryonic stem cells and their neural derivatives, determined using flow-cytometric analysis, reveal a novel CD marker for exclusion of pluripotent stem cells. Stem Cell Res 2: 113-124. doi: 10.1016/j.scr.2008.08.001.
17. Ng V Y, Ang S N, Chan J X, Choo A B (2010) Characterization of epithelial cell adhesion molecule as a surface marker on undifferentiated human embryonic stem cells. Stem Cells 28: 29-35. doi: 10.1002/stem.221.
18. Lu T Y, Lu R M, Liao M Y, Yu J, Chung C H, et al. (2010) Epithelial cell adhesion molecule regulation is associated with the maintenance of the undifferentiated phenotype of human embryonic stem cells. J Biol Chem 285: 8719-8732. doi: 10.1074/jbc.M109.077081.
19. Henderson J K, Draper J S, Baillie H S, Fishel S, Thomson J A, et al. (2002) Preimplantation human embryos and embryonic stem cells show comparable expression of stage-specific embryonic antigens. Stem Cells 20: 329-337. doi: 10.1634/stemcells.20-4-329.

Example 4

Generation of Large Genetically Diverse Cell Panels

A tissue procurement process has been established through which over 500 genetically diverse skin samples have been collected representing approximately 79% of the ethnic diversity needed to model the U.S. population (based on U.S. census data). 500 fibroblast lines have been generated from these samples and 300 iPSC lines using an automated system as described herein, with work continuing to generate more lines and to expand the sample set further. The cell lines produced are provided in 96-well microtiter plates with each well containing cells derived from a different individual.

Somatic cells are isolated, expanded, and analyzed for copy number variations (CNVs) to determine karyotype and a genomic identifier. High-content imaging is used to collect data cellular growth rates, cell counts, and morphology that guide reprogramming and differentiation. Non-genomic integrating reprogramming is accomplished using transduction of five individual mRNAs expressing Oct4, Sox2, Klf4, Lin28, and cMyc (see, for example, Warren et al., 2010). The process is performed in a chemically-defined, xeno-free, media to minimize potential sources of variability in resulting cell populations. Clonal selection is achieved using a multi-stage process including a magnetic bead based enrichment scheme where non-reprogrammed cells are depleted from the cultures of iPSCs by negative selection of CD13 and high-content imaging of surface marker Tra-1-60. The resulting iPSCs are transferred to a 96-well plate where colony growth is monitored using the automated high-content imager. For further characterization of the iPSCs, transcriptional analysis is performed by direct mRNA measurements of a set of 100 gene probes covering pluripotency, all three germ layers, sex, and housekeeping pathways. This analysis is performed on the iPSCs as well as embryoid bodies (EBs) generated from them.

Example 5

A Fully Automated, High Throughput Platform for iPS Cell Derivation and Characterization Induced pluripotent stem cells (iPSCs) have become an essential tool for modeling how causal genetic variants impact cellular function in disease and are an emerging source of tissue for transplantation medicine. Unfortunately, the preparation of somatic cells, their reprogramming and the subsequent verification of iPSC pluripotency are laborious, manual processes that limit the scale and level of reproducibility of this technology. The present Example describes a robotic platform for iPSC reprogramming that enables high-throughput conversion of skin biopsies into iPSC lines with minimal human intervention. Importantly, iPSC lines manufactured by this automated system exhibited significantly less variation than those produced manually. This robotic platform thus enables the application of iPSCs to population-scale biomedical problems including the study of complex genetic disease and the development of personalized medicines.

Introduction

The reprogramming of somatic cells into induced pluripotent stem cells (iPSCs), coupled with the development of methods for directing stem cell differentiation into relevant cell types, offers an unprecedented opportunity to study the cellular phenotypes that underlie disease (Takahashi and Yamanaka, 2006; Takahashi et al., 2007; Rubin, 2008; Colman and Dreesen, 2009; Nishikawa, Goldstein and Nierras, 2008; Daley, 2010). Study of these emerging "stem cell disease models" has led to new mechanistic insights into a wide variety of conditions ranging from neurological disorders to cardiovascular and infectious disease (Robinton and Daley, 2012).

One limitation of the application of these methods is the substantial level of variation between different stem cell lines that arises during the reprogramming progress, affecting both functional properties of the lines and their performance in disease-related studies. As a result, most successful reports have relied on evaluation of several cell lines derived from individuals harboring genetic variants of high penetrance. If stem cell technologies are to be applied to the study of common genetic variants that confer only modest effects but have been shown to be important contributors to conditions such as schizophrenia, and metabolic disease (Morris et al., 2012; Ripke et al., 2013), it will be essential to minimize variation arising during reprogramming, subsequent stem cell expansion and differentiation. Reduction in this source of variation would increase resolution of the phenotypic effects contributed by the genotype of a particular individual.

Presently, it remains unclear what fraction of or the extent to which variation between iPS cell lines arises from technical aspects of the procedure, rather than from uncontrollable, stochastic epigenetic events that occur during reprogramming. Possible contributors to functional variation include genetic background and tissue source, {reviewed in (Cahan and Daley, 2013; Nestor and Noggle, 2013); reprogramming factor stoichiometry during delivery (Carey et al., 2011); and stress during culture (Liang and Zhang, 2013). Additionally, a growing number of methods are used to deliver reprogramming factors and various cell culture media and substrates have been used for downstream expansion (Chen et al., 2014), This lack of standardization likely introduces additional variability among cell lines established by different laboratories (Newman and Cooper, 2010). As automation has improved precision and scalability in many areas of biomedical research (Meldrum, 2000; Meldrum, 2000; Lander et al., 2001), developing a fully automated platform for iPS cell derivation, expansion and differentiation would allow identification of and restriction of the factors contributing to variability in stem cell line behavior.

The present Example describes the development of three integrated robotic systems that automate the entire process of deriving iPSC lines. This integrated reprogramming platform was used to systematically explore several variables that have been reported to be important sources of variation in the reprogramming process. Importantly, automation alone was found to eliminate a significant portion of the variation in differentiation propensity exhibited between iPS cell lines.

Results

Automated Fibroblast Production

Figure 20A:
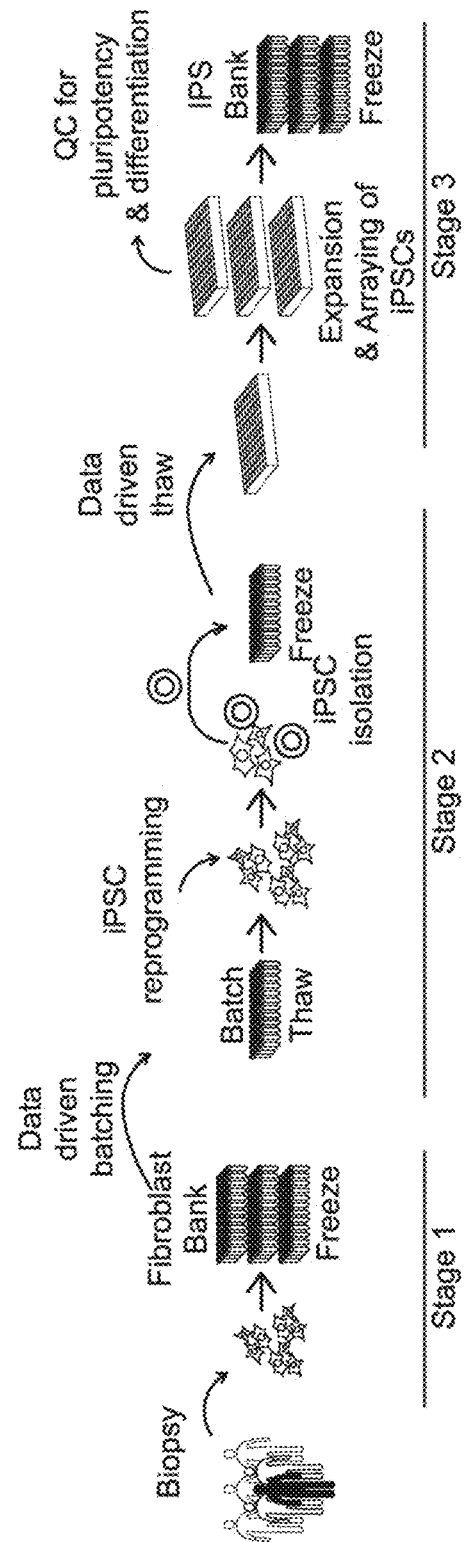
Figure 20B:

As a first step in developing an integrated and automated process for deriving iPSCs (FIG. 20A), a robotic system has been established for isolating skin fibroblasts from volunteer biopsies and tissue samples (FIG. 20A, Stage 1). This system processes tissue under quarantine conditions prior to mycoplasma testing, allowing for the expansion and freezing of fibroblasts before being transferred into a cleaner culture environment. The system is housed in a BSL II biosafety hood (FIG. 20B) and integrates a robotic liquid handler with an automated centrifuge, microscope and incubator. The biopsy processing system is complemented by a second, independent liquid handling robot connected to a luminescence plate reader, used to conduct mycoplasma detection assays.

Figure 20C:
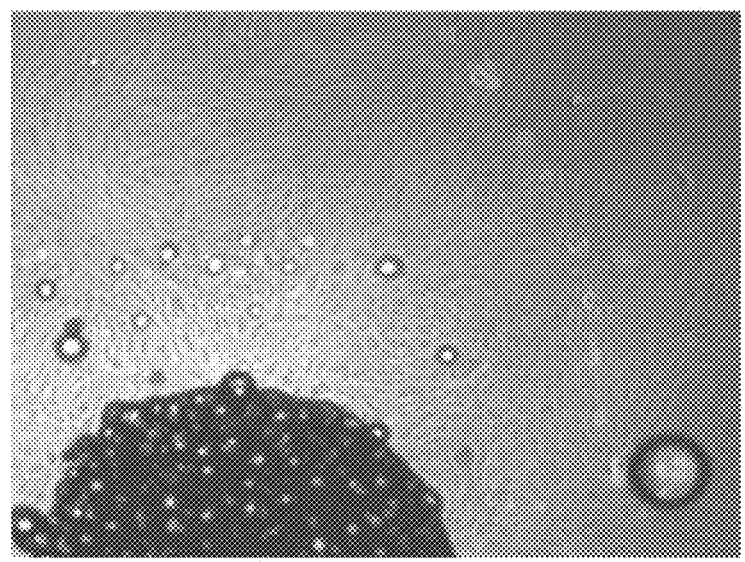
Figure 27A:
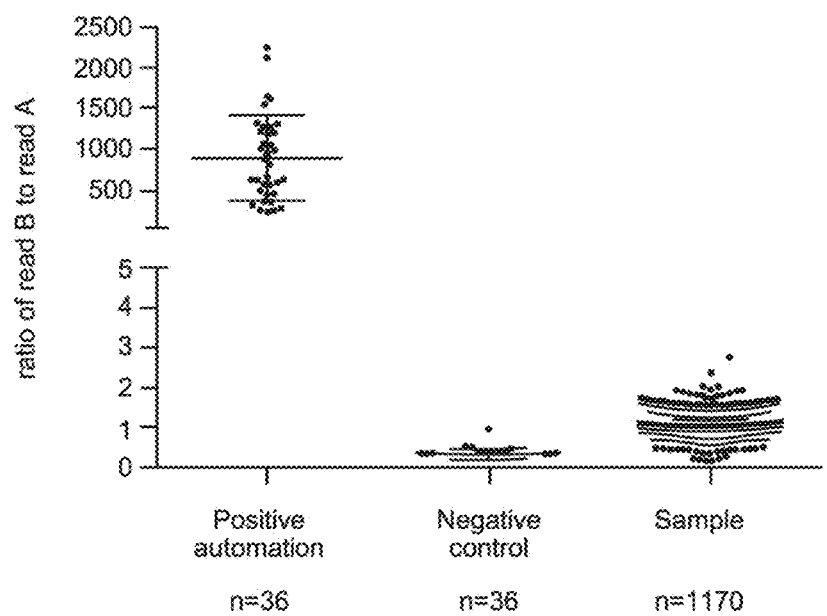
FIGS. 27A-27B.

For fibroblast derivation, biopsies and tissue samples were manually dissected and placed into individual plates filled with a low serum culture media selected to eliminate batch to batch variation in serum. In addition, low serum medium is more compatible with down-stream reprogramming using modified RNAs (Warren et al., 2010). All further maintenance, including passaging and feeding, was performed via automation. Every five days biopsy outgrowth was measured through automated image acquisition and quantification (FIGS. 20C and 20D). Media exchanges and media collection for mycoplasma testing were also handled in an automated fashion. Multi-well plates of media collected for mycoplasma testing were then placed onto the second platform for automated testing (FIG. 27A). Following completion of mycoplasma testing, fibroblast outgrowths were enzymatically passaged by the system into new plates for further expansion.

After one passage, in order to minimize population doublings and increase reprogramming potential (Utikal et al., 2009), fibroblasts were frozen into multiple 2D barcoded cryovials and banked to produce low passage frozen stocks. The automated imaging system first identified wells with outgrowth (FIG. 20Di) and area of the culture plate occupied to calculate a confluence value (FIG. 20Dii). In some experiments, DNA staining and algorithms were used for identifying and counting nuclei to extrapolate cell counts from confluence values using standard curves (FIG. 20Diii and 20Div). This allowed non-invasive calculation of growth rates of the fibroblasts. As early experiments suggested that fewer than 100,000 cells were needed for reprogramming, yields of fibroblasts from outgrowths at this early stage of growth were sufficient for the subsequent reprogramming steps (778,216 cells per passaged well of a 6-well dish s.d.=88,813, n=60). This allowed the cells to be frozen at the second passage. One vial was typically reserved for iPS generation through short-term storage within an automated −80° C. sample access manager, with the remainder banked in liquid nitrogen. An average of 363,000 fibroblasts were produced per sample (s.d. of 305,000, n=168) with minimal expansion (passaging of the biopsy outgrowth results in p1 cultures). The average total number of cells frozen into a single cryotube at the time of freezing was 121,437 cells which upon thawing had an average viability of 84%±1.43% (mean±SEM, n=167).

Figure 27B:
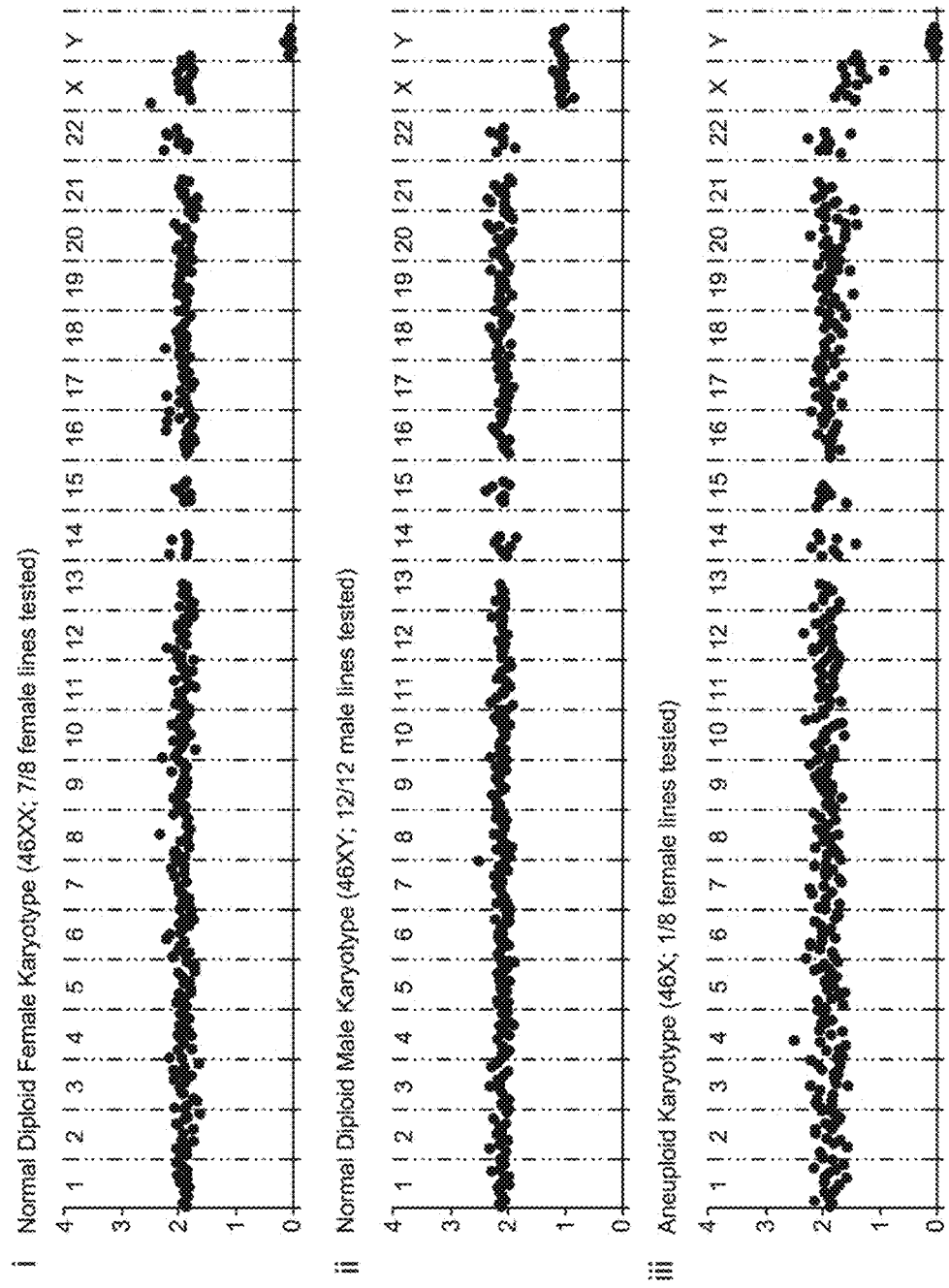

During development of the automated system, a total of 640 skin tissue samples were processed with 89.4% producing fibroblasts that were successfully frozen (n=572). Failures that arose were primarily due to either bacterial or fungal contamination (4.7%, n=30) attributable to sample handling before entering the system, and were minimally associated with equipment or manual process failures (3.2%, n=21). Only 2.7% (n=17) did not show outgrowth, which could be attributed to the small size of the biopsy, lacking an overt dermal layer. Using a Nanostring nCounter karyotyping assay that can detect aneuploidy as well as large chromosomal gains/losses (FIG. 27B), 20 randomly selected, representative fibroblast samples were tested. The majority of samples (19/20, 95%) showed a normal diploid karyotype (46XX or 46XY). Thus, the automated process can successfully derive, expand and cryopreserve high quality, low passage fibroblasts which can be banked for further processing or future use.

Figure 20E:
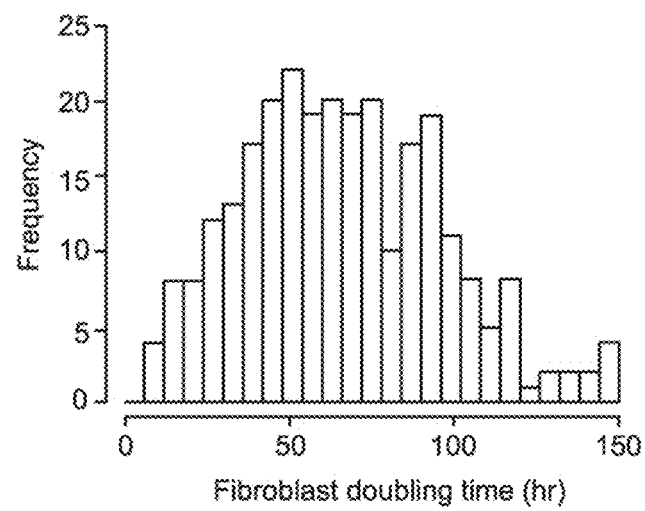
Figure 20F:
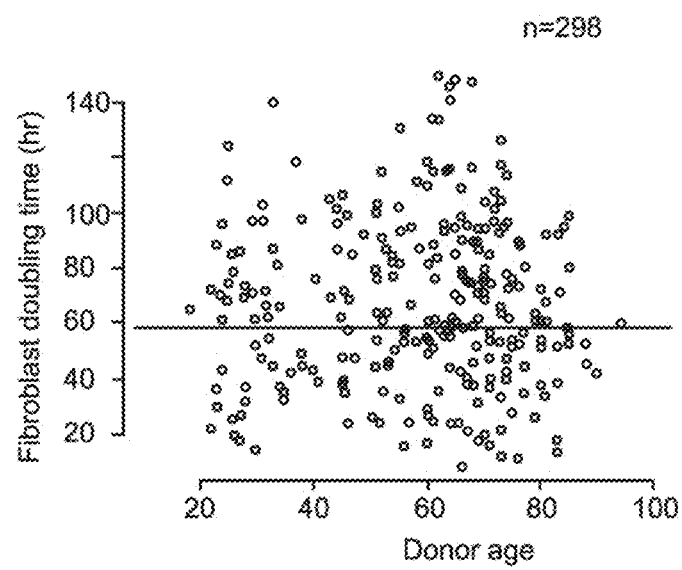
Figure 20G:
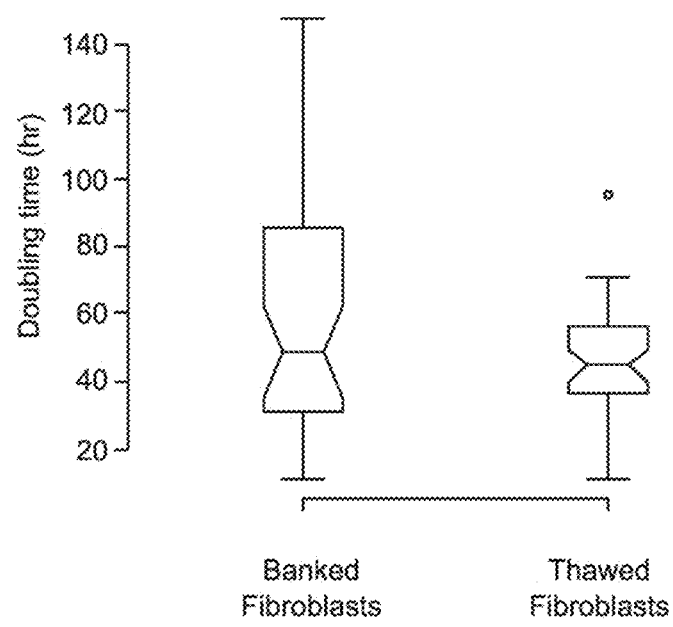

To monitor fibroblast growth rates and cell culture densities of the resulting plates, the automated imaging system was used (FIG. 20Dii). Various approaches were tested for monitoring fibroblast growth and found that confluence measurements (percent of well covered by cells) were sufficient to allow reliable tracking of growth rates. Frequent measurements allowed for doubling time calculations to be performed during log phase growth. Under these low-serum conditions, average fibroblast doubling time was 66 hours (s.d.=30.2 h, n=298). (FIG. 20E). This modest doubling time is not believed to be a product of growth on the automated system per se as when a subset of these samples was robotically fed with serum-containing media the doubling time was decreased to 45.8 hr (s.d.=16.5 h, n=33). While the mean doubling rates did not significantly differ from their growth rates prior to freezing (p=0.69), the variation decreased by almost half upon recovery in serum (% CV=61% before vs. 36% after thaw) (FIG. 20G). As doubling rate did not correlate with age (FIG. 20F), this suggests it should be possible to group samples with similar growth characteristics soon after initial outgrowth to establish cultures for downstream automated reprogramming as described below.

Automated iPS Reprogramming

Figure 21A:
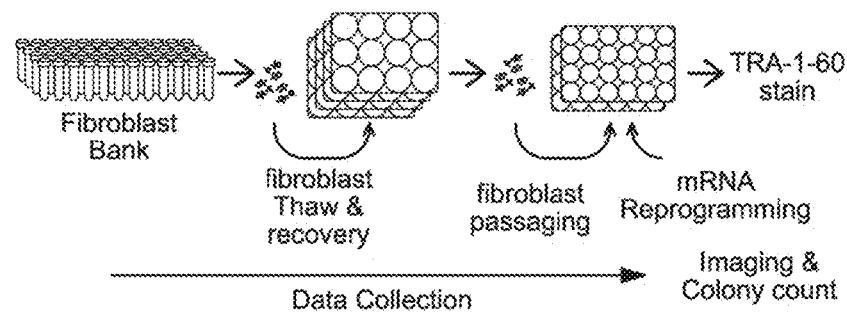
FIGS. 21A-21I. Automated reprogramming.

To enable automated reprogramming, an integrated robotic platform was constructed with the capacity to thaw fibroblast samples, deliver reprogramming factors via Sendai virus transduction (Fusaki et al., 2009) or modified mRNA transfection (Warren et al., 2010), perform magnetic selection of reprogrammed cells, and finally image cultures to identify nacent stem cell colonies after surface marker staining (FIG. 20A, Stage 2, and FIG. 21A).

Figure 28A:
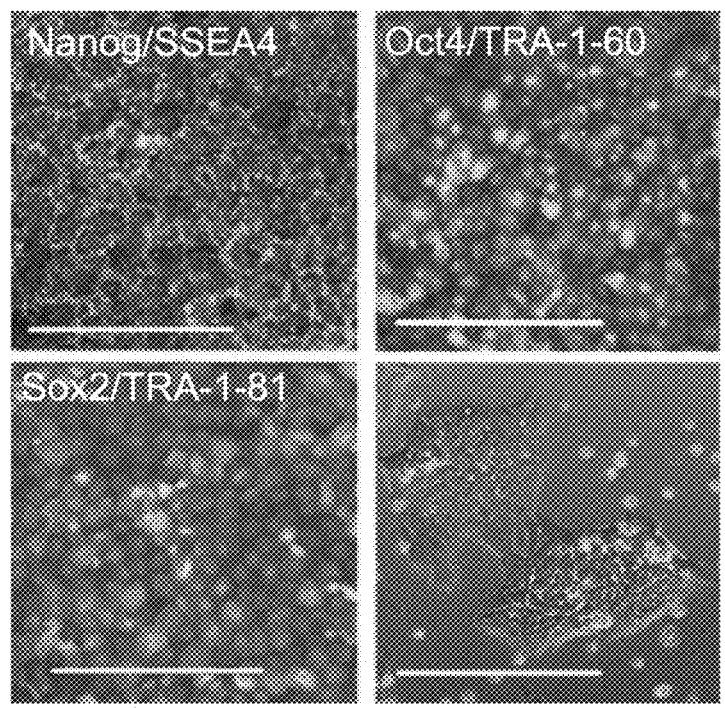
FIGS. 28A-28E. Comparisons of automated reprogramming by mRNA and Sendai.
Figure 28B:
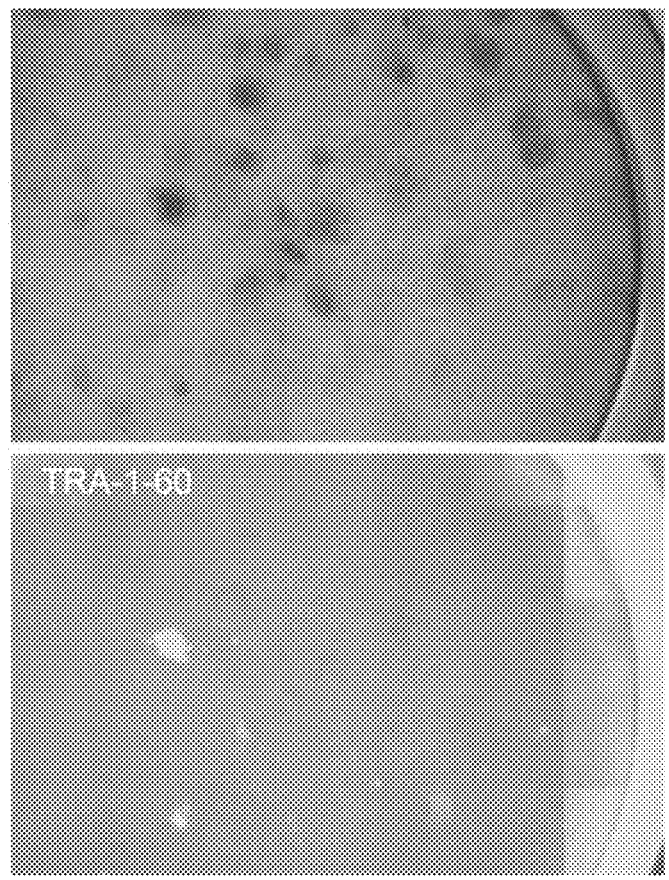
Figure 28C:
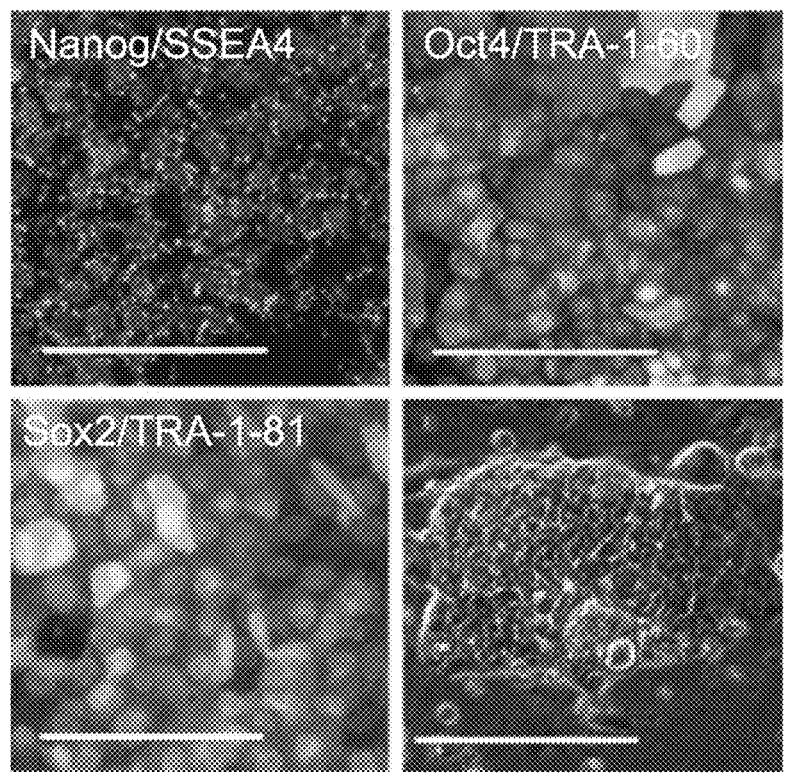
Figure 28D:
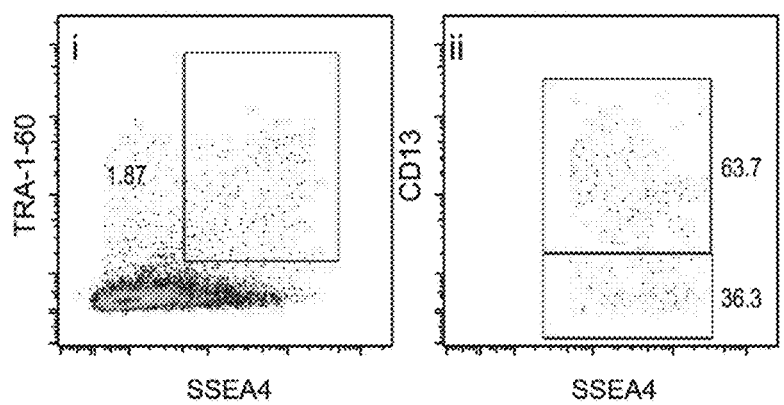
Figure 28E:
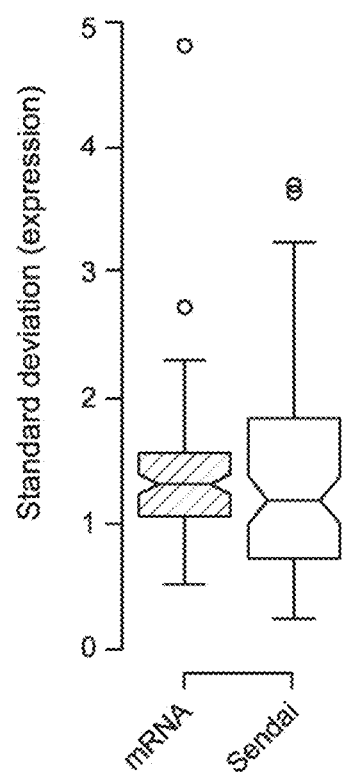

First, a viral infection method using Sendai virus (Fusaki et al., 2009) was adapted to the automated liquid handling system. Automated delivery of Sendai virus to 50,000 fibroblasts at a moiety of infection of 4 resulted in 2 to 10 TRA-1-60 positive colonies per well under feeder free conditions. Similar efficiencies were obtained by manual delivery under these conditions. Several lines were derived by manual picking of TRA-1-60 positive colonies after automated infection and appearance of colonies (FIG. 28B) before continuing the culture of the picked colonies on the automated system. Established cultures from these colonies expressed common markers of pluripotency, including Nanog, Oct4, SSEA4 and TRA-1-60 (FIG. 28C). Consistent with previous results (Kahler et al., 2013), automated Sendai infections induce TRA-1-60 positive cells that retain surface expression of a fibroblast marker with an average of 58.2% (n=12) of TRA-1-60+/SSEA4+ were also CD13+(FIG. 28D). Further, after differentiation in EB assays (see below), significant clonal variability was found in gene expression that appeared to coincide with residual Sendai transgene expression remaining in the lines between passages 5 and 10 (FIG. 28E). Between passages 11 and 12, the Sendai lines were incubated at 38.5° C. to encourage Sendai inactivation (specifically C-Myc) at which point a decrease in Sendai virus expression was observed. However, after a further 2-3 passages, the lines were reanalyzed and Sendai transgene expression had again increased. Additionally, variability in toxicity was noted among different lots and batches of virus. Together, these results suggested that, while it is possible to use Sendai virus to reprogram fibroblasts by automated methods, it was unlikely to emerge as a preferred method.

Figure 21B:
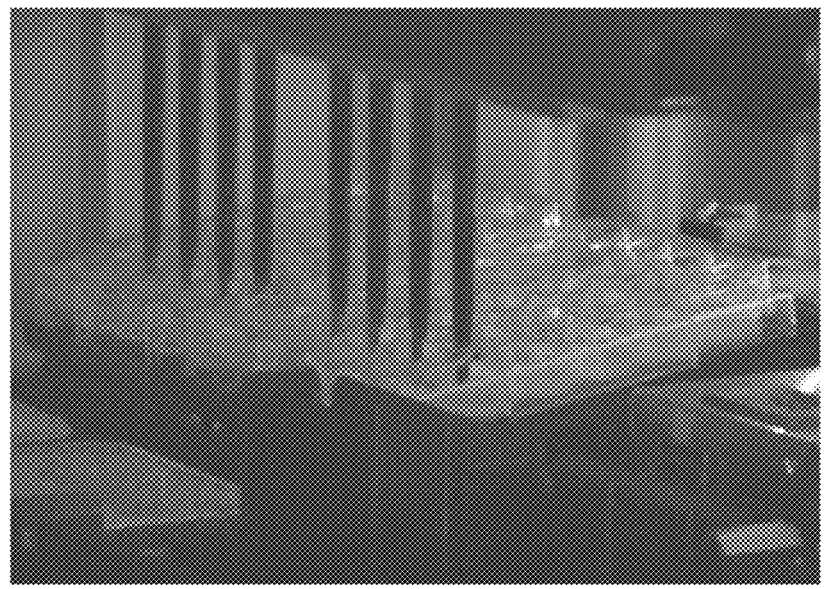

Next, transfection methods were adapted to deliver modified mRNA (Warren et al., 2010) to reprogram fibroblasts by automation. After automated passaging, fibroblasts were treated via automated media exchange with B18R to block interferon response. The liquid handling system was also used to deliver transfection mix containing miRNA (Miyoshi et al., 2011) followed by 10 daily transfections of base modified mRNA encoding Oct4, Klf4, Sox2, c-Myc, Lin-28, and nuclear GFP (nGFP) (FIG. 21B). The miRNA was also included together with the fourth mRNA transfection. Human fibroblast conditioned media was replaced daily by automated media exchanges before each transfection. Six days after final transfection the cultures were transitioned to a feeder-free hES cell culture medium using automated partial media exchanges. This integrated automated process was tested by performing 20 consecutive experimental reprogramming runs of 24 fibroblast samples in duplicate and under varying conditions, for a total of 960 independent reprogramming experiments (FIG. 21A).

Figure 21C:
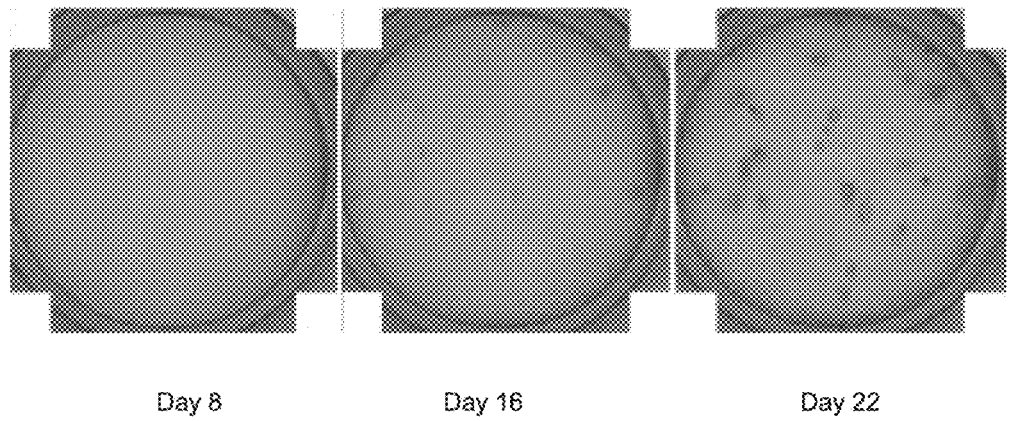
Figure 21D:
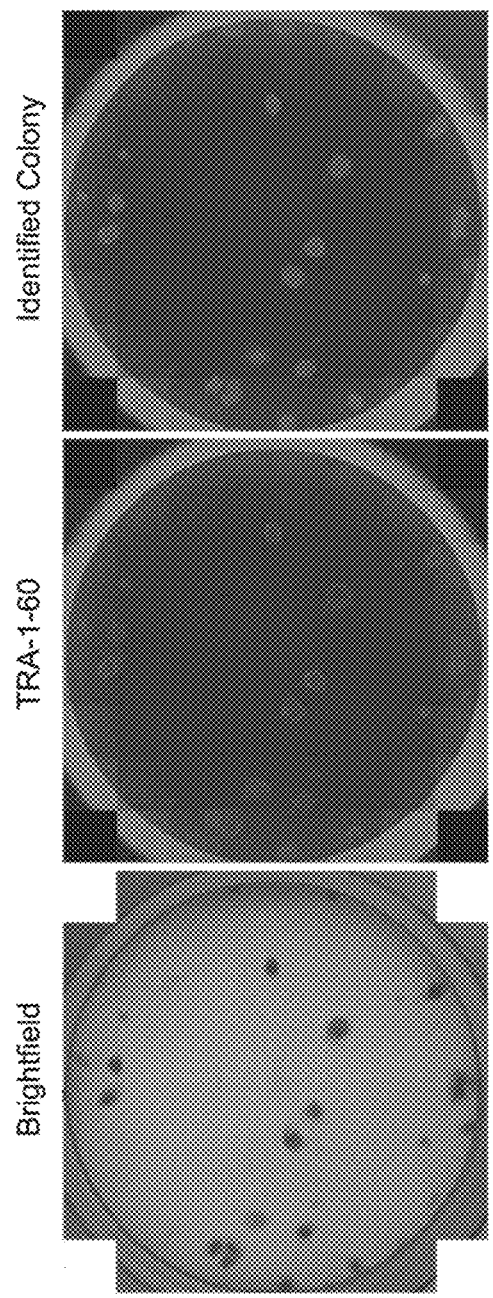
Figure 21E:
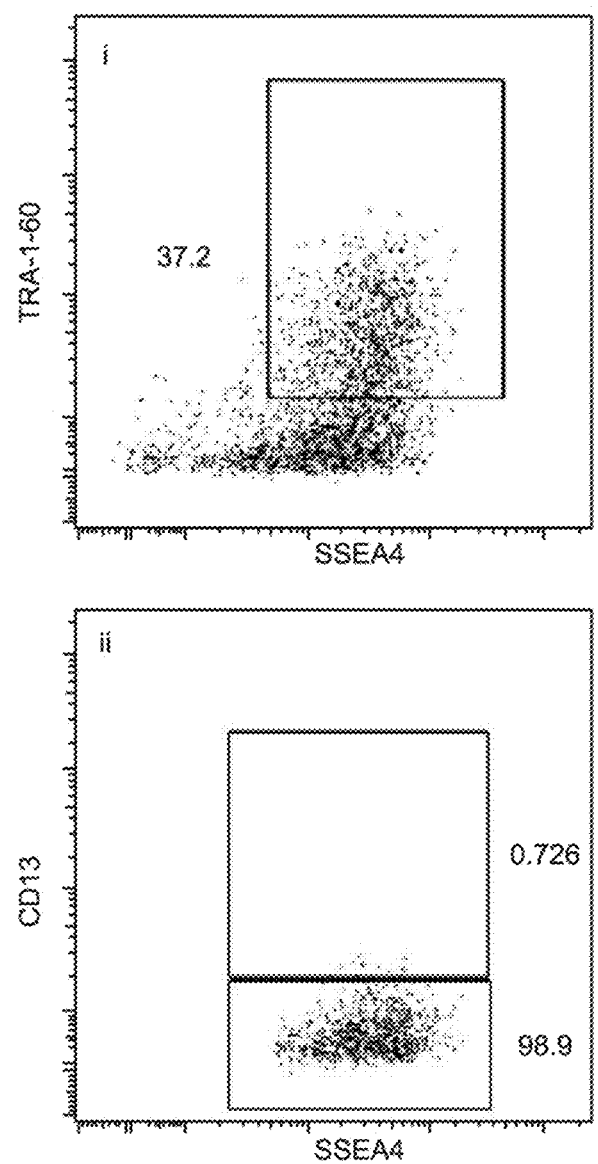
Figure 21F:
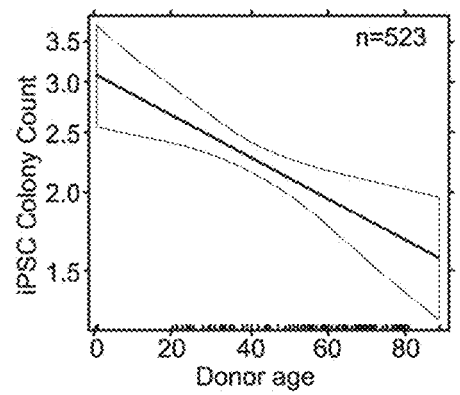
Figure 21G:
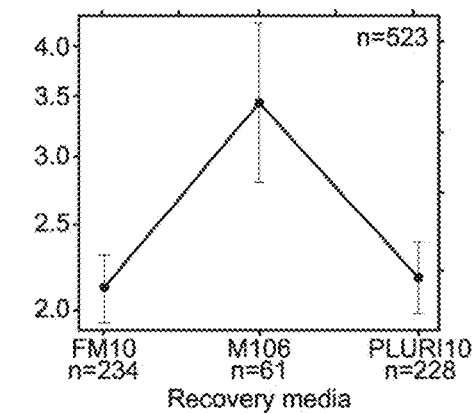
Figure 21H:
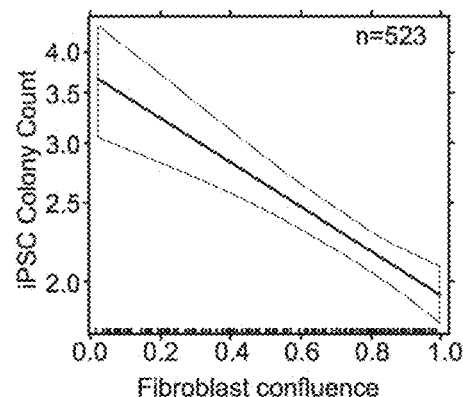
Figure 21I:
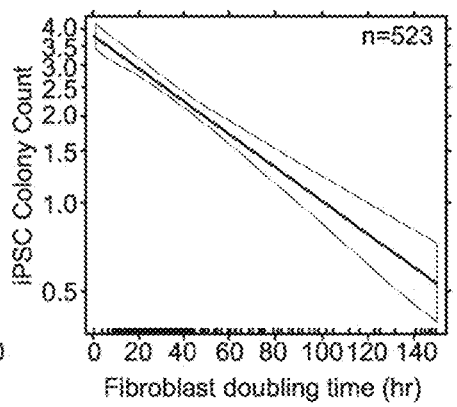

In addition to adult donor fibroblasts, BJ foreskin fibroblasts were included in each run to control for run to run variability. Following this protocol, nascent iPSC colonies were consistently observed between 16 and 22 days of culture (FIGS. 21C, 21D). Established cultures demonstrated pluripotent hESC-like morphology and expressed common markers of pluripotency, including Nanog, Oct4, Sox2, SSEA4 and TRA-1-81 (FIG. 28A). Over all runs, an average of 7 TRA-1-60+ colonies were induced per well (n=299, range 1-40 colonies). These cultures contained a high proportion of TRA-1-60+/SSEA4+ cells and an average of 9.7% (n=38) of cells retained CD13 (FIG. 21E). Reprogramming efficiency was between 0.001% and 0.16% for successful attempts per plated somatic cell, consistent with previous results obtained under feeder free conditions (Warren et al., 2012), and was slightly higher for control BJ fibroblasts (0.43%) than for adult fibroblast cultures (0.014%).

The next analysis investigated the factors that correlated with reprogramming success rates. The number of colonies produced per well was determined after mRNA mediated reprogramming production runs and several parameters were compared during fibroblast recovery and reprogramming. The number of colonies was determined by automated image based colony identification and counting after TRA-1-60 live cell surface staining of the cultures (FIG. 21D). Although fibroblasts from older donors were successfully reprogrammed, increasing donor age negatively influenced the number of colonies produced. Additionally, slower proliferation rates during reprogramming as well as the presence of serum during fibroblast recovery and passaging all had a negative impact on the number of colonies produced, when controlling for other variables included in the analysis (FIG. 21F-I). This is consistent with a transition from serum containing media to serum-free media reducing proliferation rates important for reprogramming success. Together, these results define conditions that allow for the derivation of iPSCs using this automated process.

Automated iPS Purification

Figure 22A:
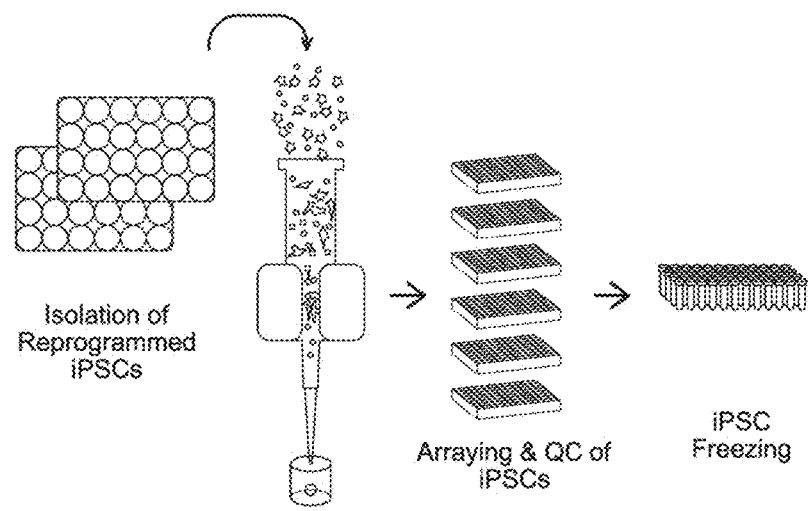
FIGS. 22A-22G. Automated iPSC purification and arraying.
Figure 22B:
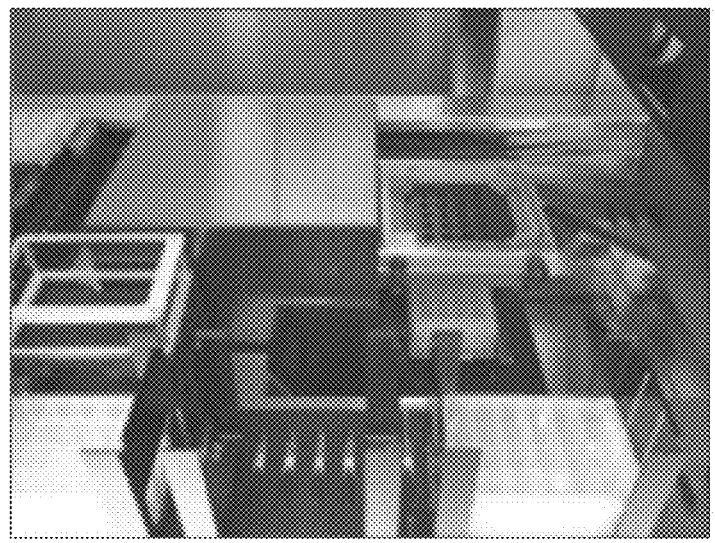
Figure 29A:
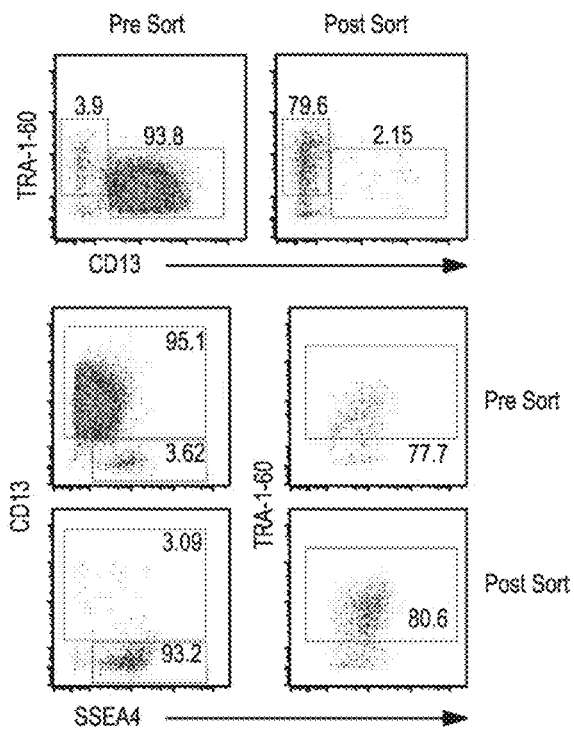
FIGS. 29A-29C.
Figure 29C:
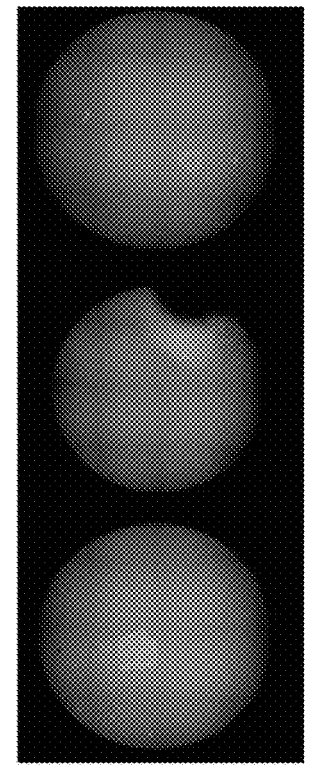
Figure 29B:
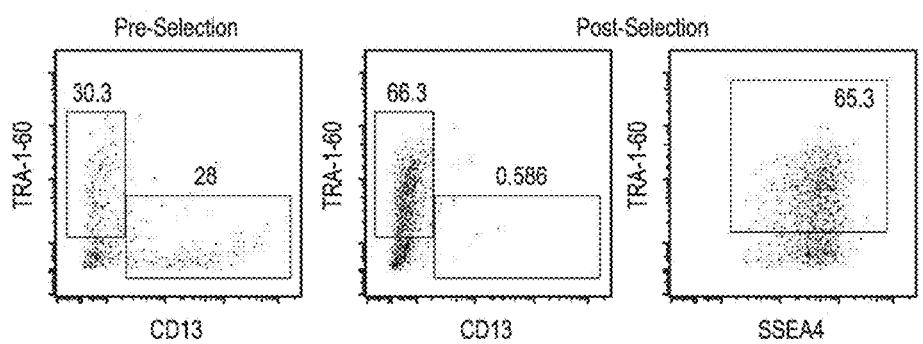

FACS methods have previously been described for enriching reprogrammed iPSCs using a standard panel of cell surface markers (Example 3 above, and Kahler et al., 2013). In particular, incompletely reprogrammed cells often retain surface expression of fibroblast specific markers. To achieve a greater throughput, reprogrammed iPS cells were enriched using automated magnetic bead based negative selection to remove incompletely reprogrammed cells (FIG. 22A). Through the integration of a MultiMACS multi-well magnetic bead separation device into the liquid handling system, negative selection was used to, in parallel process 24 lines at a time (FIG. 22B). To test the system, spike in experiments were performed with an iPS cell-to-fibroblast ratio of between 1:20 and 1:100 that demonstrated that a 6-fold fibroblast depletion and an average 47-fold iPS cell enrichment could be achieved (FIG. 29A). In practice, the magnetic bead selection process resulted in an average of ~30% CD13-/SSEA4+/TRA-1-60+ cells following completion of the automated mRNA reprogramming protocol (FIG. 29B).

Figure 22C:
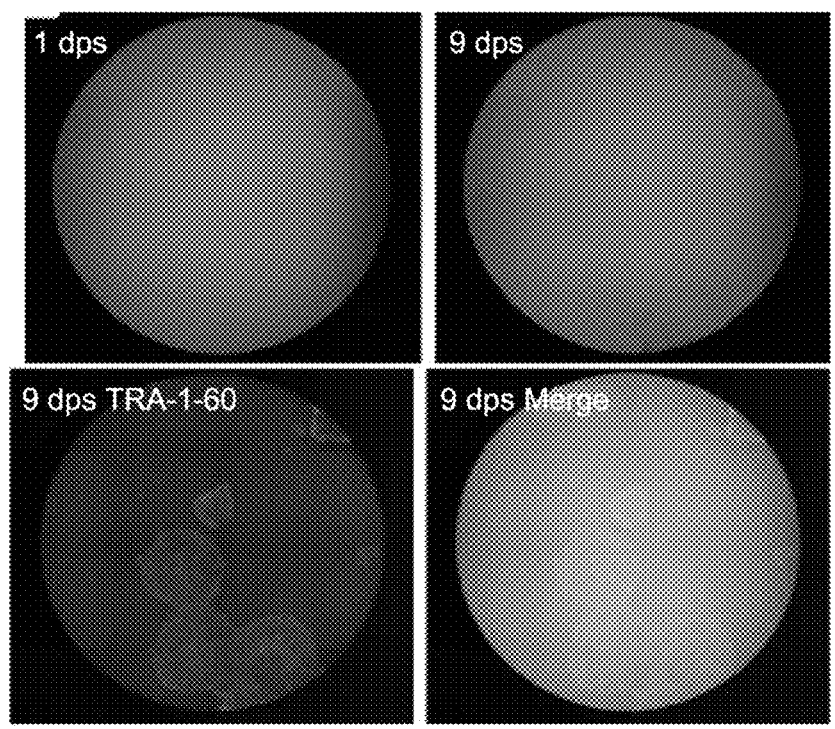
Figure 22D:
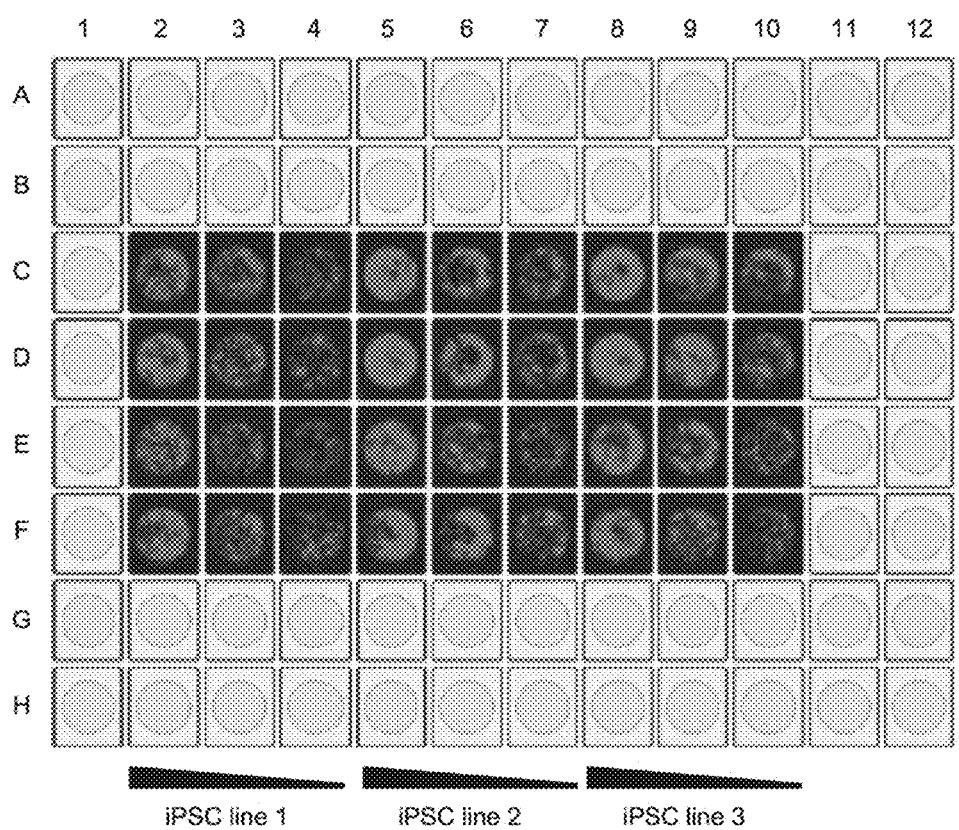
Figure 22E:
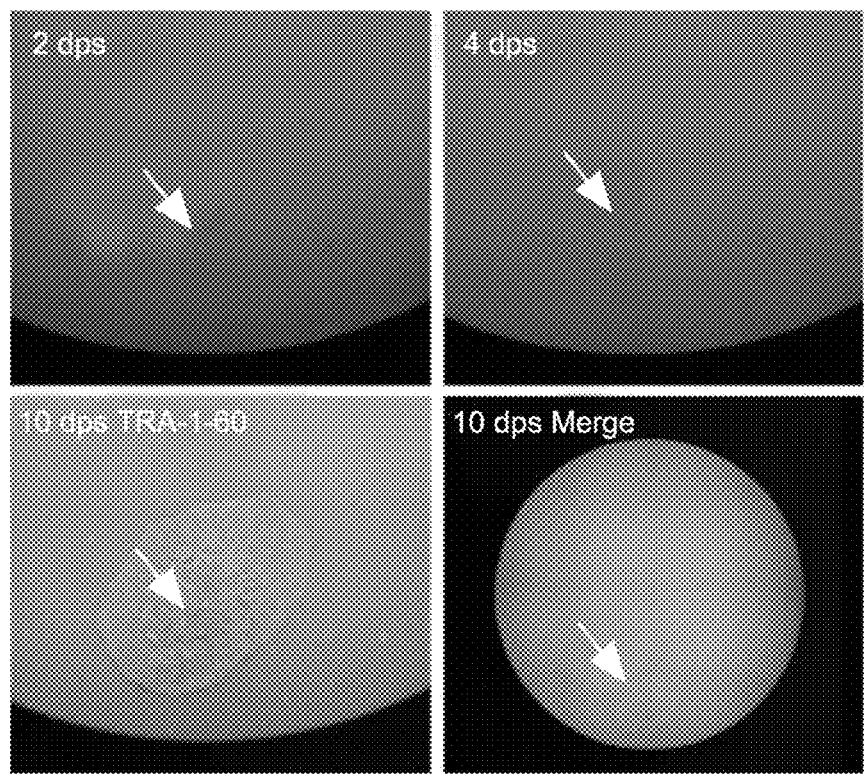
Figure 22F:
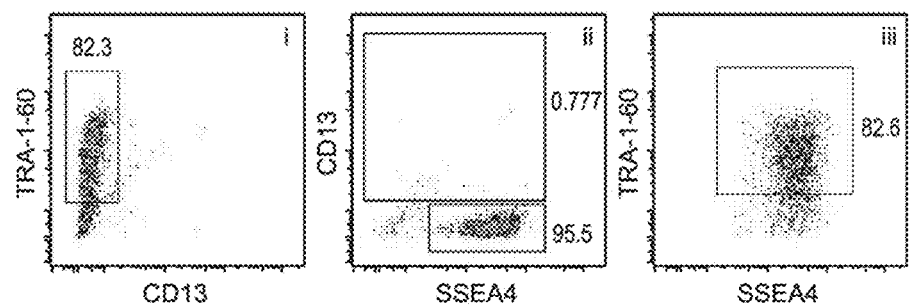
Figure 22G:
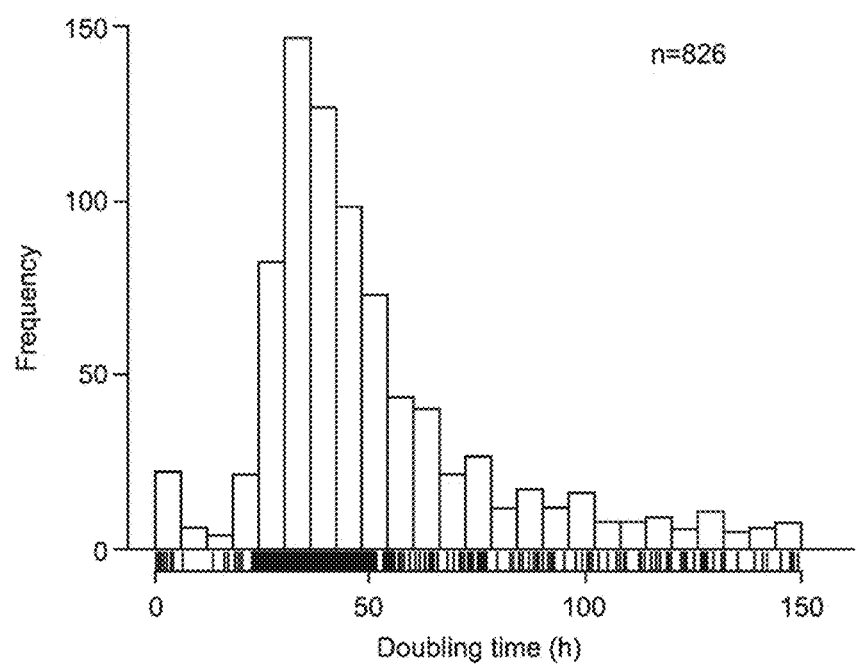
Figure 23A:
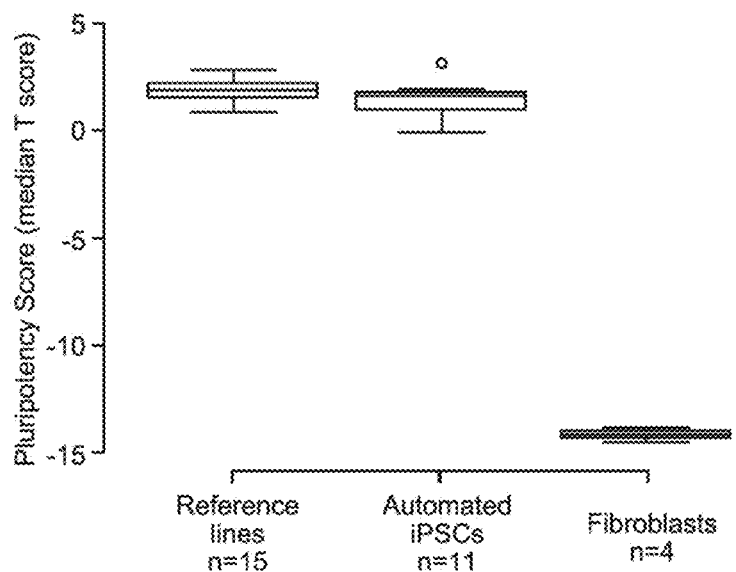
FIGS. 23A-23B. Gene expression analysis of sorted cells.
Figure 23B:
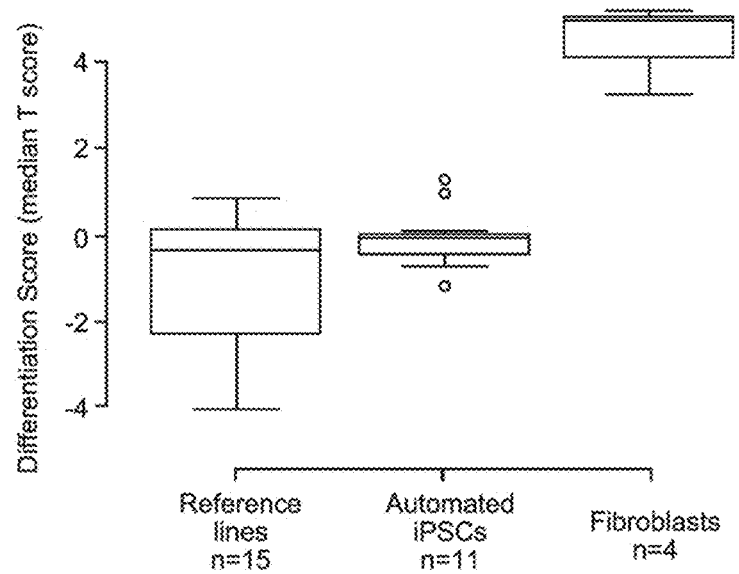
Figures 30A, 30B:
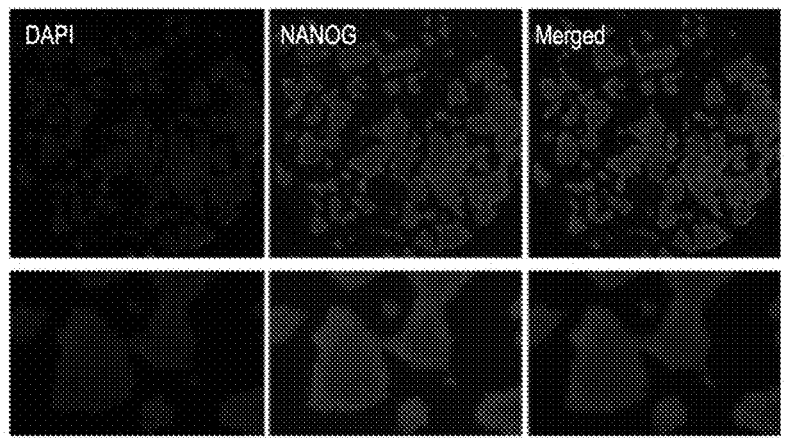
FIGS. 30A-30C.
Figure 30C:
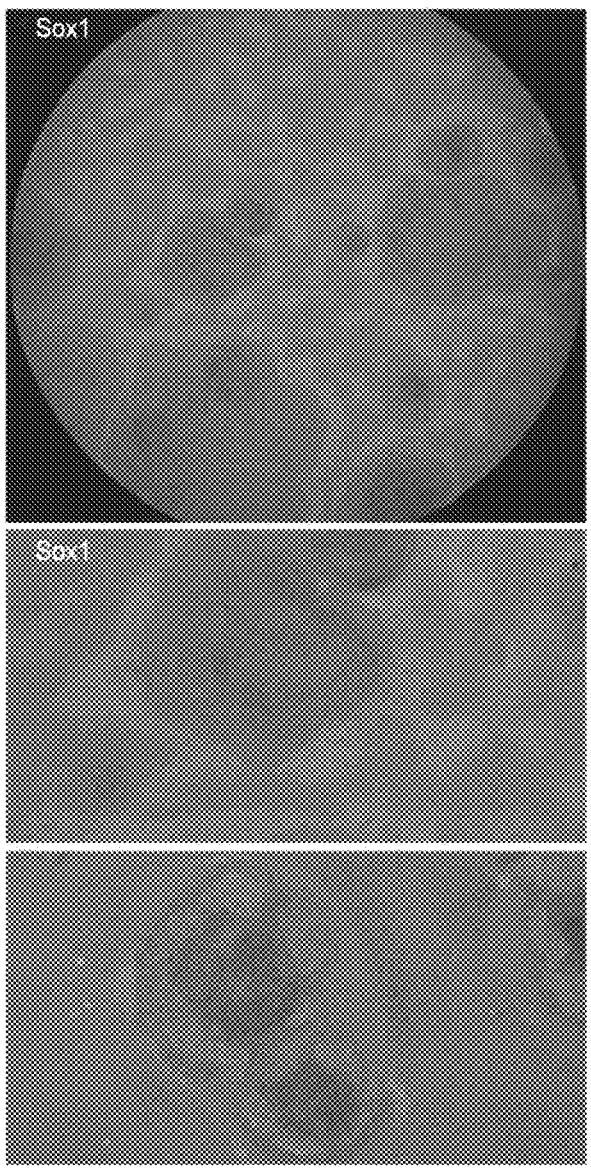

The population flow-through fraction of iPS cells by MACS was then plated into 96-well plates. The flow-through fraction was plated on an extracellular matrix in serum and feeder free conditions in a three point, two-fold serial dilution in 12 wells per initial reprogrammed well to recover colonies (FIG. 22D). Starting as single cells at the first day after sorting, TRA-1-60+colonies formed within 7-10 days (FIG. 22C) and had a typical ES cell morphology (cells with large nuclei, small amount of cytoplasm, with compact monolayer colony morphology). Doubling times, calculated from daily confluence measurements using the automated imaging system, ranged from 24-48 hrs for most lines. Sorted cells were checked daily using the Celigo automated microscope. Doubling times for most lines ranged from 24-48 hrs (FIG. 22G). Additionally, it was retrospectively established that clonal iPSC lines arose from expansion of single cells plated in single wells (FIGS. 22E and 29C). After wells with uniform confluence values were identified, three candidate wells per sample were selected and consolidated 1 well to 1 well onto 96-well plates by the robotic liquid handling methods for expansion and further quality control assays. After this passaging step, flow cytometry analysis further demonstrated that ~80% of the cells were SSEA4+/TRA-1-60+ (FIG. 22F). These passaged iPSCs reestablished typical human ES cell like colony morphology and expressed the pluripotent marker NANOG (FIG. 30B). To further ensure the negative selection had eliminated non-reprogrammed or partially reprogrammed cells, the sorted cultures were further screened by gene expression assays using a panel of pluripotency (NANOG, POU5F1, LIN28, ZFP42, SOX2) and differentiation (ANPEP, NR2F2, AFP, SOX17) marker genes. Using an analysis strategy similar to one previously described (Bock et al., 2011), performance of candidate iPSC lines were compared to an established reference panel of hESC lines (FIGS. 23A-23B). A set of newly reprogrammed and sorted iPSC lines were tested using this assay and 9 of 11 tested lines had scores consistent with the hESC reference panel. Two of the lines tested showed pluripotency scores consistent with reference standards, but showed elevated differentiation scores (FIG. 30A). This could be attributed to overgrowth of iPSCs resulting in spontaneous differentiation in these cultures (FIG. 30C). Together, these data suggest that iPSC lines purified by automated processes demonstrated characteristics of reprogrammed pluripotent cells within two passages after reprogramming. Thus, candidate iPSC lines in 96-well format can be recovered by automated single well passaging methods to consolidate and array multiple iPSC lines in parallel for expansion and further analysis.

Automated Culture of Multiple iPSC Lines in Parallel

Figure 24A:
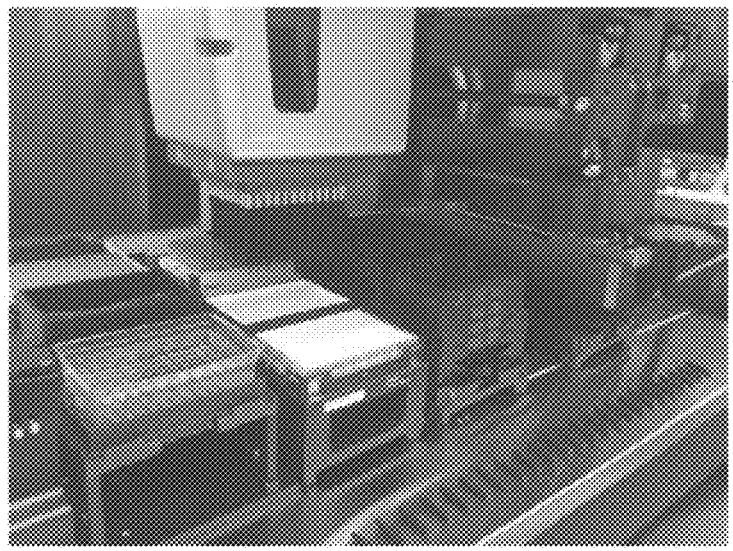
FIGS. 24A-24F. Automated parallel iPSC culture.
Figure 24B:
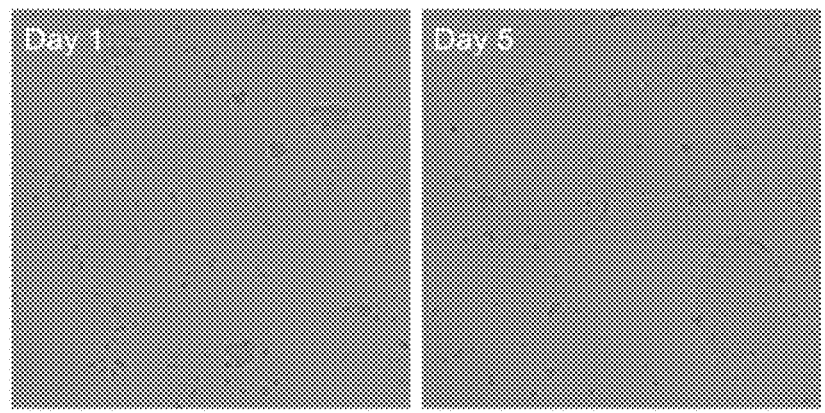
Figure 24C:
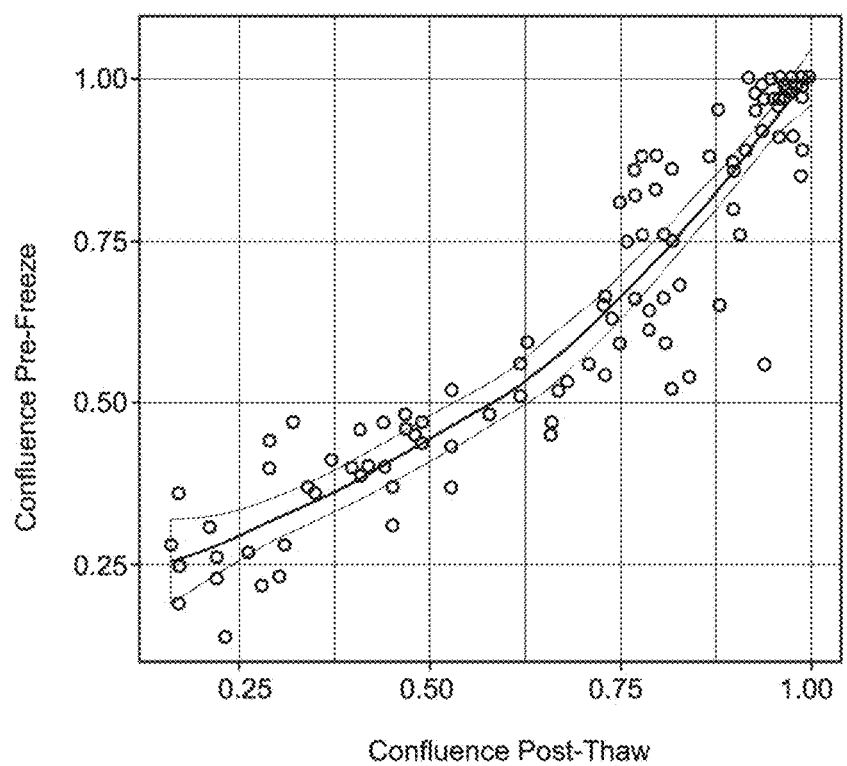
Figure 24D:
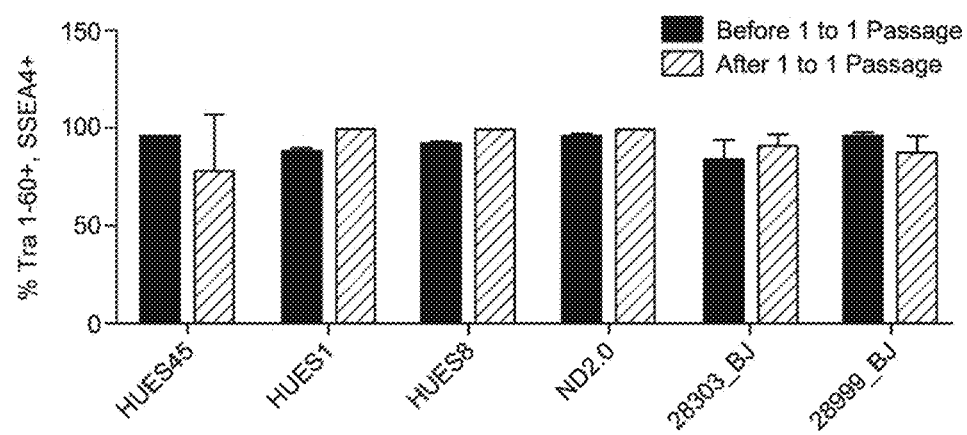
Figure 24E:
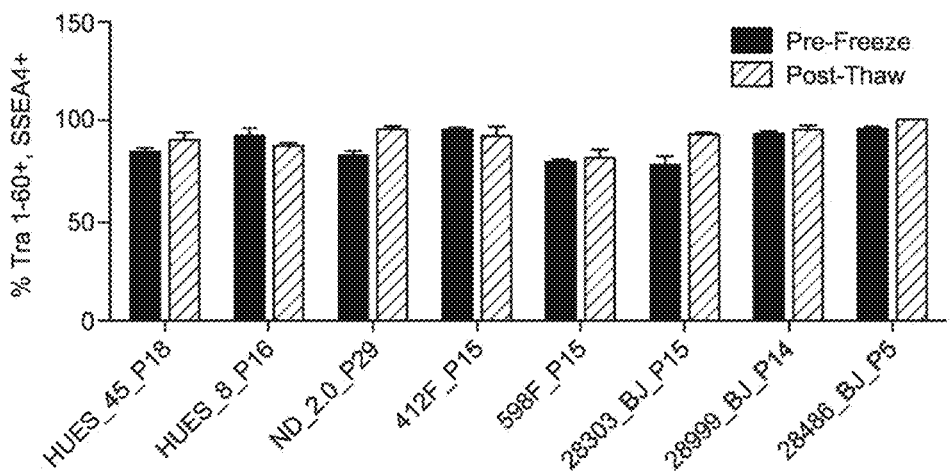
Figure 24F:
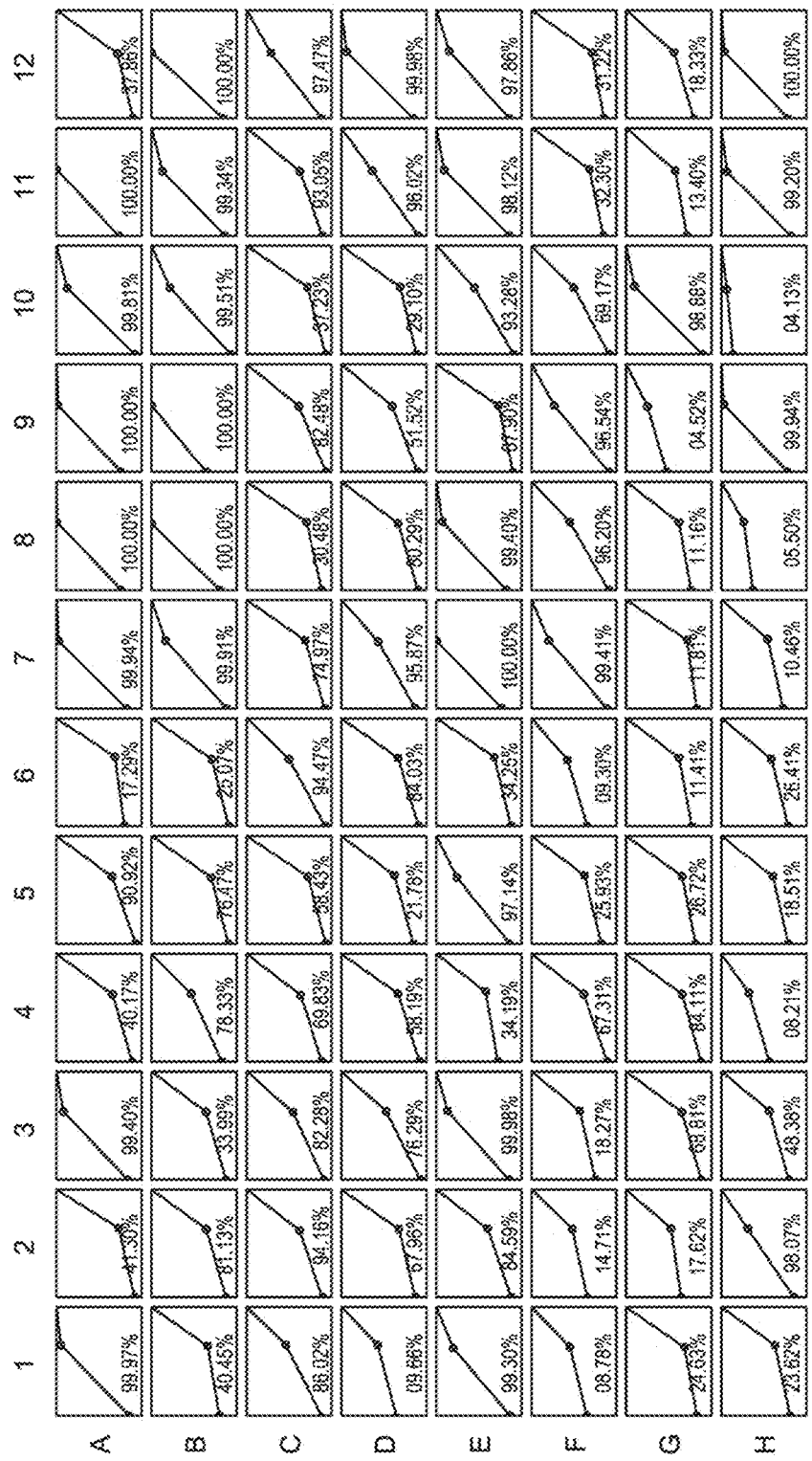
Figures 31A, 31B:
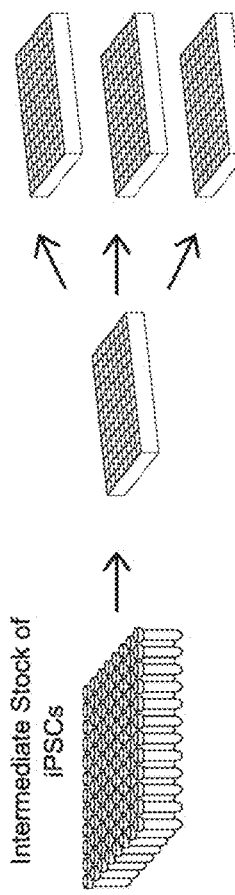
FIGS. 31A-31H.
Figure 31C:
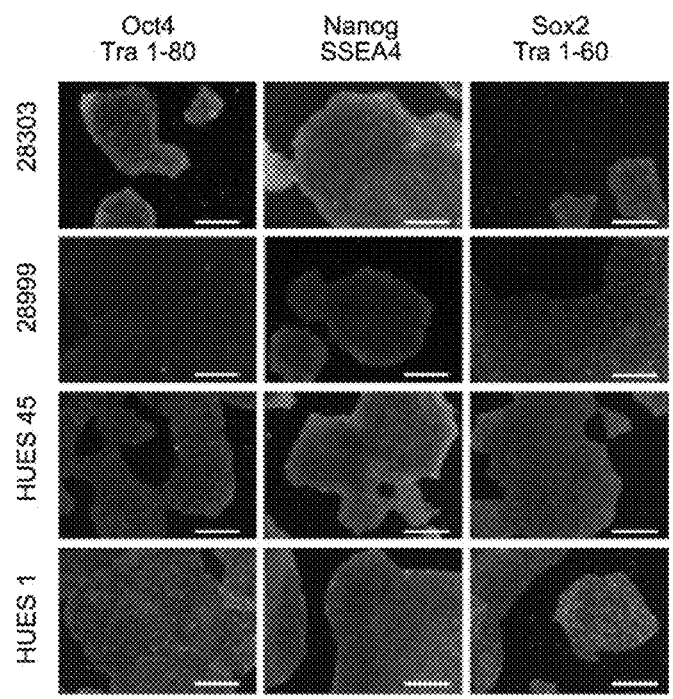
Figure 31D:
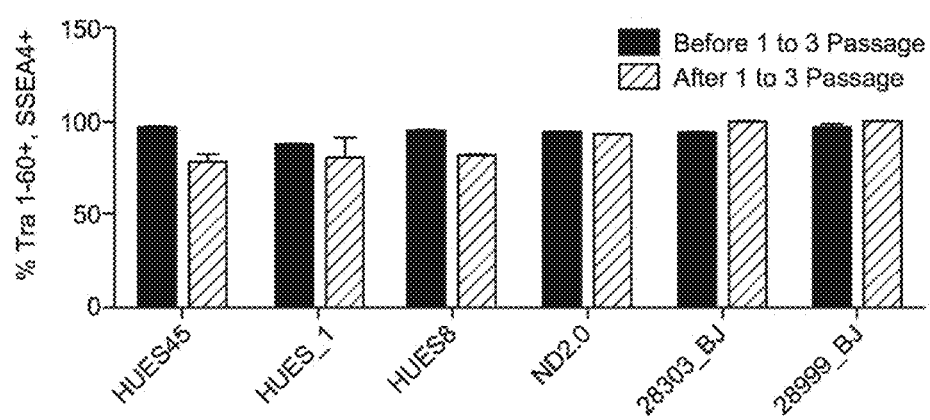

The primary aim for developing the automated process was to allow parallel derivation and culture of multiple iPS cell lines in parallel. The knowledge of growth rates and cell density at the time of consolidation combined with the ability to bin and batch cell lines and/or adjust plating characteristics at various steps was hypothesized to further enable parallel culture of cell lines with diverse growth characteristics at early passages (FIG. 22G). To enable this, automated and informatic processes were developed for cryopreservation of nascent iPSCs with similar growth characteristics (FIG. 20A Stage 3, and FIGS. 24A and 31A). After freezing in cryotubes followed by subsequent thaw, iPSCs recovered to show a normal morphology (FIG. 24B). Correlations between pre-freeze and post-thaw recovery confluencies were highest one day after the thaw (Pearson's r>0.91) and they decreased as the wells approached full confluence (Pearson's r>0.71 on day 3, >0.41 on day 6), due to overgrowth of higher confluence wells (FIG. 24C). The percentage of SSEA-4/Tra-1-60 double positive iPSCs remained consistent before and after the thaw (FIG. 24E), with subsequent passaging showing no significant differences in the percentages of the SSEA-4+/Tra-1-60+ double positive population (FIGS. 24D and 31D). Enzymatically robotically passaged cultures formed morphologically ideal colonies with well defined edges and expressed pluripotency markers POU5F1, Oct-4, Sox2, Nanog, SSEA-4, Tra1-60 and Tra 1-81 (FIG. 31C). The cultures growing in 96-well plates could be successfully maintained over 5-7 days growth and before requiring passaging (FIG. 24F). Following expansion of a single 96-well plate into three plates, between-plate variation remained low (FIG. 31B). Additionally, the wells did not lose SSEA-4+/Tra1-60+ pluripotency marker expression (FIG. 31D). Passaging rations between 1:1 and 1:15 have been successfully performed on the automated system. Together, these data indicate that after freezing, the grouping and thawing of newly derived iPSC lines, samples can successfully occur based on prior growth characteristics. Subsequent expansion of these lines does not alter either the growth or pluripotency characteristics allowing the automation of parallel culture in a multiwall format.

Figure 31E:
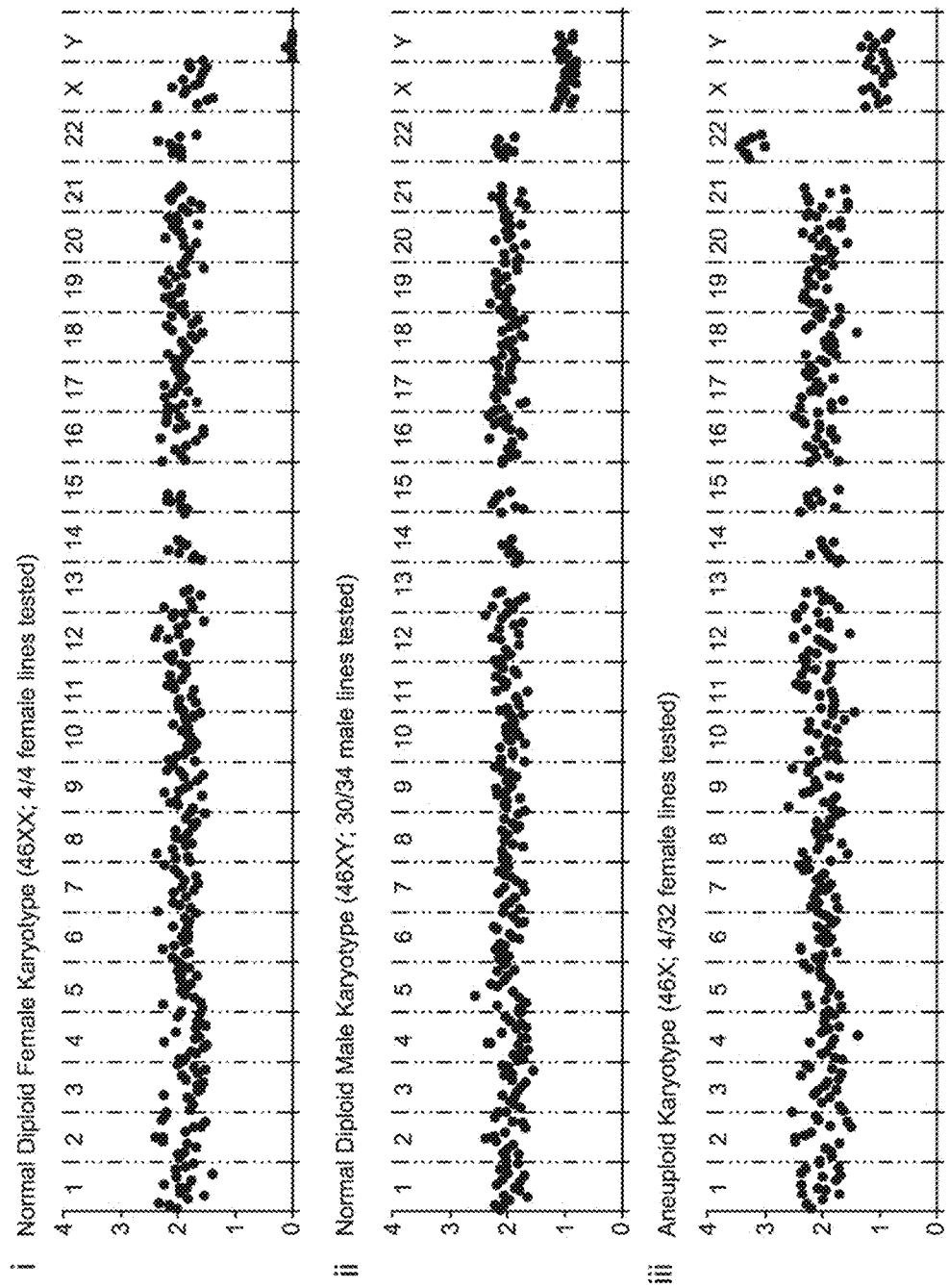
Figure 31F:
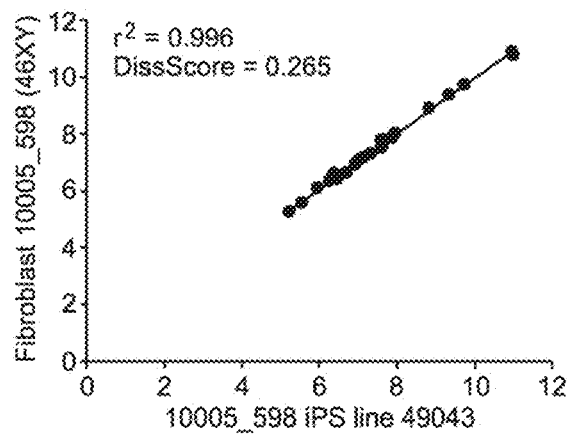
Figure 31G:
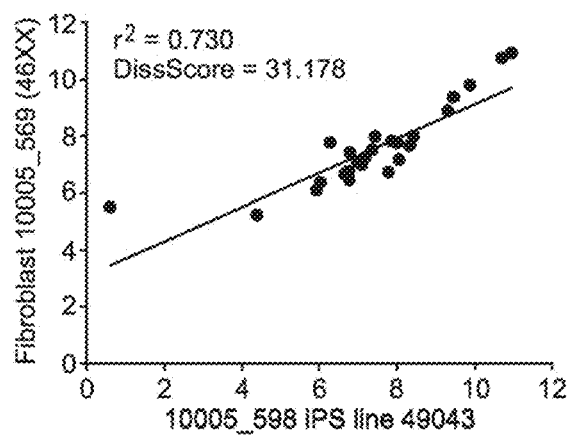
Figure 31H:
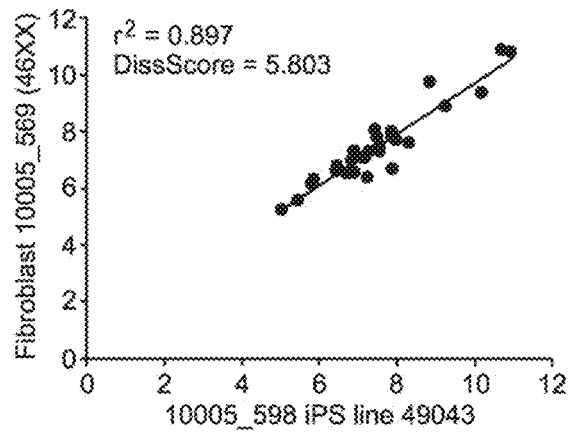

Analysis of genomic DNA was performed to track cell line identity (FIGS. 31F-31H) and to ensure that cell lines remained karyotypically normal (FIG. 31E). iPS lines were karyotyped using the Nanostring nCounter karyotyping assay that can detect aneuploidy as well as large chromosomal gains/losses commonly found during manual pluripotent stem cell culture. Whilst previous reports have stated that chromosomal abnormalities arise in approximately 20% of iPSCs (Mayshar et al., 2010), the majority of the presently described iPSCs (89%, n=38) showed a normal diploid karyotype (46, XX or 46, XY). Of the 4 abnormal lines detected, one had a chromosomal gain in the long arm of chromosome 22 (probes spanned 22q11.21-22q13.32). The remaining 3 abnormal lines all shared a common starting fibroblast population and shared a copy number gain in chromosome 17 (probes spanned 17q21.32-17q25.3), suggesting heterogeneity of the original fibroblast population that was below the threshold of detection. Together, these results suggest that it is possible to maintain iPSCs during subsequent automated passaging.

Automated Analysis of Differentiation Propensity

Figure 25A:
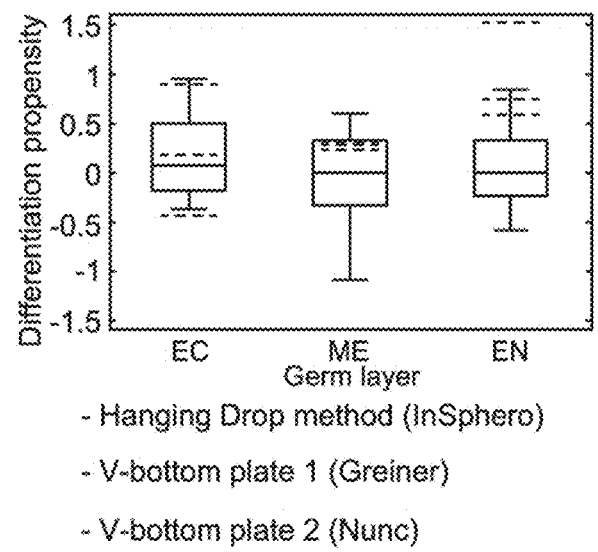
FIGS. 25A-25F. Automated Embryoid body assay.
Figure 32A:
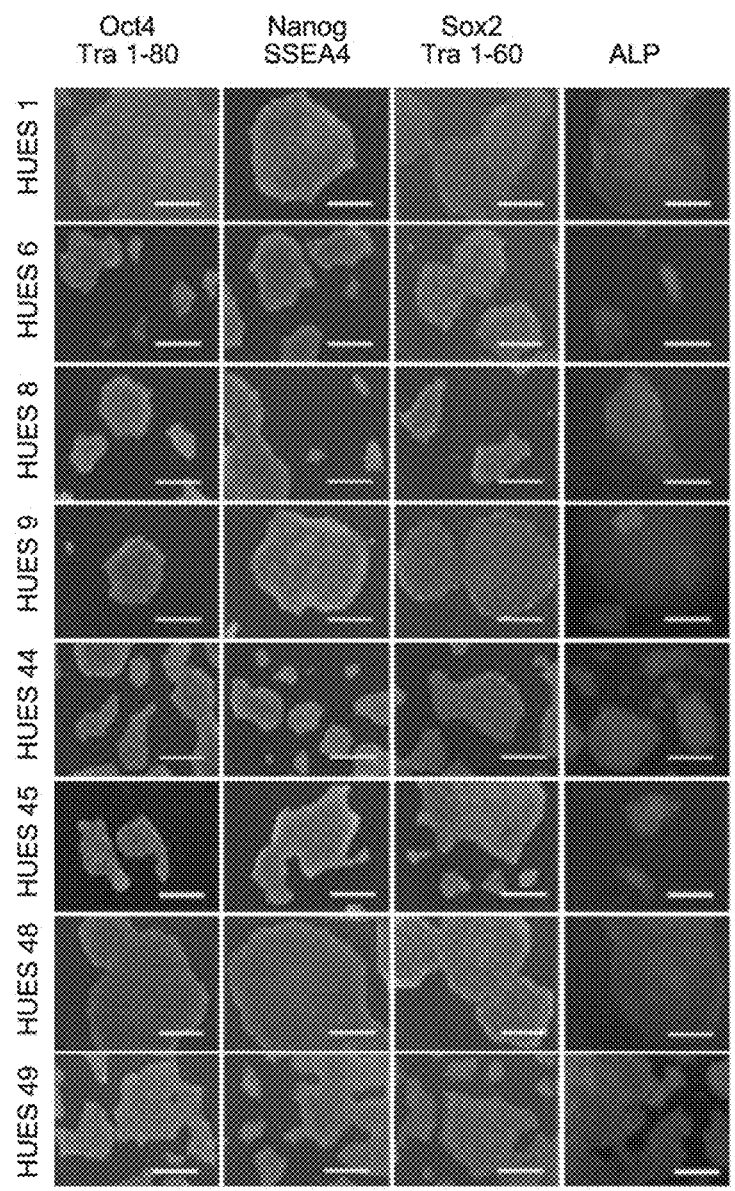
Figure 33A:
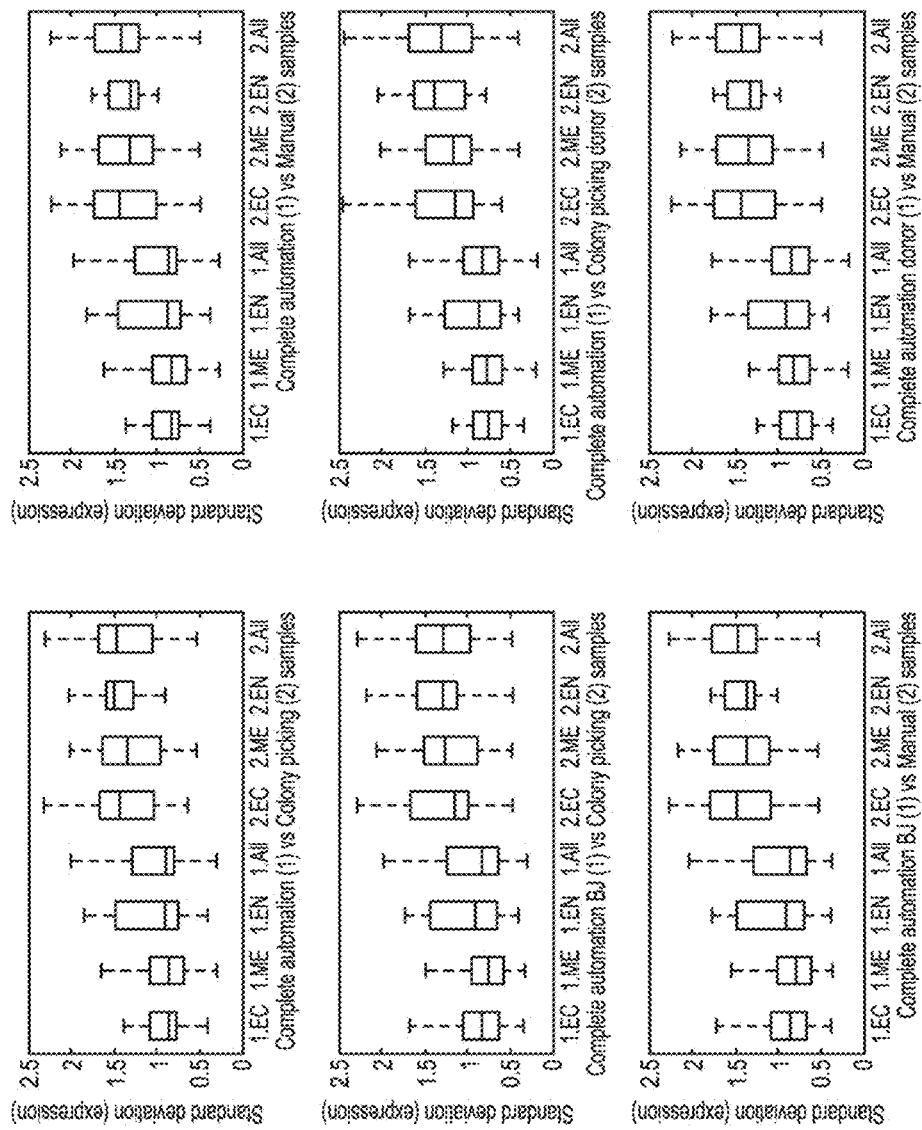
FIGS. 33A-33B.
Figure 33B:
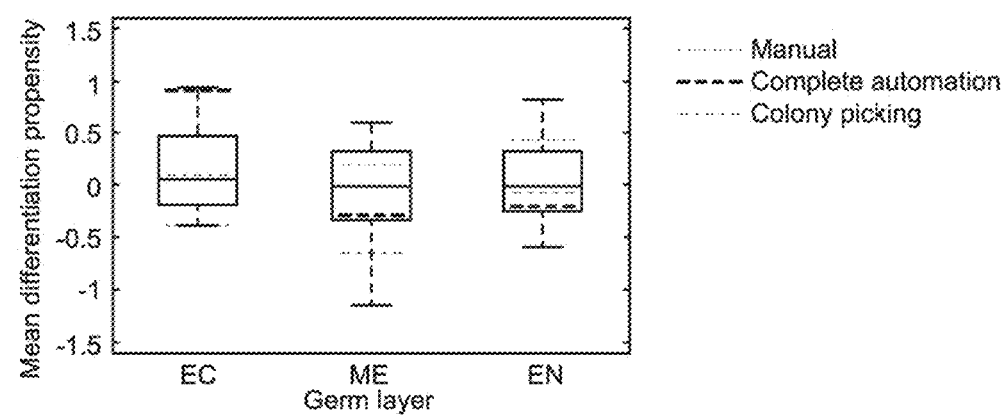

To assess the differentiation potential of robotically derived iPSCs, a robotic platform was developed to generate EBs and the ability of iPSCs to spontaneously differentiate into the three germ layers was measured. Several automation compatible methods for reproducibly forming EBs were tested followed by an automated process to harvest and lyse EBs before using a Nanostring gene expression assay to quantitatively assess germ layer differentiation as previously described (Bock et al, 2011). The previous assay was modified to include the 83 germ layer lineage genes divided into ectoderm (EC), mesoderm (ME), and endoderm (EN) gene sets as well as probes for transgene silencing and Sendai vector elimination, sex (SRY and XIST), pluripotency (Oct4, POU5F1, Sox2, Nanog, ZFP42), and housekeeping gene expression (ACTB, POLR2A, ALAS1). In initial pilot studies, hierarchical clustering of EB gene expression suggested that that samples group together according to the type of method used for the EB formation assay. EBs formed by hanging drop methods clustered separately from those produced by plating in V-bottom plates. Expression of these gene sets was measured relative to those from a control panel of EBs made from hESC lines analyzed in parallel under identical culture conditions (FIGS. 32A-32B). Pluripotency of the hESC lines used for reference standards was verified by marker staining for POU5F1, Oct4, TRA-1-80, Nanog, SSEA4, SOX2, TRA-1-60, and Alkaline Phosphatase (FIG. 32A). All lines tested exhibited scorecard differentiation propensities consistent with the ability to differentiate into the three germ layers (FIG. 32B). Germ layer lineage marker gene sets were differentially expressed between the different methods of forming EBs (FIG. 25A), with hanging drop methods generating gene expression biased towards endoderm and V-bottom plates demonstrated a more uniform differentiation potential. Together, this suggests that different methods of generating EBs may confound comparisons among lines and highlights the need for method standardization.

Figure 25B:
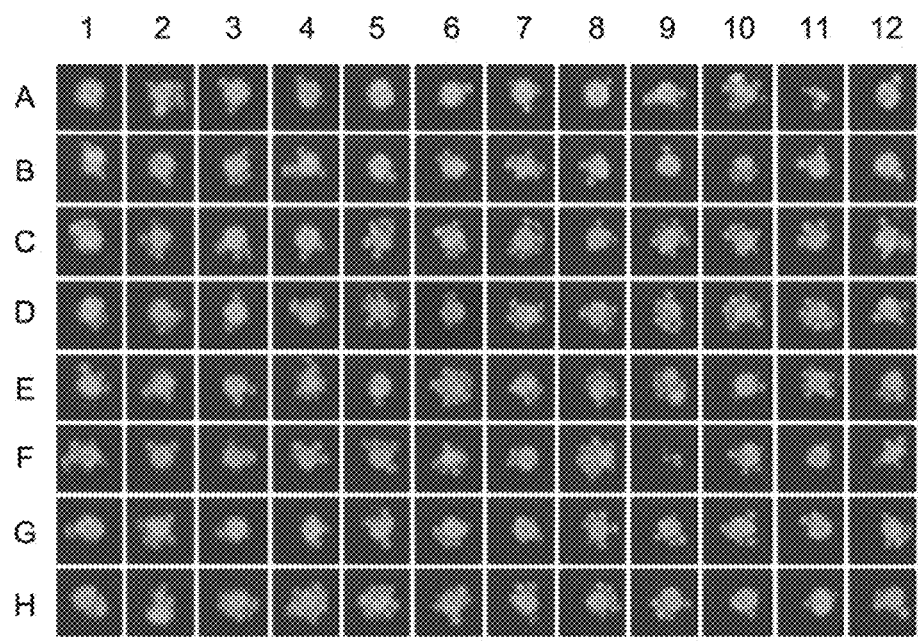
Figure 25C:
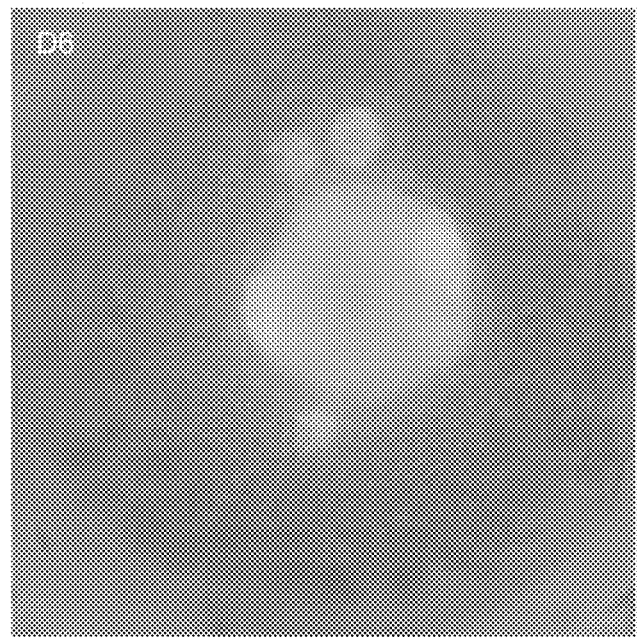
Figure 25D:
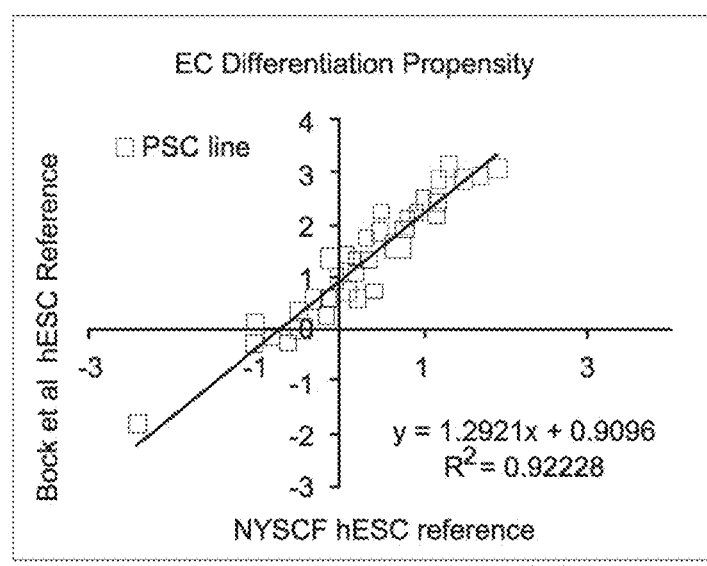
Figure 25E:
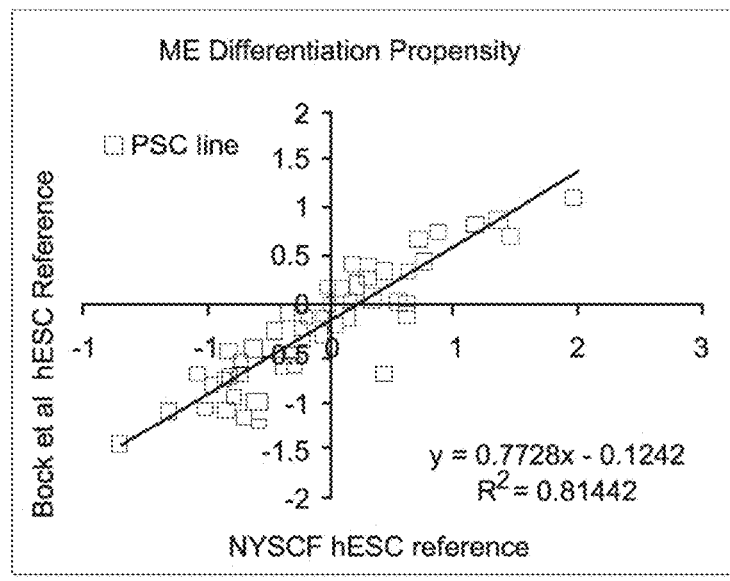
Figure 25F:
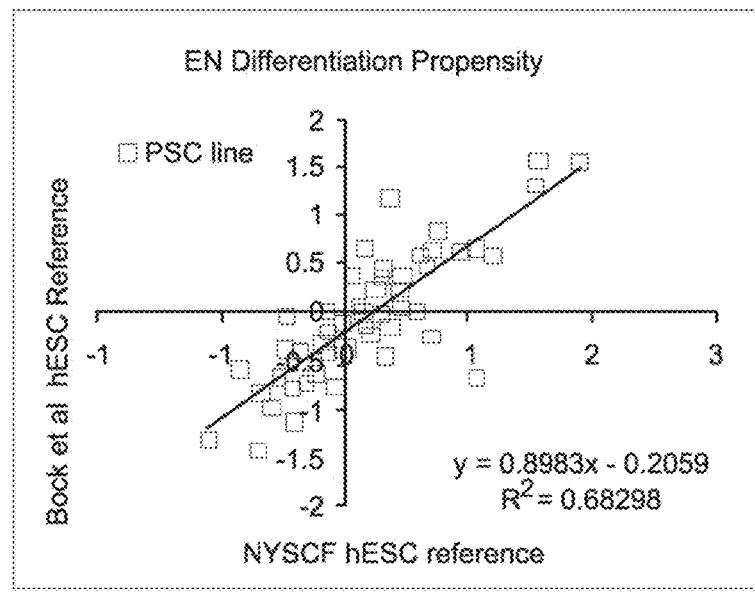

EB formation was optimized using EGFP marked iPSC lines, to seed cells from a single well of a 96-well plate into six wells of 96 well V-bottom plates (FIGS. 25B-25C). Before EBs were collected, plates were imaged using Celigo to monitor EBs formation (FIG. 25B). These automated methods allowed the iPSCs to aggregate and form embryoid bodies at the bottom of the well (FIG. 25C). While the differentiation propensity scorecard values for all samples showed excellent correlation with those previously published (Bock et al., 2011), a slight decrease was noted in correlation with previously published data from identical reference lines grown under different culture conditions (FIGS. 25D-25F), suggesting that the assay is sensitive to differentiation culture conditions. Therefore comparisons were made using reference data generated from hESCs adapted to the culture conditions used to derive iPSCs on the automated system.

Reduced Variation in Robotically Derived iPSCs

Figure 26:
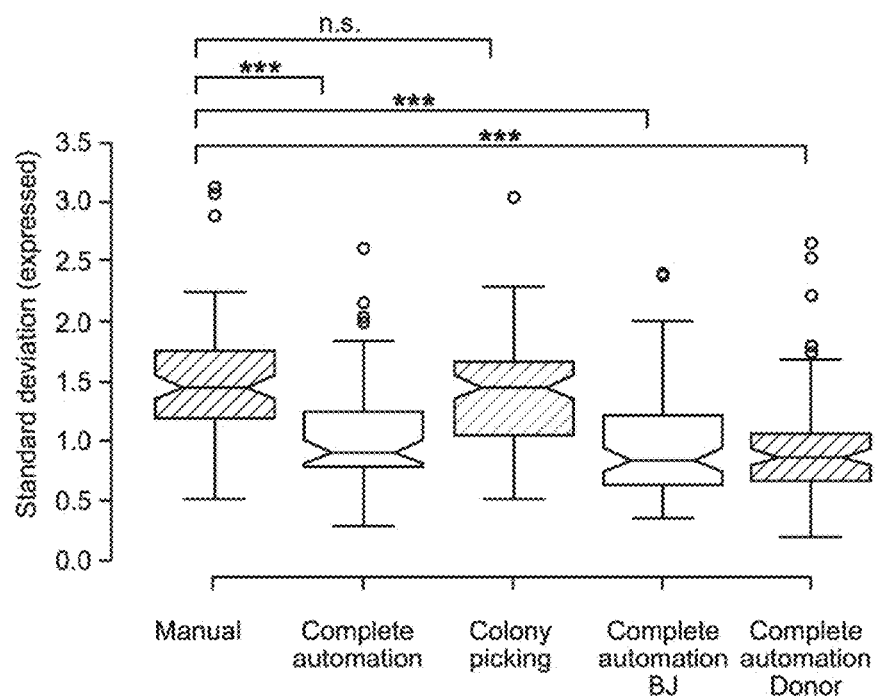
FIG. 26. Reduced variation in robotically derived iPSCs. Variance analysis of scorecard gene expression in EBs showing comparisons of standard deviation of gene expression values among samples derived on and off the automated system. Lines produced by the automated process showed significantly less variation in EB gene expression compared to lines produced by manual methods and later introduced onto the system (p value=7.08E−12, Wilcoxen signed rank test). The comparison between manually derived lines and lines reprogrammed on the automation but with manual colony picking was marginally significantly different (p value=0.023)*=p<0.05, ***=p<0.001).

Next, the propensity of robotically derived iPSCs to differentiate by the automated EB assay was measured and lineage scorecard analysis was carried out described above was used (Bock et al., 2011). Hierarchical clustering of gene expression shows overall consistency of the IPSCs generated by automation. However, the lineage scorecard differentiation assay suggested that it might be possible to distinguish among variations in methods used to derive the iPSC lines independent of genotype. It was found that iPSCs derived through complete automation of the reprogramming process showed reduced variation (as measured by comparing distributions of standard deviation of gene expression) when compared to lines reprogrammed by manual processes (p value=$7.08\times10^{-12}$, Wilcoxen signed rank test) (FIG. 26). This was true in comparisons within a single genotype (BJs, p values=$7.85\times10^{-9}$) and as well as for the patient lines (donor, p values=$9.28\times10^{-11}$) Interestingly, iPSCs initially reprogrammed robotically before having colonies manually picked and then returned to the automated system for expansion showed elevated expression similar to that found in existing manually derived iPSC lines (p value=0.023. Thus this finding suggests that manual clone selection may be an important source of variation. Additionally, lines derived by Sendai infection and manual colony picking showed similar variation to lines initially reprogrammed using automation but completed through manual colony picking (p value=0.40). This suggests that lines produced by the completely automated process show reduced variation at early time-points after derivation compared to lines derived by current manual procedures.

Discussion

This Example describes an embodiment of a fully automated platform for reprogramming easily obtainable skin cells into iPSCs. The described platform achieves reproducibility and population scale iPSC derivation and differentiation, using an automated approach based on recent advances in reprogramming and characterization methods (Bock et al., 2011; Kahler et al, 2013; Warren et al, 2010). A fully-robotic process has been established for the generation of fibroblast banks, iPSC reprogramming, as well as automated assays for assessing differentiation potential. The creation of this platform allowed assessment of the sources of functional variability between iPS cells. Importantly, sue to the use of robotics, this has been achieved with both the precision and scale that could previously not have been considered.

Most notably, manual selection of newly reprogrammed iPS cell colonies was in itself found to be a substantial contributor to cell line to cell line variation. Through automation of the reprogramming process, more than a third of the variability that existed between manually selected lines was eliminated. This finding demonstrates that at very least, a substantial portion of this variation had purely technical origins.

The large scale of the described experiments also allowed investigation of the previously raised question of whether the origin of the somatic cells and and/or their genetic background, influenced stem cell line behavior. The production of many cell lines from both a single somatic population (BJ fibroblasts) and from multiple distinct individuals allowed investigation of this issue. The results presented in this Example clearly show that the level of variability between cell lines made from many donors was not different from that found with lines from a single donor. Previous studies suggest that genetic factors could be a contributing factor to functional variance between iPS cell lines (Kajiwara et al., 2012). However, this data suggests that if these factors do contribute, the do so modestly in comparison to the technical variation that can be resolved through automation.

Although it has been cited as a potential inhibitor of reprogramming in the past, advancing age of the subject being reprogrammed was not a significant modifier of reprogramming efficiency. Instead, both the growth rate and confluence of cell cultures at the time of reprogramming were found to be the primary drivers of whether the automated approach succeeded in producing iPS cells in each individual case. This finding seems consistent with the observation that genetic factors which slow proliferation of cells inhibit reprogramming (Hanna et al, 2009).

In addition to this, the reprogramming method used for producing iPSCs had a substantial effect on cell line properties. Although aspects of iPSC production using both mRNA delivery and Sendai virus infection could be automated, incomplete eviction of Sendai virus led to a substantial change in the signature of gene expression in pluripotent cells. For this reason, plus previously discussed issues with lot to lot variation and availability, a modified mRNA reprogramming method as a standard protocol. However, the flexibility of the system allows for the future adoption of other reprogramming methods as these become available.

As described here, the integrated system has a capacity to produce approximately 384 iPSC lines per month. Running a second personnel shift using the current system could allow capacity to double, resulting in the ability to produce 768 iPSC lines per month. The advantage to this approach of automating production over a manual process, however, is that capacity can be scaled with additional systems with only a minimal increase in personnel time. The timeline for producing seed stocks of characterized iPSC lines from fibroblasts is approximately 12 weeks. Although the current automated system may not yet be ideal for clinical grade iPSC, evidence that the process can be automated suggests that a similar system tailored to the clinical grade production is now feasible. Together this increased scale and accelerated timeline should enable many large-scale projects utilizing iPSCs (McKernan and Watt, 2013).

In the future, the increased throughput of reprogramming and reduced variability between the resulting lines should open a number of new avenues for investigation. First, this approach should allow investigation of cellular phenotypes for disease states found in conditions that are caused by diverse mutations. At the moment, most studies utilizing iPSCs for disease modeling have focused on a small number of lines originating from individuals harboring either a single or small number of highly penetrant mutations. The expanded scale and reduced variation of the automated system should lead to greatly improved statistical power in addressing the question of whether a modest effect observed in culture is a direct result of the genetic background of the subject in question.

This increased sensitivity should assist in accurately assessing the impact of common variants that influence human health. Although these variants may only contribute modestly to the overall phenotype in a given individual, their prevalence in populations highlights their importance in understanding their role in disease. The ability to accurately study such variants would represent an important next phase for in vitro disease models. If there is one common process that eventually leads to cellular dysfunction in each particular disease, it may be possible to devise a single strategy for inhibiting it, providing a therapeutic for all patients. In contrast, it may be that subsets of patients follow distinct paths towards disease. If this is the case, it will be necessary to identify these distinct groups of patients so that a therapeutic strategy that is specific to the particular path their disease follows can be devised and appropriately administered. As the system described here is designed to perform standard cell culture manipulations, adaptation of this robotic technology to directed differentiation should further enable the discovery of molecular and genetic pathways that underlie our traits and disease.

Experimental Procedures

Cell Lines

Recruitment of volunteers and biopsy collection and written informed consent procedures were approved by Western Institutional Review Board. Human embryonic stem cell lines were obtained from the Harvard Stem Cell Institute. Additional reference iPSC lines BC-1, ND1.4 and 2.0 were obtained from NIH Center for Regenerative Medicine (Chen et al, 2011; Cheng et al., 2012).

Automated Systems Description

To accomplish fibroblast banking, iPSC generation, and iPSC characterization and freezing, three integrated robotic platforms were assembled from a combination of eight automated liquid handlers (Hamilton STAR and STARlet), five incubators (Thermo Cytomat), two robotic arms (Hamilton RackRunner), four automated Celigo plate imaging systems (Nexcelom Bioscience), three cryotube decappers (Hamilton), three plate centrifuges (Agilent Vspin), and one plate sealer (Agilent PlateLoc). User initiated software method scripts that communicate with the relevant instrumentation were written using custom software on the Venus platform (Hamilton) to automate individual process steps described below. Usage of shared automated devices was controlled by a custom software reservation system. Disposable conductive pipetting tips (Hamilton) were used throughout processes and tip reuse was minimized during all process steps to prevent cross contamination of cultures. Standard plate formats and tubes were used and tracked by barcode. Liquid handling procedures are tracked and logged providing process traceability.

Automated Biopsy Outgrowth and Fibroblast Cell Culture

Dermal fibroblasts were derived from donor tissue samples collected in biopsy collection medium (see extended methods below for all media formulations). Samples were washed in Biopsy Plating Media, cut into 1-2 mm pieces, added to a 6 well plate and dried for 15 minutes after which, biopsy plating medium was added to wells dropwise. Plates were left undisturbed for 10 days to allow for initial outgrowth before being transferred to the robotic system for automated culture and expansion, growth rate analysis, mycoplasma testing and freezing.

Automated Reprogramming

Automated methods were used to thaw and seed fibroblasts onto 12 well plates (Corning, #3513) then perform medium exchanges every third day until reaching 70-90% confluence. Cells were robotically dissociated using TrypLE Select CTS (Life Technologies, #A12859-01), counted by automated imaging procedure after viability staining using Hoechst (Sigma, #B2261) and Propidium Iodide (Life Technologies, #P3566) followed by cell number calculation for robotic transfer into a Geltrex™ (Life Technologies, #A14133) coated 24 well plate (Corning, #3526). Reprogramming of fibroblasts was performed using automated transfection and feeding methods to deliver modified mRNA (Stemgent, #00-0071) and conditioned Pluriton reprogramming medium supplemented with B18R (200 ng/mL) as per manufacturer's instructions. After 15-20 days following the initiation of reprogramming, cultures were transitioned to Freedom media (Life Technologies, #A14577SA) for an additional 5-10 days, after which cells were live stained with TRA-1-60 (Life Technologies, #A13828) to identify iPS colonies by the automated imaging system. Sendai virus infections were performed using an automated infection protocol with virus preparations kept cold on a chiller block located within the robotic platform.

Automated iPSC Purification

After reprogramming, iPS cells were enriched by automated depletion of non-reprogrammed fibroblasts using a MultiMACS™ system (Miltenyi Biotec, #130-050-601) integrated into a Hamilton STAR liquid handling system using anti-human fibroblast microbeads (Miltenyi Biotec, #130-050-601). The iPSCs were collected, seeded into 4 wells of a 96-well imaging plate (BD Biosciences, #353219), and serially diluted 3-fold in adjacent wells. Based upon growth rates calculated from automated imaging, well confluency levels and the presence of live TRA-1-60 surface marker expression, samples were selected and robotically cherry-picked after bulk dissociation with 0.05 mM EDTA (Life Technologies, #15575-020), and consolidated into a new Geltrex-coated 96-well plate (Corning, #3599).

Automated iPSC Passaging

Automated methods were used to perform daily feeding and imaging of consolidated iPS cell lines using Freedom medium. Upon reaching 70-90% confluence, the cell were passaged using Accutase (Life Technologies, #A11105-01). Growth medium was supplemented with Thiazovivin (1 µM; Stemgent, #04-0017) for the first 24 hrs after passaging to promote cell survival, after which cells were fed daily with growth medium.

Automated EB Formation

Cells were dissociated and plated for gravity aggregation using the automated liquid handling systems in 96 well V-bottom plates (Greiner, #651161) in the presence of human ES culture medium without bFGF (see extended methods for formulation) supplemented with 1 µM Thiazovivin for the first 24 hrs after passaging. Cell aggregates (EBs) were allowed to grow for a total of 16 days with media refreshed every 48 hrs by automated methods. EBs were imaged before being harvested and lysed using automated methods and cell lysate analyzed with custom NanoString codesets (Pluri25 and 3GL (Kahler et al., 2013 on the Nanostring nCounter system according to manufacturer's instructions.

General Methods

Pluripotency of iPSCs and hESCs was verified by immunofluorescence for the markers: Nanog (Cell Signalling Technology, #4903), Oct4 (#09-0023), Sox2 (#09-0024), SSEA4 (#09-0006), Tra 1-81 (#09-0011), Tra 1-60 (#09-00110; all Stemgent). Images were acquired using a Celigo, Nikon Eclipse TE 2000-U or Olympus BX41 fluorescent microscopes. Pluripotency was also analyzed by FACS analysis for CD-13, SSEA4 and Tra 1-60 on an ARIA-IIu™ SOU Cell Sorter as previously described (Kahler et al., 2013). DNA and RNA were isolated from cells using High Pure PCR Template Preparation kits (Roche, #11796828001), and RNeasy Micro kits (Qiagen, #74004) respectively. DNA/RNA was analyzed using a NanoString nCounter system following using NanoString's recommended procedures.

Statistical Methods

Statistical analysis was performed using custom R scripts (Team, 2014). Pluripotency/differentiation scores of candidate iPSC lines were quantified by calculating the median t-score (moderate t-test) of pluripotent/differentiation markers gene expression in comparison to the distribution of expression values for a reference set of 15 hESC lines. The previously described Scorecard method (Bock et al., 2011) was used to measure the differentiation propensity of day 16 EBs formed from robotically derived iPSCs and compared against a new reference set of 10 established hESC lines in order to maintain consistency of culturing conditions. To quantitate the variance in deriving iPSC lines using different methods, standard deviation in gene expression for cell lines was measured and grouped by different derivation methods. The analysis included all genes that were designated as markers for pluripotent, endoderm, mesoderm, and ectoderm cell state. To assess the significance of gene expression variation difference between two cell line groups, the Wilcoxen signed rank test was used.

Extended Experimental Procedures

Donor Recruitment and Biopsy Collection

Dermatology patients undergoing a regularly scheduled biopsy and volunteers from a diverse population were recruited to donate a biopsy for the generation of induced pluripotent stem cells. Volunteers free from bleeding disorders and/or prone to excessive scarring were scheduled to donate a 3 mm punch biopsy at a collaborating dermatology clinic. Prior to their participation, all participants provided their written informed consent and study approval was obtained from Western Institutional Review Board. The samples were taken from an area of the body to the doctor's discretion, usually the upper arm or leg. In addition to the biopsies, health information questionnaires were used to collect information such as health and medication history, social history and ethnic background. Upon collection, the samples and accompanying questionnaires were de-identified using a unique ID and returned to the NYSCF Human Subjects Research (HSR) staff. The information provided within the questionnaires was then transferred by the HSR staff to Redcap, a password protected database, linking the de-identified data to the anonymous sample ID for the laboratory researchers and the samples utilized for the generation of stem cell lines.

Automated Systems Description

We designed three integrated robotic platforms that fully automate the iPSC generation and characterization workflow. In brief, cells are housed in Cytomat incubators and automated method scripts call out plates onto robotic decks for processing. The first platform for fibroblast banking consists of a Hamilton Starlet liquid handler with a plate shuttle directly connecting a Cytomat C24 incubator. Additional devices such as a Celigo cell imager, an Agilent Vspin centrifuge, and a Hamilton Decapper were integrated to facilitate fibroblast growth tracking, passaging and freezing processes. The second platform for iPSC generation is a cluster of three independent liquid handling systems connected by a Hamilton Rack Runner robotic arm and rail. This format allows parallel processing on multiple systems. Each system has been customized for its intended purpose with a combination of channel pipettors, plate heaters, shakers, tilters, and cooling modules. Usage of shared automated devices such as the Hamilton Rack Runner, Cytomat C48 incubator, Celigo cell imager, Agilent Vspin, and Hamilton Decapper are controlled by a reservation system. The third platform for iPSC characterization and banking is a mirror cluster with a slightly different device configuration for optimized 96-well plate handling.

All Hamilton STAR liquid handling systems are contained within NuAire BSL II biosafety cabinets to maintain a sterile operating environment during manipulation of cell culture plates. Remaining components are enclosed in a Hepa filtered hood to maintain a sterile operating environment during transportation of cell culture plates between systems and devices.

Control, scheduling and inventory software integrate with method scripts for fully automated operation of the systems. Each method outputs detailed log and mapping files of processing steps, and Dropcam video monitoring cameras record system activity. Consumable usage and reagent barcodes are also automatically tracked on a database.

Automated Biopsy Outgrowth and Fibroblast Cell Culture

Somatic cell lines (dermal fibroblasts) were derived from patient tissue samples collected at collaborating clinics in Complete M106 media which contains Medium 106 (Life Technologies, #M-106-500), 50× Low Serum Growth Supplement (Life Technologies, #S-003-10) and 100× Antibiotic-Antimycotic (Life Technologies, #154240-062). Samples were de-identified and assigned an internal barcode for tracking identity and passage number.

Each sample was washed 3 times in Biopsy Plating Media and cleaned with a disposable scalpel and autoclaved forceps to remove blood, fat and epithelial tissue. Biopsy Plating Media contains Knockout™-DMEM (Life Technologies #10829-018), 10% FBS (Life Technologies,

100821-147), 2 mM GlutaMAX (Life Technologies, #35050-061), 0.1 mM MEM Non-Essential Amino Acids (Life Technologies, #11140-050), 1× Antibiotic-Antimycotic, 0.1 mM 2-Mercaptoethanol (Life Technologies, #21985-023) and 1% Nucleosides (Millipore, #ES-008-D). Depending on initial tissue sample size, 2-3 clean 1 mm pieces were transferred to one well of a 6 well tissue culture plate (Corning, #3516) and allowed to dry down for 15 minutes. After drying, 3 mL of biopsy plating media were added dropwise to each well containing tissue pieces and placed in a quarantine incubator for 10 days to allow for initial outgrowth undisturbed. Plates were then transferred to an automated incubator (Cytomat, Thermo Fisher) for routine cell culture on the automated system. All reagents used for automated methods were assigned internal barcodes encoding media aliquots and reagent lot numbers and scanned into individual methods.

Fibroblasts were maintained in Complete M106 media for one week and monitored by a Celigo automated imager (Nexcelom) for outgrowth before being changed into antibiotic free M106 media for 3 days. A 200 uL aliquot of fibroblast cultured media from each well of a 6 well plate, representing 1 patient sample, was robotically redistributed into a 96 well v-Bottom plate (Evergreen, #222-8031) and prepped for mycoplasma testing on system 2. System 2, a separate liquid handling robot was used to perform a mycoplasma luminescent assay using the MycoAlert Mycoplasma Detection kit (Lonza, #LT107-318) with the accompanying MycoAlert Assay Control Set (Lonza, #LT07-518) and read on an integrated BioTek Synergy HT imaging system.

Wells that passed mycoplasma detection on system 2 were enzymatically passaged using TrypLE CTS (Life Technologies, #A12859-01) into a new 6 well daughter plate, keeping source wells separate at a 1:1 ratio on system 1. Passaged cells were maintained robotically in Complete M106 on System 1 and monitored using the Celigo automated imager for doubling times and ideal freezing confluence. Upon reaching confluence, each well of the daughter plate was enzymatically passaged using TrypLE Select CTS, pooled and resuspended in 1.5 ml of CTS Syntha-a-Freeze (Life Technologies, #A13717-01). Three 500 uL aliquots of the 1.5 mL resuspended cell suspension were transferred robotically into three 2D barcoded Matrix tubes (Thermo Scientific, #3741) for cryopreservation. Matrix tubes, within their rack, were placed in a CoolBox™ 96F System (Biocision, #BCS-147). After 24 hours, one of three cryopreserved matrix tubes representing one patient sample, was transferred from the CoolBox system to an automated −80° C. Sample Access Manager (SAM, Hamilton Storage Technologies) where samples are inventoried and selected for reprogramming runs. The sample access manager inventory database allows for flexible recall and downstream process batching of tubes for reprogramming based on multiple factors including density, growth rates and disease group. The remaining two matrix tubes of the same sample were transferred from the CoolBox system to liquid nitrogen for long-term storage.

Automated Fibroblast Thawing

Fibroblasts frozen in matrix tubes, stored within the SAM were removed in batches of 20 and manually counted to determine cell number and viability. Cells were manually resuspended into matrix tubes at known cell numbers, and frozen using the Biocision CoolBox. At the point of thaw 48 matrix tubes, typically consisting of duplicates of 20 cell lines and 8 BJ fibroblast controls, were removed and placed onto System 3. Cells were thawed in a 37° C. water bath for 30 seconds, before being placed on the robot deck. Upon starting the method tubes were decapped, fibroblast growth medium consisting of DMEM (#11965), 10% FBS, Glutamax, 2-Mercaptoethanol (all Life Technologies) was added to each vial, recapped and automatically centrifuged. The supernatant was subsequently removed, and the fibroblasts resuspended in fresh media before being transferred to 4, pre-barcoded, 12 well plates (Corning, #3513). Mapping files, traced through a centralized monitoring system, were automatically generated through the use of user-generated worklists. Cells were automatically transferred, via the RackRunner, to a cytomat where cells were housed. Each 12 well plate was fed every three days, with automated imaging occurring at least three times over a 10 day growth period.

Automated Cell Seeding (12 w to 24 w Passaging)

In brief, cells grown in 12 well plates were washed and dissociated with TrypLE Select CTS. Following neutralization with fibroblast growth medium, 5% (50 µL) of the cell suspension was transferred into a 96 well BD imaging plate (BD Biosciences, #353219) pre-filled with 50 µL of PBS (Life Technologies, #14190-144) containing 5 µg/mL Hoechst 33342 (Sigma, #B2261) and 1 µg/mL Propidium Iodide (Life Technologies, #P3566). The imaging plate was centrifuged for 2 minutes, before being subjected to a cell count using the Celigo's Dead/Total application. The cell counts were auto-exported with the liquid handling software automatically calculating the exact volume of cell suspension required for transfer into daughter wells of a 24 well plate (Corning, #3526). The Dead/Total cell count and confluence readout were recorded in each method run. Following the passage, cells remaining the in the original 12 well plate were re-fed and allowed to re-expand for downstream DNA isolation.

Automated Geltrex™ Plate Coating

For Geltrex™ plate coating, 1 mL of Geltrex™ was diluted into 99 mL of pre-chilled DMEM-F12 (Life Technologies, #10565-018) and kept at 4° C. on a module in System 7. Pre-chilled plates in either 96 well or 24 well plate formats were automatically coated with 100 µL or 500 µL of the pre-chilled Geltrex™ solution respectively. Coated plates were sealed and stored for a maximum for 2 weeks at 4° C. for later use to avoid premature gelling. Prior to use, plates were incubated at 37° C. for 1 hour.

Automated Reprogramming

For initial testing with Sendai virus (Life Technologies, #A1378001), a method was established to allow automated addition of the Sendai virus to the passaged fibroblasts. Following a medium exchange into fresh fibroblast growth medium the virus, kept chilled on a cooling block on system 3, was added dropwise into each well of the 24 well plate. Cells were briefly shaken for 10 seconds, before being returned to the cytomat incubator via the RackRunner. Cells were medium exchanged daily and monitored for the presence of colonies with automated imaging via the Celigo. For mRNA transfections, an mRNA reprogramming kit (Stemgent, #00-0071) was used. In brief, 4 hours prior to miRNA transfection the day after passaging, cells were equilibrated in Pluriton NUFF-conditioned medium (Stemgent) containing 2500× supplement and 200 ng/ml B18R (both supplied with kits). Following equilibration, cells were transfected with miRNA on days 0 and 4, with mRNA transfections occurring on days 1-10. The miRNA/mRNA mix was robotically added, dropwise, to each well of the 24 well plate on system 3, followed by a 10 second shaking to disperse the mRNA mix throughout the well. Each day, prior to transfection, plates were media exchanged with pre-conditioned Pluriton medium containing supplement and B18R. After 10 transfections, cells were fed for a further 5 days with the pre-conditioned Pluriton media containing the 2500× supplement. A transition to Freedom media (Life Technologies, #A14577SA) was made with 50% medium exchanges over the subsequent 2 days and cells were further grown for up to 30 days before being sorted. Since growth of fungi and mycoplasma can be very slow, and the use of antibiotics can mask the presence of bacteria in cell cultures. The whole process of automated somatic cell reprogramming and expansion of the generated iPSC lines has been processed in antibiotic free media. Strict policies were implemented on temperature control, and non-reuse of warmed reagents as well as barcode tracking systems to prevent variations in media and growth factor quality to control environmental growth conditions during culture. Strict guidelines to maintain the sterile conditions of the liquid handling systems and integrated devices were also implemented.

Automated iPS Cell Sorting

The automated iPS cell sorting method was based on a previously developed FACS method (Kahler et al, 2013, PloS one). In brief, the worklist defined the 24-well source plate to be sorted and the 96-well destination plates that the sorted iPS cells should be seeded into. The 24-well plate was called from the Cytomat, and half of the samples were processed at a time. Cells from 12 wells were dissociated with Accutase and transferred into half of a 24-deep well harvest plate (E&K Scientific, #EK-2053-S). After a 2 minute centrifugation step, the supernatant was removed, and cell pellets were resuspended with FACS buffer. 20 µL of human anti-fibroblast magnetic beads (Miltenyi Biotec, #130-050-601) was added to cells, allowed to incubate for 15 minutes, and then washed with FACS buffer to remove the unbound antibody. Following an additional centrifugation, cells were resuspended with 500 µL of FACS buffer and applied to a column block on a magnetic separator system (MultiMACS™ Cell24 Separator Plus, Miltenyi Biotec, #130-098-637). 500 µL of FACS buffer was then applied (×3) as washes, resulting in un-reprogrammed fibroblasts staying bound to the column, with reprogrammed cells passing through and collected as a 2 mL volume in a 24-deep well collection plate. The collection plate was centrifuged for 2 minutes, supernatant was removed, and cell pellets were resuspended in 400 µL Freedom medium supplemented with 1 uM Thiazovivin (Stemgent, #04-0017). Quadruplicate aliquots of the mixture containing 100 ul of cells were seeded into 4 wells of a Geltrex pre-coated, 96-well BD black imaging plate and serially diluted over a 3-fold range. The automated method looped through again to process the second half of the 24-well source plate.

Automated Cell Consolidation

This Example describes an automated method for consolidating the iPS colonies that passed quality control measures of confluency readout (>=15%), typical human ESC morphology (e.g. cells with large nuclei, small amount of cytoplasm, and form compact monolayer colony) and TRA-1-60 surface marker expression screening (Celigo Tumorsphere Analysis). Wells in 96-well sorted plates were identified, and a cherry-picking worklist was created to dictate source and destination transfer patterns. Per run, pairs of 96-well source plates were called from the Cytomat and processed together, until the destination plate was filled. Selected wells were washed and incubated with 75 µL of 0.05 mM EDTA for 6 minutes. Automated trituration by tips promoted cell dissociation, and 100 µL of cell mixtures were transferred into a new Geltrex-coated destination plate. For the first 24 hours, cells were cultured with Freedom medium supplemented with 1 µM Thiazovivin, after which cells were fed with Freedom daily. The task of cherry picking cells from targeted wells was formulated as a combinatorial optimization, where the goal was to efficiently select target clones with good recovery and without disturbing cell integrity, according to confluency read and morphological characteristics captured the day after consolidation.

Automated iPS Cell Passaging and Expansion

For cell passage of entire 96-well plates, a worklist was created, indicating source and destination plates. All liquid-handling steps herein occurred in the entire plate at once. The source plate was placed on the deck and cell media was aspirated. Cells were washed once with Accutase before a further addition of 25 µL per well. Accutase incubation was for 5 minutes at 37° C. on a heated shaker. Cells were neutralized with 175 µL Freedom media containing 1 µM thiazovivin, and transferred to an intermediate 96-well V-bottom plate (Evergreen, #222-8031-01V). Cells were centrifuged for 5 minutes at 300 RCF before supernatants were aspirated and cells resuspended in Freedom media with 1 µM Thiazovivin. Destination plates, previously robotically coated with Geltrex™ and previously robotically pre-processed by removal of Geltrex™ suspension and addition of Freedom media with 1 µM thiazovivin, were retrieved from a Cytomat incubator and placed on the deck. Cell suspensions were transferred from the intermediate plate to the new destination plate. Destination plates were returned to the Cytomat incubator.

Automated Cell Freezing (Passage to Cryovials)

A worklist was created, indicating which 96-well plates were to be frozen into 2D barcoded Matrix tubes in Matrix racks. All liquid-handling steps use a 96-head. Media was aspirated and cells were washed with 50 µL Accutase before a further addition of 50 µL of Accutase was added per well and cells were incubated at room temperature for 12 minutes. Enzyme neutralization was performed by the addition of Freedom media containing 1 µM Thiazovivin. Cell suspensions were transferred to an intermediate 96-well V-bottom plate and centrifuged for 5 minutes at 300 RCF. The Matrix rack was automatically de-capped and replaced onto the deck. Supernatants were aspirated and cells were resuspended in 200 µL Synth-a-Freeze. Cell suspensions were transferred to the Matrix tubes before being re-capped and manually placed into a CoolBox and stored −80° C. before being transferred 24 hours later to liquid nitrogen for long term storage.

Automated Cell Thawing (Thawing of Matrix Rack with 96 Matrix Tubes)

A Geltrex coated 96 well plate was retrieved from the Cytomat incubator. Liquid handling steps were performed with a 96-head. Tubes in the Matrix rack were capped and de-capped when necessary. 700 µL of Freedom media with 1 µM Thiazovivin was added to each vial. The tubes in the Matrix rack were centrifuged for 5 minutes at 300 RCF. Supernatant was removed and cells were resuspended in 125 µL of Freedom media with thiazovivin; 100 µL was transferred to the 96 well plate. The plate was placed in the Cytomat incubator. A 10 µL volume of cell suspension remaining in each tube was used for Dead/Total cell count by the Celigo imager.

Automated EB Formation

Cells were dissociated with Accutase for 5 minutes at 37° C. and plated in suspension into 96 well V-bottom plates (Greiner, #651161) in the presence of human ES culture media without bFGF and with 1 µM Thiazovivin using System 7. Human ES media consists of Knockout™-DMEM (#10829-018), 10% Knockout Serum Replacement (#10828-028), 1% Glutamax (#35050-079), MEM nonessential amino acids (#11140-050), 0.1 mM 2-mercaptoethanol (21985-023); All Life Technologies). Cells from one individual well were dispensed into 6 daughter wells in a culture volume of 150 µL/well to create 6 total EBs per starting well. After 24 hours, 100 µL of media was removed and added fresh media without Thiazovivin. Media exchanges were performed every 48 hours. On day 16, the EBs were imaged using a Celigo to determine their presence prior to collection by the liquid handler workstation. EBs were lysed through the addition of Lysis buffer using a Bravo Automated Liquid Handling Platform (Agilent Technologies). Lysis buffer 2× contained (0.5% N-Lauroylsarcosine Sodium salt (Sigma-Aldrich, #61747), 4M Guanidine Thiocyanate (Sigma-Aldrich, #50983), 200 mM 2-mercaptoethanol (Sigma-Aldrich, #63689), 0.02 Sodium Citrate (Sigma-Aldrich, #C8532), 2% DMSO (Sigma-Aldrich, #D2650). Cell extracts were quantified with Quant-iT™ RNA Assay Kit (Life Technologies, #Q-33140). Subsequently, 100 ng of cell extract was used for gene expression analysis on the NanoString nCounter system following manufacturer's protocol. A custom codeset was used which covers 98 genes representing early differentiation markers of the three germ layers (Kahler, D J et al., 2013).

Immunofluorescence Staining

Cell lines, including hES and hiPS were rinsed twice with 1×PBS, fixed with 4% paraformaldehyde (Santa Cruz, #sc-281692) in PBS for 20 min at room temperature and permeabilized with PBS containing 0.1% Triton X-100 (herein referred to as PBST; Sigma-Aldrich, #T8787) for 30 min. Nonspecific binding sites were blocked by incubation with PBST containing 10% donkey serum (Jackson Labs, #017-000-1210) for 2 hours at room temperature. Cells were subsequently incubated overnight at 4° C. in PBST containing 10% donkey serum and specific primary antibodies: 1:500 anti-Human Oct4 (Stemgent, #09-0023), 1:100 anti-human Nanog (Cell Signaling Technologies, #4903), 1:500 anti-Human Sox2 (Stemgent, #09-0024), 1:250 anti-human SSEA4 (Abcam, #ab16287), 1:250 anti-human Tra 1-81 (Stemgent, #09-0010) 1:250 anti-human Tra 1-60 (Stemgent, #09-0010). Following 3 washes in PBS, cells were incubated with one of the following secondary antibodies: Alexa Fluor® 488 donkey anti-Mouse (#A-21202; 1:1000 dilution) and Alexa Fluor® 555 donkey anti-rabbit IgG (#A-21428; 1:1000 dilution). After washing twice with 1×PBS, the samples were incubated for 10 min with Hoechst (1 µg/ml) in PBS, followed by a final wash in PBS. Alkaline phosphatase staining was performed according to the manufacturer's instructions (SK-5100). Fluorescence images were captured with the Celigo, Nikon Eclipse TE 2000-U or Olympus BX41 fluorescent microscope.

To determine pluripotency of automated iPSCs, cells were stained for CD-13 (BD Biosciences, #555394; 1:100 dilution), SSEA-4 (BD Bioscience, #560219; 1:100 dilution), Tra 1-60 (BD Bioscience, #560173; 1:100 dilution) and DAPI (Life Technologies)(1:15000 dilution). Stained cells were analyzed on a 5 laser BD Biosciences ARIA-IIu™ SOU Cell Sorter. The resulting data were analyzed using FlowJo software (Treestar).

DNA Isolation

DNA was isolated from both iPSCs and fibroblasts. Following the passage of cells from a 12 well to a 24 well, the fibroblasts remaining within the 12 well plate were robotically cultured for 10-12 days before being manually passaged to 6 well plates. Upon reaching ~90% confluence, as monitored through the Celigo, each 6-well plate was manually treated with TypLE Select CTS and the resulting cell pellet collected in a 96 deep well plate (Corning, #3960). The trough was sealed and frozen at −80° C. until DNA extraction. iPSCs were robotically passaged from 96 well plates into 24 well plates before being robotically harvested into 24 well plates and sealed before being stored at −80° C. DNA isolation from the cell pellets was achieved using the High Pure Template PCR Template Preparation Kit (Roche, #11796828001) as per the manufacturer's instructions with the following modifications: 1) cells were treated with 4 µL of RNase (Qiagen, #19101) for 2 minutes whilst resuspended in PBS; 2) DNA was eluted in 30 µL of water.

Cell Line Karyotyping and ID Testing

Cell lines were karyotyped and an identification record of each line was made using Nanostring technology. Karyotyping was undertaken using the Nanostring nCounter Human Karyotype Panel (Nanostring Technologies, USA) and performed as per the manufacturer's instructions. In brief, the protocol is as follows: 600 ng of genomic DNA was Alu1 digested at 37° C. for 2 hours, before being denatured at 95° C. for 5 minutes. To prevent renaturing samples were kept on ice. A total of 300 ng of Alu1-digested DNA per sample was mixed with hybridization buffer, capture and reporter codes. Following a 16 hour incubation at 65° C., samples were transferred to a Nanostring Prep station where hybridized DNA was bound to an imaging cartridge before imaging. Using reference samples, a copy number was calculated for each chromosome following normalization of the data using nSolver (Nanostring Technologies, USA) and Microsoft Excel. The same protocol was used for a proprietary codeset that allows the identification of genomic repeat elements. This codeset is based upon 28 previously identified Copy Number Polymorphic regions. (Tyson, C. et al. Expansion of a 12-kb VNTR containing the REXO1L1 gene cluster underlies the microscopically visible euchromatic variant of 8q21.2. Eur J Hum Genet 22, 458-463 (2014)). A dissimilarity score between a given pair of samples was calculated as the sum of squared differences between the samples' normalized, log-transformed probe values.

Gene expression analysis was performed using either a custom nCounter code set for pluripotency (Pluri25) or a custom nCounter code set for early differentiation markers into all three germ layers (3GL) previously described in (Kahler. D J et al., 2013). Cell extract containing 100 ng of RNA per sample, previously quantified with Quant-iT™ RNA Assay Kit (Life Technologies), was mixed with hybridization buffer, capture and reporter probes. Following a 16 hour incubation at 65° C., samples were transferred to a Nanostring Prep station, where hybridized fluorescently-labeled RNA was bound to an imaging cartridge before imaging. Data was normalized using nSolver (Nanostring Technologies, USA). Clustering was performed using the R software. R Core Team (2013). R: A language and environment for statistical computing. R Foundation for Statistical Computing, Vienna, Austria. ISBN 3-900051-07-0.

References for Example 5

Bock, C., Kiskinis, E., Verstappen, G., Gu, H., Boulting, G., Smith, Z. D., Ziller, M., Croft, G. F., Amoroso, M. W., Oakley, D. H., et al. (2011). Reference Maps of Human ES and iPS Cell Variation Enable High-Throughput Characterization of Pluripotent Cell Lines. Cell 144, 439-452.

Cahan, P., and Daley, G. Q. (2013). Origins and implications of pluripotent stem cell variability and heterogeneity. Nature Reviews Molecular Cell Biology 14, 357-368.

Carey, B. W., Markoulaki, S., Hanna, J. H., Faddah, D. A., Buganim, Y., Kim, J., Ganz, K., Steine, E. J., Cassady, J. P., Creyghton, M. P., et al. (2011). Reprogramming factor stoichiometry influences the epigenetic state and biological properties of induced pluripotent stem cells. Cell Stem Cell 9, 588-598.

Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Chemically defined conditions for human iPSC derivation and culture. Nature Methods 8, 424-429.

Chen, Kevin G., Mallon, Barbara S., McKay, Ronald D., and Robey, Pamela G. (2014). Human Pluripotent Stem Cell Culture: Considerations for Maintenance, Expansion, and Therapeutics. Cell Stem Cell 14, 13-26.

Cheng, L., Hansen, N. F., Zhao, L., Du, Y., Zou, C., Donovan, F. X., Chou, B.-K., Zhou, G., Li, S., Dowey, S. N., et al. (2012). Low Incidence of DNA Sequence Variation in Human Induced Pluripotent Stem Cells Generated by Nonintegrating Plasmid Expression. Stem Cell 10, 337-344.

Colman, A., and Dreesen, 0. (2009). Pluripotent stem cells and disease modeling. Cell Stem Cell 5, 244-247.

Daley, G. Q. (2010). Stem cells: roadmap to the clinic. The Journal of Clinical Investigation 120, 8-10.

Fusaki, N., Ban, H., Nishiyama, A., Saeki, K., and Hasegawa, M. (2009). Efficient induction of transgene-free human pluripotent stem cells using a vector based on Sendai virus, an RNA virus that does not integrate into the host genome. Proceedings of the Japan Academy Series B, Physical and biological sciences 85, 348-362.

Hanna, J., Saha, K., Pando, B., van Zon, J., Lengner, C. J., Creyghton, M. P., van Oudenaarden, A., and Jaenisch, R. (2009). Direct cell reprogramming is a stochastic process amenable to acceleration. Nature 462, 595-601.

Kahler, D. J., Ahmad, F. S., Ritz, A., Hua, H., Moroziewicz, D. N., Sproul, A. A., Dusenberry, C. R., Shang, L., Paull, D., Zimmer, M., et al. (2013). Improved methods for reprogramming human dermal fibroblasts using fluorescence activated cell sorting. PLoS One 8, e59867.

Kajiwara, M., Aoi, T., Okita, K., Takahashi, R., Inoue, H., Takayama, N., Endo, H., Eto, K., Toguchida, J., Uemoto, S., et al. (2012). Donor-dependent variations in hepatic differentiation from human-induced pluripotent stem cells. Proceedings of the National Academy of Sciences 109, 12538-12543.

Lander, E. S., Linton, L. M., Birren, B., Nusbaum, C., Zody, M. C., Baldwin, J., Devon, K., Dewar, K., Doyle, M., FitzHugh, W., et al. (2001). Initial sequencing and analysis of the human genome. Nature 409, 860-921.

Liang, G., and Zhang, Y. (2013). Genetic and Epigenetic Variations in iPSCs: Potential Causes and Implications for Application. Cell Stem Cell 13, 149-159.

Mayshar, Y., Ben-David, U., Lavon, N., Biancotti, J.-C., Yakir, B., Clark, A. T., Plath, K., Lowry, W. E., and Benvenisty, N. (2010). Identification and classification of chromosomal aberrations in human induced pluripotent stem cells. Cell stem cell 7, 521-531.

McKernan, R., and Watt, F. M. (2013). Nat Biotechnol. In What is the point of large-scale collections of human induced pluripotent stem cells? (United States), pp. 875-877.

Meldrum, D. (2000a). Automation for Genomics, Part One: Preparation for Sequencing. Genome Research 10, 1081-1092.

Meldrum, D. (2000b). Automation for Genomics, Part Two: Sequencers, Microarrays, and Future Trends. Genome Research 10, 1288-1303.

Miyoshi, N., Ishii, H., Nagano, H., Haraguchi, N., Dewi, D. L., Kano, Y., Nishikawa, S., Tanemura, M., Mimori, K., Tanaka, F., et al. (2011). Reprogramming of mouse and human cells to pluripotency using mature microRNAs. Cell Stem Cell 8, 633-638.

Morris, A. P., Voight, B. F., Teslovich, T. M., Ferreira, T., Segrè, A. V., Steinthorsdottir, V., Strawbridge, R. J., Khan, H., Grallert, H., Mahajan, A., et al. (2012). Large-scale association analysis provides insights into the genetic architecture and pathophysiology of type 2 diabetes. Nat Genet 44, 981-990.

Nestor, M. W., and Noggle, S. A. (2013). Standardization of human stem cell pluripotency using bioinformatics. Stem Cell Research & Therapy 4, 37.

Newman, A. M., and Cooper, J. B. (2010). Lab-specific gene expression signatures in pluripotent stem cells. Cell Stem Cell 7, 258-262.

Nishikawa, S.-i., Goldstein, R. A., and Nierras, C. R. (2008). The promise of human induced pluripotent stem cells for research and therapy. Nature Reviews Molecular Cell Biology 9, 725-729.

Ripke, S., O'Dushlaine, C., Chambert, K., Moran, J. L., Kahler, A. K., Akterin, S., Bergen, S. E., Collins, A. L., Crowley, J. J., Fromer, M., et al. (2013). Genome-wide association analysis identifies 13 new risk loci for schizophrenia. Nat Genet 45, 1150-1159.

Robinton, D. A., and Daley, G. Q. (2012). The promise of induced pluripotent stem cells in research and therapy. Nature 481, 295-305.

Rubin, L. L. (2008). Stem cells and drug discovery: the beginning of a new era? Cell 132, 549-552.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Team, R. C. (2014). R: A Language and Environment for Statistical Computing. R Foundation for Statistical Computing, Vienna, Austria, 2012 (ISBN 3-900051-07-0).

Utikal, J., Polo, J. M., Stadtfeld, M., Maherali, N., Kulalert, W., Walsh, R. M., Khalil, A., Rheinwald, J. G., and Hochedlinger, K. (2009). Immortalization eliminates a roadblock during cellular reprogramming into iPS cells. Nature 460, 1145-1148.

Warren, L., Manos, P. D., Ahfeldt, T., Loh, Y.-H., Li, H., Lau, F., Ebina, W., Mandal, P. K., Smith, Z. D., Meissner, A., et al. (2010). Highly Efficient Reprogramming to Pluripotency and Directed Differentiation of Human Cells with Synthetic Modified mRNA. Cell Stem Cell 7, 618-630.

Warren, L., Ni, Y., Wang, J., and Guo, X. (2012). Feeder-free derivation of human induced pluripotent stem cells with messenger RNA. Sci Rep 2, 657.

While several exemplary embodiments of the invention have been described, the invention is not limited to these embodiments.

What is claimed is:

1. A method for the automated generation and/or manipulation of stem cells, the method comprising:
   a) providing an automated system having controller software,
   b) culturing multiple different samples of cells, wherein the cells comprise adult somatic cells,
   c) determining the proliferation rate or cell doubling time of individual cell samples from among the multiple different samples of cells utilizing an automated device having controller software for determining the proliferation rate or cell doubling time,
   d) freezing individual cell samples from among the multiple different samples of cells,
   e) selecting from the individual cell samples a subset of samples having similar proliferation rates or cell doubling times,
   f) thawing the subset of samples selected in step (e),
   g) plating the subset of samples in a multi-well plate,
   h) culturing the subset of samples until they reach a desired confluency,
   i) contacting the cultured subset of samples with one or more reprogramming factors in order to produce iPSCs, and
   j) sorting the iPSCs and consolidating the sorted iPSCs to produce a pooled iPSC sample, wherein (a) to (j) are performed on the automated system via the controller software.

2. The method of claim 1, wherein the cells are derived from human donors.

3. The method of claim 1, wherein the adult somatic cells are fibroblasts.

4. The method of claim 1, wherein the individual cell samples in the subset of samples have proliferation rates or cell doubling times that are within 10% of one another.

5. The method of claim 1, wherein the culturing of step (h) is performed in low serum medium.

6. The method of claim 1, wherein the step of selecting a subset of samples further comprises selecting samples based the age, sex, race, ethnicity, diagnosis, genotype, phenotype, blood type, HLA type, treatment history, or drug response profile of the cell sample or of the donor from which the cell sample was obtained.

7. The method of claim 1, comprising contacting the pooled iPSCs with one or more differentiation factors thereby producing differentiated cells.

8. The method of claim 1, comprising generating embryoid bodies (EBs) from the pooled iPSCs.

9. The method of claim 8, wherein generating embryoid bodies (EBs) comprises plating iPSCs in V-bottom plates.

\* \* \* \* \*